US009561268B2

(12) United States Patent
Ceddia et al.

(10) Patent No.: US 9,561,268 B2
(45) Date of Patent: Feb. 7, 2017

(54) IMMUNOGENIC COMPOSITION

(71) Applicant: GLAXOSMITHKLINE BIOLOGICALS S.A., Rixensart (BE)

(72) Inventors: Francesca Ceddia, Rixensart (BE); William Paul Hausdorff, Rixensart (BE); Vincent Verlant, Rixensart (BE); Carine Ysebaert, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 67 days.

(21) Appl. No.: 13/826,696

(22) Filed: Mar. 14, 2013

(65) Prior Publication Data

US 2014/0105926 A1    Apr. 17, 2014

(30) Foreign Application Priority Data

Oct. 17, 2012  (GB) .................................. 1218660.7

(51) Int. Cl.
| | |
|---|---|
| *A61K 39/02* | (2006.01) |
| *A61K 39/09* | (2006.01) |
| *A61K 39/102* | (2006.01) |
| *A61K 39/00* | (2006.01) |

(52) U.S. Cl.
CPC ........... *A61K 39/092* (2013.01); *A61K 39/102* (2013.01); *A61K 2039/55505* (2013.01); *A61K 2039/55566* (2013.01); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 8,945,577 B2 | 2/2015 | Blais et al. | |
| 2009/0010959 A1 | 1/2009 | Biemans et al. | |
| 2011/0071279 A1 | 3/2011 | Hausdorff et al. | |
| 2014/0105927 A1* | 4/2014 | Verlant ...................... | 424/190.1 |
| 2014/0193451 A1 | 7/2014 | Verlant | |
| 2015/0166613 A1 | 6/2015 | Blais et al. | |
| 2015/0175670 A1 | 6/2015 | Blais et al. | |

FOREIGN PATENT DOCUMENTS

| | | |
|---|---|---|
| WO | 02/22168 | 3/2002 |
| WO | 2007/008527 | 1/2007 |
| WO | 2007/084053 | 7/2007 |
| WO | 2009/000826 | 12/2008 |
| WO | 2010/071986 | 7/2010 |
| WO | 2011/075823 | 6/2011 |
| WO | 2012/075428 | 6/2012 |
| WO | 2012/139225 | 10/2012 |
| WO | 2012/156391 | 11/2012 |
| WO | PCT/EP2013/071477 | 10/2013 |
| WO | PCT/EP2013/071483 | 10/2013 |

OTHER PUBLICATIONS

Van de Loo et al. (Proc. Natl. Acad. Sci 1995).*
Broun et al. (Science 1998).*
Prymula, et al., Pneumococcal capsular polysaccharides conjugated to protein D for prevention of acute otitis media caused by both *Streptococcus pneumoniae* and non-typable Haemophuilus influenzae: a randomised double-blind study, Lancet 367:740-748 (2006).
Croxtall and Keating, et al., Pneumococcal Polysaccharide Protein D-Conjugate Vaccine (Synflorix; PhiD-CV), Pediatr Drugs 11(5):349-357 (2009).
Prymula, et al., Effect of vaccination with pneumococcal capsular polysaccharides conjugated to Haemophilus influenzae-derived protein D on nasopharyngeal carriage of *Streptococcus pneumoniae* and H. influenzae in children under 2 years of age, Vaccine 28:71-78 (2010).
Peeters, et al., Effect of Carrier Priming on Immunogenicity of Saccharide-Protein Conjugate Vaccines, Infect & Immun 59(10):3504-3510 (1991).
Rennels, et al., Safety and Immunogenicity of Heptavalent Pneumococcal Vaccine Conjugated to CRM197 in United States Infants, Pediatrics 101(4): 604-611 (1998).
Choo, et al., Immunogenicity and reactogenicity of a pneumococcal conjugate vaccine administered combined with a Haemophilus influenzae type b conjugate vaccine in United Kingdom infants, Pediatr Infect Dis J 19(9):854-862 (2000).
Prymula, et al., Pneumococcal capsular polysaccharides conjugated to protein D for prevention of acute otitis media caused by both *Streptococcus pneumoniae* and non-typable Haemophilus influenzae: a randomised double-blind efficacy study, Lancet 367:740-748 (2006).
Prymula, et al., Effect of vaccination with pneumococcal capsular polysaccharides conjugated to Haemophilus influenzae-derived protein D on nasopharyngeal carriage of Streptococcus pneumoniae and H. influenzae in children under 2 years of age, Vaccine 28(1):71-78 (2009).
Bryant, et al., Safety and Immunogenicity of a 13-Valent Pneumococcal Conjugate Vaccine, Pediatrics 125 (5):866-875 (2010).
Sharma Sharad, et al., CD4+ T-cell responses among adults and young children in response to *Streptococcus pneumoniae* and Haemophilus influenzae vaccine candidate protein antigens, Vaccine 31(30): 3090-3097 (2013).
International Search Report for corresponding PCT/EP2013/071472.
International Search Report for Application PCT/EP2013/071477 filed Oct. 15, 2013.
International Search Report for Application PCT/EP2013/071483 filed Oct. 15, 2013.
Nowak-Wegrzyn, et al., Serum Opsonic Activity in Infants with Sickle-Cell Disease Immunized with Pneumococcal Polysaccharide Protein Conjugate Vaccine, Clinical and Vaccine Immunology 7(5):788-793 (2000).

(Continued)

Primary Examiner — J. Hines
Assistant Examiner — Khatol Shahnan Shah
(74) Attorney, Agent, or Firm — Barbara J. Carter

(57) ABSTRACT

The present invention relates to immunogenic compositions comprising one or more *Streptococcus pneumoniae* capsular saccharide conjugates and a protein component comprising Protein E and/or PilA from *Haemophilus influenzae*.

19 Claims, 29 Drawing Sheets

(56) References Cited

OTHER PUBLICATIONS

A phase II, randomized, controlled, observer-blind study to assess the safety, reactogenicity and immunogenicity of GlaxoSmithKline (GSK) Biologicals' *Streptococcus pneumoniae* protein containing vaccine formulations when administered according to a 0-2-6 month schedule, in healthy children aged 12-2, International Clinical Trials Registry Platform, Mar. 19, 2011 XP055097477, Retrieved from the Internet: URL:htt;://apps.who.int/trialsearch/trial.aspx?trialid=EUCTR2009-012701-19-CZ [retrieved on Jan. 21, 2014] the whole document.

Hausdorff, et al., Need for and development of a protein-based pneumococcal vaccine, Nov. 18, 2011, XP002724490, Retrieved from the Internet: URL:http://www.meningitis.org/assets/x/53980 [retrieved on Apr. 1, 2014] p. 25.

Leroux-Roels, Safety/reactogenicity results of a phase I clinical trial of an investigational pneumococcal protein-based vaccine in adults (poster n° 231), 8th International Symposium on Pneumococci and Pneumococcal Diseases, Mar. 11, 2012-Mar. 15, 2012, XP055111237, Iguacu Falls, Brazil, p. 543.

Pauksens, et al., Randomized Controlled Study of Pneumococcal Vaccine Formulations containing PhtD and dPly Proteins with Alum or Adjuvant System AS02V in Elderly Adults: Safety and Immunogenicity, Clinical and Vaccine Immunology, Mar. 1, 2014, XP055111053, ISN: 1556-6811, DOI: 10.1128/CVI.00807-13 the whole document.

Prymula, et al., Safety and immunogenicity of an investigational vaccine containing two common pneumococcal proteins given to Czech toddlers (poster n° 274), 8th International Symposium on Pneumococci and Pneumococcal Diseases, Mar. 11, 2012-Mar. 15, 2012, XP055111237, Iguacu Falls, Brazil, p. 586.

Leroux-Roels, et al., Safety, reactogenicity and immunogenicity of a novel pneumococcal protein-based vaccine in adults: a phase I/II randomized clinical study, Vaccine (2014) http://dx.doi.org/10.1016/j.vaccine.2014.02.052.

* cited by examiner (a)

(b)

(a) Experiment 1

(b) Experiment 2

(c) Experiment 3

| Construct ID | % fusion protein gel #1 | % fusion protein gel #2 | % fusion protein gel #3 | Average % fusion protein | SD deviation |
|---|---|---|---|---|---|
| LVL291 | 9.3 | 8.98 | 9.43 | 9.24 | 0.231588716 |
| LVL702 | 7.2 | 8.85 | 8.37 | 8.14 | 0.848704896 |
| LVL736 | 11.16 | 10.2 | 11.94 | 11.10 | 0.871550343 |
| LVL737 | 8.18 | 8.33 | 9.32 | 8.61 | 0.619435227 |
| LVL738 | 8.56 | 8.55 | 7.97 | 8.36 | 0.337786915 |
| LVL739 | 8.91 | 8.88 | 9.21 | 9.00 | 0.182482876 |
| LVL740 | 7.69 | 7.49 | 8 | 7.73 | 0.256969518 |

SEQUENCE LISTING

```
<160> NUMBER OF SEQ ID NOS: 220

<210> SEQ ID NO 1
<211> LENGTH: 25
<212> TYPE: PRT
<213> ORGANISM: Haemophilus influenzae

<400> SEQUENCE: 1

Pro Lys Arg Tyr Ala Arg Ser Val Arg Gln Tyr Lys Ile Leu Asn Cys
1               5                   10                  15

Ala Asn Tyr His Leu Thr Gln Val Arg
            20                  25

<210> SEQ ID NO 2
<211> LENGTH: 7
<212> TYPE: PRT
<213> ORGANISM: Artificial Sequence
<220> FEATURE:
<223> OTHER INFORMATION: synthetic construct

<400> SEQUENCE: 2

Met His His His His His His
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Gly Gly His His His His His His
1               5

<210> SEQ ID NO 4
<211> LENGTH: 160
<212> TYPE: PRT
<213> ORGANISM: Haemophilus influenzae

<400> SEQUENCE: 4

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95
```

-continued

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

<210> SEQ ID NO 5
<211> LENGTH: 160
<212> TYPE: PRT
<213> ORGANISM: Haemophilus influenzae

<400> SEQUENCE: 5

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

<210> SEQ ID NO 6
<211> LENGTH: 160
<212> TYPE: PRT
<213> ORGANISM: Haemophilus influenzae

<400> SEQUENCE: 6

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
                100                 105                 110

```
Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 7
<211> LENGTH: 160
<212> TYPE: PRT
<213> ORGANISM: Haemophilus influenzae

<400> SEQUENCE: 7

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 8
<211> LENGTH: 160
<212> TYPE: PRT
<213> ORGANISM: Haemophilus influenzae

<400> SEQUENCE: 8

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125
```

```
Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 9
<211> LENGTH: 160
<212> TYPE: PRT
<213> ORGANISM: Haemophilus influenzae

<400> SEQUENCE: 9

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 10
<211> LENGTH: 160
<212> TYPE: PRT
<213> ORGANISM: Haemophilus influenzae

<400> SEQUENCE: 10

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Met Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
        130                 135                 140
```

```
Gln Ile Ile Cys Ala Asn Tyr Gly Lys Ala Phe Ser Val Asp Lys Lys
145                 150                 155                 160
```

<210> SEQ ID NO 11
<211> LENGTH: 160
<212> TYPE: PRT
<213> ORGANISM: Haemophilus influenzae

<400> SEQUENCE: 11

```
Met Lys Lys Ile Ile Leu Thr Leu Ser Leu Gly Leu Leu Thr Ala Cys
 1               5                  10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160
```

<210> SEQ ID NO 12
<211> LENGTH: 159
<212> TYPE: PRT
<213> ORGANISM: Haemophilus influenzae

<400> SEQUENCE: 12

```
Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Met Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Val Asp Asn Gln Glu Pro Gln Ile
50                  55                  60

Val His Phe Asp Ala Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
        115                 120                 125

His Thr Leu Ser Leu Thr Pro Asp Thr Thr Leu Tyr Asn Ala Ala Gln
    130                 135                 140

Ile Ile Cys Ala Asn Tyr Gly Lys Ala Phe Ser Val Asp Lys Lys
145                 150                 155
```

<210> SEQ ID NO 13
<211> LENGTH: 160
<212> TYPE: PRT
<213> ORGANISM: Haemophilus influenzae

<400> SEQUENCE: 13

Met Lys Lys Ile Ile Leu Thr Leu Ser Leu Gly Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 14
<211> LENGTH: 160
<212> TYPE: PRT
<213> ORGANISM: Haemophilus influenzae

<400> SEQUENCE: 14

Met Lys Lys Ile Ile Leu Thr Leu Ser Leu Gly Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 15

```
<211> LENGTH: 194
<212> TYPE: PRT
<213> ORGANISM: Haemophilus influenzae

<400> SEQUENCE: 15

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Gln Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Ile Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Asn
145                 150                 155                 160

Lys Lys Ile Cys Thr Leu Ile Ser Leu Asn Phe Ile Gln Leu Leu Gly
                165                 170                 175

Cys Arg Glu Tyr Ser Ile Phe Leu Gln Leu Leu Leu Phe Tyr Cys Trp
            180                 185                 190

His Phe

<210> SEQ ID NO 16
<211> LENGTH: 195
<212> TYPE: PRT
<213> ORGANISM: Haemophilus influenzae

<400> SEQUENCE: 16

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140
```

```
Gln Ile Ile Cys Ala Asn Tyr Gly Lys Ala Phe Ser Val Asp Lys Lys
145                 150                 155                 160

Ile Lys Lys Ile Cys Thr Leu Ile Ser Leu Asn Phe Ile Gln Leu Leu
            165                 170                 175

Gly Cys Arg Glu Tyr Ser Ile Phe Leu Gln Leu Leu Leu Phe Tyr Cys
        180                 185                 190

Trp His Phe
    195

<210> SEQ ID NO 17
<211> LENGTH: 160
<212> TYPE: PRT
<213> ORGANISM: Haemophilus influenzae

<400> SEQUENCE: 17

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Met Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 18
<211> LENGTH: 160
<212> TYPE: PRT
<213> ORGANISM: Haemophilus influenzae

<400> SEQUENCE: 18

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110
```

```
Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 19
<211> LENGTH: 160
<212> TYPE: PRT
<213> ORGANISM: Haemophilus influenzae

<400> SEQUENCE: 19

Met Lys Lys Ile Ile Leu Thr Leu Ser Leu Gly Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
        100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160

<210> SEQ ID NO 20
<211> LENGTH: 160
<212> TYPE: PRT
<213> ORGANISM: Haemophilus influenzae

<400> SEQUENCE: 20

Met Lys Lys Ile Ile Leu Thr Leu Ser Leu Gly Leu Thr Ala Cys
1               5                   10                  15

Ser Ala Gln Thr Gln Lys Val Glu Gln Asn Asp Val Lys Leu Thr Ala
            20                  25                  30

Pro Thr Asp Val Arg Ser Gly Phe Val Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
        100                 105                 110

Asp Glu Phe Trp Gly Gln Gly Leu Arg Ala Ala Pro Lys Lys Gln Lys
            115                 120                 125
```

```
Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Leu Val Asp Lys Lys
145                 150                 155                 160

<210> SEQ ID NO 21
<211> LENGTH: 160
<212> TYPE: PRT
<213> ORGANISM: Haemophilus influenzae

<400> SEQUENCE: 21

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 22
<211> LENGTH: 160
<212> TYPE: PRT
<213> ORGANISM: Haemophilus influenzae

<400> SEQUENCE: 22

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140
```

Gln Ile Ile Cys Ala Asn Tyr Gly Lys Ala Phe Ser Val Asp Lys Lys
145                 150                 155                 160

<210> SEQ ID NO 23
<211> LENGTH: 160
<212> TYPE: PRT
<213> ORGANISM: Haemophilus influenzae

<400> SEQUENCE: 23

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Glu Ala Phe Ser Val Asp Lys Lys
145                 150                 155                 160

<210> SEQ ID NO 24
<211> LENGTH: 160
<212> TYPE: PRT
<213> ORGANISM: Haemophilus influenzae

<400> SEQUENCE: 24

Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Pro
            20                  25                  30

Pro Thr Asp Val Arg Ser Gly Tyr Val Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 25
<211> LENGTH: 160
<212> TYPE: PRT
<213> ORGANISM: Haemophilus influenzae

<400> SEQUENCE: 25

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

<210> SEQ ID NO 26
<211> LENGTH: 160
<212> TYPE: PRT
<213> ORGANISM: Haemophilus influenzae

<400> SEQUENCE: 26

Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
            20                  25                  30

Pro Thr Asp Val Arg Ser Gly Tyr Val Arg Leu Val Lys Asn Ala Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 27
<211> LENGTH: 160

```
<212> TYPE: PRT
<213> ORGANISM: Haemophilus influenzae

<400> SEQUENCE: 27

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Ile Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 28
<211> LENGTH: 160
<212> TYPE: PRT
<213> ORGANISM: Haemophilus influenzae

<400> SEQUENCE: 28

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 29
<211> LENGTH: 160
<212> TYPE: PRT
<213> ORGANISM: Haemophilus influenzae
```

```
<400> SEQUENCE: 29

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Thr Val Val Asn Leu Asp Lys Gly Leu Tyr Val
65              70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 30
<211> LENGTH: 160
<212> TYPE: PRT
<213> ORGANISM: Haemophilus influenzae

<400> SEQUENCE: 30

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65              70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 31
<211> LENGTH: 160
<212> TYPE: PRT
<213> ORGANISM: Haemophilus influenzae

<400> SEQUENCE: 31

Met Lys Lys Ile Ile Leu Thr Leu Ser Leu Gly Leu Leu Thr Ala Cys
```

```
                1               5                   10                  15
Ser Ala Gln Ile Gln Lys Ala Lys Gln Asn Asp Val Lys Leu Ala Pro
                    20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
            50                  55                  60

Ile Val His Phe Asp Ala Val Val Asn Leu Asp Lys Gly Leu Tyr Val
 65                 70                  75                  80

Tyr Pro Glu Pro Lys Arg Tyr Ala Arg Ser Val Arg Gln Tyr Lys Ile
                    85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Glu Ala Phe Ser Val Asp Lys Lys
145                 150                 155                 160

<210> SEQ ID NO 32
<211> LENGTH: 160
<212> TYPE: PRT
<213> ORGANISM: Haemophilus influenzae

<400> SEQUENCE: 32

Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Val Lys Leu Ala Pro
                    20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
            50                  55                  60

Ile Val His Phe Asp Ala Val Val Asn Leu Asp Lys Gly Leu Tyr Val
 65                 70                  75                  80

Tyr Pro Glu Pro Lys Arg Tyr Ala Arg Ser Val Arg Gln Tyr Lys Ile
                    85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 33
<211> LENGTH: 160
<212> TYPE: PRT
<213> ORGANISM: Haemophilus influenzae

<400> SEQUENCE: 33

Met Lys Lys Ile Ile Leu Thr Leu Ser Leu Gly Leu Leu Thr Ala Cys
 1               5                   10                  15

Ser Ala Gln Thr Gln Lys Val Glu Gln Asn Asp Val Lys Leu Thr Pro
```

```
                    20                  25                  30

Pro Thr Asp Val Arg Ser Gly Tyr Val Arg Leu Val Lys Asn Val Asn
                35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 34
<211> LENGTH: 160
<212> TYPE: PRT
<213> ORGANISM: Haemophilus influenzae

<400> SEQUENCE: 34

Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 35
<211> LENGTH: 160
<212> TYPE: PRT
<213> ORGANISM: Haemophilus influenzae

<400> SEQUENCE: 35

Met Lys Lys Ile Ile Leu Thr Leu Ser Leu Gly Leu Leu Thr Ala Cys
 1               5                   10                  15

Ser Ala Gln Ile Gln Lys Ala Lys Gln Asn Asp Val Lys Leu Ala Pro
                20                  25                  30

Pro Thr Asp Val Arg Ser Gly Tyr Ile Arg Leu Val Lys Asn Val Asn
```

```
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

<210> SEQ ID NO 36
<211> LENGTH: 160
<212> TYPE: PRT
<213> ORGANISM: Haemophilus influenzae

<400> SEQUENCE: 36

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

<210> SEQ ID NO 37
<211> LENGTH: 160
<212> TYPE: PRT
<213> ORGANISM: Haemophilus influenzae

<400> SEQUENCE: 37

Met Lys Lys Ile Ile Leu Thr Leu Ser Leu Gly Leu Leu Thr Ala Cys
  1               5                  10                  15

Ser Ala Gln Thr Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
```

```
                50                  55                  60
Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 38
<211> LENGTH: 160
<212> TYPE: PRT
<213> ORGANISM: Haemophilus influenzae

<400> SEQUENCE: 38

Met Lys Lys Ile Ile Leu Thr Leu Ser Leu Gly Leu Leu Thr Ala Cys
 1                   5                  10                  15

Ser Ala Gln Thr Gln Lys Val Glu Gln Asn Asp Val Lys Leu Thr Ala
                 20                  25                  30

Pro Ala Asp Val Arg Ser Gly Tyr Val Arg Leu Val Lys Asn Val Asn
                 35                  40                  45

Tyr Tyr Ile Asp Ser Glu Ser Ile Trp Val Asp Asn Gln Glu Pro Gln
                 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 39
<211> LENGTH: 159
<212> TYPE: PRT
<213> ORGANISM: Haemophilus influenzae

<400> SEQUENCE: 39

Met Lys Lys Ile Ile Leu Thr Leu Ser Leu Gly Leu Leu Thr Ala Cys
 1                   5                  10                  15

Ser Ala Gln Ile Gln Lys Ala Lys Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
                 50                  55                  60

Ile Val His Phe Asp Ala Val Val Asn Leu Asp Lys Gly Leu Tyr Val
```

```
                65                  70                  75                  80
Tyr Pro Glu Pro Lys Arg Tyr Ala Arg Ser Val Arg Tyr Lys Ile Leu
                    85                  90                  95

Asn Cys Ala Asn Tyr His Leu Thr Gln Val Arg Thr Asp Phe Tyr Asp
                100                 105                 110

Glu Phe Trp Gly Gln Gly Leu Arg Ala Ala Pro Lys Lys Gln Lys Lys
                115                 120                 125

His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys
145                 150                 155

<210> SEQ ID NO 40
<211> LENGTH: 159
<212> TYPE: PRT
<213> ORGANISM: Haemophilus influenzae

<400> SEQUENCE: 40

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Tyr Lys Ile Leu
                    85                  90                  95

Asn Cys Ala Asn Tyr His Leu Thr Gln Val Arg Thr Asp Phe Tyr Asp
                100                 105                 110

Glu Phe Trp Gly Gln Gly Leu Arg Ala Ala Pro Lys Lys Gln Lys Lys
                115                 120                 125

His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys
145                 150                 155

<210> SEQ ID NO 41
<211> LENGTH: 160
<212> TYPE: PRT
<213> ORGANISM: Haemophilus influenzae

<400> SEQUENCE: 41

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
```

```
            85                  90                  95
Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 42
<211> LENGTH: 160
<212> TYPE: PRT
<213> ORGANISM: Haemophilus influenzae

<400> SEQUENCE: 42

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 43
<211> LENGTH: 160
<212> TYPE: PRT
<213> ORGANISM: Haemophilus influenzae

<400> SEQUENCE: 43

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
```

```
                    100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 44
<211> LENGTH: 160
<212> TYPE: PRT
<213> ORGANISM: Haemophilus influenzae

<400> SEQUENCE: 44

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 45
<211> LENGTH: 160
<212> TYPE: PRT
<213> ORGANISM: Haemophilus influenzae

<400> SEQUENCE: 45

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Ser Leu Arg Ala Ala Pro Lys Lys Gln Lys
```

```
                115                 120                 125
Lys His Thr Leu Ser Leu Thr Pro Asp Thr Thr Leu Tyr Asn Ala Ala
        130                 135                 140
Gln Ile Ile Cys Ala Asn Tyr Gly Lys Ala Phe Ser Val Asp Lys Lys
145                 150                 155                 160

<210> SEQ ID NO 46
<211> LENGTH: 160
<212> TYPE: PRT
<213> ORGANISM: Haemophilus influenzae

<400> SEQUENCE: 46

Met Lys Lys Ile Ile Leu Thr Leu Ser Leu Gly Leu Leu Thr Ala Cys
1               5                   10                  15
Ser Ala Gln Thr Gln Lys Val Glu Gln Asn Asp Val Lys Leu Thr Pro
            20                  25                  30
Pro Thr Asp Val Arg Ser Gly Tyr Val Arg Leu Val Lys Asn Val Asn
        35                  40                  45
Tyr Tyr Ile Asp Ser Glu Ser Ile Trp Val Asp Asn Gln Glu Pro Gln
50                  55                  60
Ile Val His Phe Asp Ala Val Val Asn Leu Asp Lys Gly Leu Tyr Val
65                  70                  75                  80
Tyr Pro Glu Pro Lys Arg Tyr Ala Arg Ser Val Arg Gln Tyr Lys Ile
                85                  90                  95
Leu Asn Cys Ala Asn Tyr His Leu Thr Gln Val Arg Thr Asp Phe Tyr
            100                 105                 110
Asp Glu Phe Trp Gly Gln Gly Leu Arg Ala Ala Pro Lys Lys Gln Lys
        115                 120                 125
Lys His Thr Leu Ser Leu Thr Pro Asp Thr Thr Val Tyr Asn Ala Ala
        130                 135                 140
Gln Ile Ile Cys Ala Asn Tyr Gly Lys Ala Phe Ser Val Asp Lys Lys
145                 150                 155                 160

<210> SEQ ID NO 47
<211> LENGTH: 160
<212> TYPE: PRT
<213> ORGANISM: Haemophilus influenzae

<400> SEQUENCE: 47

Met Lys Lys Ile Ile Leu Thr Leu Ser Leu Gly Leu Leu Thr Ala Cys
1               5                   10                  15
Ser Ala Gln Thr Gln Lys Val Glu Gln Asn Asp Val Lys Leu Thr Pro
            20                  25                  30
Pro Thr Asp Val Arg Ser Gly Tyr Val Arg Leu Val Lys Asn Val Asn
        35                  40                  45
Tyr Tyr Ile Asp Ser Glu Ser Ile Trp Val Asp Asn Gln Glu Pro Gln
50                  55                  60
Ile Val His Phe Asp Ala Val Val Asn Leu Asp Lys Gly Leu Tyr Val
65                  70                  75                  80
Tyr Pro Glu Pro Lys Arg Tyr Ala Arg Ser Val Arg Gln Tyr Lys Ile
                85                  90                  95
Leu Asn Cys Ala Asn Tyr His Leu Thr Gln Val Arg Thr Asp Phe Tyr
            100                 105                 110
Asp Glu Phe Trp Gly Gln Gly Leu Arg Ala Ala Pro Lys Lys Gln Lys
        115                 120                 125
Lys His Thr Leu Ser Leu Thr Pro Asp Thr Thr Val Tyr Asn Ala Ala
```

Gln Ile Ile Cys Ala Asn Tyr Gly Lys Ala Phe Ser Val Asp Lys Lys
145                 150                 155                 160

<210> SEQ ID NO 48
<211> LENGTH: 160
<212> TYPE: PRT
<213> ORGANISM: Haemophilus influenzae

<400> SEQUENCE: 48

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 49
<211> LENGTH: 160
<212> TYPE: PRT
<213> ORGANISM: Haemophilus influenzae

<400> SEQUENCE: 49

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys

<210> SEQ ID NO 50
<211> LENGTH: 160
<212> TYPE: PRT
<213> ORGANISM: Haemophilus influenzae

<400> SEQUENCE: 50

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 51
<211> LENGTH: 160
<212> TYPE: PRT
<213> ORGANISM: Haemophilus influenzae

<400> SEQUENCE: 51

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

```
<210> SEQ ID NO 52
<211> LENGTH: 160
<212> TYPE: PRT
<213> ORGANISM: Haemophilus influenzae

<400> SEQUENCE: 52

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
 50                  55                  60

Ile Val His Phe Asp Ala Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
             85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 53
<211> LENGTH: 160
<212> TYPE: PRT
<213> ORGANISM: Haemophilus influenzae

<400> SEQUENCE: 53

Met Lys Lys Ile Ile Leu Thr Leu Ser Leu Gly Leu Leu Thr Ala Cys
  1               5                  10                  15

Ser Ala Gln Ile Gln Lys Ala Glu Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
 50                  55                  60

Ile Val His Phe Asp Thr Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
             85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 54
<211> LENGTH: 160
<212> TYPE: PRT
```

<213> ORGANISM: Haemophilus influenzae

<400> SEQUENCE: 54

| Met | Lys | Lys | Ile | Ile | Leu | Thr | Leu | Ser | Leu | Gly | Leu | Leu | Thr | Ala | Cys |
| 1 | | | | 5 | | | | | 10 | | | | | 15 | |

Ser Ala Gln Thr Gln Lys Ala Glu Gln Asn Asp Val Lys Leu Ala Pro
         20                  25                  30

Pro Thr Asp Val Arg Ser Gly Tyr Ile Arg Leu Val Lys Asn Val Asn
             35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
             85                  90                  95

Leu Asn Cys Ala Asn Tyr His Leu Thr Gln Ile Arg Thr Asp Phe Tyr
             100                 105                 110

Asp Glu Phe Trp Gly Gln Gly Leu Arg Ala Ala Pro Lys Lys Gln Lys
             115                 120                 125

Lys His Thr Leu Ser Leu Thr Pro Asp Thr Thr Leu Tyr Asn Ala Ala
         130                 135                 140

Gln Ile Ile Cys Ala Asn Tyr Gly Lys Ala Phe Ser Val Asp Lys Lys
145                 150                 155                 160

<210> SEQ ID NO 55
<211> LENGTH: 160
<212> TYPE: PRT
<213> ORGANISM: Haemophilus influenzae

<400> SEQUENCE: 55

| Met | Lys | Lys | Ile | Ile | Leu | Thr | Leu | Ser | Leu | Gly | Leu | Leu | Thr | Ala | Cys |
| 1 | | | | 5 | | | | | 10 | | | | | 15 | |

Ser Ala Gln Ile Gln Lys Ala Lys Gln Asn Asp Val Lys Leu Ala Pro
         20                  25                  30

Pro Thr Asp Val Arg Ser Gly Tyr Ile Arg Leu Val Lys Asn Val Asn
             35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
             85                  90                  95

Leu Asn Cys Ala Asn Tyr His Leu Thr Gln Val Arg Thr Asp Phe Tyr
             100                 105                 110

Asp Glu Phe Trp Gly Gln Gly Leu Arg Ala Ala Pro Lys Lys Gln Lys
             115                 120                 125

Lys His Thr Leu Ser Leu Thr Pro Asp Thr Thr Leu Tyr Asn Ala Ala
         130                 135                 140

Gln Ile Ile Cys Ala Asn Tyr Gly Glu Ala Phe Ser Val Asp Lys Lys
145                 150                 155                 160

<210> SEQ ID NO 56
<211> LENGTH: 160
<212> TYPE: PRT
<213> ORGANISM: Haemophilus influenzae

<400> SEQUENCE: 56

```
Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                      55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 57
<211> LENGTH: 159
<212> TYPE: PRT
<213> ORGANISM: Haemophilus influenzae

<400> SEQUENCE: 57

Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Met Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Val Asp Asn Gln Glu Pro Gln Ile
50                      55                  60

Val His Phe Asp Ala Val Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
                100                 105                 110

Glu Phe Trp Gly Gln Gly Leu Arg Ala Ala Pro Lys Lys Gln Lys Lys
            115                 120                 125

His Thr Leu Ser Leu Thr Pro Asp Thr Thr Leu Tyr Asn Ala Ala Gln
        130                 135                 140

Ile Ile Cys Ala Asn Tyr Gly Lys Ala Phe Ser Val Asp Lys Lys
145                 150                 155

<210> SEQ ID NO 58
<211> LENGTH: 149
<212> TYPE: PRT
<213> ORGANISM: Haemophilus influenzae

<400> SEQUENCE: 58

Met Lys Leu Thr Thr Gln Gln Thr Leu Lys Lys Gly Phe Thr Leu Ile
 1               5                   10                  15
```

```
Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 59
<211> LENGTH: 149
<212> TYPE: PRT
<213> ORGANISM: Haemophilus influenzae

<400> SEQUENCE: 59

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Ala Gly Asn Gly Thr Leu Asp Gly Met Ser
                100                 105                 110

Tyr Thr Leu Thr Ala Glu Gly Asp Ser Ala Lys Gly Val Thr Trp Lys
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 60
<211> LENGTH: 149
<212> TYPE: PRT
<213> ORGANISM: Haemophilus influenzae

<400> SEQUENCE: 60

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30
```

```
Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 61
<211> LENGTH: 149
<212> TYPE: PRT
<213> ORGANISM: Haemophilus influenzae

<400> SEQUENCE: 61

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Lys Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Gly Lys Pro Ser Ser Cys Ser Gly Gly Ser Asn Gly Ile Ala
 65                  70                  75                  80

Ala Asp Ile Thr Thr Ala Lys Gly Tyr Val Ala Ser Val Ile Thr Gln
                 85                  90                  95

Ser Gly Gly Ile Thr Val Lys Gly Asp Gly Thr Leu Ala Asn Met Glu
                100                 105                 110

Tyr Ile Leu Gln Ala Ala Gly Asn Ala Ala Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 62
<211> LENGTH: 149
<212> TYPE: PRT
<213> ORGANISM: Haemophilus influenzae

<400> SEQUENCE: 62

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
            35                  40                  45
```

```
Leu Gln Ala Ser Ala Pro Tyr Lys Ala Asp Val Glu Leu Cys Val Tyr
     50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 63
<211> LENGTH: 149
<212> TYPE: PRT
<213> ORGANISM: Haemophilus influenzae

<400> SEQUENCE: 63

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ser Asp Val Glu Leu Cys Val Tyr
     50                  55                  60

Ser Thr Gly Lys Pro Ser Thr Cys Ser Gly Gly Ser Asn Gly Ile Ala
 65                  70                  75                  80

Ala Asp Ile Thr Thr Val Lys Gly Tyr Val Lys Ser Val Thr Thr Ser
                 85                  90                  95

Asn Gly Ala Ile Thr Val Ala Gly Asn Gly Thr Leu Asp Gly Met Ser
                100                 105                 110

Tyr Thr Leu Thr Ala Glu Gly Asp Ser Ala Lys Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 64
<211> LENGTH: 149
<212> TYPE: PRT
<213> ORGANISM: Haemophilus influenzae

<400> SEQUENCE: 64

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
     50                  55                  60
```

```
Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
             85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 65
<211> LENGTH: 149
<212> TYPE: PRT
<213> ORGANISM: Haemophilus influenzae

<400> SEQUENCE: 65

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
             85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 66
<211> LENGTH: 149
<212> TYPE: PRT
<213> ORGANISM: Haemophilus influenzae

<400> SEQUENCE: 66

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80
```

Ala Asp Ile Thr Thr Ala Lys Gly Tyr Val Lys Ser Val Thr Thr Ser
            85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
            130                 135                 140

Gly Ser Val Thr Gln
145

<210> SEQ ID NO 67
<211> LENGTH: 149
<212> TYPE: PRT
<213> ORGANISM: Haemophilus influenzae

<400> SEQUENCE: 67

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Lys Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Ile Thr Asn Cys Met Gly Gly Lys Asn Gly Ile Ala
65              70                  75                  80

Ala Asp Ile Thr Thr Ala Lys Gly Tyr Val Ala Ser Val Lys Thr Gln
            85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Ala Gly Val Thr Trp Thr
            115                 120                 125

Thr Thr Cys Lys Gly Thr Asp Ala Ser Leu Phe Pro Ala Asn Phe Cys
            130                 135                 140

Gly Ser Ile Thr Gln
145

<210> SEQ ID NO 68
<211> LENGTH: 149
<212> TYPE: PRT
<213> ORGANISM: Haemophilus influenzae

<400> SEQUENCE: 68

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65              70                  75                  80

Ala Asp Ile Thr Thr Ala Lys Gly Tyr Val Ala Ser Val Lys Thr Gln
            85                  90                  95

```
Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 69
<211> LENGTH: 149
<212> TYPE: PRT
<213> ORGANISM: Haemophilus influenzae

<400> SEQUENCE: 69

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Ser Cys Thr Gly Gly Lys Asn Gly Ile Ala
65                  70                  75                  80

Ala Asp Ile Lys Thr Ala Lys Gly Tyr Val Ala Ser Val Ile Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Ala Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145

<210> SEQ ID NO 70
<211> LENGTH: 149
<212> TYPE: PRT
<213> ORGANISM: Haemophilus influenzae

<400> SEQUENCE: 70

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110
```

```
Tyr Ile Leu Gln Ala Ser Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 71
<211> LENGTH: 149
<212> TYPE: PRT
<213> ORGANISM: Haemophilus influenzae

<400> SEQUENCE: 71

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Ser Cys Thr Gly Gly Lys Asn Gly Ile Ala
65                  70                  75                  80

Ala Asp Ile Lys Thr Ala Lys Gly Tyr Val Ala Ser Val Ile Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Ala Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Lys
145

<210> SEQ ID NO 72
<211> LENGTH: 149
<212> TYPE: PRT
<213> ORGANISM: Haemophilus influenzae

<400> SEQUENCE: 72

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
            115                 120                 125
```

```
Thr Thr Cys Lys Gly Thr Asp Ala Ser Leu Phe Pro Ala Asn Phe Cys
    130                 135                 140

Gly Ser Val Thr Gln
145

<210> SEQ ID NO 73
<211> LENGTH: 149
<212> TYPE: PRT
<213> ORGANISM: Haemophilus influenzae

<400> SEQUENCE: 73

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ser Val Ser Glu Leu
             35                  40                  45

Leu Gln Ala Ser Ala Pro Tyr Lys Ser Asp Val Glu Leu Cys Val Tyr
         50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 74
<211> LENGTH: 149
<212> TYPE: PRT
<213> ORGANISM: Haemophilus influenzae

<400> SEQUENCE: 74

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140
```

```
Gly Ser Val Thr Gln
145

<210> SEQ ID NO 75
<211> LENGTH: 149
<212> TYPE: PRT
<213> ORGANISM: Haemophilus influenzae

<400> SEQUENCE: 75

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Glu Ala Ser Leu Phe Pro Ala Asn Phe Cys
130                 135                 140

Gly Ser Val Thr Gln
145

<210> SEQ ID NO 76
<211> LENGTH: 149
<212> TYPE: PRT
<213> ORGANISM: Haemophilus influenzae

<400> SEQUENCE: 76

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ser Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
130                 135                 140

Arg Ser Val Thr Lys
145
```

```
<210> SEQ ID NO 77
<211> LENGTH: 149
<212> TYPE: PRT
<213> ORGANISM: Haemophilus influenzae

<400> SEQUENCE: 77

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
                35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 78
<211> LENGTH: 149
<212> TYPE: PRT
<213> ORGANISM: Haemophilus influenzae

<400> SEQUENCE: 78

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
                35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
                100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
130                 135                 140

Arg Ser Val Thr Lys
145

<210> SEQ ID NO 79
```

<211> LENGTH: 149
<212> TYPE: PRT
<213> ORGANISM: Haemophilus influenzae

<400> SEQUENCE: 79

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Glu Ala Ser Leu Phe Pro Ala Asn Phe Cys
    130                 135                 140

Gly Ser Val Thr Gln
145
```

<210> SEQ ID NO 80
<211> LENGTH: 149
<212> TYPE: PRT
<213> ORGANISM: Haemophilus influenzae

<400> SEQUENCE: 80

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Glu Ala Ser Leu Phe Pro Ala Asn Phe Cys
    130                 135                 140

Gly Ser Val Thr Gln
145
```

<210> SEQ ID NO 81
<211> LENGTH: 149
<212> TYPE: PRT
<213> ORGANISM: Haemophilus influenzae

<400> SEQUENCE: 81

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ser Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Lys
        115                 120                 125

Thr Thr Cys Lys Gly Thr Asp Ala Ser Leu Phe Pro Ala Asn Phe Cys
    130                 135                 140

Gly Ser Val Thr Lys
145

<210> SEQ ID NO 82
<211> LENGTH: 149
<212> TYPE: PRT
<213> ORGANISM: Haemophilus influenzae

<400> SEQUENCE: 82

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 83
<211> LENGTH: 149
<212> TYPE: PRT
<213> ORGANISM: Haemophilus influenzae

<400> SEQUENCE: 83

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Ser Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 84
<211> LENGTH: 149
<212> TYPE: PRT
<213> ORGANISM: Haemophilus influenzae

<400> SEQUENCE: 84

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 85
<211> LENGTH: 149
<212> TYPE: PRT
<213> ORGANISM: Haemophilus influenzae

<400> SEQUENCE: 85

Met Lys Leu Thr Thr Gln Gln Thr Leu Lys Lys Gly Phe Thr Leu Ile
1               5                   10                  15

```
Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Ile Ser Glu Leu
        35                  40                  45

Leu Gln Ala Ser Ala Pro Tyr Lys Ser Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
        130                 135                 140

Arg Ser Val Thr Lys
145

<210> SEQ ID NO 86
<211> LENGTH: 149
<212> TYPE: PRT
<213> ORGANISM: Haemophilus influenzae

<400> SEQUENCE: 86

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Glu Ala Ser Leu Phe Pro Ala Asn Phe Cys
        130                 135                 140

Gly Ser Val Thr Gln
145

<210> SEQ ID NO 87
<211> LENGTH: 149
<212> TYPE: PRT
<213> ORGANISM: Haemophilus influenzae

<400> SEQUENCE: 87

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30
```

```
Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 88
<211> LENGTH: 149
<212> TYPE: PRT
<213> ORGANISM: Haemophilus influenzae

<400> SEQUENCE: 88

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ser Asp Val Glu Leu Cys Val Tyr
        50                  55                  60

Ser Thr Gly Lys Pro Ser Thr Cys Ser Gly Gly Ser Asn Gly Ile Ala
 65                  70                  75                  80

Ala Asp Ile Thr Thr Val Lys Gly Tyr Val Lys Ser Val Thr Thr Ser
                85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 89
<211> LENGTH: 149
<212> TYPE: PRT
<213> ORGANISM: Haemophilus influenzae

<400> SEQUENCE: 89

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45
```

```
Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 90
<211> LENGTH: 149
<212> TYPE: PRT
<213> ORGANISM: Haemophilus influenzae

<400> SEQUENCE: 90

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
         35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 91
<211> LENGTH: 149
<212> TYPE: PRT
<213> ORGANISM: Haemophilus influenzae

<400> SEQUENCE: 91

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
         35                  40                  45

Leu Gln Ala Ser Ala Pro Tyr Lys Ala Asp Val Glu Leu Cys Val Tyr
    50                  55                  60
```

```
Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Arg Met Ser
            100                 105                 110

Tyr Thr Leu Thr Ala Glu Gly Asp Ser Ala Lys Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 92
<211> LENGTH: 149
<212> TYPE: PRT
<213> ORGANISM: Haemophilus influenzae

<400> SEQUENCE: 92

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60

Ser Thr Gly Lys Pro Ser Ser Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 93
<211> LENGTH: 149
<212> TYPE: PRT
<213> ORGANISM: Haemophilus influenzae

<400> SEQUENCE: 93

Met Lys Leu Thr Thr Gln Thr Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ser Asp Val Glu Leu Cys Val Tyr
         50                  55                  60

Ser Thr Asn Glu Thr Thr Asn Cys Thr Gly Gly Lys Asn Gly Ile Ala
 65                  70                  75                  80
```

```
Ala Asp Ile Thr Thr Ala Lys Gly Tyr Val Ala Ser Val Ile Thr Gln
                85                  90                  95

Ser Gly Gly Ile Thr Val Lys Gly Asn Gly Thr Leu Thr Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Ile Thr Gln
145

<210> SEQ ID NO 94
<211> LENGTH: 149
<212> TYPE: PRT
<213> ORGANISM: Haemophilus influenzae

<400> SEQUENCE: 94

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 95
<211> LENGTH: 149
<212> TYPE: PRT
<213> ORGANISM: Haemophilus influenzae

<400> SEQUENCE: 95

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95
```

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 96
<211> LENGTH: 149
<212> TYPE: PRT
<213> ORGANISM: Haemophilus influenzae

<400> SEQUENCE: 96

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
            115                 120                 125

Thr Thr Cys Lys Gly Thr Asp Thr Ser Leu Phe Pro Ala Asn Phe Cys
        130                 135                 140

Gly Ser Val Thr Gln
145

<210> SEQ ID NO 97
<211> LENGTH: 149
<212> TYPE: PRT
<213> ORGANISM: Haemophilus influenzae

<400> SEQUENCE: 97

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 98
<211> LENGTH: 149
<212> TYPE: PRT
<213> ORGANISM: Haemophilus influenzae

<400> SEQUENCE: 98

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 99
<211> LENGTH: 149
<212> TYPE: PRT
<213> ORGANISM: Haemophilus influenzae

<400> SEQUENCE: 99

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

```
Thr Thr Cys Lys Gly Thr Asp Ala Ser Leu Phe Pro Ala Asn Phe Cys
    130                 135                 140

Arg Ser Val Thr Lys
145

<210> SEQ ID NO 100
<211> LENGTH: 149
<212> TYPE: PRT
<213> ORGANISM: Haemophilus influenzae

<400> SEQUENCE: 100

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
                35                  40                  45

Leu Gln Ala Ser Ala Pro Tyr Lys Ala Asp Val Glu Leu Cys Val Tyr
 50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
                100                 105                 110

Tyr Ile Leu Gln Ala Lys Gly Asn Ala Thr Ala Gly Val Thr Trp Thr
                115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 101
<211> LENGTH: 149
<212> TYPE: PRT
<213> ORGANISM: Haemophilus influenzae

<400> SEQUENCE: 101

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
                35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Lys Asn Gly Ile Ala
 65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
                115                 120                 125

Thr Thr Cys Lys Gly Thr Asp Ala Ser Leu Phe Pro Ala Asn Phe Cys
    130                 135                 140
```

Gly Ser Val Thr Gln
145

<210> SEQ ID NO 102
<211> LENGTH: 149
<212> TYPE: PRT
<213> ORGANISM: Haemophilus influenzae

<400> SEQUENCE: 102

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 103
<211> LENGTH: 149
<212> TYPE: PRT
<213> ORGANISM: Haemophilus influenzae

<400> SEQUENCE: 103

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

```
<210> SEQ ID NO 104
<211> LENGTH: 149
<212> TYPE: PRT
<213> ORGANISM: Haemophilus influenzae

<400> SEQUENCE: 104

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 105
<211> LENGTH: 149
<212> TYPE: PRT
<213> ORGANISM: Haemophilus influenzae

<400> SEQUENCE: 105

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 106
<211> LENGTH: 149
```

```
<212> TYPE: PRT
<213> ORGANISM: Haemophilus influenzae
<220> FEATURE:
<221> NAME/KEY: VARIANT
<222> LOCATION: (1)...(149)
<223> OTHER INFORMATION: Xaa = glutamine or leucine

<400> SEQUENCE: 106

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Xaa Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 107
<211> LENGTH: 149
<212> TYPE: PRT
<213> ORGANISM: Haemophilus influenzae

<400> SEQUENCE: 107

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 108
```

-continued

```
<211> LENGTH: 149
<212> TYPE: PRT
<213> ORGANISM: Haemophilus influenzae

<400> SEQUENCE: 108

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 109
<211> LENGTH: 149
<212> TYPE: PRT
<213> ORGANISM: Haemophilus influenzae

<400> SEQUENCE: 109

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 110
<211> LENGTH: 149
<212> TYPE: PRT
<213> ORGANISM: Haemophilus influenzae
```

<400> SEQUENCE: 110

| Met | Lys | Leu | Thr | Thr | Leu | Gln | Thr | Leu | Lys | Lys | Gly | Phe | Thr | Leu | Ile |
|---|---|---|---|---|---|---|---|---|---|---|---|---|---|---|---|
| 1 | | | | 5 | | | | | 10 | | | | | 15 | |

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
 50                  55                  60

Ser Thr Gly Lys Pro Ser Thr Cys Ser Gly Gly Asn Asn Gly Ile Ala
 65                  70                  75                  80

Ala Asp Ile Lys Thr Ala Lys Gly Tyr Val Ala Ser Val Lys Thr Gln
                 85                  90                  95

Ser Gly Gly Ile Thr Val Lys Gly Asp Gly Thr Leu Ala Asn Met Glu
             100                 105                 110

Tyr Ile Leu Gln Ala Thr Gly Asn Ala Ala Thr Gly Val Thr Trp Thr
             115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 111
<211> LENGTH: 149
<212> TYPE: PRT
<213> ORGANISM: Haemophilus influenzae

<400> SEQUENCE: 111

Met Lys Leu Thr Thr Gln Gln Thr Leu Lys Lys Gly Phe Thr Leu Ile
 1               5                  10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
 50                  55                  60

Ser Thr Asn Glu Thr Thr Ser Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Gly Met Ser
             100                 105                 110

Tyr Thr Leu Thr Ala Glu Gly Asp Ser Ala Lys Gly Val Thr Trp Lys
             115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 112
<211> LENGTH: 149
<212> TYPE: PRT
<213> ORGANISM: Haemophilus influenzae

<400> SEQUENCE: 112

-continued

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Ser Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Lys
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 113
<211> LENGTH: 149
<212> TYPE: PRT
<213> ORGANISM: Haemophilus influenzae

<400> SEQUENCE: 113

```
Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 114
<211> LENGTH: 149
<212> TYPE: PRT
<213> ORGANISM: Haemophilus influenzae

<400> SEQUENCE: 114

```
Met Lys Leu Thr Thr Leu Gln Thr Leu Lys Lys Gly Phe Thr Leu Ile
1               5                   10                  15
```

```
Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 115
<211> LENGTH: 149
<212> TYPE: PRT
<213> ORGANISM: Haemophilus influenzae

<400> SEQUENCE: 115

```
Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 116
<211> LENGTH: 149
<212> TYPE: PRT
<213> ORGANISM: Haemophilus influenzae

<400> SEQUENCE: 116

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30
```

```
Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Glu Ala Ser Leu Phe Pro Ala Asn Phe Cys
        130                 135                 140

Gly Ser Val Thr Gln
145

<210> SEQ ID NO 117
<211> LENGTH: 149
<212> TYPE: PRT
<213> ORGANISM: Haemophilus influenzae

<400> SEQUENCE: 117

Met Lys Leu Thr Thr Leu Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Asn Asn Gly Ile Ala
 65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 118
<211> LENGTH: 149
<212> TYPE: PRT
<213> ORGANISM: Haemophilus influenzae

<400> SEQUENCE: 118

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
            35                  40                  45
```

```
Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
                100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
        130                 135                 140

Arg Ser Val Thr Lys
145
```

<210> SEQ ID NO 119
<211> LENGTH: 149
<212> TYPE: PRT
<213> ORGANISM: Haemophilus influenzae

<400> SEQUENCE: 119

```
Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
        50                  55                  60

Ser Thr Asn Glu Ala Thr Lys Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
                100                 105                 110

Tyr Ile Leu Gln Ala Ser Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145
```

<210> SEQ ID NO 120
<211> LENGTH: 149
<212> TYPE: PRT
<213> ORGANISM: Haemophilus influenzae

<400> SEQUENCE: 120

```
Met Lys Leu Thr Thr Leu Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
        50                  55                  60
```

```
Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 121
<211> LENGTH: 149
<212> TYPE: PRT
<213> ORGANISM: Haemophilus influenzae

<400> SEQUENCE: 121

Met Lys Leu Thr Thr Gln Gln Thr Leu Lys Lys Gly Phe Thr Leu Ile
 1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ser Val Ser Glu Leu
             35                  40                  45

Leu Gln Ala Ser Ala Pro Tyr Lys Ser Asp Val Glu Leu Cys Val Tyr
         50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 122
<211> LENGTH: 144
<212> TYPE: PRT
<213> ORGANISM: Haemophilus influenzae

<400> SEQUENCE: 122

Ser Ala Gln Ile Gln Lys Ala Glu Gln Asn Asp Val Lys Leu Ala Pro
 1               5                  10                  15

Pro Thr Asp Val Arg Ser Gly Tyr Ile Arg Leu Val Lys Asn Val Asn
                 20                  25                  30

Tyr Tyr Ile Asp Ser Glu Ser Ile Trp Val Asp Asn Gln Glu Pro Gln
             35                  40                  45

Ile Val His Phe Asp Ala Val Val Asn Leu Asp Lys Gly Leu Tyr Val
         50                  55                  60

Tyr Pro Glu Pro Lys Arg Tyr Ala Arg Ser Val Arg Gln Tyr Lys Ile
 65                  70                  75                  80
```

```
Leu Asn Cys Ala Asn Tyr His Leu Thr Gln Val Arg Thr Asp Phe Tyr
                85                  90                  95

Asp Glu Phe Trp Gly Gln Gly Leu Arg Ala Ala Pro Lys Lys Gln Lys
            100                 105                 110

Lys His Thr Leu Ser Leu Thr Pro Asp Thr Thr Leu Tyr Asn Ala Ala
        115                 120                 125

Gln Ile Ile Cys Ala Asn Tyr Gly Glu Ala Phe Ser Val Asp Lys Lys
    130                 135                 140

<210> SEQ ID NO 123
<211> LENGTH: 143
<212> TYPE: PRT
<213> ORGANISM: Haemophilus influenzae

<400> SEQUENCE: 123

Ala Gln Ile Gln Lys Ala Glu Gln Asn Asp Val Lys Leu Ala Pro Pro
1               5                   10                  15

Thr Asp Val Arg Ser Gly Tyr Ile Arg Leu Val Lys Asn Val Asn Tyr
            20                  25                  30

Tyr Ile Asp Ser Glu Ser Ile Trp Val Asp Asn Gln Glu Pro Gln Ile
        35                  40                  45

Val His Phe Asp Ala Val Val Asn Leu Asp Lys Gly Leu Tyr Val Tyr
    50                  55                  60

Pro Glu Pro Lys Arg Tyr Ala Arg Ser Val Arg Gln Tyr Lys Ile Leu
65                  70                  75                  80

Asn Cys Ala Asn Tyr His Leu Thr Gln Val Arg Thr Asp Phe Tyr Asp
                85                  90                  95

Glu Phe Trp Gly Gln Gly Leu Arg Ala Ala Pro Lys Lys Gln Lys Lys
            100                 105                 110

His Thr Leu Ser Leu Thr Pro Asp Thr Thr Leu Tyr Asn Ala Ala Gln
        115                 120                 125

Ile Ile Cys Ala Asn Tyr Gly Glu Ala Phe Ser Val Asp Lys Lys
    130                 135                 140

<210> SEQ ID NO 124
<211> LENGTH: 142
<212> TYPE: PRT
<213> ORGANISM: Haemophilus influenzae

<400> SEQUENCE: 124

Gln Ile Gln Lys Ala Glu Gln Asn Asp Val Lys Leu Ala Pro Pro Thr
1               5                   10                  15

Asp Val Arg Ser Gly Tyr Ile Arg Leu Val Lys Asn Val Asn Tyr Tyr
            20                  25                  30

Ile Asp Ser Glu Ser Ile Trp Val Asp Asn Gln Glu Pro Gln Ile Val
        35                  40                  45

His Phe Asp Ala Val Val Asn Leu Asp Lys Gly Leu Tyr Val Tyr Pro
    50                  55                  60

Glu Pro Lys Arg Tyr Ala Arg Ser Val Arg Gln Tyr Lys Ile Leu Asn
65                  70                  75                  80

Cys Ala Asn Tyr His Leu Thr Gln Val Arg Thr Asp Phe Tyr Asp Glu
                85                  90                  95

Phe Trp Gly Gln Gly Leu Arg Ala Ala Pro Lys Lys Gln Lys Lys His
            100                 105                 110

Thr Leu Ser Leu Thr Pro Asp Thr Thr Leu Tyr Asn Ala Ala Gln Ile
        115                 120                 125
```

Ile Cys Ala Asn Tyr Gly Glu Ala Phe Ser Val Asp Lys Lys
    130                 135                 140

<210> SEQ ID NO 125
<211> LENGTH: 141
<212> TYPE: PRT
<213> ORGANISM: Haemophilus influenzae

<400> SEQUENCE: 125

Ile Gln Lys Ala Glu Gln Asn Asp Val Lys Leu Ala Pro Pro Thr Asp
  1               5                  10                  15

Val Arg Ser Gly Tyr Ile Arg Leu Val Lys Asn Val Asn Tyr Tyr Ile
             20                  25                  30

Asp Ser Glu Ser Ile Trp Val Asp Asn Gln Glu Pro Gln Ile Val His
         35                  40                  45

Phe Asp Ala Val Val Asn Leu Asp Lys Gly Leu Tyr Val Tyr Pro Glu
     50                  55                  60

Pro Lys Arg Tyr Ala Arg Ser Val Arg Gln Tyr Lys Ile Leu Asn Cys
 65                  70                  75                  80

Ala Asn Tyr His Leu Thr Gln Val Arg Thr Asp Phe Tyr Asp Glu Phe
                 85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
        115                 120                 125

Cys Ala Asn Tyr Gly Glu Ala Phe Ser Val Asp Lys Lys
    130                 135                 140

<210> SEQ ID NO 126
<211> LENGTH: 139
<212> TYPE: PRT
<213> ORGANISM: Haemophilus influenzae

<400> SEQUENCE: 126

Lys Ala Glu Gln Asn Asp Val Lys Leu Ala Pro Pro Thr Asp Val Arg
  1               5                  10                  15

Ser Gly Tyr Ile Arg Leu Val Lys Asn Val Asn Tyr Tyr Ile Asp Ser
             20                  25                  30

Glu Ser Ile Trp Val Asp Asn Gln Glu Pro Gln Ile Val His Phe Asp
         35                  40                  45

Ala Val Val Asn Leu Asp Lys Gly Leu Tyr Val Tyr Pro Glu Pro Lys
     50                  55                  60

Arg Tyr Ala Arg Ser Val Arg Gln Tyr Lys Ile Leu Asn Cys Ala Asn
 65                  70                  75                  80

Tyr His Leu Thr Gln Val Arg Thr Asp Phe Tyr Asp Glu Phe Trp Gly
                 85                  90                  95

Gln Gly Leu Arg Ala Ala Pro Lys Lys Gln Lys Lys His Thr Leu Ser
            100                 105                 110

Leu Thr Pro Asp Thr Thr Leu Tyr Asn Ala Ala Gln Ile Ile Cys Ala
        115                 120                 125

Asn Tyr Gly Glu Ala Phe Ser Val Asp Lys Lys
    130                 135

<210> SEQ ID NO 127
<211> LENGTH: 110
<212> TYPE: PRT
<213> ORGANISM: Haemophilus influenzae

<400> SEQUENCE: 127

Thr Lys Lys Ala Ala Val Ser Glu Leu Leu Gln Ala Ser Ala Pro Tyr
1               5                   10                  15

Lys Ala Asp Val Glu Leu Cys Val Tyr Ser Thr Asn Glu Thr Thr Asn
                20                  25                  30

Cys Thr Gly Gly Lys Asn Gly Ile Ala Ala Asp Ile Thr Thr Ala Lys
            35                  40                  45

Gly Tyr Val Lys Ser Val Thr Thr Ser Asn Gly Ala Ile Thr Val Lys
50                  55                      60

Gly Asp Gly Thr Leu Ala Asn Met Glu Tyr Ile Leu Gln Ala Thr Gly
65              70                  75                      80

Asn Ala Ala Thr Gly Val Thr Trp Thr Thr Cys Lys Gly Thr Asp
                85                  90                  95

Ala Ser Leu Phe Pro Ala Asn Phe Cys Gly Ser Val Thr Gln
            100                 105                 110

<210> SEQ ID NO 128
<211> LENGTH: 25
<212> TYPE: PRT
<213> ORGANISM: Haemophilus influenzae

<400> SEQUENCE: 128

Pro Lys Arg Tyr Ala Arg Ser Val Arg Gln Tyr Lys Ile Leu Asn Cys
1               5                   10                  15

Ala Asn Tyr His Leu Thr Gln Val Arg
                20                  25

<210> SEQ ID NO 129
<211> LENGTH: 66
<212> TYPE: DNA
<213> ORGANISM: Artificial Sequence
<220> FEATURE:
<223> OTHER INFORMATION: pelB signal peptide

<400> SEQUENCE: 129
atgaaatacc tgctgccgac cgctgctgct ggtctgctgc tcctcgctgc ccagccggcg    60
atggcc                                                              66

<210> SEQ ID NO 130
<211> LENGTH: 22
<212> TYPE: PRT
<213> ORGANISM: Artificial Sequence
<220> FEATURE:
<223> OTHER INFORMATION: pelB signal peptide

<400> SEQUENCE: 130

Met Lys Tyr Leu Leu Pro Thr Ala Ala Ala Gly Leu Leu Leu Leu Ala
1               5                   10                  15

Ala Gln Pro Ala Met Ala
                20

<210> SEQ ID NO 131
<211> LENGTH: 57
<212> TYPE: DNA
<213> ORGANISM: Artificial Sequence
<220> FEATURE:
<223> OTHER INFORMATION: FlgI signal peptide

<400> SEQUENCE: 131
atgattaaat ttctctctgc attaattctt ctactggtca cgacggcggc tcaggct      57

<210> SEQ ID NO 132
<211> LENGTH: 19
<212> TYPE: PRT
<213> ORGANISM: Artificial Sequence
<220> FEATURE:
<223> OTHER INFORMATION: FlgI signal peptide

<400> SEQUENCE: 132

Met Ile Lys Phe Leu Ser Ala Leu Ile Leu Leu Leu Val Thr Thr Ala
 1               5                  10                  15

Ala Gln Ala

<210> SEQ ID NO 133
<211> LENGTH: 69
<212> TYPE: DNA
<213> ORGANISM: Artificial Sequence
<220> FEATURE:
<223> OTHER INFORMATION: NadA signal peptide

<400> SEQUENCE: 133
atgaaacact tccatccaa agtactgacc acagccatcc ttgccacttt ctgtagcggc     60
gcactggca                                                            69

<210> SEQ ID NO 134
<211> LENGTH: 23
<212> TYPE: PRT
<213> ORGANISM: Artificial Sequence
<220> FEATURE:
<223> OTHER INFORMATION: NadA signal peptide

<400> SEQUENCE: 134

Met Lys His Phe Pro Ser Lys Val Leu Thr Thr Ala Ile Leu Ala Thr
 1               5                  10                  15

Phe Cys Ser Gly Ala Leu Ala
            20

<210> SEQ ID NO 135
<211> LENGTH: 852
<212> TYPE: DNA
<213> ORGANISM: Artificial Sequence
<220> FEATURE:
<223> OTHER INFORMATION: LVL312

<400> SEQUENCE: 135
atgattaaat ttctctctgc attaattctt ctactggtca cgacggcggc tcaggctgag     60
actaaaaaag cagcggtatc tgaattactg caagcgtcag cgccttataa ggctgatgtg    120
gaattatgtg tatatagcac aaatgaaaca acaaactgta cgggtggaaa aaatggtatt    180
gcagcagata taaccacagc aaaaggctat gtaaaatcag tgacaacaag caacggtgca    240
ataacagtaa aagggggatgg cacattggca aatatggaat atattttgca agctacaggt    300
aatgctgcaa caggtgtaac ttggacaaca acttgcaaag aacggatgc ctctttattt    360 ccagcaaatt tttgcggaag tgtcacacaa ggcggcgcgc agattcagaa ggctgaacaa    420
aatgatgtga agctggcacc gccgactgat gtacgaagcg gatatatacg tttggtaaag    480
aatgtgaatt attcatcga tagtgaatcg atctgggtgg ataaccaaga gccacaaatt    540
gtacattttg atgcagtggt gaatttagat aagggattgt atgtttatcc tgagcctaaa    600
cgttatgcac gttctgttcg tcagtataag atcttgaatt gtgcaaatta tcatttaact    660
caagtacgaa ctgatttcta tgatgaattt tggggacagg gtttgcgggc agcacctaaa    720

-continued

```
aagcaaaaga aacatacgtt aagtttaaca cctgatacaa cgctttataa tgctgctcag    780
attatttgtg cgaactatgg tgaagcattt tcagttgata aaaaaggcgg ccaccaccac    840
caccaccact aa                                                        852
```

<210> SEQ ID NO 136
<211> LENGTH: 283
<212> TYPE: PRT
<213> ORGANISM: Artificial Sequence
<220> FEATURE:
<223> OTHER INFORMATION: LVL312

<400> SEQUENCE: 136

```
Met Ile Lys Phe Leu Ser Ala Leu Ile Leu Leu Val Thr Thr Ala
 1               5                  10                  15

Ala Gln Ala Glu Thr Lys Lys Ala Ala Val Ser Glu Leu Leu Gln Ala
            20                  25                  30

Ser Ala Pro Tyr Lys Ala Asp Val Glu Leu Cys Val Tyr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Thr Cys
            100                 105                 110

Lys Gly Thr Asp Ala Ser Leu Phe Pro Ala Asn Phe Cys Gly Ser Val
        115                 120                 125

Thr Gln Gly Gly Ala Gln Ile Gln Lys Ala Glu Gln Asn Asp Val Lys
    130                 135                 140

Leu Ala Pro Pro Thr Asp Val Arg Ser Gly Tyr Ile Arg Leu Val Lys
145                 150                 155                 160

Asn Val Asn Tyr Tyr Ile Asp Ser Glu Ser Ile Trp Val Asp Asn Gln
                165                 170                 175

Glu Pro Gln Ile Val His Phe Asp Ala Val Val Asn Leu Asp Lys Gly
            180                 185                 190

Leu Tyr Val Tyr Pro Glu Pro Lys Arg Tyr Ala Arg Ser Val Arg Gln
        195                 200                 205

Tyr Lys Ile Leu Asn Cys Ala Asn Tyr His Leu Thr Gln Val Arg Thr
    210                 215                 220

Asp Phe Tyr Asp Glu Phe Trp Gly Gln Gly Leu Arg Ala Ala Pro Lys
225                 230                 235                 240

Lys Gln Lys Lys His Thr Leu Ser Leu Thr Pro Asp Thr Thr Leu Tyr
                245                 250                 255

Asn Ala Ala Gln Ile Ile Cys Ala Asn Tyr Gly Glu Ala Phe Ser Val
            260                 265                 270

Asp Lys Lys Gly Gly His His His His His
        275                 280
```

<210> SEQ ID NO 137
<211> LENGTH: 855
<212> TYPE: DNA
<213> ORGANISM: Artificial Sequence
<220> FEATURE:
<223> OTHER INFORMATION: LVL291

<400> SEQUENCE: 137

```
atgaaatacc tgctgccgac cgctgctgct ggtctgctgc tcctcgctgc ccagccggcg    60
atggcccaga ttcagaaggc tgaacaaaat gatgtgaagc tggcaccgcc gactgatgta   120
cgaagcggat atatacgttt ggtaaagaat gtgaattatt acatcgatag tgaatcgatc   180
tgggtggata ccaagagcc acaaattgta cattttgatg cagtggtgaa tttagataag   240
ggattgtatg tttatcctga gcctaaacgt tatgcacgtt ctgttcgtca gtataagatc   300
ttgaattgtg caaattatca tttaactcaa gtacgaactg atttctatga tgaattttgg   360
ggacagggtt tgcgggcagc acctaaaaag caaagaaac atacgttaag tttaacacct   420
gatacaacgc tttataatgc tgctcagatt atttgtgcga actatggtga agcatttca   480
gttgataaaa aaggcggcac taaaaaagca gcggtatctg aattactgca agcgtcagcg   540
cctataagg ctgatgtgga attatgtgta tatagcacaa atgaaacaac aaactgtacg   600
ggtggaaaaa atggtattgc agcagatata accacagcaa aaggctatgt aaaatcagtg   660
acaacaagca acggtgcaat aacagtaaaa ggggatggca cattggcaaa tatgaatat    720
attttgcaag ctacaggtaa tgctgcaaca ggtgtaactt ggacaacaac ttgcaaagga   780
acggatgcct ctttatttcc agcaaatttt tgcggaagtg tcacacaagg cggccaccac   840
caccaccacc actaa                                                    855
```

<210> SEQ ID NO 138
<211> LENGTH: 284
<212> TYPE: PRT
<213> ORGANISM: Artificial Sequence
<220> FEATURE:
<223> OTHER INFORMATION: LVL291

<400> SEQUENCE: 138

```
Met Lys Tyr Leu Leu Pro Thr Ala Ala Ala Gly Leu Leu Leu Leu Ala
1               5                   10                  15
Ala Gln Pro Ala Met Ala Gln Ile Gln Lys Ala Glu Gln Asn Asp Val
            20                  25                  30
Lys Leu Ala Pro Pro Thr Asp Val Arg Ser Gly Tyr Ile Arg Leu Val
        35                  40                  45
Lys Asn Val Asn Tyr Tyr Ile Asp Ser Glu Ser Ile Trp Val Asp Asn
    50                  55                  60
Gln Glu Pro Gln Ile Val His Phe Asp Ala Val Val Asn Leu Asp Lys
65                  70                  75                  80
Gly Leu Tyr Val Tyr Pro Glu Pro Lys Arg Tyr Ala Arg Ser Val Arg
                85                  90                  95
Gln Tyr Lys Ile Leu Asn Cys Ala Asn Tyr His Leu Thr Gln Val Arg
            100                 105                 110
Thr Asp Phe Tyr Asp Glu Phe Trp Gly Gln Gly Leu Arg Ala Ala Pro
        115                 120                 125
Lys Lys Gln Lys Lys His Thr Leu Ser Leu Thr Pro Asp Thr Thr Leu
    130                 135                 140
Tyr Asn Ala Ala Gln Ile Ile Cys Ala Asn Tyr Gly Glu Ala Phe Ser
145                 150                 155                 160
Val Asp Lys Lys Gly Gly Thr Lys Lys Ala Val Ser Glu Leu Leu
                165                 170                 175
Gln Ala Ser Ala Pro Tyr Lys Ala Asp Val Glu Leu Cys Val Tyr Ser
            180                 185                 190
Thr Asn Glu Thr Thr Asn Cys Thr Gly Gly Lys Asn Gly Ile Ala Ala
        195                 200                 205
```

```
Asp Ile Thr Thr Ala Lys Gly Tyr Val Lys Ser Val Thr Thr Ser Asn
    210                 215                 220

Gly Ala Ile Thr Val Lys Gly Asp Gly Thr Leu Ala Asn Met Glu Tyr
225                 230                 235                 240

Ile Leu Gln Ala Thr Gly Asn Ala Ala Thr Gly Val Thr Trp Thr Thr
                245                 250                 255

Thr Cys Lys Gly Thr Asp Ala Ser Leu Phe Pro Ala Asn Phe Cys Gly
                260                 265                 270

Ser Val Thr Gln Gly Gly His His His His His
            275                 280

<210> SEQ ID NO 139
<211> LENGTH: 852
<212> TYPE: DNA
<213> ORGANISM: Artificial Sequence
<220> FEATURE:
<223> OTHER INFORMATION: LVL268

<400> SEQUENCE: 139
atgaaatacc tgctgccgac cgctgctgct ggtctgctgc tcctcgctgc ccagccggcg      60
atggccgata ttcagaaggc tgaacaaaat gatgtgaagc tggcaccgcc gactgatgta    120
cgaagcggat atatacgttt ggtaaagaat gtgaattatt acatcgatag tgaatcgatc    180
tgggtggata ccaagagcc acaaattgta cattttgatg cagtggtgaa tttagataag    240
ggattgtatg tttatcctga gcctaaacgt tatgcacgtt ctgttcgtca gtataagatc    300
ttgaattgtg caaattatca tttaactcaa gtacgaactg atttctatga tgaattttgg    360
ggacagggtt tgcgggcagc acctaaaaag caaagaaac atacgttaag tttaacacct    420
gatacaacgc tttataatgc tgctcagatt atttgtgcga actatggtga agcattttca    480
gttgataaaa aaggcggcac taaaaaagca gcggtatctg aattactgca agcgtcagcg    540
ccttataagg ctgatgtgga attatgtgta tatagcacaa atgaaacaac aaactgtacg    600
ggtggaaaaa atggtattgc agcagatata accacagcaa aaggctatgt aaaatcagtg    660
acaacaagca acggtgcaat aacagtaaaa gggatggca cattggcaaa tatggaatat    720 atttttgcaag ctacaggtaa tgctgcaaca ggtgtaactt ggacaacaac ttgcaaagga    780
acggatgcct cttattcc agcaaatttt tgcggaagtg tcacacaagg cggccaccac    840
caccaccacc ac                                                        852

<210> SEQ ID NO 140
<211> LENGTH: 284
<212> TYPE: PRT
<213> ORGANISM: Artificial Sequence
<220> FEATURE:
<223> OTHER INFORMATION: LVL268

<400> SEQUENCE: 140

Met Lys Tyr Leu Leu Pro Thr Ala Ala Ala Gly Leu Leu Leu Leu Ala
1               5                   10                  15

Ala Gln Pro Ala Met Ala Asp Ile Gln Lys Ala Glu Gln Asn Asp Val
            20                  25                  30

Lys Leu Ala Pro Pro Thr Asp Val Arg Ser Gly Tyr Ile Arg Leu Val
        35                  40                  45

Lys Asn Val Asn Tyr Tyr Ile Asp Ser Glu Ser Ile Trp Val Asp Asn
    50                  55                  60

Gln Glu Pro Gln Ile Val His Phe Asp Ala Val Val Asn Leu Asp Lys
```

Gly Leu Tyr Val Tyr Pro Glu Pro Lys Arg Tyr Ala Arg Ser Val Arg
 65                  70                  75                  80

Gln Tyr Lys Ile Leu Asn Cys Ala Asn Tyr His Leu Thr Gln Val Arg
             85                  90                  95

Thr Asp Phe Tyr Asp Glu Phe Trp Gly Gln Gly Leu Arg Ala Ala Pro
        100                 105                 110

Lys Lys Gln Lys Lys His Thr Leu Ser Leu Thr Pro Asp Thr Thr Leu
    115                 120                 125

Tyr Asn Ala Ala Gln Ile Ile Cys Ala Asn Tyr Gly Glu Ala Phe Ser
130                 135                 140

Val Asp Lys Lys Gly Thr Lys Lys Ala Ala Val Ser Glu Leu Leu
145                 150                 155                 160

Gln Ala Ser Ala Pro Tyr Lys Ala Asp Val Glu Leu Cys Val Tyr Ser
                165                 170                 175

Thr Asn Glu Thr Thr Asn Cys Thr Gly Gly Lys Asn Gly Ile Ala Ala
            180                 185                 190

Asp Ile Thr Thr Ala Lys Gly Tyr Val Lys Ser Val Thr Thr Ser Asn
        195                 200                 205

Gly Ala Ile Thr Val Lys Gly Asp Gly Thr Leu Ala Asn Met Glu Tyr
    210                 215                 220

Ile Leu Gln Ala Thr Gly Asn Ala Ala Thr Gly Val Thr Trp Thr Thr
225                 230                 235                 240

Thr Cys Lys Gly Thr Asp Ala Ser Leu Phe Pro Ala Asn Phe Cys Gly
                245                 250                 255

Ser Val Thr Gln Gly Gly His His His His His
            260                 265                 270

<210> SEQ ID NO 141
<211> LENGTH: 867
<212> TYPE: DNA
<213> ORGANISM: Artificial Sequence
<220> FEATURE:
<223> OTHER INFORMATION: LVL269

<400> SEQUENCE: 141
atgaaacact tccatccaa gtactgacc acagccatcc ttgccacttt ctgtagcggc     60
gcactggcag ccacaaacga cgacgataag gctgaacaaa atgatgtgaa gctggcaccg    120
ccgactgatg tacgaagcgg atatatacgt ttggtaaaga atgtgaatta ttacatcgat    180
agtgaatcga tctgggtgga taaccaagag ccacaaattg tacattttga tgcagtggtg    240
aatttagata agggattgta tgtttatcct gagcctaaac gttatgcacg ttctgttcgt    300
cagtataaga tcttgaattg tgcaaattat catttaactc aagtacgaac tgatttctat    360
gatgaatttt ggggacaggg tttgcgggca gcacctaaaa agcaaaagaa acatacgtta    420
agtttaacac ctgatacaac gctttataat gctgctcaga ttatttgtgc gaactatggt    480
gaagcatttt cagttgataa aaaggcggc actaaaaaag cagcggtatc tgaattactg    540
caagcgtcag cgccttataa ggctgatgtg gaattatgtg tatatagcac aaatgaaaca    600
acaaactgta cgggtggaaa aaatggtatt gcagcagata taaccacagc aaaaggctat    660
gtaaaatcag tgacaacaag caacggtgca ataacagtaa aggggatgg cacattggca    720
aatatggaat atatttttgca agctacaggt aatgctgcaa caggtgtaac ttggacaaca    780
acttgcaaag gaacggatgc ctcttttattt ccagcaaatt tttgcggaag tgtcacacaa    840

```
ggcggccacc accaccacca ccactaa                                          867
```

<210> SEQ ID NO 142
<211> LENGTH: 288
<212> TYPE: PRT
<213> ORGANISM: Artificial Sequence
<220> FEATURE:
<223> OTHER INFORMATION: LVL269

<400> SEQUENCE: 142

| Met | Lys | His | Phe | Pro | Ser | Lys | Val | Leu | Thr | Thr | Ala | Ile | Leu | Ala | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Phe Cys Ser Gly Ala Leu Ala Ala Thr Asn Asp Asp Lys Ala Glu
            20                  25                  30

Gln Asn Asp Val Lys Leu Ala Pro Pro Thr Asp Val Arg Ser Gly Tyr
            35                  40                  45

Ile Arg Leu Val Lys Asn Val Asn Tyr Tyr Ile Asp Ser Glu Ser Ile
        50                  55                  60

Trp Val Asp Asn Gln Glu Pro Gln Ile Val His Phe Asp Ala Val Val
65                  70                  75                  80

Asn Leu Asp Lys Gly Leu Tyr Val Tyr Pro Glu Pro Lys Arg Tyr Ala
                85                  90                  95

Arg Ser Val Arg Gln Tyr Lys Ile Leu Asn Cys Ala Asn Tyr His Leu
            100                 105                 110

Thr Gln Val Arg Thr Asp Phe Tyr Asp Glu Phe Trp Gly Gln Gly Leu
        115                 120                 125

Arg Ala Ala Pro Lys Lys Gln Lys Lys His Thr Leu Ser Leu Thr Pro
130                 135                 140

Asp Thr Thr Leu Tyr Asn Ala Ala Gln Ile Ile Cys Ala Asn Tyr Gly
145                 150                 155                 160

Glu Ala Phe Ser Val Asp Lys Lys Gly Gly Thr Lys Lys Ala Ala Val
                165                 170                 175

Ser Glu Leu Leu Gln Ala Ser Ala Pro Tyr Lys Ala Asp Val Glu Leu
            180                 185                 190

Cys Val Tyr Ser Thr Asn Glu Thr Thr Asn Cys Thr Gly Gly Lys Asn
        195                 200                 205

Gly Ile Ala Ala Asp Ile Thr Thr Ala Lys Gly Tyr Val Lys Ser Val
    210                 215                 220

Thr Thr Ser Asn Gly Ala Ile Thr Val Lys Gly Asp Gly Thr Leu Ala
225                 230                 235                 240

Asn Met Glu Tyr Ile Leu Gln Ala Thr Gly Asn Ala Ala Thr Gly Val
                245                 250                 255

Thr Trp Thr Thr Thr Cys Lys Gly Thr Asp Ala Ser Leu Phe Pro Ala
            260                 265                 270

Asn Phe Cys Gly Ser Val Thr Gln Gly Gly His His His His His
        275                 280                 285

<210> SEQ ID NO 143
<211> LENGTH: 792
<212> TYPE: DNA
<213> ORGANISM: Artificial Sequence
<220> FEATURE:
<223> OTHER INFORMATION: LVL270

<400> SEQUENCE: 143

```
atgcaccacc accaccacca cagcgcgcag attcagaagg ctgaacaaaa tgatgtgaag    60
ctggcaccgc cgactgatgt acgaagcgga tatatacgtt tggtaaagaa tgtgaattat   120
```

```
tacatcgata gtgaatcgat ctgggtggat aaccaagagc cacaaattgt acattttgat    180
gcagtggtga atttagataa gggattgtat gtttatcctg agcctaaacg ttatgcacgt    240
tctgttcgtc agtataagat cttgaattgt gcaaattatc atttaactca agtacgaact    300
gatttctatg atgaattttg gggacagggt ttgcgggcag cacctaaaaa gcaaaagaaa    360
catacgttaa gtttaacacc tgatacaacg ctttataatg ctgctcagat tatttgtgcg    420
aactatggtg aagcattttc agttgataaa aaaggcggca ctaaaaaagc agcggtatct    480
gaattactgc aagcgtcagc gccttataag gctgatgtgg aattatgtgt atatagcaca    540
aatgaaacaa caaactgtac gggtggaaaa aatggtattg cagcagatat aaccacagca    600
aaaggctatg taaatcagt gacaacaagc aacggtgcaa taacagtaaa aggggatggc    660
acattggcaa atatggaata tattttgcaa gctacaggta atgctgcaac aggtgtaact    720
tggacaacaa cttgcaaagg aacggatgcc tctttatttc cagcaaattt ttgcggaagt    780
gtcacacaat aa                                                        792
```

<210> SEQ ID NO 144
<211> LENGTH: 263
<212> TYPE: PRT
<213> ORGANISM: Artificial Sequence
<220> FEATURE:
<223> OTHER INFORMATION: LVL270

<400> SEQUENCE: 144

```
Met His His His His His Ser Ala Gln Ile Gln Lys Ala Glu Gln
  1               5                  10                  15

Asn Asp Val Lys Leu Ala Pro Pro Thr Asp Val Arg Ser Gly Tyr Ile
             20                  25                  30

Arg Leu Val Lys Asn Val Asn Tyr Tyr Ile Asp Ser Glu Ser Ile Trp
         35                  40                  45

Val Asp Asn Gln Glu Pro Gln Ile Val His Phe Asp Ala Val Val Asn
     50                  55                  60

Leu Asp Lys Gly Leu Tyr Val Tyr Pro Glu Pro Lys Arg Tyr Ala Arg
 65                  70                  75                  80

Ser Val Arg Gln Tyr Lys Ile Leu Asn Cys Ala Asn Tyr His Leu Thr
                 85                  90                  95

Gln Val Thr Asp Phe Tyr Asp Glu Phe Trp Gly Gln Gly Leu Arg
            100                 105                 110

Ala Ala Pro Lys Lys Gln Lys Lys His Thr Leu Ser Leu Thr Pro Asp
        115                 120                 125

Thr Thr Leu Tyr Asn Ala Ala Gln Ile Ile Cys Ala Asn Tyr Gly Glu
    130                 135                 140

Ala Phe Ser Val Asp Lys Lys Gly Gly Thr Lys Lys Ala Ala Val Ser
145                 150                 155                 160

Glu Leu Leu Gln Ala Ser Ala Pro Tyr Lys Ala Asp Val Glu Leu Cys
                165                 170                 175

Val Tyr Ser Thr Asn Glu Thr Thr Asn Cys Thr Gly Gly Lys Asn Gly
            180                 185                 190

Ile Ala Ala Asp Ile Thr Thr Ala Lys Gly Tyr Val Lys Ser Val Thr
        195                 200                 205

Thr Ser Asn Gly Ala Ile Thr Val Lys Gly Asp Gly Thr Leu Ala Asn
    210                 215                 220

Met Glu Tyr Ile Leu Gln Ala Thr Gly Asn Ala Ala Thr Gly Val Thr
225                 230                 235                 240
```

Trp Thr Thr Thr Cys Lys Gly Thr Asp Ala Ser Leu Phe Pro Ala Asn
            245                 250                 255

Phe Cys Gly Ser Val Thr Gln
            260

<210> SEQ ID NO 145
<211> LENGTH: 852
<212> TYPE: DNA
<213> ORGANISM: Artificial Sequence
<220> FEATURE:
<223> OTHER INFORMATION: LVL315

<400> SEQUENCE: 145

| | | | | | | |
|---|---|---|---|---|---|---|
| atgaaatacc | tgctgccgac | cgctgctgct | ggtctgctgc | tcctcgctgc | ccagccggcg | 60 |
| atggccatgg | ataaggctga | acaaaatgat | gtgaagctgg | caccgccgac | tgatgtacga | 120 |
| agcggatata | tacgtttggt | aaagaatgtg | aattattaca | tcgatagtga | atcgatctgg | 180 |
| gtggataacc | aagagccaca | aattgtacat | tttgatgcag | tggtgaattt | agataaggga | 240 |
| ttgtatgttt | atcctgagcc | taaacgttat | gcacgttctg | ttcgtcagta | taagatcttg | 300 |
| aattgtgcaa | attatcattt | aactcaagta | cgaactgatt | tctatgatga | attttgggga | 360 |
| cagggtttgc | gggcagcacc | taaaaagcaa | agaaacata | cgttaagttt | aacacctgat | 420 |
| acaacgcttt | ataatgctgc | tcagattatt | tgtgcgaact | atggtgaagc | attttcagtt | 480 |
| gataaaaaag | gcggcactaa | aaaagcagcg | gtatctgaat | tactgcaagc | gtcagcgcct | 540 |
| tataaggctg | atgtggaatt | atgtgtatat | agcacaaatg | aaacaacaaa | ctgtacgggt | 600 |
| ggaaaaaatg | gtattgcagc | agatataacc | acagcaaaag | gctatgtaaa | atcagtgaca | 660 |
| acaagcaacg | gtgcaataac | agtaaaaggg | gatggcacat | ggcaaaatat | ggaatatatt | 720 |
| ttgcaagcta | caggtaatgc | tgcaacaggt | gtaacttgga | caacaacttg | caaaggaacg | 780 |
| gatgcctctt | tatttccagc | aaatttttgc | ggaagtgtca | cacaaggcgg | ccaccaccac | 840 |
| caccaccact | aa | | | | | 852 |

<210> SEQ ID NO 146
<211> LENGTH: 283
<212> TYPE: PRT
<213> ORGANISM: Artificial Sequence
<220> FEATURE:
<223> OTHER INFORMATION: LVL315

<400> SEQUENCE: 146

Met Lys Tyr Leu Leu Pro Thr Ala Ala Ala Gly Leu Leu Leu Leu Ala
 1               5                  10                  15

Ala Gln Pro Ala Met Ala Met Asp Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
    50                  55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys

|       | 115 |       |       | 120 |       |       | 125 |       |
| ----- | --- | ----- | ----- | --- | ----- | ----- | --- | ----- |

Lys Gln Lys Lys His Thr Leu Ser Leu Thr Pro Asp Thr Thr Leu Tyr
130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
            165                 170                 175

Ala Ser Ala Pro Tyr Lys Ala Asp Val Glu Leu Cys Val Tyr Ser Thr
            180                 185                 190

Asn Glu Thr Thr Asn Cys Thr Gly Gly Lys Asn Gly Ile Ala Ala Asp
            195                 200                 205

Ile Thr Thr Ala Lys Gly Tyr Val Lys Ser Val Thr Ser Asn Gly
    210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
            260                 265                 270

Val Thr Gln Gly Gly His His His His His His
            275                 280

<210> SEQ ID NO 147
<211> LENGTH: 831
<212> TYPE: DNA
<213> ORGANISM: Artificial Sequence
<220> FEATURE:
<223> OTHER INFORMATION: LVL317

<400> SEQUENCE: 147

```
atgaaatacc tgctgccgac cgctgctgct ggtctgctgc tcctcgctgc ccagccggcg     60
atggcccaga ttcagaaggc tgaacaaaat gatgtgaagc tggcaccgcc gactgatgta    120
cgaagcggat atatacgttt ggtaaagaat gtgaattatt acatcgatag tgaatcgatc    180
tgggtggata ccaagagcc acaaattgta cattttgatg cagtggtgaa tttagataag     240
ggattgtatg tttatcctga gcctaaacgt tatgcacgtt ctgttcgtca gtataagatc    300
ttgaattgtg caaattatca tttaactcaa gtacgaactg attctctatga tgaattttgg   360
ggacagggtt tgcgggcagc acctaaaaag caaagaaac atacgttaag tttaacacct     420
gatacaacgc tttataatgc tgctcagatt atttgtgcga actatggtga agcatttca    480
gttgataaaa aaggcggcac taaaaaagca gcggtatctg aattactgca agcgtcagcg    540
ccttataagg ctgatgtgga attatgtgta tatagcacaa atgaaacaac aaactgtacg    600
ggtggaaaaa atggtattgc agcagatata accacagcaa aaggctatgt aaaatcagtg   660
acaacaagca acggtgcaat aacagtaaaa gggatggca cattggcaaa tatggaatat   720
attttgcaag ctacaggtaa tgctgcaaca ggtgtaactt ggacaacaac ttgcaaagga   780
acggatgcct ctttatttcc agcaaatttt tgcggaagtg tcacacaata a            831
```

<210> SEQ ID NO 148
<211> LENGTH: 276
<212> TYPE: PRT
<213> ORGANISM: Artificial Sequence
<220> FEATURE:
<223> OTHER INFORMATION: LVL317

<400> SEQUENCE: 148

```
Met Lys Tyr Leu Leu Pro Thr Ala Ala Ala Gly Leu Leu Leu Ala
  1               5                  10                  15

Ala Gln Pro Ala Met Ala Gln Ile Gln Lys Ala Glu Gln Asn Asp Val
             20                  25                  30

Lys Leu Ala Pro Pro Thr Asp Val Arg Ser Gly Tyr Ile Arg Leu Val
         35                  40                  45

Lys Asn Val Asn Tyr Tyr Ile Asp Ser Glu Ser Ile Trp Val Asp Asn
 50                  55                  60

Glu Pro Gln Ile Val His Phe Asp Ala Val Val Asn Leu Asp Lys
 65                  70                  75                  80

Gly Leu Tyr Val Tyr Pro Glu Pro Lys Arg Tyr Ala Arg Ser Val Arg
                 85                  90                  95

Gln Tyr Lys Ile Leu Asn Cys Ala Asn Tyr His Leu Thr Gln Val Arg
                100                 105                 110

Thr Asp Phe Tyr Asp Glu Phe Trp Gly Gln Gly Leu Arg Ala Ala Pro
            115                 120                 125

Lys Lys Gln Lys Lys His Thr Leu Ser Leu Thr Pro Asp Thr Thr Leu
130                 135                 140

Tyr Asn Ala Ala Gln Ile Ile Cys Ala Asn Tyr Gly Glu Ala Phe Ser
145                 150                 155                 160

Val Asp Lys Lys Gly Gly Thr Lys Lys Ala Val Ser Glu Leu Leu
                165                 170                 175

Gln Ala Ser Ala Pro Tyr Lys Ala Asp Val Glu Leu Cys Val Tyr Ser
                180                 185                 190

Thr Asn Glu Thr Thr Asn Cys Thr Gly Gly Lys Asn Gly Ile Ala Ala
            195                 200                 205

Asp Ile Thr Thr Ala Lys Gly Tyr Val Lys Ser Val Thr Thr Ser Asn
210                 215                 220

Gly Ala Ile Thr Val Lys Gly Asp Gly Thr Leu Ala Asn Met Glu Tyr
225                 230                 235                 240

Ile Leu Gln Ala Thr Gly Asn Ala Ala Thr Gly Val Thr Trp Thr Thr
                245                 250                 255

Thr Cys Lys Gly Thr Asp Ala Ser Leu Phe Pro Ala Asn Phe Cys Gly
            260                 265                 270

Ser Val Thr Gln
            275

<210> SEQ ID NO 149
<211> LENGTH: 828
<212> TYPE: DNA
<213> ORGANISM: Artificial Sequence
<220> FEATURE:
<223> OTHER INFORMATION: LVL318

<400> SEQUENCE: 149
atgaaatacc tgctgccgac cgctgctgct ggtctgctgc tcctcgctgc ccagccggcg      60
atggccatgg ataaggctga acaaaatgat gtgaagctgg caccgccgac tgatgtacga     120
agcggatata tacgtttggt aaagaatgtg aattattaca tcgatagtga atcgatctgg     180
gtggataacc aagagccaca aattgtacat tttgatgcag tggtgaattt agataaggga     240
ttgtatgttt atcctgagcc taaacgttat gcacgttctg ttcgtcagta taagatcttg     300
aattgtgcaa attatcattt aactcaagta cgaactgatt tctatgatga attttgggga     360
cagggtttgc gggcagcacc taaaaagcaa aagaaacata cgttaagttt aacacctgat     420
```

```
acaacgcttt ataatgctgc tcagattatt tgtgcgaact atggtgaagc atttcagtt    480 gataaaaaag gcggcactaa aaaagcagcg gtatctgaat tactgcaagc gtcagcgcct    540
tataaggctg atgtggaatt atgtgtatat agcacaaatg aaacaacaaa ctgtacgggt    600
ggaaaaaatg gtattgcagc agatataacc acagcaaaag ctatgtaaa atcagtgaca     660 acaagcaacg gtgcaataac agtaaaaggg gatggcacat tggcaaatat ggaatatatt    720
ttgcaagcta caggtaatgc tgcaacaggt gtaacttgga caacaacttg caaaggaacg    780
gatgcctctt tatttccagc aaattttgc ggaagtgtca cacaataa                  828
```

<210> SEQ ID NO 150
<211> LENGTH: 275
<212> TYPE: PRT
<213> ORGANISM: Artificial Sequence
<220> FEATURE:
<223> OTHER INFORMATION: LVL318

<400> SEQUENCE: 150

```
Met Lys Tyr Leu Leu Pro Thr Ala Ala Ala Gly Leu Leu Leu Leu Ala
 1               5                  10                  15

Ala Gln Pro Ala Met Ala Met Asp Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
    50                  55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
           100                 105                 110

Asp Phe Tyr Asp Glu Phe Trp Gly Gln Gly Leu Arg Ala Ala Pro Lys
       115                 120                 125

Lys Gln Lys Lys His Thr Leu Ser Leu Thr Pro Asp Thr Thr Leu Tyr
130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175

Ala Ser Ala Pro Tyr Lys Ala Asp Val Glu Leu Cys Val Tyr Ser Thr
           180                 185                 190

Asn Glu Thr Thr Asn Cys Thr Gly Gly Lys Asn Gly Ile Ala Ala Asp
       195                 200                 205

Ile Thr Thr Ala Lys Gly Tyr Val Lys Ser Val Thr Ser Asn Gly
   210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
           260                 265                 270

Val Thr Gln
       275
```

```
<210> SEQ ID NO 151
<211> LENGTH: 483
<212> TYPE: DNA
<213> ORGANISM: Haemophilus influenzae

<400> SEQUENCE: 151
atgaaaaaaa ttattttaac attatcactt gggttactta ccgcttgttc tgctcaaatc    60
caaaaggctg aacaaaatga tgtgaagctg gcaccgccga ctgatgtacg aagcggatat   120
atacgtttgg taaagaatgt gaattattac atcgatagtg aatcgatctg ggtgataac   180 caagagccac aaattgtaca ttttgatgct gtggtgaatt tagataggg attgtatgtt   240 tatcctgagc ctaaacgtta tgcacgttct gttcgtcagt ataagatttt gaattgtgca   300
aattatcatt taactcaaat acgaactgat ttctatgatg aattttgggg acagggtttg   360
cgggcagcac ctaaaaagca aagaaacat acgttaagtt taacacctga tacaacgctt   420
tataatgctg ctcagattat ttgtgcaaat tatggtaaag catttcagt tgataaaaaa    480 taa                                                                483

<210> SEQ ID NO 152
<211> LENGTH: 160
<212> TYPE: PRT
<213> ORGANISM: Haemophilus influenzae

<400> SEQUENCE: 152

Met Lys Lys Ile Ile Leu Thr Leu Ser Leu Gly Leu Leu Thr Ala Cys
  1               5                  10                  15

Ser Ala Gln Ile Gln Lys Ala Glu Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
     50                  55                  60

Ile Val His Phe Asp Ala Val Val Asn Leu Asp Arg Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 153
<211> LENGTH: 480
<212> TYPE: DNA
<213> ORGANISM: Haemophilus influenzae

<400> SEQUENCE: 153
atgaaaaaaa ttattttaac attatcactt gggttactta ctgcctgttc tgctcaaatc    60
caaaaggcta acaaaatga tgtgaagctg gcaccgccga ctgatgtacg aagcggatat   120
atacgtttgg taaagaatgt gaattattac atcgatagtg aatcgatctg ggtgataac   180 caagagccac aaattgtaca ttttgatgca gtggtgaatt tagataaggg attgtatgtt   240
```

```
tatcctgagc ctaaacgtta tgcacgttct gttcgtcagt ataagatctt gaattgtgca    300
aattatcatt taactcaagt acgaactgat ttctatgatg aatttcgggg acagggtttg    360
cgggcagcac ctaaaaagca aagaaacat acgttaagtt taacacctga tacaacgctt    420
tataatgctg ctcagattat ttgtgcgaac tatggtgaag cattttcagt tgataaaaaa    480
```

<210> SEQ ID NO 154
<211> LENGTH: 160
<212> TYPE: PRT
<213> ORGANISM: Haemophilus influenzae

<400> SEQUENCE: 154

```
Met Lys Lys Ile Ile Leu Thr Leu Ser Leu Gly Leu Leu Thr Ala Cys
 1               5                  10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160
```

<210> SEQ ID NO 155
<211> LENGTH: 91
<212> TYPE: DNA
<213> ORGANISM: Artificial Sequence
<220> FEATURE:
<223> OTHER INFORMATION: primer

<400> SEQUENCE: 155

```
cacacacata tgattaaatt tctctctgca ttaattcttc tactggtcac gacggcggct    60
caggctgaga ctaaaaaagc agcggtatct g                                    91
```

<210> SEQ ID NO 156
<211> LENGTH: 66
<212> TYPE: DNA
<213> ORGANISM: Artificial Sequence
<220> FEATURE:
<223> OTHER INFORMATION: primer

<400> SEQUENCE: 156

```
tgtgtgaagc ttttagtggt ggtggtggtg gtggccgcct tgtgtgacac ttccgcaaaa    60
atttgc                                                                66
```

<210> SEQ ID NO 157
<211> LENGTH: 58
<212> TYPE: DNA
<213> ORGANISM: Artificial Sequence

```
<220> FEATURE:
<223> OTHER INFORMATION: primer

<400> SEQUENCE: 157
tttgcggaag tgtcacacaa ggcggcgcgc agattcagaa ggctgaacaa aatgatgt        58

<210> SEQ ID NO 158
<211> LENGTH: 58
<212> TYPE: DNA
<213> ORGANISM: Artificial Sequence
<220> FEATURE:
<223> OTHER INFORMATION: primer

<400> SEQUENCE: 158
acatcatttt gttcagcctt ctgaatctgc gcgccgcctt gtgtgacact tccgcaaa        58

<210> SEQ ID NO 159
<211> LENGTH: 59
<212> TYPE: DNA
<213> ORGANISM: Artificial Sequence
<220> FEATURE:
<223> OTHER INFORMATION: primer

<400> SEQUENCE: 159
tgtgtgaagc ttttagtggt ggtggtggtg gtggccgcct tttttatcaa ctgaaaatg       59

<210> SEQ ID NO 160
<211> LENGTH: 65
<212> TYPE: DNA
<213> ORGANISM: Artificial Sequence
<220> FEATURE:
<223> OTHER INFORMATION: primer

<400> SEQUENCE: 160
cacacacata tgcaccacca ccaccaccac agcgcgcaga ttcagaaggc tgaacaaaat      60
gatgt                                                                 65

<210> SEQ ID NO 161
<211> LENGTH: 46
<212> TYPE: DNA
<213> ORGANISM: Artificial Sequence
<220> FEATURE:
<223> OTHER INFORMATION: primer

<400> SEQUENCE: 161
cattttcagt tgataaaaaa ggcggcacta aaaagcagc ggtatc                     46

<210> SEQ ID NO 162
<211> LENGTH: 46
<212> TYPE: DNA
<213> ORGANISM: Artificial Sequence
<220> FEATURE:
<223> OTHER INFORMATION: primer

<400> SEQUENCE: 162
gataccgctg ctttttagt gccgcctttt ttatcaactg aaaatg                     46

<210> SEQ ID NO 163
<211> LENGTH: 35
<212> TYPE: DNA
<213> ORGANISM: Artificial Sequence
<220> FEATURE:
<223> OTHER INFORMATION: primer

<400> SEQUENCE: 163
```
tgtgtgaagc ttttattgtg tgacacttcc gcaaa    35

<210> SEQ ID NO 164
<211> LENGTH: 104
<212> TYPE: DNA
<213> ORGANISM: Artificial Sequence
<220> FEATURE:
<223> OTHER INFORMATION: primer

<400> SEQUENCE: 164
cacacacata tgaaatacct gctgccgacc gctgctgctg gtctgctgct cctcgctgcc    60
cagccggcga tggcccagat tcagaaggct gaacaaaatg atgt    104

<210> SEQ ID NO 165
<211> LENGTH: 49
<212> TYPE: DNA
<213> ORGANISM: Artificial Sequence
<220> FEATURE:
<223> OTHER INFORMATION: primer

<400> SEQUENCE: 165
gcattttcag ttgataaaaa aggcggcact aaaaaagcag cggtatctg    49

<210> SEQ ID NO 166
<211> LENGTH: 49
<212> TYPE: DNA
<213> ORGANISM: Artificial Sequence
<220> FEATURE:
<223> OTHER INFORMATION: primer

<400> SEQUENCE: 166
cagataccgc tgcttttttta gtgccgcctt ttttatcaac tgaaaatgc    49

<210> SEQ ID NO 167
<211> LENGTH: 104
<212> TYPE: DNA
<213> ORGANISM: Artificial Sequence
<220> FEATURE:
<223> OTHER INFORMATION: primer

<400> SEQUENCE: 167
cacacacata tgaaatacct gctgccgacc gctgctgctg gtctgctgct cctcgctgcc    60
cagccggcga tggccgatat tcagaaggct gaacaaaatg atgt    104

<210> SEQ ID NO 168
<211> LENGTH: 115
<212> TYPE: DNA
<213> ORGANISM: Artificial Sequence
<220> FEATURE:
<223> OTHER INFORMATION: primer

<400> SEQUENCE: 168
cacacacata tgaaacactt tccatccaaa gtactgacca cagccatcct tgccactttc    60
tgtagcggcg cactggcagc cacaaacgac gacgataagg ctgaacaaaa tgatg    115

<210> SEQ ID NO 169
<211> LENGTH: 35
<212> TYPE: DNA
<213> ORGANISM: Artificial Sequence
<220> FEATURE:
<223> OTHER INFORMATION: primer

<400> SEQUENCE: 169
gccggcgatg gccatggata aggctgaaca aaatg    35

<210> SEQ ID NO 170
<211> LENGTH: 35
<212> TYPE: DNA
<213> ORGANISM: Artificial Sequence
<220> FEATURE:
<223> OTHER INFORMATION: primer

<400> SEQUENCE: 170
cattttgttc agccttatcc atggccatcg ccggc                                35

<210> SEQ ID NO 171
<211> LENGTH: 34
<212> TYPE: DNA
<213> ORGANISM: Artificial Sequence
<220> FEATURE:
<223> OTHER INFORMATION: primer

<400> SEQUENCE: 171
ggaagtgtca cacaataagg cggccaccac cacc                                 34

<210> SEQ ID NO 172
<211> LENGTH: 34
<212> TYPE: DNA
<213> ORGANISM: Artificial Sequence
<220> FEATURE:
<223> OTHER INFORMATION: primer

<400> SEQUENCE: 172
ggtggtggtg gccgccttat tgtgtgacac ttcc                                 34

<210> SEQ ID NO 173
<211> LENGTH: 54
<212> TYPE: DNA
<213> ORGANISM: Artificial Sequence
<220> FEATURE:
<223> OTHER INFORMATION: primer

<400> SEQUENCE: 173
gaattccata tgcaccatca ccatcaccat actaaaaaag cagcggtatc tgaa           54

<210> SEQ ID NO 174
<211> LENGTH: 32
<212> TYPE: DNA
<213> ORGANISM: Artificial Sequence
<220> FEATURE:
<223> OTHER INFORMATION: primer

<400> SEQUENCE: 174
gcgccgctcg agtcattgtg tgacacttcc gc                                   32

<210> SEQ ID NO 175
<211> LENGTH: 43
<212> TYPE: DNA
<213> ORGANISM: Artificial Sequence
<220> FEATURE:
<223> OTHER INFORMATION: primer

<400> SEQUENCE: 175
gcccagccgg cgatggccca gatccagaag gctgaacaaa atg                       43

<210> SEQ ID NO 176
<211> LENGTH: 43
<212> TYPE: DNA
<213> ORGANISM: Artificial Sequence
<220> FEATURE:

<223> OTHER INFORMATION: primer

<400> SEQUENCE: 176
cattttgttc agccttctgg atctgggcca tcgccggctg ggc        43

<210> SEQ ID NO 177
<211> LENGTH: 254
<212> TYPE: PRT
<213> ORGANISM: Artificial Sequence
<220> FEATURE:
<223> OTHER INFORMATION: Fusion protein

<400> SEQUENCE: 177

Gln Ile Gln Lys Ala Glu Gln Asn Asp Val Lys Leu Ala Pro Pro Thr
 1               5                  10                  15

Asp Val Arg Ser Gly Tyr Ile Arg Leu Val Lys Asn Val Asn Tyr Tyr
            20                  25                  30

Ile Asp Ser Glu Ser Ile Trp Val Asp Asn Gln Glu Pro Gln Ile Val
        35                  40                  45

His Phe Asp Ala Val Val Asn Leu Asp Lys Gly Leu Tyr Val Tyr Pro
    50                  55                  60

Glu Pro Lys Arg Tyr Ala Arg Ser Val Arg Gln Tyr Lys Ile Leu Asn
65                  70                  75                  80

Cys Ala Asn Tyr His Leu Thr Gln Val Arg Thr Asp Phe Tyr Asp Glu
                85                  90                  95

Phe Trp Gly Gln Gly Leu Arg Ala Ala Pro Lys Lys Gln Lys Lys His
            100                 105                 110

Thr Leu Ser Leu Thr Pro Asp Thr Thr Leu Tyr Asn Ala Ala Gln Ile
        115                 120                 125

Ile Cys Ala Asn Tyr Gly Glu Ala Phe Ser Val Asp Lys Lys Gly Gly
    130                 135                 140

Thr Lys Lys Ala Ala Val Ser Glu Leu Leu Gln Ala Ser Ala Pro Tyr
145                 150                 155                 160

Lys Ala Asp Val Glu Leu Cys Val Tyr Ser Thr Asn Glu Thr Thr Asn
                165                 170                 175

Cys Thr Gly Gly Lys Asn Gly Ile Ala Ala Asp Ile Thr Thr Ala Lys
            180                 185                 190

Gly Tyr Val Lys Ser Val Thr Thr Ser Asn Gly Ala Ile Thr Val Lys
        195                 200                 205

Gly Asp Gly Thr Leu Ala Asn Met Glu Tyr Ile Leu Gln Ala Thr Gly
    210                 215                 220

Asn Ala Ala Thr Gly Val Thr Trp Thr Thr Thr Cys Lys Gly Thr Asp
225                 230                 235                 240

Ala Ser Leu Phe Pro Ala Asn Phe Cys Gly Ser Val Thr Gln
                245                 250

<210> SEQ ID NO 178
<211> LENGTH: 6
<212> TYPE: PRT
<213> ORGANISM: Artificial Sequence
<220> FEATURE:
<223> OTHER INFORMATION: Synthetic construct

<400> SEQUENCE: 178

Ala Thr Asn Asp Asp Asp
 1               5

<210> SEQ ID NO 179

```
<211> LENGTH: 138
<212> TYPE: PRT
<213> ORGANISM: Haemophilus influenzae

<400> SEQUENCE: 179

Ala Glu Gln Asn Asp Val Lys Leu Ala Pro Pro Thr Asp Val Arg Ser
 1               5                  10                  15

Gly Tyr Ile Arg Leu Val Lys Asn Val Asn Tyr Tyr Ile Asp Ser Glu
            20                  25                  30

Ser Ile Trp Val Asp Asn Gln Glu Pro Gln Ile Val His Phe Asp Ala
        35                  40                  45

Val Val Asn Leu Asp Lys Gly Leu Tyr Val Tyr Pro Glu Pro Lys Arg
 50                  55                  60

Tyr Ala Arg Ser Val Arg Gln Tyr Lys Ile Leu Asn Cys Ala Asn Tyr
 65                  70                  75                  80

His Leu Thr Gln Val Arg Thr Asp Phe Tyr Asp Glu Phe Trp Gly Gln
                85                  90                  95

Gly Leu Arg Ala Ala Pro Lys Lys Gln Lys Lys His Thr Leu Ser Leu
            100                 105                 110

Thr Pro Asp Thr Thr Leu Tyr Asn Ala Ala Gln Ile Ile Cys Ala Asn
        115                 120                 125

Tyr Gly Glu Ala Phe Ser Val Asp Lys Lys
130                 135

<210> SEQ ID NO 180
<211> LENGTH: 137
<212> TYPE: PRT
<213> ORGANISM: Haemophilus influenzae

<400> SEQUENCE: 180

Glu Gln Asn Asp Val Lys Leu Ala Pro Pro Thr Asp Val Arg Ser Gly
 1               5                  10                  15

Tyr Ile Arg Leu Val Lys Asn Val Asn Tyr Tyr Ile Asp Ser Glu Ser
            20                  25                  30

Ile Trp Val Asp Asn Gln Glu Pro Gln Ile Val His Phe Asp Ala Val
        35                  40                  45

Val Asn Leu Asp Lys Gly Leu Tyr Val Tyr Pro Glu Pro Lys Arg Tyr
 50                  55                  60

Ala Arg Ser Val Arg Gln Tyr Lys Ile Leu Asn Cys Ala Asn Tyr His
 65                  70                  75                  80

Leu Thr Gln Val Arg Thr Asp Phe Tyr Asp Glu Phe Trp Gly Gln Gly
                85                  90                  95

Leu Arg Ala Ala Pro Lys Lys Gln Lys Lys His Thr Leu Ser Leu Thr
            100                 105                 110

Pro Asp Thr Thr Leu Tyr Asn Ala Ala Gln Ile Ile Cys Ala Asn Tyr
        115                 120                 125

Gly Glu Ala Phe Ser Val Asp Lys Lys
130                 135

<210> SEQ ID NO 181
<211> LENGTH: 849
<212> TYPE: DNA
<213> ORGANISM: Artificial Sequence
<220> FEATURE:
<223> OTHER INFORMATION: LVL702

<400> SEQUENCE: 181
atgaaatacc tgctgccgac cgctgctgct ggtctgctgc tcctcgctgc ccagccggcg      60
```

```
atggccattc agaaggctga acaaaatgat gtgaagctgg caccgccgac tgatgtacga    120
agcggatata tacgtttggt aaagaatgtg aattattaca tcgatagtga atcgatctgg    180
gtggataacc aagagccaca aattgtacat tttgatgcag tggtgaattt agataaggga    240
ttgtatgttt atcctgagcc taaacgttat gcacgttctg ttcgtcagta aagatcttg     300 aattgtgcaa attatcattt aactcaagta cgaactgatt tctatgatga attttgggga    360
cagggtttgc gggcagcacc taaaaagcaa aagaaacata cgttaagttt aacacctgat    420
acaacgcttt ataatgctgc tcagattatt tgtgcgaact atggtgaagc attttcagtt    480
gataaaaaag gcggcactaa aaaagcagcg gtatctgaat tactgcaagc gtcagcgcct    540
tataaggctg atgtggaatt atgtgtatat agcacaaatg aaacaacaaa ctgtacgggt    600
ggaaaaaatg gtattgcagc agatataacc acagcaaaag gctatgtaaa atcagtgaca    660
acaagcaacg gtgcaataac agtaaaaggg gatggcacat tggcaaatat ggaatatatt    720
ttgcaagcta caggtaatgc tgcaacaggt gtaacttgga caacaacttg caaaggaacg    780
gatgcctctt tatttccagc aaattttgc ggaagtgtca cacaaggcgg ccaccaccac    840
caccaccac                                                            849
```

<210> SEQ ID NO 182
<211> LENGTH: 283
<212> TYPE: PRT
<213> ORGANISM: Artificial Sequence
<220> FEATURE:
<223> OTHER INFORMATION: LVL702

<400> SEQUENCE: 182

```
Met Lys Tyr Leu Leu Pro Thr Ala Ala Gly Leu Leu Leu Leu Ala
 1               5                  10                  15

Ala Gln Pro Ala Met Ala Ile Gln Lys Ala Glu Gln Asn Asp Val Lys
                20                  25                  30

Leu Ala Pro Pro Thr Asp Val Arg Ser Gly Tyr Ile Arg Leu Val Lys
            35                  40                  45

Asn Val Asn Tyr Tyr Ile Asp Ser Glu Ser Ile Trp Val Asp Asn Gln
        50                  55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175

Ala Ser Ala Pro Tyr Lys Ala Asp Val Glu Leu Cys Val Tyr Ser Thr
            180                 185                 190

Asn Glu Thr Thr Asn Cys Thr Gly Gly Lys Asn Gly Ile Ala Ala Asp
        195                 200                 205

Ile Thr Thr Ala Lys Gly Tyr Val Lys Ser Val Thr Thr Ser Asn Gly
```

```
                  210                 215                 220
Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
                260                 265                 270

Val Thr Gln Gly Gly His His His His His His
            275                 280
```

<210> SEQ ID NO 183
<211> LENGTH: 858
<212> TYPE: DNA
<213> ORGANISM: Artificial Sequence
<220> FEATURE:
<223> OTHER INFORMATION: LVL736

<400> SEQUENCE: 183

```
atgaaatacc tgctgccgac cgctgctgct ggtctgctgc tcctcgctgc ccagccggcg      60
atggccagcg cccagattca gaaggctgaa caaaatgatg tgaagctggc accgccgact     120
gatgtacgaa gcggatatat acgtttggta agaatgtgaa attattacat cgatagtgaa     180
tcgatctggg tggataacca agagccacaa attgtacatt ttgatgcagt ggtgaattta     240
gataagggat tgtatgttta tcctgagcct aaacgttatg cacgttctgt tcgtcagtat     300
aagatcttga attgtgcaaa ttatcattta actcaagtac gaactgattt ctatgatgaa     360
ttttggggac agggtttgcg ggcagcacct aaaaagcaaa agaaacatac gttaagttta     420
acacctgata acgcttta taatgctgct cagattattt gtgcgaacta tggtgaagca     480
tttcagttg ataaaaaagg cggcactaaa aaagcagcgg tatctgaatt actgcaagcg     540
tcagcgcctt ataaggctga tgtggaatta tgtgtatata gcacaaatga acaacaaac     600
tgtacgggtg gaaaaaatgg tattgcagca gatataacca cagcaaaagg ctatgtaaaa     660
tcagtgacaa caagcaacgg tgcaataaca gtaaaggggg atggcacatt ggcaaatatg     720
gaatatattt tgcaagctac aggtaatgct gcaacaggtg taacttggac aacaacttgc     780
aaaggaacgg atgcctcttt atttccagca aattttttgcg gaagtgtcac acaaggcggc     840
caccaccacc accaccac                                                    858
```

<210> SEQ ID NO 184
<211> LENGTH: 286
<212> TYPE: PRT
<213> ORGANISM: Artificial Sequence
<220> FEATURE:
<223> OTHER INFORMATION: LVL736

<400> SEQUENCE: 184

```
Met Lys Tyr Leu Leu Pro Thr Ala Ala Ala Gly Leu Leu Leu Leu Ala
1               5                   10                  15

Ala Gln Pro Ala Met Ala Ser Ala Gln Ile Gln Lys Ala Glu Gln Asn
                20                  25                  30

Asp Val Lys Leu Ala Pro Pro Thr Asp Val Arg Ser Gly Tyr Ile Arg
            35                  40                  45

Leu Val Lys Asn Val Asn Tyr Tyr Ile Asp Ser Glu Ser Ile Trp Val
        50                  55                  60

Asp Asn Gln Glu Pro Gln Ile Val His Phe Asp Ala Val Val Asn Leu
65                  70                  75                  80
```

```
Asp Lys Gly Leu Tyr Val Tyr Pro Glu Pro Lys Arg Tyr Ala Arg Ser
             85                  90                  95
Val Arg Gln Tyr Lys Ile Leu Asn Cys Ala Asn Tyr His Leu Thr Gln
        100                 105                 110
Val Arg Thr Asp Phe Tyr Asp Glu Phe Trp Gly Gln Gly Leu Arg Ala
        115                 120                 125
Ala Pro Lys Lys Gln Lys Lys His Thr Leu Ser Leu Thr Pro Asp Thr
    130                 135                 140
Thr Leu Tyr Asn Ala Ala Gln Ile Ile Cys Ala Asn Tyr Gly Glu Ala
145                 150                 155                 160
Phe Ser Val Asp Lys Lys Gly Gly Thr Lys Lys Ala Ala Val Ser Glu
                165                 170                 175
Leu Leu Gln Ala Ser Ala Pro Tyr Lys Ala Asp Val Glu Leu Cys Val
            180                 185                 190
Tyr Ser Thr Asn Glu Thr Thr Asn Cys Thr Gly Gly Lys Asn Gly Ile
        195                 200                 205
Ala Ala Asp Ile Thr Thr Ala Lys Gly Tyr Val Lys Ser Val Thr Thr
    210                 215                 220
Ser Asn Gly Ala Ile Thr Val Lys Gly Asp Gly Thr Leu Ala Asn Met
225                 230                 235                 240
Glu Tyr Ile Leu Gln Ala Thr Gly Asn Ala Ala Thr Gly Val Thr Trp
                245                 250                 255
Thr Thr Thr Cys Lys Gly Thr Asp Ala Ser Leu Phe Pro Ala Asn Phe
            260                 265                 270
Cys Gly Ser Val Thr Gln Gly Gly His His His His His
        275                 280                 285

<210> SEQ ID NO 185
<211> LENGTH: 855
<212> TYPE: DNA
<213> ORGANISM: Artificial Sequence
<220> FEATURE:
<223> OTHER INFORMATION: LVL737

<400> SEQUENCE: 185
atgaaatacc tgctgccgac cgctgctgct ggtctgctgc tcctcgctgc ccagccggcg    60
atggccgccc agattcagaa ggctgaacaa aatgatgtga agctggcacc gccgactgat   120
gtacgaagcg atatatacg tttggtaaag aatgtgaatt attacatcga tagtgaatcg   180
atctgggtgg ataaccaaga gccacaaatt gtacattttg atgcagtggt gaatttagat   240
aagggattgt atgtttatcc tgagcctaaa cgttatgcac gttctgttcg tcagtataag   300
atcttgaatt gtgcaaatta tcatttaact caagtacgaa ctgatttcta tgatgaattt   360
tggggacagg gtttgcgggc agcacctaaa agcaaaaga acatacgtt aagtttaaca   420 cctgatacaa cgctttataa tgctgctcag attatttgtg cgaactatgg tgaagcattt   480
tcagttgata aaaaggcgg cactaaaaaa gcagcggtat ctgaattact gcaagcgtca   540
gcgccttata aggctgatgt ggaattatgt gtatatagca caatgaaaac aacaaactgt   600
acgggtggaa aaaatggtat tgcagcagat ataaccacag caaaaggcta tgtaaaatca   660
gtgacaacaa gcaacggtgc aataacagta aaaggggatg gcacattggc aaatatggaa   720
tatattttgc aagctacagg taatgctgca acaggtgtaa cttggacaac aacttgcaaa   780
ggaacggatg cctctttatt tccagcaaat ttttgcggaa gtgtcacaca aggcggccac   840
caccaccacc accac                                                    855
```

<210> SEQ ID NO 186
<211> LENGTH: 285
<212> TYPE: PRT
<213> ORGANISM: Artificial Sequence
<220> FEATURE:
<223> OTHER INFORMATION: LVL737

<400> SEQUENCE: 186

```
Met Lys Tyr Leu Leu Pro Thr Ala Ala Ala Gly Leu Leu Leu Leu Ala
 1               5                  10                  15

Ala Gln Pro Ala Met Ala Ala Gln Ile Gln Lys Ala Glu Gln Asn Asp
            20                  25                  30

Val Lys Leu Ala Pro Pro Thr Asp Val Arg Ser Gly Tyr Ile Arg Leu
        35                  40                  45

Val Lys Asn Val Asn Tyr Tyr Ile Asp Ser Glu Ser Ile Trp Val Asp
 50                  55                  60

Asn Gln Glu Pro Gln Ile Val His Phe Asp Ala Val Val Asn Leu Asp
 65                  70                  75                  80

Lys Gly Leu Tyr Val Tyr Pro Glu Pro Lys Arg Tyr Ala Arg Ser Val
                85                  90                  95

Arg Gln Tyr Lys Ile Leu Asn Cys Ala Asn Tyr His Leu Thr Gln Val
            100                 105                 110

Arg Thr Asp Phe Tyr Asp Glu Phe Trp Gly Gln Gly Leu Arg Ala Ala
        115                 120                 125

Pro Lys Lys Gln Lys Lys His Thr Leu Ser Leu Thr Pro Asp Thr Thr
130                 135                 140

Leu Tyr Asn Ala Ala Gln Ile Ile Cys Ala Asn Tyr Gly Glu Ala Phe
145                 150                 155                 160

Ser Val Asp Lys Lys Gly Gly Thr Lys Lys Ala Ala Val Ser Glu Leu
                165                 170                 175

Leu Gln Ala Ser Ala Pro Tyr Lys Ala Asp Val Glu Leu Cys Val Tyr
            180                 185                 190

Ser Thr Asn Glu Thr Thr Asn Cys Thr Gly Gly Lys Asn Gly Ile Ala
        195                 200                 205

Ala Asp Ile Thr Thr Ala Lys Gly Tyr Val Lys Ser Val Thr Thr Ser
    210                 215                 220

Asn Gly Ala Ile Thr Val Lys Gly Asp Gly Thr Leu Ala Asn Met Glu
225                 230                 235                 240

Tyr Ile Leu Gln Ala Thr Gly Asn Ala Ala Thr Gly Val Thr Trp Thr
                245                 250                 255

Thr Thr Cys Lys Gly Thr Asp Ala Ser Leu Phe Pro Ala Asn Phe Cys
            260                 265                 270

Gly Ser Val Thr Gln Gly Gly His His His His His
        275                 280                 285
```

<210> SEQ ID NO 187
<211> LENGTH: 843
<212> TYPE: DNA
<213> ORGANISM: Artificial Sequence
<220> FEATURE:
<223> OTHER INFORMATION: LVL738

<400> SEQUENCE: 187

```
atgaaatacc tgctgccgac cgctgctgct ggtctgctgc tcctcgctgc ccagccggcg    60
atggccaagg ctgaacaaaa tgatgtgaag ctggcaccgc cgactgatgt acgaagcgga   120
tatatacgtt tggtaaagaa tgtgaattat tacatcgata gtgaatcgat ctgggtggat   180
```

```
aaccaagagc cacaaattgt acattttgat gcagtggtga atttagataa gggattgtat    240
gtttatcctg agcctaaacg ttatgcacgt tctgttcgtc agtataagat cttgaattgt    300
gcaaattatc atttaactca agtacgaact gatttctatg atgaattttg gggacagggt    360
ttgcgggcag cacctaaaaa gcaaagaaaa catacgttaa gtttaacacc tgatacaacg    420
ctttataatg ctgctcagat tatttgtgcg aactatggtg aagcattttc agttgataaa    480
aaaggcggca ctaaaaaagc agcggtatct gaattactgc aagcgtcagc gccttataag    540
gctgatgtgg aattatgtgt atatagcaca aatgaaacaa caaactgtac gggtggaaaa    600
aatggtattg cagcagatat aaccacagca aaaggctatg taaaatcagt gacaacaagc    660
aacggtgcaa taacagtaaa aggggatggc acattggcaa atatggaata tattttgcaa    720
gctacaggta atgctgcaac aggtgtaact tggacaacaa cttgcaaagg aacggatgcc    780
tctttatttc cagcaaattt ttgcggaagt gtcacacaag gcggccacca ccaccaccac    840
cac                                                                  843
```

```
<210> SEQ ID NO 188
<211> LENGTH: 281
<212> TYPE: PRT
<213> ORGANISM: Artificial Sequence
<220> FEATURE:
<223> OTHER INFORMATION: LVL738

<400> SEQUENCE: 188
```

| | | | | | | | | | | | | | | |
|---|---|---|---|---|---|---|---|---|---|---|---|---|---|---|
| Met | Lys | Tyr | Leu | Leu | Pro | Thr | Ala | Ala | Gly | Leu | Leu | Leu | Leu | Ala |
| 1 | | | | 5 | | | | | 10 | | | | | 15 |
| Ala | Gln | Pro | Ala | Met | Ala | Lys | Ala | Glu | Gln | Asn | Asp | Val | Lys | Leu | Ala |
| | | | 20 | | | | | 25 | | | | | 30 | |
| Pro | Pro | Thr | Asp | Val | Arg | Ser | Gly | Tyr | Ile | Arg | Leu | Val | Lys | Asn | Val |
| | | 35 | | | | | 40 | | | | | 45 | | |
| Asn | Tyr | Tyr | Ile | Asp | Ser | Glu | Ser | Ile | Trp | Val | Asp | Asn | Gln | Glu | Pro |
| | 50 | | | | | 55 | | | | | 60 | | | |
| Gln | Ile | Val | His | Phe | Asp | Ala | Val | Val | Asn | Leu | Asp | Lys | Gly | Leu | Tyr |
| 65 | | | | | 70 | | | | | 75 | | | | | 80 |
| Val | Tyr | Pro | Glu | Pro | Lys | Arg | Tyr | Ala | Arg | Ser | Val | Arg | Gln | Tyr | Lys |
| | | | | 85 | | | | | 90 | | | | | 95 | |
| Ile | Leu | Asn | Cys | Ala | Asn | Tyr | His | Leu | Thr | Gln | Val | Arg | Thr | Asp | Phe |
| | | | 100 | | | | | 105 | | | | | 110 | | |
| Tyr | Asp | Glu | Phe | Trp | Gly | Gln | Gly | Leu | Arg | Ala | Ala | Pro | Lys | Lys | Gln |
| | | 115 | | | | | 120 | | | | | 125 | | | |
| Lys | Lys | His | Thr | Leu | Ser | Leu | Thr | Pro | Asp | Thr | Thr | Leu | Tyr | Asn | Ala |
| 130 | | | | | 135 | | | | | 140 | | | | | |
| Ala | Gln | Ile | Ile | Cys | Ala | Asn | Tyr | Gly | Glu | Ala | Phe | Ser | Val | Asp | Lys |
| 145 | | | | | 150 | | | | | 155 | | | | | 160 |
| Lys | Gly | Gly | Thr | Lys | Lys | Ala | Ala | Val | Ser | Glu | Leu | Leu | Gln | Ala | Ser |
| | | | | 165 | | | | | 170 | | | | | 175 | |
| Ala | Pro | Tyr | Lys | Ala | Asp | Val | Glu | Leu | Cys | Val | Tyr | Ser | Thr | Asn | Glu |
| | | | 180 | | | | | 185 | | | | | 190 | | |
| Thr | Thr | Asn | Cys | Thr | Gly | Gly | Lys | Asn | Gly | Ile | Ala | Ala | Asp | Ile | Thr |
| | | 195 | | | | | 200 | | | | | 205 | | | |
| Thr | Ala | Lys | Gly | Tyr | Val | Lys | Ser | Val | Thr | Thr | Ser | Asn | Gly | Ala | Ile |
| | 210 | | | | | 215 | | | | | 220 | | | | |
| Thr | Val | Lys | Gly | Asp | Gly | Thr | Leu | Ala | Asn | Met | Glu | Tyr | Ile | Leu | Gln |
| 225 | | | | | 230 | | | | | 235 | | | | | 240 |

Ala Thr Gly Asn Ala Ala Thr Gly Val Thr Trp Thr Thr Thr Cys Lys
            245                 250                 255

Gly Thr Asp Ala Ser Leu Phe Pro Ala Asn Phe Cys Gly Ser Val Thr
        260                 265                 270

Gln Gly Gly His His His His His His
    275                 280

<210> SEQ ID NO 189
<211> LENGTH: 840
<212> TYPE: DNA
<213> ORGANISM: Artificial Sequence
<220> FEATURE:
<223> OTHER INFORMATION: LVL739

<400> SEQUENCE: 189
atgaaatacc tgctgccgac cgctgctgct ggtctgctgc tcctcgctgc ccagccggcg    60
atggccgctg aacaaaatga tgtgaagctg gcaccgccga ctgatgtacg aagcggatat   120
atacgtttgg taaagaatgt gaattattac atcgatagtg aatcgatctg ggtggataac   180
caagagccac aaattgtaca ttttgatgca gtggtgaatt tagataaggg attgtatgtt   240
tatcctgagc ctaaacgtta tgcacgttct gttcgtcagt ataagatctt gaattgtgca   300
aattatcatt taactcaagt acgaactgat ttctatgatg aattttgggg acagggtttg   360
cgggcagcac ctaaaaagca aagaaacat acgttaagtt taacacctga tacaacgctt   420
tataatgctg ctcagattat ttgtgcgaac tatggtgaag catttttcagt tgataaaaaa   480 ggcggcacta aaaagcagc ggtatctgaa ttactgcaag cgtcagcgcc ttataaggct   540
gatgtggaat atgtgtata tagcacaaat gaaacaacaa actgtacggg tggaaaaaat   600
ggtattgcag cagatataac cacagcaaaa ggctatgtaa aatcagtgac aacaagcaac   660
ggtgcaataa cagtaaaagg ggatggcaca ttggcaaata tggaatatat tttgcaagct   720
acaggtaatg ctgcaacagg tgtaacttgg acaacaactt gcaaaggaac ggatgcctct   780
ttatttccag caaatttttg cggaagtgtc acacaaggcg gccaccacca ccaccaccac   840

<210> SEQ ID NO 190
<211> LENGTH: 280
<212> TYPE: PRT
<213> ORGANISM: Artificial Sequence
<220> FEATURE:
<223> OTHER INFORMATION: LVL739

<400> SEQUENCE: 190

Met Lys Tyr Leu Leu Pro Thr Ala Ala Ala Gly Leu Leu Leu Leu Ala
1               5                   10                  15

Ala Gln Pro Ala Met Ala Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Gln Lys
         115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

Gly Gly Thr Lys Lys Ala Ala Val Ser Glu Leu Leu Gln Ala Ser Ala
                165                 170                 175

Pro Tyr Lys Ala Asp Val Glu Leu Cys Val Tyr Ser Thr Asn Glu Thr
            180                 185                 190

Thr Asn Cys Thr Gly Gly Lys Asn Gly Ile Ala Ala Asp Ile Thr Thr
        195                 200                 205

Ala Lys Gly Tyr Val Lys Ser Val Thr Thr Ser Asn Gly Ala Ile Thr
    210                 215                 220

Val Lys Gly Asp Gly Thr Leu Ala Asn Met Glu Tyr Ile Leu Gln Ala
225                 230                 235                 240

Thr Gly Asn Ala Ala Thr Gly Val Thr Trp Thr Thr Thr Cys Lys Gly
                245                 250                 255

Thr Asp Ala Ser Leu Phe Pro Ala Asn Phe Cys Gly Ser Val Thr Gln
            260                 265                 270

Gly Gly His His His His His His
        275                 280

<210> SEQ ID NO 191
<211> LENGTH: 837
<212> TYPE: DNA
<213> ORGANISM: Artificial Sequence
<220> FEATURE:
<223> OTHER INFORMATION: LVL740

<400> SEQUENCE: 191
atgaaatacc tgctgccgac cgctgctgct ggtctgctgc tcctcgctgc ccagccggcg      60
atggccgaac aaaatgatgt gaagctggca ccgccgactg atgtacgaag cggatatata     120
cgtttggtaa agaatgtgaa ttattacatc gatagtgaat cgatctgggt ggataaccaa     180
gagccacaaa ttgtacattt tgatgcagtg gtgaatttag ataagggatt gtatgtttat     240
cctgagccta acgttatgc acgttctgtt cgtcagtata agatcttgaa ttgtgcaaat      300
tatcatttaa ctcaagtacg aactgatttc tatgatgaat tttggggaca gggtttgcgg     360
gcagcaccta aaagcaaaa gaaacatacg ttaagtttaa cacctgatac aacgctttat     420
aatgctgctc agattatttg tgcgaactat ggtgaagcat tttcagttga taaaaaaggc     480
ggcactaaaa aagcagcggt atctgaatta ctgcaagcgt cagcgcctta taggctgat     540 gtggaattat gtgtatatag cacaaatgaa acaacaaact gtacgggtgg aaaaaatggt     600
attgcagcag atataaccac agcaaaaggc tatgtaaaat cagtgacaac aagcaacggt     660
gcaataacag taaaggggga tggcacattg gcaaatatgg aatatatttt gcaagctaca     720
ggtaatgctg caacaggtgt aacttggaca acaacttgca aggaacgga tgcctcttta     780 tttccagcaa attttttgcgg aagtgtcaca caaggcggcc accaccacca ccaccac     837

<210> SEQ ID NO 192
<211> LENGTH: 279
<212> TYPE: PRT
<213> ORGANISM: Artificial Sequence
<220> FEATURE:
<223> OTHER INFORMATION: LVL740

<400> SEQUENCE: 192

Met Lys Tyr Leu Leu Pro Thr Ala Ala Gly Leu Leu Leu Ala
1               5                   10                  15

Ala Gln Pro Ala Met Ala Glu Gln Asn Asp Val Lys Leu Ala Pro Pro
            20                  25                  30

Thr Asp Val Arg Ser Gly Tyr Ile Arg Leu Val Lys Asn Val Asn Tyr
                35                  40                  45

Tyr Ile Asp Ser Glu Ser Ile Trp Val Asp Asn Gln Glu Pro Gln Ile
50                  55                  60

Val His Phe Asp Ala Val Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
                115                 120                 125

His Thr Leu Ser Leu Thr Pro Asp Thr Thr Leu Tyr Asn Ala Ala Gln
            130                 135                 140

Ile Ile Cys Ala Asn Tyr Gly Glu Ala Phe Ser Val Asp Lys Lys Gly
145                 150                 155                 160

Gly Thr Lys Lys Ala Ala Val Ser Glu Leu Leu Gln Ala Ser Ala Pro
                165                 170                 175

Tyr Lys Ala Asp Val Glu Leu Cys Val Tyr Ser Thr Asn Glu Thr Thr
            180                 185                 190

Asn Cys Thr Gly Gly Lys Asn Gly Ile Ala Ala Asp Ile Thr Thr Ala
            195                 200                 205

Lys Gly Tyr Val Lys Ser Val Thr Thr Ser Asn Gly Ala Ile Thr Val
            210                 215                 220

Lys Gly Asp Gly Thr Leu Ala Asn Met Glu Tyr Ile Leu Gln Ala Thr
225                 230                 235                 240

Gly Asn Ala Ala Thr Gly Val Thr Trp Thr Thr Thr Cys Lys Gly Thr
            245                 250                 255

Asp Ala Ser Leu Phe Pro Ala Asn Phe Cys Gly Ser Val Thr Gln Gly
            260                 265                 270

Gly His His His His His His
        275

<210> SEQ ID NO 193
<211> LENGTH: 825
<212> TYPE: DNA
<213> ORGANISM: Artificial Sequence
<220> FEATURE:
<223> OTHER INFORMATION: LVL735

<400> SEQUENCE: 193

```
atgaaatacc tgctgccgac cgctgctgct ggtctgctgc tcctcgctgc ccagccggcg    60
atggccattc agaaggctga acaaaatgat gtgaagctgg caccgccgac tgatgtacga   120
agcggatata tacgtttggt aaagaatgtg aattattaca tcgatagtga atcgatctgg   180
gtggataacc aagagccaca aattgtacat tttgatgcag tggtgaattt agataaggga   240
ttgtatgttt atcctgagcc taaacgttat gcacgttctg ttcgtcagta taagatcttg   300
aattgtgcaa attatcattt aactcaagta cgaactgatt tctatgatga attttgggga   360
cagggtttgc gggcagcacc taaaaagcaa aagaaacata cgttaagttt aacacctgat   420
```

```
acaacgcttt ataatgctgc tcagattatt tgtgcgaact atggtgaagc attttcagtt    480
gataaaaaag gcggcactaa aaaagcagcg gtatctgaat tactgcaagc gtcagcgcct    540
tataaggctg atgtggaatt atgtgtatat agcacaaatg aaacaacaaa ctgtacgggt    600
ggaaaaaatg gtattgcagc agatataacc acagcaaaag ctatgtaaa atcagtgaca     660 acaagcaacg gtgcaataac agtaaaaggg gatggcacat tggcaaatat ggaatatatt    720
ttgcaagcta caggtaatgc tgcaacaggt gtaacttgga caacaacttg caaaggaacg    780
gatgcctctt tatttccagc aaattttgc ggaagtgtca cacaa                    825
```

<210> SEQ ID NO 194
<211> LENGTH: 275
<212> TYPE: PRT
<213> ORGANISM: Artificial Sequence
<220> FEATURE:
<223> OTHER INFORMATION: LVL735

<400> SEQUENCE: 194

```
Met Lys Tyr Leu Leu Pro Thr Ala Ala Gly Leu Leu Leu Leu Ala
 1               5                  10                  15

Ala Gln Pro Ala Met Ala Ile Gln Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
 50                  55                  60

Glu Pro Gln Ile Val His Phe Asp Ala Val Val Asn Leu Asp Lys Gly
 65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175

Ala Ser Ala Pro Tyr Lys Ala Asp Val Glu Leu Cys Val Tyr Ser Thr
            180                 185                 190

Asn Glu Thr Thr Asn Cys Thr Gly Gly Lys Asn Gly Ile Ala Ala Asp
        195                 200                 205

Ile Thr Thr Ala Lys Gly Tyr Val Lys Ser Val Thr Thr Ser Asn Gly
    210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
            260                 265                 270

Val Thr Gln
        275
```

<210> SEQ ID NO 195
<211> LENGTH: 834
<212> TYPE: DNA
<213> ORGANISM: Artificial Sequence
<220> FEATURE:
<223> OTHER INFORMATION: LVL778

<400> SEQUENCE: 195

```
atgaaatacc tgctgccgac cgctgctgct ggtctgctgc tcctcgctgc ccagccggcg      60
atggccagcg cccagattca gaaggctgaa caaaatgatg tgaagctggc accgccgact     120
gatgtacgaa gcggatatat acgtttggta agaatgtgaa attattacat cgatagtgaa     180
tcgatctggg tggataacca agagccacaa attgtacatt ttgatgcagt ggtgaattta     240
gataagggat tgtatgttta tcctgagcct aaacgttatg cacgttctgt tcgtcagtat     300
aagatcttga attgtgcaaa ttatcattta actcaagtac gaactgattt ctatgatgaa     360
ttttggggac agggtttgcg ggcagcacct aaaaagcaaa agaaacatac gttaagttta     420
acacctgata caacgcttta taatgctgct cagattattt gtgcgaacta tggtgaagca     480
ttttcagttg ataaaaaagg cggcactaaa aaagcagcgg tatctgaatt actgcaagcg     540
tcagcgcctt ataaggctga tgtggaatta tgtgtatata gcacaaatga acaacaaac     600 tgtacgggtg gaaaaaatgg tattgcagca gatataacca cagcaaaagg ctatgtaaaa     660
tcagtgacaa caagcaacgg tgcaataaca gtaaaagggg atggcacatt ggcaaatatg     720
gaatatattt tgcaagctac aggtaatgct gcaacaggtg taacttggac aacaacttgc     780
aaaggaacgg atgcctcttt atttccagca aattttgcg aagtgtcac acaa            834
```

<210> SEQ ID NO 196
<211> LENGTH: 278
<212> TYPE: PRT
<213> ORGANISM: Artificial Sequence
<220> FEATURE:
<223> OTHER INFORMATION: LVL778

<400> SEQUENCE: 196

```
Met Lys Tyr Leu Leu Pro Thr Ala Ala Ala Gly Leu Leu Leu Ala
 1               5                  10                  15

Ala Gln Pro Ala Met Ala Ser Ala Gln Ile Gln Lys Ala Glu Gln Asn
                20                  25                  30

Asp Val Lys Leu Ala Pro Pro Thr Asp Val Arg Ser Gly Tyr Ile Arg
            35                  40                  45

Leu Val Lys Asn Val Asn Tyr Tyr Ile Asp Ser Glu Ser Ile Trp Val
    50                  55                  60

Asp Asn Gln Glu Pro Gln Ile Val His Phe Asp Ala Val Val Asn Leu
65                  70                  75                  80

Asp Lys Gly Leu Tyr Val Tyr Pro Glu Pro Lys Arg Tyr Ala Arg Ser
                85                  90                  95

Val Arg Gln Tyr Lys Ile Leu Asn Cys Ala Asn Tyr His Leu Thr Gln
            100                 105                 110

Val Arg Thr Asp Phe Tyr Asp Glu Phe Trp Gly Gln Gly Leu Arg Ala
        115                 120                 125

Ala Pro Lys Lys Gln Lys Lys His Thr Leu Ser Leu Thr Pro Asp Thr
    130                 135                 140

Thr Leu Tyr Asn Ala Ala Gln Ile Ile Cys Ala Asn Tyr Gly Glu Ala
145                 150                 155                 160

Phe Ser Val Asp Lys Lys Gly Gly Thr Lys Lys Ala Ala Val Ser Glu
```

```
                    165                 170                 175
Leu Leu Gln Ala Ser Ala Pro Tyr Lys Ala Asp Val Glu Leu Cys Val
            180                 185                 190

Tyr Ser Thr Asn Glu Thr Thr Asn Cys Thr Gly Gly Lys Asn Gly Ile
        195                 200                 205

Ala Ala Asp Ile Thr Thr Ala Lys Gly Tyr Val Lys Ser Val Thr Thr
    210                 215                 220

Ser Asn Gly Ala Ile Thr Val Lys Gly Asp Gly Thr Leu Ala Asn Met
225                 230                 235                 240

Glu Tyr Ile Leu Gln Ala Thr Gly Asn Ala Ala Thr Gly Val Thr Trp
                245                 250                 255

Thr Thr Thr Cys Lys Gly Thr Asp Ala Ser Leu Phe Pro Ala Asn Phe
            260                 265                 270

Cys Gly Ser Val Thr Gln
            275

<210> SEQ ID NO 197
<211> LENGTH: 831
<212> TYPE: DNA
<213> ORGANISM: Artificial Sequence
<220> FEATURE:
<223> OTHER INFORMATION: LVL779

<400> SEQUENCE: 197
atgaaatacc tgctgccgac cgctgctgct ggtctgctgc tcctcgctgc ccagccggcg      60
atggccgccc agattcagaa ggctgaacaa aatgatgtga agctggcacc gccgactgat     120
gtacgaagcg gatatatacg tttggtaaag aatgtgaatt attacatcga tagtgaatcg     180
atctgggtgg ataaccaaga gccacaaatt gtacattttg atgcagtggt gaatttagat     240
aagggattgt atgtttatcc tgagcctaaa cgttatgcac gttctgttcg tcagtataag     300
atcttgaatt gtgcaaatta tcatttaact caagtacgaa ctgatttcta tgatgaattt     360
tggggacagg gtttgcgggc agcacctaaa aagcaaaaga acatacgtt aagtttaaca      420 cctgatacaa cgctttataa tgctgctcag attatttgtg cgaactatgg tgaagcattt     480
tcagttgata aaaaaggcgg cactaaaaaa gcagcggtat ctgaattact gcaagcgtca     540 gcgcctttata ggctgatgt ggaattatgt gtatatagca caaatgaaac aacaaactgt     600
acgggtggaa aaaatggtat tgcagcagat ataaccacag caaaaggcta tgtaaaatca     660
gtgacaacaa gcaacggtgc aataacagta aaggggatg gcacattggc aaatatggaa      720
tatattttgc aagctacagg taatgctgca acaggtgtaa cttggacaac aacttgcaaa     780
ggaacggatg cctctttatt tccagcaaat ttttgcggaa gtgtcacaca a              831

<210> SEQ ID NO 198
<211> LENGTH: 277
<212> TYPE: PRT
<213> ORGANISM: Artificial Sequence
<220> FEATURE:
<223> OTHER INFORMATION: LVL779

<400> SEQUENCE: 198

Met Lys Tyr Leu Leu Pro Thr Ala Ala Ala Gly Leu Leu Leu Leu Ala
  1               5                  10                  15

Ala Gln Pro Ala Met Ala Ala Gln Ile Gln Lys Ala Glu Gln Asn Asp
            20                  25                  30

Val Lys Leu Ala Pro Pro Thr Asp Val Arg Ser Gly Tyr Ile Arg Leu
        35                  40                  45
```

Val Lys Asn Val Asn Tyr Tyr Ile Asp Ser Glu Ser Ile Trp Val Asp
 50                  55                  60

Asn Gln Glu Pro Gln Ile Val His Phe Asp Ala Val Val Asn Leu Asp
 65                  70                  75                  80

Lys Gly Leu Tyr Val Tyr Pro Glu Pro Lys Arg Tyr Ala Arg Ser Val
                 85                  90                  95

Arg Gln Tyr Lys Ile Leu Asn Cys Ala Asn Tyr His Leu Thr Gln Val
            100                 105                 110

Arg Thr Asp Phe Tyr Asp Glu Phe Trp Gly Gln Gly Leu Arg Ala Ala
        115                 120                 125

Pro Lys Lys Gln Lys Lys His Thr Leu Ser Leu Thr Pro Asp Thr Thr
    130                 135                 140

Leu Tyr Asn Ala Ala Gln Ile Ile Cys Ala Asn Tyr Gly Glu Ala Phe
145                 150                 155                 160

Ser Val Asp Lys Lys Gly Gly Thr Lys Lys Ala Val Ser Glu Leu
                165                 170                 175

Leu Gln Ala Ser Ala Pro Tyr Lys Ala Asp Val Glu Leu Cys Val Tyr
            180                 185                 190

Ser Thr Asn Glu Thr Thr Asn Cys Thr Gly Gly Lys Asn Gly Ile Ala
        195                 200                 205

Ala Asp Ile Thr Thr Ala Lys Gly Tyr Val Lys Ser Val Thr Thr Ser
    210                 215                 220

Asn Gly Ala Ile Thr Val Lys Gly Asp Gly Thr Leu Ala Asn Met Glu
225                 230                 235                 240

Tyr Ile Leu Gln Ala Thr Gly Asn Ala Ala Thr Gly Val Thr Trp Thr
                245                 250                 255

Thr Thr Cys Lys Gly Thr Asp Ala Ser Leu Phe Pro Ala Asn Phe Cys
            260                 265                 270

Gly Ser Val Thr Gln
        275

<210> SEQ ID NO 199
<211> LENGTH: 819
<212> TYPE: DNA
<213> ORGANISM: Artificial Sequence
<220> FEATURE:
<223> OTHER INFORMATION: LVL780

<400> SEQUENCE: 199
atgaaatacc tgctgccgac cgctgctgct ggtctgctgc tcctcgctgc ccagccggcg    60
atggccaagg ctgaacaaaa tgatgtgaag ctggcaccgc cgactgatgt acgaagcgga   120
tatatacgtt tggtaaagaa tgtgaattat tacatcgata gtgaatcgat ctgggtggat   180
aaccaagagc cacaaattgt acattttgat gcagtggtga atttagataa gggattgtat   240
gtttatcctg agcctaaacg ttatgcacgt tctgttcgtc agtataagat cttgaattgt   300
gcaaattatc atttaactca agtacgaact gatttctatg atgaattttg gggacagggt   360
ttgcgggcag cacctaaaaa gcaaagaaa catacgttaa gtttaacacc tgatacaacg   420
ctttataatg ctgctcagat tatttgtgcg aactatggtg aagcattttc agttgataaa   480
aaaggcggca ctaaaaaagc agcggtatct gaattactgc aagcgtcagc gccttataag   540
gctgatgtgg aattatgtgt atatagcaca aatgaaacaa caaactgtac gggtggaaaa   600
aatggtattg cagcagatat aaccacagca aaaggctatg taaaatcagt gacaacaagc   660
aacggtgcaa taacagtaaa aggggatggc acattggcaa atatggaata tattttgcaa   720
gctacaggta atgctgcaac aggtgtaact tggacaacaa cttgcaaagg aacggatgcc    780
tctttatttc cagcaaattt ttgcggaagt gtcacacaa    819

<210> SEQ ID NO 200
<211> LENGTH: 273
<212> TYPE: PRT
<213> ORGANISM: Artificial Sequence
<220> FEATURE:
<223> OTHER INFORMATION: LVL780

<400> SEQUENCE: 200

```
Met Lys Tyr Leu Leu Pro Thr Ala Ala Ala Gly Leu Leu Leu Leu Ala
 1               5                  10                  15

Ala Gln Pro Ala Met Ala Lys Ala Glu Gln Asn Asp Val Lys Leu Ala
            20                  25                  30

Pro Pro Thr Asp Val Arg Ser Gly Tyr Ile Arg Leu Val Lys Asn Val
        35                  40                  45

Asn Tyr Tyr Ile Asp Ser Glu Ser Ile Trp Val Asp Asn Gln Glu Pro
    50                  55                  60

Gln Ile Val His Phe Asp Ala Val Val Asn Leu Asp Lys Gly Leu Tyr
65                  70                  75                  80

Val Tyr Pro Glu Pro Lys Arg Tyr Ala Arg Ser Val Arg Gln Tyr Lys
                85                  90                  95

Ile Leu Asn Cys Ala Asn Tyr His Leu Thr Gln Val Arg Thr Asp Phe
            100                 105                 110

Tyr Asp Glu Phe Trp Gly Gln Gly Leu Arg Ala Ala Pro Lys Lys Gln
        115                 120                 125

Lys Lys His Thr Leu Ser Leu Thr Pro Asp Thr Thr Leu Tyr Asn Ala
    130                 135                 140

Ala Gln Ile Ile Cys Ala Asn Tyr Gly Glu Ala Phe Ser Val Asp Lys
145                 150                 155                 160

Lys Gly Gly Thr Lys Lys Ala Ala Val Ser Glu Leu Leu Gln Ala Ser
                165                 170                 175

Ala Pro Tyr Lys Ala Asp Val Glu Leu Cys Val Tyr Ser Thr Asn Glu
            180                 185                 190

Thr Thr Asn Cys Thr Gly Gly Lys Asn Gly Ile Ala Ala Asp Ile Thr
        195                 200                 205

Thr Ala Lys Gly Tyr Val Lys Ser Val Thr Thr Ser Asn Gly Ala Ile
    210                 215                 220

Thr Val Lys Gly Asp Gly Thr Leu Ala Asn Met Glu Tyr Ile Leu Gln
225                 230                 235                 240

Ala Thr Gly Asn Ala Ala Thr Gly Val Thr Trp Thr Thr Thr Cys Lys
                245                 250                 255

Gly Thr Asp Ala Ser Leu Phe Pro Ala Asn Phe Cys Gly Ser Val Thr
            260                 265                 270

Gln
```

<210> SEQ ID NO 201
<211> LENGTH: 816
<212> TYPE: DNA
<213> ORGANISM: Artificial Sequence
<220> FEATURE:
<223> OTHER INFORMATION: LVL781

<400> SEQUENCE: 201
atgaaatacc tgctgccgac cgctgctgct ggtctgctgc tcctcgctgc ccagccggcg    60

```
atggccgctg aacaaaatga tgtgaagctg gcaccgccga ctgatgtacg aagcggatat    120
atacgtttgg taaagaatgt gaattattac atcgatagtg aatcgatctg ggtggataac    180
caagagccac aaattgtaca ttttgatgca gtggtgaatt tagataaggg attgtatgtt    240
tatcctgagc ctaaacgtta tgcacgttct gttcgtcagt ataagatctt gaattgtgca    300
aattatcatt taactcaagt acgaactgat ttctatgatg aattttgggg acagggtttg    360
cgggcagcac ctaaaaagca aagaaacat acgttaagtt taacacctga tacaacgctt    420
tataatgctg ctcagattat ttgtgcgaac tatggtgaag cattttcagt tgataaaaaa    480
ggcggcacta aaaagcagc ggtatctgaa ttactgcaag cgtcagcgcc ttataaggct    540
gatgtggaat tatgtgtata tagcacaaat gaaacaacaa actgtacggg tggaaaaaat    600
ggtattgcag cagatataac cacagcaaaa ggctatgtaa aatcagtgac aacaagcaac    660
ggtgcaataa cagtaaaagg ggatggcaca ttggcaaata tggaatatat tttgcaagct    720
acaggtaatg ctgcaacagg tgtaacttgg acaacaactt gcaaaggaac ggatgcctct    780
ttatttccag caaattttg cggaagtgtc acacaa                              816
```

<210> SEQ ID NO 202
<211> LENGTH: 272
<212> TYPE: PRT
<213> ORGANISM: Artificial Sequence
<220> FEATURE:
<223> OTHER INFORMATION: LVL781

<400> SEQUENCE: 202

```
Met Lys Tyr Leu Leu Pro Thr Ala Ala Ala Gly Leu Leu Leu Leu Ala
 1               5                  10                  15

Ala Gln Pro Ala Met Ala Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

Gly Gly Thr Lys Lys Ala Ala Val Ser Glu Leu Leu Gln Ala Ser Ala
                165                 170                 175

Pro Tyr Lys Ala Asp Val Glu Leu Cys Val Tyr Ser Thr Asn Glu Thr
            180                 185                 190

Thr Asn Cys Thr Gly Gly Lys Asn Gly Ile Ala Ala Asp Ile Thr Thr
        195                 200                 205

Ala Lys Gly Tyr Val Lys Ser Val Thr Thr Ser Asn Gly Ala Ile Thr
    210                 215                 220
```

Val Lys Gly Asp Gly Thr Leu Ala Asn Met Glu Tyr Ile Leu Gln Ala
225                 230                 235                 240

Thr Gly Asn Ala Ala Thr Gly Val Thr Trp Thr Thr Thr Cys Lys Gly
            245                 250                 255

Thr Asp Ala Ser Leu Phe Pro Ala Asn Phe Cys Gly Ser Val Thr Gln
            260                 265                 270

<210> SEQ ID NO 203
<211> LENGTH: 813
<212> TYPE: DNA
<213> ORGANISM: Artificial Sequence
<220> FEATURE:
<223> OTHER INFORMATION: LVL782

<400> SEQUENCE: 203

| | | | | | |
|---|---|---|---|---|---|
| atgaaatacc | tgctgccgac | cgctgctgct | ggtctgctgc | tcctcgctgc | ccagccggcg | 60 |
| atggccgaac | aaaatgatgt | gaagctggca | ccgccgactg | atgtacgaag | cggatatata | 120 |
| cgtttggtaa | agaatgtgaa | ttattacatc | gatagtgaat | cgatctgggt | ggataaccaa | 180 |
| gagccacaaa | ttgtacattt | tgatgcagtg | gtgaatttag | ataagggatt | gtatgtttat | 240 |
| cctgagccta | aacgttatgc | acgttctgtt | cgtcagtata | agatcttgaa | ttgtgcaaat | 300 |
| tatcatttaa | ctcaagtacg | aactgatttc | tatgatgaat | tttggggaca | gggtttgcgg | 360 |
| gcagcaccta | aaaagcaaaa | gaaacatacg | ttaagtttaa | cacctgatac | aacgctttat | 420 |
| aatgctgctc | agattatttg | tgcgaactat | ggtgaagcat | tttcagttga | taaaaaaggc | 480 |
| ggcactaaaa | aagcagcggt | atctgaatta | ctgcaagcgt | cagcgcctta | taaggctgat | 540 |
| gtggaattat | gtgtatatag | cacaaatgaa | acaacaaact | gtacgggtgg | aaaaaatggt | 600 |
| attgcagcag | atataaccac | agcaaaaggc | tatgtaaaat | cagtgacaac | aagcaacggt | 660 |
| gcaataacag | taaaagggga | tggcacattg | gcaaatatgg | aatatatttt | gcaagctaca | 720 |
| ggtaatgctg | caacaggtgt | aacttggaca | acaacttgca | aaggaacgga | tgcctcttta | 780 |
| tttccagcaa | attttttgcgg | aagtgtcaca | caa | | | 813 |

<210> SEQ ID NO 204
<211> LENGTH: 271
<212> TYPE: PRT
<213> ORGANISM: Artificial Sequence
<220> FEATURE:
<223> OTHER INFORMATION: LVL782

<400> SEQUENCE: 204

Met Lys Tyr Leu Leu Pro Thr Ala Ala Ala Gly Leu Leu Leu Leu Ala
1               5                   10                  15

Ala Gln Pro Ala Met Ala Glu Gln Asn Asp Val Lys Leu Ala Pro Pro
            20                  25                  30

Thr Asp Val Arg Ser Gly Tyr Ile Arg Leu Val Lys Asn Val Asn Tyr
            35                  40                  45

Tyr Ile Asp Ser Glu Ser Ile Trp Val Asp Asn Gln Glu Pro Gln Ile
    50                  55                  60

Val His Phe Asp Ala Val Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys

```
            115                 120                 125
His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys Gly
145                 150                 155                 160

Gly Thr Lys Lys Ala Ala Val Ser Glu Leu Leu Gln Ala Ser Ala Pro
                165                 170                 175

Tyr Lys Ala Asp Val Glu Leu Cys Val Tyr Ser Thr Asn Glu Thr Thr
            180                 185                 190

Asn Cys Thr Gly Gly Lys Asn Gly Ile Ala Ala Asp Ile Thr Thr Ala
        195                 200                 205

Lys Gly Tyr Val Lys Ser Val Thr Thr Ser Asn Gly Ala Ile Thr Val
210                 215                 220

Lys Gly Asp Gly Thr Leu Ala Asn Met Glu Tyr Ile Leu Gln Ala Thr
225                 230                 235                 240

Gly Asn Ala Ala Thr Gly Val Thr Trp Thr Thr Thr Cys Lys Gly Thr
                245                 250                 255

Asp Ala Ser Leu Phe Pro Ala Asn Phe Cys Gly Ser Val Thr Gln
            260                 265                 270
```

<210> SEQ ID NO 205
<211> LENGTH: 95
<212> TYPE: DNA
<213> ORGANISM: Artificial Sequence
<220> FEATURE:
<223> OTHER INFORMATION: primer

<400> SEQUENCE: 205
gatatacata tgaaatacct gctgccgacc gctgctgctg gtctgctgct cctcgctgcc      60
cagccggcga tggccattca gaaggctgaa caaaa      95

<210> SEQ ID NO 206
<211> LENGTH: 39
<212> TYPE: DNA
<213> ORGANISM: Artificial Sequence
<220> FEATURE:
<223> OTHER INFORMATION: primer

<400> SEQUENCE: 206
ggccgcaagc ttttagtggt ggtggtggtg gtggccgcc      39

<210> SEQ ID NO 207
<211> LENGTH: 30
<212> TYPE: DNA
<213> ORGANISM: Artificial Sequence
<220> FEATURE:
<223> OTHER INFORMATION: primer

<400> SEQUENCE: 207
ggccgcaagc ttttattgtg tgacacttcc      30

<210> SEQ ID NO 208
<211> LENGTH: 42
<212> TYPE: DNA
<213> ORGANISM: Artificial Sequence
<220> FEATURE:
<223> OTHER INFORMATION: primer

<400> SEQUENCE: 208
gctgcccagc cggcgatggc caaggctgaa caaaatgatg tg      42

<210> SEQ ID NO 209
<211> LENGTH: 42
<212> TYPE: DNA
<213> ORGANISM: Artificial Sequence
<220> FEATURE:
<223> OTHER INFORMATION: primer

<400> SEQUENCE: 209
cacatcattt tgttcagcct tggccatcgc cggctgggca gc          42

<210> SEQ ID NO 210
<211> LENGTH: 43
<212> TYPE: DNA
<213> ORGANISM: Artificial Sequence
<220> FEATURE:
<223> OTHER INFORMATION: primer

<400> SEQUENCE: 210
gctgcccagc cggcgatggc cgctgaacaa aatgatgtga agc         43

<210> SEQ ID NO 211
<211> LENGTH: 43
<212> TYPE: DNA
<213> ORGANISM: Artificial Sequence
<220> FEATURE:
<223> OTHER INFORMATION: primer

<400> SEQUENCE: 211
gcttcacatc attttgttca gcggccatcg ccggctgggc agc         43

<210> SEQ ID NO 212
<211> LENGTH: 43
<212> TYPE: DNA
<213> ORGANISM: Artificial Sequence
<220> FEATURE:
<223> OTHER INFORMATION: primer

<400> SEQUENCE: 212
gctgcccagc cggcgatggc cgaacaaaat gatgtgaagc tgg         43

<210> SEQ ID NO 213
<211> LENGTH: 43
<212> TYPE: DNA
<213> ORGANISM: Artificial Sequence
<220> FEATURE:
<223> OTHER INFORMATION: primer

<400> SEQUENCE: 213
ccagcttcac atcattttgt tcggccatcg ccggctgggc agc         43

<210> SEQ ID NO 214
<211> LENGTH: 43
<212> TYPE: DNA
<213> ORGANISM: Artificial Sequence
<220> FEATURE:
<223> OTHER INFORMATION: primer

<400> SEQUENCE: 214
gctgcccagc cggcgatggc cgcccagatt cagaaggctg aac         43

<210> SEQ ID NO 215
<211> LENGTH: 43
<212> TYPE: DNA
<213> ORGANISM: Artificial Sequence
<220> FEATURE:
<223> OTHER INFORMATION: primer

<400> SEQUENCE: 215
gttcagcctt ctgaatctgg gcggccatcg ccggctgggc agc                43

<210> SEQ ID NO 216
<211> LENGTH: 46
<212> TYPE: DNA
<213> ORGANISM: Artificial Sequence
<220> FEATURE:
<223> OTHER INFORMATION: primer

<400> SEQUENCE: 216
gctgcccagc cggcgatggc cagcgcccag attcagaagg ctgaac             46

<210> SEQ ID NO 217
<211> LENGTH: 46
<212> TYPE: DNA
<213> ORGANISM: Artificial Sequence
<220> FEATURE:
<223> OTHER INFORMATION: primer

<400> SEQUENCE: 217
gttcagcctt ctgaatctgg gcgctggcca tcgccggctg ggcagc             46

<210> SEQ ID NO 218
<211> LENGTH: 30
<212> TYPE: DNA
<213> ORGANISM: Artificial Sequence
<220> FEATURE:
<223> OTHER INFORMATION: primer

<400> SEQUENCE: 218
cacacacata tgaaatacct gctgccgacc                               30

<210> SEQ ID NO 219
<211> LENGTH: 253
<212> TYPE: PRT
<213> ORGANISM: Artificial Sequence
<220> FEATURE:
<223> OTHER INFORMATION: FUSION PROTEIN

<400> SEQUENCE: 219

```
Ile Gln Lys Ala Glu Gln Asn Asp Val Lys Leu Ala Pro Pro Thr Asp
  1               5                  10                  15

Val Arg Ser Gly Tyr Ile Arg Leu Val Lys Asn Val Asn Tyr Tyr Ile
             20                  25                  30

Asp Ser Glu Ser Ile Trp Val Asp Asn Gln Glu Pro Gln Ile Val His
         35                  40                  45

Phe Asp Ala Val Val Asn Leu Asp Lys Gly Leu Tyr Val Tyr Pro Glu
     50                  55                  60

Pro Lys Arg Tyr Ala Arg Ser Val Arg Gln Tyr Lys Ile Leu Asn Cys
 65                  70                  75                  80

Ala Asn Tyr His Leu Thr Gln Val Arg Thr Asp Phe Tyr Asp Glu Phe
                 85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
        115                 120                 125

Cys Ala Asn Tyr Gly Glu Ala Phe Ser Val Asp Lys Lys Gly Gly Thr
    130                 135                 140

Lys Lys Ala Ala Val Ser Glu Leu Leu Gln Ala Ser Ala Pro Tyr Lys
```

```
                145                 150                 155                 160
Ala Asp Val Glu Leu Cys Val Tyr Ser Thr Asn Glu Thr Thr Asn Cys
                    165                 170                 175

Thr Gly Gly Lys Asn Gly Ile Ala Ala Asp Ile Thr Thr Ala Lys Gly
                    180                 185                 190

Tyr Val Lys Ser Val Thr Thr Ser Asn Gly Ala Ile Thr Val Lys Gly
                    195                 200                 205

Asp Gly Thr Leu Ala Asn Met Glu Tyr Ile Leu Gln Ala Thr Gly Asn
                    210                 215                 220

Ala Ala Thr Gly Val Thr Trp Thr Thr Thr Cys Lys Gly Thr Asp Ala
225                 230                 235                 240

Ser Leu Phe Pro Ala Asn Phe Cys Gly Ser Val Thr Gln
                    245                 250

<210> SEQ ID NO 220
<211> LENGTH: 818
<212> TYPE: PRT
<213> ORGANISM: Streptococcus pneumoniae

<400> SEQUENCE: 220

Ser Tyr Glu Leu Gly Arg His Gln Ala Gly Gln Val Lys Lys Glu Ser
1               5                   10                  15

Asn Arg Val Ser Tyr Ile Asp Gly Asp Gln Ala Gly Gln Lys Ala Glu
                20                  25                  30

Asn Leu Thr Pro Asp Glu Val Ser Lys Arg Glu Gly Ile Asn Ala Glu
                35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Ile Ile
65                  70                  75                  80

Ser Glu Glu Leu Leu Met Lys Asp Pro Asn Tyr Gln Leu Lys Asp Ser
                85                  90                  95

Asp Ile Val Asn Glu Ile Lys Gly Gly Tyr Val Ile Lys Val Asp Gly
                100                 105                 110

Lys Tyr Tyr Val Tyr Leu Lys Asp Ala Ala His Ala Asp Asn Ile Arg
            115                 120                 125

Thr Lys Glu Glu Ile Lys Arg Gln Lys Gln Glu His Ser His Asn His
        130                 135                 140

Gly Gly Gly Ser Asn Asp Gln Ala Val Val Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
                180                 185                 190

Tyr Ile Pro Lys Asn Glu Leu Ser Ala Ser Glu Leu Ala Ala Ala Glu
            195                 200                 205

Ala Tyr Trp Asn Gly Lys Gln Gly Ser Arg Pro Ser Ser Ser Ser Ser
        210                 215                 220

Tyr Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270
```

```
Ser Asp Gly Leu Ile Phe Asp Pro Ala Gln Ile Thr Ser Arg Thr Ala
        275                 280                 285

Arg Gly Val Ala Val Pro His Gly Asn His Tyr His Phe Ile Pro Tyr
290                 295                 300

Glu Gln Met Ser Glu Leu Glu Lys Arg Ile Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Pro Ser Pro Gln Pro Ala Pro
            340                 345                 350

Asn Pro Gln Pro Ala Pro Ser Asn Pro Ile Asp Glu Lys Leu Val Lys
        355                 360                 365

Glu Ala Val Arg Lys Val Gly Asp Gly Tyr Val Phe Glu Glu Asn Gly
    370                 375                 380

Val Ser Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
        435                 440                 445

Lys Gly Arg Gln Val Asp Phe Glu Ala Leu Asp Asn Leu Leu Glu Arg
    450                 455                 460

Leu Lys Asp Val Pro Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Asp Glu Ile Gln Val Ala Lys Leu Ala
            500                 505                 510

Gly Lys Tyr Thr Thr Glu Asp Gly Tyr Ile Phe Asp Pro Arg Asp Ile
        515                 520                 525

Thr Ser Asp Glu Gly Asp Ala Tyr Val Thr Pro His Met Thr His Ser
530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Ser Thr Asp His
            565                 570                 575

Gln Asp Ser Gly Asn Thr Glu Ala Lys Gly Ala Glu Ala Ile Tyr Asn
        580                 585                 590

Arg Val Lys Ala Ala Lys Lys Val Pro Leu Asp Arg Met Pro Tyr Asn
    595                 600                 605

Leu Gln Tyr Thr Val Glu Val Lys Asn Gly Ser Leu Ile Ile Pro His
610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Thr Leu Glu Asp Leu Leu Ala Thr Val
                645                 650                 655

Lys Tyr Tyr Val Glu His Pro Asn Glu Arg Pro His Ser Asp Asn Gly
            660                 665                 670

Phe Gly Asn Ala Ser Asp His Val Arg Lys Asn Lys Val Asp Gln Asp
        675                 680                 685

Ser Lys Pro Asp Glu Asp Lys Glu His Asp Glu Val Ser Glu Pro Thr
```

```
              690                 695                 700
His Pro Glu Ser Asp Glu Lys Glu Asn His Ala Gly Leu Asn Pro Ser
705                     710                 715                 720

Ala Asp Asn Leu Tyr Lys Pro Ser Thr Asp Thr Glu Glu Thr Glu Glu
                725                 730                 735

Glu Ala Glu Asp Thr Thr Asp Glu Ala Glu Ile Pro Gln Val Glu Asn
                740                 745                 750

Ser Val Ile Asn Ala Lys Ile Ala Asp Ala Glu Ala Leu Leu Glu Lys
            755                 760                 765

Val Thr Asp Pro Ser Ile Arg Gln Asn Ala Met Glu Thr Leu Thr Gly
        770                 775                 780

Leu Lys Ser Ser Leu Leu Leu Gly Thr Lys Asp Asn Asn Thr Ile Ser
785                 790                 795                 800

Ala Glu Val Asp Ser Leu Leu Ala Leu Leu Lys Glu Ser Gln Pro Ala
                805                 810                 815

Pro Ile
```

IMMUNOGENIC COMPOSITION

This application is a United States 111(a) application which claims priority from Provisional Application Serial Number 1218660.7, filed in the United Kingdom Oct. 17, 2012, the contents of which is herein incorporated by reference in its entirety.

SEQUENCE LISTING

This application contains sequences, listed in an electronic Sequence Listing entitled VB65265T_Seq_List, 258 KB, created on Nov. 12, 2013, the contents and sequences of which are hereby incorporated by reference herein.

TECHNICAL FIELD

The present invention relates to immunogenic compositions comprising one or more *Streptococcus pneumoniae* capsular saccharide conjugates and a protein component comprising Protein E and/or PilA from *Haemophilus influenzae*.

BACKGROUND

Non-typeable *Haemophilus influenzae* (NTHi) is an important and common respiratory pathogen that causes otitis media in infants and children. NTHi is, after *Streptococcus pneumoniae*, the most common cause of acute otitis media in children (J. Immunology 183: 2593-2601 (2009), Pediatrics 113:1451-1465 (2004)). It is an important cause of sinusitis in children and adults. (Current Infectious Disease Reports 11:177-182 (2009)). It has been associated with increased risk of exacerbations in chronic obstructive pulmonary disease (COPD) in adults. (Journal of Chronic Obstructive Pulmonary Disease 3:109-115 (2006)). In addition, non-typeable *H. influenzae* causes community-acquired pneumonia in adults and may cause pneumonia in children in developing countries. (Current Infectious Disease Reports 11:177-182 (2009)).

*Streptococcus pneumoniae* (*S. pneumoniae*), also known as the pneumococcus, is a Gram-positive bacterium. *S. pneumoniae* is a major public health problem all over the world and is responsible for considerable morbidity and mortality, especially among infants, the elderly and immunocompromised persons. *S. pneumoniae* causes a wide range of important human pathologies including community-acquired pneumonia, acute sinusitis, otitis media, meningitis, bacteremia, septicemia, osteomyelitis, septic arthritis, endocarditis, peritonitis, pericarditis, cellulitis, and brain abscess. *S. pneumoniae* is estimated to be the causal agent in 3,000 cases of meningitis, 50,000 cases of bacteremia, 500,000 cases of pneumonia, and 7,000,000 cases of otitis media annnually in the United States alone (Reichler, M. R. et al., 1992, J. Infect. Dis. 166: 1346; Stool, S. E. and Field, M. J., 1989 Pediatr. Infect. Dis J. 8: S11). Mortality rates due to pneumococcal disease are especially high in children younger than 5 years of age from both developed and developing countries. The elderly, the immunocompromised and patients with other underlying conditions (diabetes, asthma) are also particularly susceptible to disease.

The major clinical syndromes caused by *S. pneumoniae* are widely recognized and discussed in standard medical textbooks (Fedson D S, Muscher D M. In: Plotkin S A, Orenstein W A, editors. Vaccines. 4th edition. Philadelphia WB Saunders Co, 2004a: 529-588). For instance, Invasive pneumococcal disease (IPD) is defined as any infection in which *S. pneumoniae* is isolated from the blood or another normally sterile site (Musher D M. *Streptococcus pneumoniae*. In Mandell G L, Bennett J E, Dolin R (eds). Principles and Practice of Infectious diseases (5th ed). New York, Churchill Livingstone, 2001, p 2128-2147).

Chronic obstructive pulmonary disease is a chronic inflammatory disease of the lungs and a major cause of morbidity and mortality worldwide. Approximately one in 20 deaths in 2005 in the US had COPD as the underlying cause. (Drugs and Aging 26:985-999 (2009)). It is projected that in 2020 COPD will rise to the fifth leading cause of disability adjusted life years, chronic invalidating diseases, and to the third most important cause of mortality (Lancet 349:1498-1504 (1997)).

Thus a need for combination vaccines against *Streptococcus pneumoniae* and *Haemophilus influenzae* exists.

Protein E (PE) is an outer membrane lipoprotein with adhesive properties. It plays a role in the adhesion/invasion of non-typeable *Haemophilus influenzae* (NTHi) to epithelial cells. (J. Immunology 183: 2593-2601 (2009); The Journal of Infectious Diseases 199:522-531 (2009), Microbes and Infection 10:87-96 (2008)). It is highly conserved in both encapsulated *Haemophilus influenzae* and non-typeable *H. influenzae* and has a conserved epithelial binding domain. (The Journal of Infectious Diseases 201: 414-419 (2010)). Thirteen different point mutations have been described in different *Haemophilus* species when compared with *Haemophilus influenzae* Rd as a reference strain. Its expression is observed on both logarithmic growing and stationary phase bacteria. (WO2007/084053).

Protein E is also involved in human complement resistance through binding vitronectin. (Immunology 183: 2593-2601 (2009)). PE, by the binding domain PKRYARSVRQ YKILNCANYH LTQVR (SEQ ID NO. 1, corresponding to amino acids 84-108 of SEQ ID NO. 4), binds vitronectin which is an important inhibitor of the terminal complement pathway. (J. Immunology 183:2593-2601 (2009)).

Pilin A (PilA) is likely the major pilin subunit of *H. influenzae* Type IV Pilus (Tfp) involved in twitching motility (Infection and Immunity, 73: 1635-1643 (2005)). NTHi PilA is a conserved adhesin expressed in vivo. It has been shown to be involved in NTHi adherence, colonization and biofilm formation. (Molecular Microbiology 65: 1288-1299 (2007)).

The inventors have found that PilA and PE may be beneficially present in an immunogenic composition for prevention of *H. influenzae* and furthermore that PilA and Protein E can be added to a composition comprising *S. pneumoniae* capsular saccharides in order to provide an immunogenic composition which can prevent *H. influenzae* and *S. pneumoniae* infection. The skilled person would be aware of the effect of carrier-induced epitopic suppression, and know that generally simultaneous exposure to multiple conjugate antigens can result in either enhanced or diminished immune responses (Plotkin et al, Vaccines fourth addition 2003).

BRIEF SUMMARY

The inventors have found that PilA, PE (or fragments thereof) and saccharides from *Streptococcus pneumoniae* may be beneficially combined in an immunogenic composition to provide effective protection against *H. influenzae* and *S. pneumoniae*.

Accordingly in a first aspect there is provided an immunogenic composition comprising 1 or more (e.g. 7, 8, 9, 10, 11, 12, 13, 14, 15, 16, 17, 18, 19 or 20) *Streptococcus pneumoniae* capsular saccharide conjugates and a protein component comprising Protein E or an immunogenic fragment of Protein E and/or PilA (or an immunogenic fragment of PilA) from *Haemophilus influenzae*.

In a second aspect there is provided a vaccine comprising an immunogenic composition of the invention and a pharmaceutically acceptable excipient.

In a third aspect there is provided a method of immunising a subject against diseases caused by *Streptococcus pneumoniae* infection comprising administering to the subject a therapeutically effective dose of the immunogenic composition of the invention or the vaccine of the invention.

In a fourth aspect there is provided a method of immunising a subject against diseases caused by *Haemophilus influenzae* infection comprising administering to the subject a therapeutically effective dose of the immunogenic composition of the invention or the vaccine of the invention.

In a fifth aspect there is provided an immunogenic composition of the invention or a vaccine of the invention for use in the treatment or prevention of diseases caused by *Streptococcus pneumoniae* infection.

In a sixth aspect there is provided an immunogenic composition of the invention or a vaccine of the invention for use in the treatment or prevention of diseases caused by *Haemophilus influenzae* infection.

In a seventh aspect there is provided a use of the immunogenic composition of the invention or the vaccine of the invention in the manufacture of a medicament for the treatment or prevention of diseases caused by *Streptococcus pneumoniae* infection.

In an eighth aspect there is provided a use of the immunogenic composition of the invention or the vaccine of the invention in the manufacture of a medicament for the treatment or prevention of diseases caused by *Haemophilus influenzae* infection.

DETAILED DESCRIPTION

Figure 1:
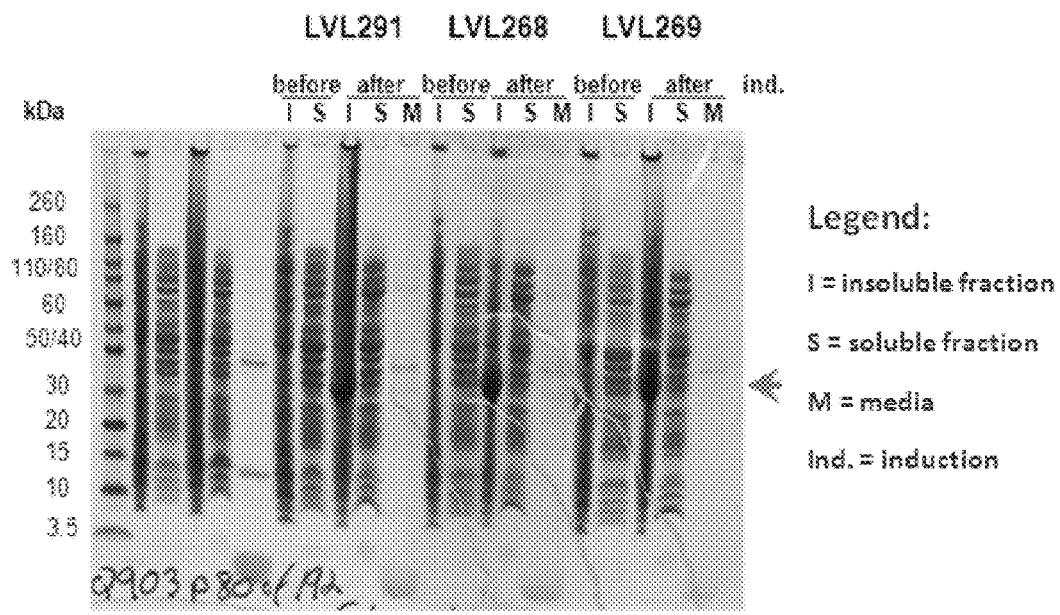
FIG. 1. SDS-PAGE of induced bacterial extracts for fusion protein constructs LVL291, LVL268 and LVL269. Insoluble fraction (I), Soluble fraction (S) and Culture Media fraction (M) were loaded for LVL291, LVL268 and LVL269 before and after induction (ind).

In a first aspect, the present invention relates to an immunogenic composition comprising 1 or more (e.g. 7, 8, 9, 10, 11, 12, 13, 14, 15, 16, 17, 18, 19 or 20) *Streptococcus pneumoniae* capsular saccharide conjugates and a protein component comprising Protein E (or an immunogenic fragment thereof) and/or PilA (or an immunogenic fragment thereof) from *Haemophilus influenzae*.

The term "protein component" relates to a sequence of amino acids comprising Protein E (or an immunogenic fragment thereof) and/or PilA (or an immunogenic fragment thereof), the protein component may comprise Protein E alone, PilA alone, an immunogenic fragment of Protein E alone, an immunogenic fragment of PilA alone, Protein E and PilA, an immunogenic fragment of Protein E and PilA, an immunogenic fragment of Protein E and an immunogenic fragment of PilA or Protein E and an immunogenic fragment of PilA (for example as a fusion protein). The protein component may further comprise additional sequences.

Protein E

As used herein "Protein E", "protein E", "Prot E", and "PE" mean Protein E from *H. influenzae*. Protein E may consist of or comprise the amino acid sequence of SEQ ID NO. 4 (MKKIILTLSL GLLTACSAQI QKAEQNDVKL APPTDVRSGY IRLVKNVNYY IDSESIWVDN QEPQIVHFDA VVNLDKGLYV YPEPKRYARS VRQYKILNCA NYHLTQVRTD FYDEFWGQGL RAAPKKQKKH TLSLTPDTTL YNAAQIICAN YGEAFSVDKK) as well as sequences with at least or exactly 75%, 77%, 80%, 85%, 90%, 95%, 97%, 99% or 100% identity, over the entire length, to SEQ ID NO. 4. Comparison of 53 sequences of Protein E from *Haemophilus influenzae* (Table 1, SEQ ID NO. 5-SEQ ID NO. 57) demonstrated approximately 77% to approximately 100% identity to Protein E as set forth in SEQ ID NO. 4. For example, in the amino acid sequence of Protein E, amino acid #20 may be isoleucine (I) or threonine (T); amino acid #23 may be alanine (A) or valine (V); amino acid #24 may be lysine (K) or glutamic acid (E); amino acid #31 may be alanine (A) or threonine (T); amino acid #32 may be proline (P) or alanine (A); amino acid #34 may be threonine (T) or alanine (A); amino acid #37 may be arginine (R) or glutamine (Q); amino acid #47 may be valine (V) or alanine (A); amino acid #57 may be tryptophane (W) or may be absent (−); amino acid #70 may be alanine (A) or threonine (T); amino acid #93 may be glutamine (Q) or absent (−); amino acid #109 may be threonine (T) or isoleucine (I); amino acid #119 may be glycine (G) or serine (S); amino acid #153 may be glutamic acid (E) or lysine (K); amino acid #156 may be serine (S) or leucine (L); amino acid #160 may be lysine (K) or asparagine (N); amino acid #161 may be lysine (K), isoleucine (I) or absent (−); amino acids #162-#195 may be absent, or as set forth in SEQ ID NO. 15 (with (−) indicating amino acid #166 is absent) or as set forth in SEQ ID NO. 16; or any combination thereof.

Protein E may consist of or comprise an amino acid sequence that differs from SEQ ID NO. 4 at any one or more amino acid selected from the group consisting of: amino acid #20, amino acid #23, amino acid #24, amino acid #31, amino acid #32, amino acid #34, amino acid #37, amino acid #47, amino acid #57, amino acid #70, amino acid #93, amino acid #109, amino acid #119, amino acid #153, amino acid #156, amino acid #160, amino acid #161 and amino acids #162-#195, wherein amino acid #20 is threonine (T); amino acid #23 is valine (V); amino acid #24 is lysine (K); amino acid #31 is threonine (T); amino acid #32 is alanine (A); amino acid #34 is alanine (A); amino acid #37 is glutamine (Q); amino acid #47 is alanine (A); amino acid #57 is absent (−); amino acid #70 is threonine (T); amino acid #93 is absent (−); amino acid #109 is isoleucine (I); amino acid #119 is serine (S); amino acid #153 is lysine (K); amino acid #156 is leucine (L); amino acid #160 is asparagine (N); amino acid #161 is lysine (K) or isoleucine (I); or amino acids #162-#195 are as set forth in SEQ ID NO. 15 (with (−) indicating amino acid #166 is absent) or as set forth in SEQ ID NO. 16.

TABLE 1

Protein E amino acid sequences from 53 strains of *Haemophilus influenzae* (SEQ ID NO. 5 - SEQ ID NO. 57).

| Strain Name | Protein E sequence |
|---|---|
| 3224A | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 5) |
| RdKW20 | MKKIILTLSLGLLTACSAQIQKAEQNDVKLAPPTDVRSGYIRLVKNVNYYIDSES IWVDNQEPQIVHFDAVVNLDRGLYVYPEPKRYARSVRQYKILNCANYHLTQIR TDFYDEFWGQGLRAAPKKQKKHTLSLTPDTTLYNAAQIICANYGKAFSVDKK (SEQ ID NO. 6) |
| 86-028NP | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 7) |
| R2846 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 8) |
| R2866 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 9) |
| 3655 | MKKIILTLSLGLLTACSAQIQKAEQNDMKLAPPTDVRSGYIRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 10) |
| PittAA | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 11) |
| PittEE | MKKIILTLSLGLLTACSAQIQKAEQNDMKLAPPTDVRSGYIRLVKNVNYYIDSE SI-VDNQEPQ IVHFDAVVNLDKGLYVYPEPKRYARSVRQYKILNCANYHLTQVRTDFYDEFW GQGLRAAPKKQKKHTLSLTPDTTLYNAAQIICANYGKAFSVDKK(SEQ ID NO. 12) |
| PittHH | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 13) |
| PittII | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 14) |
| R3021 | MKKIILTLSLGLLTACSAQTQKAEQNDVKLTPPTDVQSGYVRLVKNVNYYIDSE SIWVDNQEPQIVHFDAVVNLDKGLYVYPEPKRYARSVRQYKILNCANYHLTQ VRIDFYDEFWGQGLRAAPKKQKKHTLSLTPDTTLYNAAQIICANYGKAFSVDK NKKICT-LISLNFIQLLGCREYSIFLQLLLFYC WHF (SEQ ID NO. 15) |
| 22.4-21 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK KIKKICTLISLNFIQLLGCREYSIFLQLLLFYCWHF (SEQ ID NO. 16) |
| 3219C | MKKIILTLSLGLLTACSAQIQKAEQNDMKLAPPTDVRSGYIRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 17) |
| 3185 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 18) |
| 3241A | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV |

TABLE 1-continued

Protein E amino acid sequences from 53 strains of *Haemophilus influenzae* (SEQ ID NO. 5 - SEQ ID NO. 57).

| Strain Name | Protein E sequence |
|---|---|
| | RTDFYDEFWGQGLRAAPKKQKKHTLSLTPDTTLYNAAQIICANYGEAFSVDK K (SEQ ID NO. 19) |
| 038144S1 | MKKIILTLSLGLLTACSAQTQKVEQNDVKLTAPTDVRSGFVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFLVDK K (SEQ ID NO. 20) |
| 810956 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 21) |
| 821246 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQIR TDFYDEFWGQGLRAAPKKQKKHTLSLTPDTTLYNAAQIICANYGKAFSVDKK (SEQ ID NO. 22) |
| 840645 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 23) |
| 902550Z19 | MKKIILTLSLGLLTACSAQTQKVEQNDVKLTPPTDVRSGYVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 24) |
| A840177 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 25) |
| A860514 | MKKIILTLSLGLLTACSAQTQKVEQNDVKLTAPTDVRSGYVRLVKNANYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 26) |
| A950014 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RIDFYDEFWGQGLRAAPKKQKKHTLSLTPDTTLYNAAQIICANYGKAFSVDKK (SEQ ID NO. 27) |
| 306543X4 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K(SEQ ID NO. 28) |
| A930105 | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQGLRAAPKKQKKHTLSLTPDTTLYNAAQIICANYGKAFSVDK K(SEQ ID NO. 29) |
| 901905U | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 30) |
| A920030 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 31) |
| 32216 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 32) |
| 27W116791N | MKKIILTLSLGLLTACSAQTQKVEQNDVKLTPPTDVRSGYVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 33) |

TABLE 1-continued

Protein E amino acid sequences from 53 strains of *Haemophilus influenzae* (SEQ ID NO. 5 - SEQ ID NO. 57).

| Strain Name | Protein E sequence |
|---|---|
| N218 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 34) |
| N163 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 35) |
| N162 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 36) |
| N107 | MKKIILTLSLGLLTACSAQTQKAEQNDVKLAPPTDVRSGYIRLVKNVNYYIDSE SIWVDNQEPQIVHFDAVVNLDKGLYVYPEPKRYARSVRQYKILNCANYHLTQI RTDFYDEFWGQGLRAAPKKQKKHTLSLTPDTTLYNAAQIICANYGKAFSVDK K (SEQ ID NO. 37) |
| N91 | MKKIILTLSLGLLTACSAQTQKVEQNDVKLTAPADVRSGYVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 38) |
| D211PG | MKKIILTLSLGLLTACSAQIQKAKQNDVKLAPPTDVRSGYIRLVKNVNYYIDSES IWVDNQEPQIVHFDAVVNLDKGLYVYPEPKRYARSVR- YKILNCANYHLTQVRTDFYDEFWGQGLRAAPKKQK KHTLSLTPDTTLYNAAQIICANYGEAFSVDKK (SEQ ID NO. 39) |
| D211PD | MKKIILTLSLGLLTACSAQIQKAKQNDVKLAPPTDVRSGYIRLVKNVNYYIDSES IWVDNQEPQIVHFDAVVNLDKGLYVYPEPKRYARSVR- YKILNCANYHLTQVRTDFYDEFWGQGLRAAPKKQK KHTLSLTPDTTLYNAAQIICANYGEAFSVDKK (SEQ ID NO. 40) |
| D201PG | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 41) |
| D201PD | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 42) |
| D198PG | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 43) |
| D198PD | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 44) |
| D195PD | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQSLRAAPKKQKKHTLSLTPDTTLYNAAQIICANYGKAFSVDKK (SEQ ID NO. 45) |
| D189PG | MKKIILTLSLGLLTACSAQTQKVEQNDVKLTPPTDVRSGYVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTVYNAAQIICANYGKAFSVD KK (SEQ ID NO. 46) |
| D189PD | MKKIILTLSLGLLTACSAQTQKVEQNDVKLTPPTDVRSGYVRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTVYNAAQIICANYGKAFSVD KK (SEQ ID NO. 47) |

TABLE 1-continued

Protein E amino acid sequences from 53 strains of *Haemophilus influenzae* (SEQ ID NO. 5 - SEQ ID NO. 57).

| Strain Name | Protein E sequence |
|---|---|
| D129CG | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 48) |
| D124PG | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 49) |
| D124PD | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQGLRAAPKKQKKHTLSLTPDTTLYNAAQIICANYGKAFSVDK K(SEQ ID NO. 50) |
| D58PG | MKKIILTLSLGLLTACSAQTQKAEQNDVKLTPPTDVRSGYIRLVKNVNYYIDSE SIWVDNQEPQIVHFDAVVNLDKGLYVYPEPKRYARSVRQYKILNCANYHLTQ VRTDFYDEFWGQGLRAAPKKQKKHTLSLTPDTTLYNAAQIICANYGKAFSVD KK (SEQ ID NO. 51) |
| D330D | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 52) |
| BS433 | MKKIILTLSLGLLTACSAQIQKAEQNDVKLAPPTDVRSGYIRLVKNVNYYIDSES IWVDNQEPQIVHFDTVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 53) |
| BS432 | MKKIILTLSLGLLTACSAQTQKAEQNDVKLAPPTDVRSGYIRLVKNVNYYIDSE SIWVDNQEPQIVHFDAVVNLDKGLYVYPEPKRYARSVRQYKILNCANYHLTQI RTDFYDEFWGQGLRAAPKKQKKHTLSLTPDTTLYNAAQIICANYGKAFSVDK K(SEQ ID NO. 54) |
| 1714 | MKKIILTLSLGLLTACSAQIQKAKQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGEAFSVDK K (SEQ ID NO. 55) |
| 1128 | MKKIILTLSLGLLTACSAQIQKAEQNDVKLAPPTDVRSGYIRLVKNVNYYIDSES IWVDNQEPQIVHFDAVVNLDKGLYVYPEPKRYARSVRQYKILNCANYHLTQV RTDFYDEFWGQGLRAAPKKQKKHTLSLTPDTTLYNAAQIICANYGKAFSVDK K (SEQ ID NO. 56) |
| BS430 | MKKIILTLSLGLLTACSAQIQKAEQNDMKLAPPTDVRSGYIRLVKNVNYYIDSE SI-VDNQEPQ IVHFDAVVNLDKGLYVYPEPKRYARSVRQYKILNCANYHLTQVRTDFYDEFW GQGLRAAPKKQKKHTLSLTPDTTLYNAAQIICANYGKAFSVDKK (SEQ ID NO. 57) |

- indicates amino acid is absent.

Protein E may be Protein E from *H. influenzae* strain 3224A, RdKW20, 86-028NP, R2846, R2866, 3655, PittAA, PittEE, PittHH, PittII, R3021, 22.4-21, 3219C, 3185, 3241A, 038144S1, 810956, 821246, 840645, 902550Z19, A840177, A860514, A950014, 306543X4, A930105, 901905U, A920030, 3221B, 27W116791N, N218, N163, N162, N107, N91, D211PG, D211PD, D201PG, D201PD, D198PG, D198PD, D195PD, D189PG, D189PD, D129CG, D124PG, D124PD, D58PG, D330D, BS433, BS432, 1714, 1128 or BS430. Protein E may be Protein E as set forth in any of SEQ ID NO. 5-SEQ ID NO. 57.

Protein E may be a sequence with at least 95% or 98%, 99% identity, over the entire length, to any of SEQ ID NO. 4-SEQ ID NO. 57. Protein E may be a sequence with at least 95% identity, over the entire length, to any of the sequences set forth in Table 1, SEQ ID NO. 5-SEQ ID NO. 57.

Immunogenic fragments of Protein E comprise immunogenic fragments of at least 7, 10, 15, 20, 25, 30 or 50 contiguous amino acids of SEQ ID NO. 4. In one embodiment the fragment is less than 150, 125, 100, 75, or 60 amino acids of Protein E, for example in one embodiment the immunogenic composition of the invention comprises less than 150, 125, 100, 75 or 60 amino acids of Protein E. The immunogenic fragments may elicit antibodies which can bind SEQ ID NO. 4. The immunogenic fragment may comprise a B and/or T cell epitope of SEQ ID NO:4.

Immunogenic fragments of Protein E may comprise immunogenic fragments of at least 7, 10, 15, 20, 25, 30 or 50 contiguous amino acids of any of SEQ ID NO. 4-SEQ ID NO. 57. The immunogenic fragments may elicit antibodies which can bind the full length sequence from which the fragment is derived. The immunogenic fragment may comprise a B and/or T cell epitope of SEQ ID NO:4-SEQ ID NO. 57. In one embodiment the immunogenic fragment of Protein E is selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125) and amino acids 22-160 of SEQ ID NO. 4 (SEQ ID NO. 126). In another embodiment, the immunogenic fragment of protein E is selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). In a further embodiment, the immunogenic fragment of Protein E from *H. influenzae* is selected from the group consisting of amino acids 17-160 of SEQ ID NO. 4 (SEQ ID NO. 122), amino acids 18-160 of SEQ ID NO. 4 (SEQ ID NO. 123), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). More specifically, in one embodiment, the immunogenic fragment is SEQ ID NO. 124, amino acids 19-160 of SEQ ID NO. 4. In an additional embodiment, the immunogenic fragment is SEQ ID NO. 125, amino acids 20-160 of SEQ ID NO. 5. In another embodiment, the immunogenic fragment is an immunogenic fragment of Protein E from *H. influenzae* selected from the group consisting of amino acids 23-160 of SEQ ID NO. 4 (SEQ ID NO. 179) and amino acids 24-160 of SEQ ID NO. 4 (SEQ ID NO. 180).

Protein E contains an epithelial cell binding region (PKRYARSVRQ YKILNCANYH LTQVR, SEQ ID NO. 128) that has been reported to be conserved among more than 100 clinical NTHi isolates, encapsulated *H. influenzae*, and culture collection strains analyzed (Singh et al, J. Infect. Dis. 201(3):414-9 (2010)). Singh et al. reported that Protein E was highly conserved in both NTHi and encapsulated *H. influenzae* (96.9%-100% identity without the signal peptide). In one embodiment, the fragment of Protein E comprises the binding region of SEQ ID NO. 128 (PKRYARSVRQ YKILNCANYH LTQVR)

```
Protein E - SEQ ID NO. 4
MKKIILTLSL GLLTACSAQI QKAEQNDVKL APPTDVRSGY IRLVKNVNYY IDSESIWVDN

QEPQIVHFDA VVNLDKGLYV YPEPKRYARS VRQYKILNCA NYHLTQVRTD FYDEFWGQGL

RAAPKKQKKH TLSLTPDTTL YNAAQIICAN YGEAFSVDKK

Amino acids 17-160 of Protein E from SEQ ID NO. 4 - SEQ ID NO. 122
      SAQI QKAEQNDVKL APPTDVRSGY IRLVKNVNYY IDSESIWVDN QEPQIVHFDA

VVNLDKGLYV YPEPKRYARS VRQYKILNCA NYHLTQVRTD FYDEFWGQGL RAAPKKQKKH

TLSLTPDTTL YNAAQIICAN YGEAFSVDKK

Amino acids 18-160 of Protein E from SEQ ID NO. 4 - SEQ ID NO. 123
       AQI QKAEQNDVKL APPTDVRSGY IRLVKNVNYY IDSESIWVDN QEPQIVHFDA

VVNLDKGLYV YPEPKRYARS VRQYKILNCA NYHLTQVRTD FYDEFWGQGL RAAPKKQKKH

TLSLTPDTTL YNAAQIICAN YGEAFSVDKK

Amino acids 19-160 of Protein E from SEQ ID NO. 4 - SEQ ID NO. 124
        QI QKAEQNDVKL APPTDVRSGY IRLVKNVNYY IDSESIWVDN QEPQIVHFDA

VVNLDKGLYV YPEPKRYARS VRQYKILNCA NYHLTQVRTD FYDEFWGQGL RAAPKKQKKH

TLSLTPDTTL YNAAQIICAN YGEAFSVDKK

Amino acids 20-160 of Protein E from SEQ ID NO. 4 - SEQ ID NO. 125
         I QKAEQNDVKL APPTDVRSGY IRLVKNVNYY IDSESIWVDN QEPQIVHFDA

VVNLDKGLYV YPEPKRYARS VRQYKILNCA NYHLTQVRTD FYDEFWGQGL RAAPKKQKKH

TLSLTPDTTL YNAAQIICAN YGEAFSVDKK

Amino acids 22-160 of Protein E from SEQ ID NO. 4 - SEQ ID NO. 126
           KAEQNDVKL APPTDVRSGY IRLVKNVNYY

IDSESIWVDN QEPQIVHFDA VVNLDKGLYV YPEPKRYARS VRQYKILNCA NYHLTQVRTD

FYDEFWGQGL RAAPKKQKKH TLSLTPDTTL YNAAQIICAN YGEAFSVDKK

Amino acids 23-160 of Protein E from SEQ ID NO. 4 - SEQ ID NO. 179
           AEQNDVKL APPTDVRSGY IRLVKNVNYY

IDSESIWVDN QEPQIVHFDA VVNLDKGLYV YPEPKRYARS VRQYKILNCA NYHLTQVRTD

FYDEFWGQGL RAAPKKQKKH TLSLTPDTTL YNAAQIICAN YGEAFSVDKK
```

Amino acids 24-160 Protein E from SEQ ID NO. 4 - SEQ ID NO. 180
    EQNDVKL APPTDVRSGY IRLVKNVNYY

IDSESIWVDN QEPQIVHFDA VVNLDKGLYV YPEPKRYARS VRQYKILNCA NYHLTQVRTD

FYDEFWGQGL RAAPKKQKKH TLSLTPDTTL YNAAQIICAN YGEAFSVDKK

In one embodiment the Protein E or an immunogenic fragment thereof is capable of eliciting an immune response which recognizes SEQ ID NO:4. Whether or not a first protein is capable of eliciting an immune response which recognizes a second protein can be determined using an ELISA assay (for example the ELISA described in example 22).

PilA

As used herein "PilA" means Pilin A from *H. influenzae*. PilA may consist of or comprise the protein sequence of SEQ ID NO. 58 (MKLTTQQTLK KGFTLIELMI VIAI-IAILAT IAIPSYQNYT KKAAVSELLQ ASAPYKADVE LCVYSTNETT NCTGGKNGIA ADITTAKGYV KSVTTSNGAI TVKGDGTLAN MEYILQATGN AAT-GVTWTTT CKGTDASLFP ANFCGSVTQ) as well as sequences with 80% to 100% identity to SEQ ID NO. 58. For example, PilA may be at least 80%, 85%, 90%, 95%, 97% or 100% identical to SEQ ID NO. 58. Full length comparison of 64 sequences of PilA from *Haemophilus influenzae* (Table 2, SEQ ID NO. 58-SEQ ID NO. 121) demonstrated approximately 80% to 100% identity to PilA as set forth in SEQ ID NO. 58. For example, in the amino acid sequence of PilA, amino acid #6 may be glutamine (Q) or leucine (L); amino acid #7 may be glutamine (Q) or threonine (T); amino acid #37 may be glutamine (Q) or lysine (K); amino acid #44 may be alanine (A) or serine (S); amino acid #57 may be alanine (A) or serine (S); amino acid #67 may be asparagine (N) or glycine (G); amino acid #68 may be glutamic acid (E) or lysine (K); amino acid #69 may be threonine (T) or proline (P); amino acid #71 may be lysine (K), asparagine (N), serine (S) or threonine (T); amino acid #73 may be threonine (T), serine (S) or methionine (M); amino acid #76 may be lysine (K), serine (S) or asparagine (N); amino acid #84 may be threonine (T) or lysine (K); amino acid #86 may be alanine (A) or valine (V); amino acid #91 may be lysine (K) or alanine (A); amino acid #94 may be threonine (T), isoleucine (I) or lysine (K); amino acid #96 may be serine (S) or glutamine (Q); amino acid #97 may be asparagine (N) or serine (S); amino acid #99 may be alanine (A) or glycine (G); amino acid #103 may be alanine (A) or lysine (K); amino acid #109 may be aspartic acid (D), alanine (A) or threonine (T); amino acid #110 may be glycine (G), asparagine (N), or arginine (R); amino acid #112 may be serine (S) or glutamic acid (E); amino acid #114 may be threonine (T) or isoleucine (I); amino acid #116 may be threonine (T) or glutamine (Q); amino acid #118 may be glutamic acid (E), threonine (T), alanine (A), lysine (K) or serine (S); amino acid #121 may be serine (S) or alanine (A); amino acid #122 may be alanine (A) or threonine (T); amino acid #123 may be lysine (K), threonine (T) or alanine (A); amino acid #128 may be lysine (K) or threonine (T); amino acid #135 may be aspartic acid (D) or glutamic acid (E); amino acid #136 may be alanine (A) or threonine (T); amino acid #145 may be glycine (G) or arginine (R); amino acid #149 may be glutamine (Q) or lysine (K); or any combination thereof.

PilA may consist of or comprise an amino acid sequence that differs from SEQ ID NO. 58 at any one or more amino acid selected from the group consisting of amino acid #6, amino acid #7, amino acid #37, amino acid #44, amino acid #57, amino acid #67, amino acid #68, amino acid #69, amino acid #71, amino acid #73, amino acid #76, amino acid #84, amino acid #86, amino acid #91, amino acid #94, amino acid #96, amino acid #97, amino acid #99, amino acid #103, amino acid #109, amino acid #110, amino acid #112, amino acid #114, amino acid #116, amino acid #118 amino acid, #121, amino acid #122, amino acid #123, amino acid #128, amino acid #135, amino acid #136, amino acid #145 and amino acid #149, wherein amino acid #6 is leucine (L); amino acid #7 is threonine (T); amino acid #37 is lysine (K); amino acid #44 is serine (S); amino acid #57 is serine (S); amino acid #67 is glycine (G); amino acid #68 is lysine (K); amino acid #69 is proline (P); amino acid #71 is lysine (K), serine (S) or threonine (T); amino acid #73 is serine (S) or methionine (M); amino acid #76 is serine (S) or asparagine (N); amino acid #84 is lysine (K); amino acid #86 is valine (V); amino acid #91 is alanine (A); amino acid #94 is isoleucine (I) or lysine (K); amino acid #96 is glutamine (Q); amino acid #97 is serine (S); amino acid #99 is glycine (G); amino acid #103 is alanine (A); amino acid #109 is aspartic acid (D) or threonine (T); amino acid #110 is glycine (G) or arginine (R); amino acid #112 is serine (S); amino acid #114 is threonine (T); amino acid #116 is threonine (T); amino acid #118 is glutamic acid (E), alanine (A), lysine (K) or serine (S); amino acid #121 is serine (S); amino acid #122 is threonine (T); amino acid #123 is lysine (K) or alanine (A); amino acid #128 is lysine (K); amino acid #135 is glutamic acid (E); amino acid #136 is threonine (T); amino acid #145 is arginine (R); amino acid #149 is lysine (K).

TABLE 2

Pilin A amino acid sequences from 64 strains of *Haemophilus influenzae* (SEQ ID NO. 58 - SEQ ID NO. 121)

| Strain Name | PilA sequence |
|---|---|
| 86-028NP | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 58) |
| NTHi3219C | MKLTTQQTLKKGFTLIELMIVIAIIAILATIAIPSYQNYTKKAAVSELLQASAPYKA DVELCVYSTNETTKCTGGKNGIAADITTAKGYVKSVTTSNGAITVAGNGTLDG MSYTLTAEGDSAKGVTWKTTCKGTDASLFPANFCGSVTQ (SEQ ID NO. 59) |

TABLE 2-continued

Pilin A amino acid sequences from 64 strains of Haemophilus influenzae (SEQ ID NO. 58 - SEQ ID NO. 121)

| Strain Name | PilA sequence |
|---|---|
| NTHi3224A | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 60) |
| NTHi12 | MKLTTQQTLKKGFTLIELMIVIAIIAILATIAIPSYKNYTKKAAVSELLQASAPYKA DVELCVYSTGKPSSCSGGSNGIAADITTAKGYVASVITQSGGITVKGDGTLAN MEYILQAAGNAAAGVTWTTTCKGTDASLFPANFCGSVTQ (SEQ ID NO. 61) |
| NTHi44 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 62) |
| NTHi67 | MKLTTQQTLKKGFTLIELMIVIAIIAILATIAIPSYQNYTKKAAVSELLQASAPYKS DVELCVYSTGKPSTCSGGSNGIAADITTVKGYVKSVTTSNGAITVAGNGTLDG MSYTLTAEGDSAKGVTWTTTCKGTDASLFPANFCGSVTQ (SEQ ID NO. 63) |
| 1054MEE | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 64) |
| 1729MEE | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 65) |
| 1728MEE | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 66) |
| 1885MEE | MKLTTQQTLKKGFTLIELMIVIAIIAILATIAIPSYKNYTKKAAVSELLQASAPYKA DVELCVYSTNEITNCMGGKNGIAADITTAKGYVASVKTQSGGITVKGDGTLAN MEYILQATGNAAAGVTWTTTCKGTDASLFPANFCGSITQ (SEQ ID NO. 67) |
| 1060MEE | MKLTTQQTLKKGFTLIELMIVIAIIAILATIAIPSYQNYTKKASVSELLQASAPYKA DVELCVYSTNETTNCTGGKNGIAADITTAKGYVASVKTQSGGITVKGNGTLAN MEYILQAKGNATAGVTWTTTCKGTDASLFPANFCRSVTK (SEQ ID NO. 68) |
| RdKW20 | MKLTTLQTLKKGFTLIELMIVIAIIAILATIAIPSYQNYTKKAAVSELLQASAPYKA DVELCVYSTNETTSCTGGKNGIAADIKTAKGYVASVITQSGGITVKGNGTLAN MEYILQAKGNAAAGVTWTTTCKGTDASLFPANFCGSVTK (SEQ ID NO. 69) |
| 214NP | MKLTTQQTLKKGFTLIELMIVIAIIAILATIAIPSYQNYTKKAAVSELLQASAPYKA DVELCVYSTGKPSSCSGGSNGIAADITTAKGYVKSVTTSNGAITVKGDGTLAN MEYILQASGNAATGVTWTTTCKGTDASLFPANFCGSVTQ (SEQ ID NO. 70) |
| 1236MEE | MKLTTLQTLKKGFTLIELMIVIAIIAILATIAIPSYQNYTKKAAVSELLQASAPYKA DVELCVYSTNETTSCTGGKNGIAADIKTAKGYVASVITQSGGITVKGNGTLAN MEYILQAKGNAAAGVTWTTTCKGTDASLFPANFCGSVTK (SEQ ID NO. 71) |
| 1714MEE | MKLTTLQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQATGNAATGVTWTTTCKGTDASLFPANFCGSVTQ (SEQ ID NO. 72) |
| 1128MEE | MKLTTQQTLKKGFTLIELMIVIAIIAILATIAIPSYQNYTKKASVSELLQASAPYKS DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 73) |
| R2846 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 74) |
| R2866 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTEASLFPANFCGSVTQ (SEQ ID NO. 75) |
| 3655 | MKLTTQQTLKKGFTLIELMIVIAIIAILATIAIPSYQNYTKKASVSELLQASAPYKA DVELCVYSTNETTNCTGGKNGIAADITTAKGYVASVKTQSGGITVKGNGTLAN MEYILQAKGNATAGVTWTTTCKGTDASLFPANFCRSVTK (SEQ ID NO. 76) |
| PittAA | MKLTTLQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQATGNAATGVTWTTTCKGTDASLFPANFCGSVTQ (SEQ ID NO. 77) |

TABLE 2-continued

Pilin A amino acid sequences from 64 strains of Haemophilus influenzae (SEQ ID NO. 58 - SEQ ID NO. 121)

| Strain Name | PilA sequence |
|---|---|
| PittGG | MKLTTQQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 78) |
| PittII | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGDGTLAN MEYILQATGNAATGVTWTTTCKGTEASLFPANFCGSVTQ (SEQ ID NO. 79) |
| R3021 | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGDGTLAN MEYILQATGNAATGVTWTTTCKGTEASLFPANFCGSVTQ (SEQ ID NO. 80) |
| 22.4-21 | MKLTTQQTLKKGFTLIELMIVIAIIAILATIAIPSYQNYTKKAAVSELLQASAPYKS DVELCVYSTGKPSTCSGGSNGIAADITTAKGYVKSVTTSNGAITVAGNGTLDG MSYTLTAEGDSAKGVTWKTTCKGTDASLFPANFCGSVTK (SEQ ID NO. 81) |
| 3185A | MKLTTQQTLKKGFTLIELMIVIAIIAILATIAIPSYQNYTKKAAVSELLQASAPYKA DVELCVYSTNEATKCTGGKNGIAADITTAKGYVKSVTTSNGAITVKGDGTLAN MEYILQASGNAATGVTWTTTCKGTDASLFPANFCGSVTQ (SEQ ID NO. 82) |
| 3221B | MKLTTQQTLKKGFTLIELMIVIAIIAILATIAIPSYQNYTKKAAVSELLQASAPYKA DVELCVYSTNEATKCTGGKNGIAADITTAKGYVKSVTTSNGAITVKGDGTLAN MEYILQASGNAATGVTWTTTCKGTDASLFPANFCGSVTQ (SEQ ID NO. 83) |
| 3241A | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 84) |
| 038144S1 | MKLTTQQTLKKGFTLIELMIVIAIIAILATIAIPSYQNYTKKAAISELLQASAPYKSD VELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 85) |
| 821246 | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGDGTLAN MEYILQATGNAATGVTWTTTCKGTEASLFPANFCGSVTQ (SEQ ID NO. 86) |
| 840645 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 87) |
| 902550Z19 | MKLTTQQTLKKGFTLIELMIVIAIIAILATIAIPSYQNYTKKAAVSELLQASAPYKS DVELCVYSTGKPSTCSGGSNGIAADITTVKGYVKSVTTSNGAITVAGNGTLDG MSYTLTAEGDSAKGVTWTTTCKGTDASLFPANFCGSVTQ (SEQ ID NO. 88) |
| A840177 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 89) |
| A920030 | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGNGTLAN MEYILQATGNAATGVTWTTTCKGTDASLFPANFCGSVTQ (SEQ ID NO. 90) |
| A950014 | MKLTTQQTLKKGFTLIELMIVIAIIAILATIAIPSYQNYTKKAAVSELLQASAPYKA DVELCVYSTGKPSTCSGGSNGIAADITTAKGYVKSVTTSNGAITVAGNGTLDR MSYTLTAEGDSAKGVTWTTTCKGTDASLFPANFCGSVTQ (SEQ ID NO. 91) |
| 901905U | MKLTTQQTLKKGFTLIELMIVIAIIAILATIAIPSYQNYTKKAAVSELLQASAPYKA DVELCVYSTGKPSSCSGGSNGIAADITTAKGYVKSVTTSNGAITVKGDGTLAN MEYILQASGNAATGVTWTTTCKGTDASLFPANFCGSVTQ (SEQ ID NO. 92) |
| A920029 | MKLTTQTTLKKGFTLIELMIVIAIIAILATIAIPSYQNYTKKAAVSELLQASAPYKS DVELCVYSTNETTNCTGGKNGIAADITTAKGYVASVITQSGGITVKGNGTLTN MEYILQATGNAATGVTWTTTCKGTDASLFPANFCGSITQ (SEQ ID NO. 93) |
| A930105 | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 94) |
| 306543X4 | MKLTTQQTLKKGFTLIELMIVIAIIAILATIAIPSYQNYTKKAAVSELLQASAPYKA DVELCVYSTGKPSSCSGGSNGIAADITTAKGYVKSVTTSNGAITVKGDGTLAN MEYILQASGNAATGVTWTTTCKGTDASLFPANFCGSVTQ (SEQ ID NO. 95) |

TABLE 2-continued

Pilin A amino acid sequences from 64 strains of Haemophilus influenzae (SEQ ID NO. 58 - SEQ ID NO. 121)

| Strain Name | PilA sequence |
|---|---|
| N218 | MKLTTQQTLKKGFTLIELMIVIAIIAILATIAIPSYQNYTKKAAVSELLQASAPYKA DVELCVYSTNEATKCTGGKNGIAADITTAKGYVKSVTTSNGAITVKGDGTLAN MEYILQASGNAATGVTWTTTCKGTDTSLFPANFCGSVTQ (SEQ ID NO. 96) |
| N163 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 97) |
| N162 | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGNGTLAN MEYILQATGNAATGVTWTTTCKGTDASLFPANFCGSVTQ (SEQ ID NO. 98) |
| N120 | MKLTTQQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 99) |
| N107 | MKLTTQQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 100) |
| N92 | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 101) |
| N91 | MKLTTQQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 102) |
| D219PG | MKLTTQQTLKKGFTLIELMIVIAIIAILATIAIPSYQNYTKKAAVSELLQASAPYKA DVELCVYSTNEATKCTGGKNGIAADITTAKGYVKSVTTSNGAITVKGDGTLAN MEYILQASGNAATGVTWTTTCKGTDASLFPANFCGSVTQ (SEQ ID NO. 103) |
| D211PG | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 104) |
| D211PD | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 105) |
| D204CD | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILXATGNAATGVTWTTTCKGTDASLFPANFCGSVTQ (SEQ ID NO. 106) |
| D198PG | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 107) |
| D198PD | MKLTTQQTLKKGFTLIELMIVIAIIAILATIAIPSYQNYTKKAAVSELLQASAPYKA DVELCVYSTNETTNCTGGKNGIAADITTAKGYVKSVTTSNGAITVKGDGTLAN MEYILQATGNAATGVTWTTTCKGTDASLFPANFCGSVTQ (SEQ ID NO. 108) |
| D195PD | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 109) |
| D195CD | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 110) |
| D189PG | MKLTTQQTLKKGFTLIELMIVIAIIAILATIAIPSYQNYTKKAAVSELLQASAPYKA DVELCVYSTNETTSCTGGKNGIAADITTAKGYVKSVTTSNGAITVAGNGTLDG MSYTLTAEGDSAKGVTWKTTCKGTDASLFPANFCGSVTQ (SEQ ID NO. 111) |
| D189PD | MKLTTQQTLKKGFTLIELMIVIAIIAILATIAIPSYQNYTKKAAVSELLQASAPYKA DVELCVYSTNETTSCTGGKNGIAADITTAKGYVKSVTTSNGAITVAGNGTLDG MSYTLTAEGDSAKGVTWKTTCKGTDASLFPANFCGSVTQ (SEQ ID NO. 112) |
| D124PG | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 113) |

TABLE 2-continued

Pilin A amino acid sequences from 64 strains of Haemophilus influenzae (SEQ ID NO. 58 - SEQ ID NO. 121)

| Strain Name | PilA sequence |
|---|---|
| D124PD | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 114) |
| D124CG | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 115) |
| D58PG | MKLTTQQTLKKGFTLIELMIVIAIIAILATIAIPSYQNYTKKAAVSELLQASAPYKA DVELCVYSTNETTNCTGGKNGIAADITTAKGYVASVKTQSGGITVKGDGTLAN MEYILQATGNAATGVTWTTTCKGTEASLFPANFCGSVTQ (SEQ ID NO. 116) |
| BS433 | MKLTTLQTLKKGFTLIELMIVIAIIAILATIAIPSYQNYTKKAAVSELLQASAPYKA DVELCVYSTGKPSTCSGGNNGIAADIKTAKGYVASVKTQSGGITVKGDGTLA NMEYILQATGNAATGVTWTTTCKGTDASLFPANFCGSVTQ (SEQ ID NO. 117) |
| BS432 | MKLTTQQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 118) |
| BS430 | MKLTTQQTLKKGFTLIELMIVIAIIAILATIAIPSYQNYTKKAAVSELLQASAPYKA DVELCVYSTNEATKCTGGKNGIAADITTAKGYVKSVTTSNGAITVKGDGTLAN MEYILQASGNAATGVTWTTTCKGTDASLFPANFCGSVTQ (SEQ ID NO. 119) |
| 1714 | MKLTTLQTLKKGFTLIELMIVIAIIAILATIAIPSYQNYTKKAAVSELLQASAPYKA DVELCVYSTGKPSTCSGGSNGIAADITTAKGYVASVKTQSGGITVKGNGTLAN MEYILQATGNAATGVTWTTTCKGTDASLFPANFCGSVTQ (SEQ ID NO. 120) |
| 1128 | MKLTTQQTLKKGFTLIELMIVIAIIAILATIAIPSYQNYTKKASVSELLQASAPYKS DVELCVYSTGKPSTCSGGSNGIAADITTAKGYVASVKTQSGGITVKGNGTLAN MEYILQAKGNATAGVTWTTTCKGTDASLFPANFCRSVTK (SEQ ID NO. 121) |

PilA may be PilA from *H. influenzae* strain NTHi3219C, NTHi3224A, NTHi12, NTHi44, NTHi67, 1054MEE, 1729MEE, 1728MEE, 1885MEE, 1060MEE, RdKW20, 214NP, 1236MEE, 1714MEE, 1128MEE, 86-028NP, R2846, R2866, 3655, PittAA, PittGG, PittII, R3021, 22.4-21, 3185A, 3221B, 3241A, 038144S1, 821246, 840645, 902550Z19, A840177, A920030, A950014, 901905U, A920029, A930105, 306543X4, N218, N163, N162, N120, N107, N92, N91, D219PG, D211PG, D211PD, D204CD, D198PG, D198PD, D195PD, D195CD, D189PG, D189PD, D124PG, D124PD, D124CG, D58PG, BS433, BS432, BS430, 1714 or 1128. An amino acid sequence for PilA from *H. influenzae* strain D204CD is set forth in SEQ ID NO. 106, wherein X at position #116 is either glutamine (Q) or leucine (L); ambiguity as to the amino acid at position #116 could be cleared up by technical resolution of the second nucleotide encoding amino acid #116, clarifying the PilA sequence for strain D204CD. PilA may be PilA as set forth in any of SEQ ID NO. 58-SEQ ID NO. 121.

PilA may be a sequence with at least 95%, 98%, or 99% identity, over the entire length, to any of SEQ ID NO. 58-SEQ ID NO. 121 (as set out in Table 2).

Immunogenic fragments of PilA comprise immunogenic fragments of at least 7, 10, 15, 20, 25, 30 or 50 contiguous amino acids of SEQ ID NO. 58-SEQ ID NO. 121. The immunogenic fragments may elicit antibodies which can bind the full length sequence from which the fragment is derived. The immunogenic fragments may comprise a B and/or T cell epitope of SEQ ID NO. 58-SEQ ID NO:121.

For example, immunogenic fragments of PilA comprise immunogenic fragments of at least 7, 10, 15, 20, 25, 30 or 50 contiguous amino acids of SEQ ID NO. 58. In one embodiment the immunogenic fragment of PilA comprises less than 150, 125, 100, 75, or 60 amino acids of PilA, in a further embodiment the immunogenic composition comprises less than 150, 125, 100, 75 or 60 amino acids of PilA. The immunogenic fragments may elicit antibodies which can bind SEQ ID NO. 58. The immunogenic fragments may comprise a B and/or T cell epitope of SEQ ID NO:58.

In one embodiment the immunogenic fragment of PilA is a fragment from *H. influenzae* strain 86-028NP wherein PilA is SEQ ID NO. 58.

PilA from *H. influenzae* strain 86-028NP - SEQ ID NO. 58
MKLTTQQTLK KGFTLIELMI VIAIIAILAT IAIPSYQNYT
KKAAVSELLQ ASAPYKADVE LCVYSTNETT NCTGGKNGIA
ADITTAKGYV KSVTTSNGAI TVKGDGTLAN MEYILQATGN
AATGVTWTTT CKGTDASLFP ANFCGSVTQL In another embodiment, the immunogenic fragment of PilA is approximately at least 75%, 80%, 85%, 90%, 95%, 98% or 99% identical to SEQ ID NO. 127. More specifically, in one embodiment the immunogenic fragment of PilA is SEQ ID NO. 127, a fragment consisting of amino acids 40-149 of SEQ ID NO. 58.

```
Amino acids 40-149 of PilA from H. influenzae
strain 86-028NP - SEQ ID NO. 127.
T KKAAVSELLQ ASAPYKADVE LCVYSTNETT NCTGGKNGIA

ADITTAKGYV KSVTTSNGAI TVKGDGTLAN MEYILQATGN

AATGVTWTTT CKGTDASLFP ANFCGSVTQ
```

In another embodiment, the immunogenic fragment of PilA consists of amino acids 40-149 from any of SEQ ID NO. 58-SEQ ID NO. 121. In an additional embodiment, the immunogenic fragment is at least 95% identical to amino acids 40-149 from any of SEQ ID NO. 58-SEQ ID NO. 121.

Identity between polypeptides may be calculated by various algorithms. For example, the Needle program, from the EMBOSS package (Free software; EMBOSS: The European Molecular Biology Open Software Suite (2000). Trends in Genetics 16(6): 276-277) and the Gap program from the GCG® package (Accelrys Inc.) may be used. This Gap program is an implementation of the Needleman-Wunsch algorithm described in: Needleman, S. B. and Wunsch, C. D. (1970) J. Mol. Biol. 48, 443-453. The BLOSUM62 scoring matrix has been used, and the gap open and extension penalties were respectively 8 and 2.

Looking at the computed alignment, identical residues between two compared sequences can be observed. A percentage of identity can be computed by (1) calculating the number of identities divided by the length of the alignment, multiplied by 100 (for example, for the Needle program analysis), (2) calculating the number of identities divided by the length of the longest sequence, multiplied by 100, (3) calculating the number of identities divided by the length of the shortest sequence, multiplied by 100, or (4) calculating the number of identities divided by the number of aligned residues, multiplied by 100 (a residue is aligned if it is in front of another) (for example, for the Gap program analysis).

In one embodiment the PilA is capable of eliciting an immune response which recognizes SEQ ID NO. 58.

Protein E/PilA Fusion Protein

In one embodiment Protein E and PilA are present in a fusion protein. In a further embodiment the fusion protein has formula (I):

$$L-(X)_m-(R_1)_n-A-(Y)_o-B-(Z)_p \quad \text{(formula I)}$$

wherein:
X is a signal peptide or MHHHHHH (SEQ ID NO: 2);
m is 0 or 1;
$R_1$ is an amino acid;
n is 0, 1, 2, 3, 4, 5 or 6;
A is Protein E from *Haemophilus influenzae* or an immunogenic fragment thereof, or PilA from *Haemophilus influenzae* or an immunogenic fragment thereof;
Y is selected from the group consisting of GG, SG, SS and $(G)_h$ wherein h is 4, 5, 6, 7, 8, 9, or 10;
o is 0 or 1;
B is PilA from *Haemophilus influenzae* or an immunogenic fragment thereof, or Protein E from *Haemophilus influenzae* or an immunogenic fragment thereof;
Z is GGHHHHHH (SEQ ID NO: 3); and
p is 0 or 1.

In one embodiment, the fusion proteins of formula (I) are defined wherein X is selected from the group consisting of the signal sequence from CcmH (cytochrome c membrane protein H), DsbA (periplasmic protein disulfide isomerise I), DsbB (disulfide bond membrane protein B), FlgI (flagellar peptidoglycan ring protein), FocC (F1c Chaperone protein), MalE (maltose transporter subunit E), NadA (quinolinate synthase subunit A), NikA (nickel ABC transporter component A), NspA (Neisserial surface protein A), Omp26 (outer membrane protein 26), OmpA (outer membrane protein A), OspA (outer surface protein A), pelB (pectate lyase B), PhoA (bacterial alkaline phosphatase), PhtD (poly histidine triad protein D), PhtE (poly histidine triad protein E), SfmC (periplasmic pilin chaperone), Sip1 (surface immunogenic protein), TolB (Tol-Pal Cell Envelope Complex Component B), TorA (trimethylamine N-oxide reductase system subunit A), TorT (trimethylamine N-oxide reductase system periplasmic protein T) and YraI (putative periplasmic pilin chaperone); or any subgroup thereof. In one embodiment, X is a co-translational signal peptide or a post-translational signal peptide. In one embodiment X is the signal sequence from FlgI (flgI sp). In another particular embodiment, X is the signal sequence from pelB (pelB sp). In another embodiment, X is a post-translational signal peptide. In another embodiment, X is selected from the group consisting of the signal sequence from FlgI, NadA and pelB.

In one embodiment, the fusion proteins of formula (I) are defined wherein m is 1. In another embodiment, m is 0.

In one particular embodiment, $R_1$ and n are defined wherein $(R_1)_n$ is 1 to 6 amino acids enriched in small, usually hydrophilic, amino acids. Hydrophilic amino acids include glutamic acid (E), aspartic acid (D) and asparagine (N).

In one embodiment, the fusion proteins of formula (I) are defined wherein n is selected from the group consisting of 0, 1, 2 and 6. In one particular embodiment, $R_1$ and n are defined wherein $(R_1)_n$ is selected from the group consisting of D, E, ATNDDD (SEQ ID NO. 178) and MD, or any subset thereof.

In one particular embodiment, n is selected from the group consisting of 1, 2 and 6. In one particular embodiment, n is 0.

In one embodiment, the fusion proteins of formula (I) are defined wherein A is Protein E from *H. influenzae*. In another embodiment, the fusion proteins of formula (I) are defined wherein A is Protein E as encoded by an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 5 through SEQ ID NO. 57. In another embodiment, the fusion proteins of formula (I) are defined wherein A is Protein E, wherein Protein E is approximately at least 75%, 80%, 85%, 90%, 92%, 95%, 98% or 99% identical to the Protein E amino acid sequence set forth in SEQ ID NO: 4. In another embodiment, A is Protein E wherein Protein E is approximately 90% to 100% identical to the Protein E amino acid sequence set forth in SEQ ID NO: 4. In another embodiment, A is Protein E wherein Protein E is at least 95% identical to the Protein E amino acid sequence set forth in SEQ ID NO: 4. In additional embodiment, A is Protein E wherein Protein E is at least 95% identical to Protein E as set for in any of SEQ ID NO. 4-SEQ ID NO. 57. In a particular embodiment, A is Protein E having the amino acid sequence set forth in SEQ ID NO. 4.

In another embodiment, the fusion proteins of formula (I) are defined wherein A is an immunogenic fragment of Protein E from *H. influenzae*. In another embodiment, A is an immunogenic fragment of Protein E wherein Protein E has an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, A is an immunogenic fragment of Protein E, wherein Protein E is approximately 75%, 80%, 85%, 90%, 92%, 95%, 98% or 99% identical to the amino acid sequence set forth in SEQ ID NO: 4. In another embodiment, A is an immunogenic fragment of Protein E, wherein Protein E is approximately 90% to 100% identical to SEQ ID NO. 4. In an additional embodiment, A is an immunogenic fragment of Protein E, wherein Protein E is at least 95% identical to any of SEQ ID NO. 4-SEQ ID NO. 57. More specifically, in one embodiment, A is an immunogenic fragment of Protein E, wherein Protein E is at least 93%, 95%, 98%, 99% or 100% identical to SEQ ID NO. 124. In a particular embodiment, A is an immunogenic fragment of Protein E wherein Protein E is SEQ ID NO. 4.

In another embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125) and amino acids 22-160 of SEQ ID NO. 4 (SEQ ID NO. 126). In another embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). In a further embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). More specifically, in one embodiment, A is SEQ ID NO. 124, amino acids 19-160 of SEQ ID NO. 4. In an additional embodiment, A is SEQ ID NO. 125, amino acids 20-160 of SEQ ID NO. 5. In another embodiment, A is immunogenic fragment of Protein E from *H. influenzae* selected from the group consisting of amino acids 23-160 of SEQ ID NO. 4 (SEQ ID NO. 179) and amino acids 24-160 of SEQ ID NO. 4 (SEQ ID NO. 180).

```
Protein E - SEQ ID NO. 4
MKKIILTLSL GLLTACSAQI QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 17-160 of Protein E from SEQ ID NO.
4 - SEQ ID NO. 122
SAQI QKAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 18-160 of Protein E from SEQ ID NO.
4 - SEQ ID NO. 123
AQI QKAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 19-160 of Protein E from SEQ ID NO.
4 - SEQ ID NO. 124
QI QKAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 20-160 of Protein E from SEQ ID NO.
4 - SEQ ID NO. 125
I QKAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 22-160 of Protein E from SEQ ID NO.
4 - SEQ ID NO. 126
KAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 23-160 of Protein E from SEQ ID NO.
4 - SEQ ID NO. 179
AEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK

Amino acids 24-160 Protein E from SEQ ID NO. 4 -
SEQ ID NO. 180
EQNDVKL APPTDVRSGY IRLVKNVNYY IDSESIWVDN

QEPQIVHFDA VVNLDKGLYV YPEPKRYARS VRQYKILNCA
```

-continued

```
NYHLTQVRTD FYDEFWGQGL RAAPKKQKKH TLSLTPDTTL

YNAAQIICAN YGEAFSVDKK
```

In another embodiment, the fusion proteins of formula (I) are defined wherein A is PilA from *H. influenzae*. In another embodiment, the fusion proteins of formula (I) are defined wherein A is PilA from *H. influenzae* having an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, A is PilA wherein PilA is approximately at least 75%, 80%, 85%, 90%, 92%, 95%, 98% or 99% identical to SEQ ID NO. 58. In another embodiment, A is PilA wherein PilA is at least 95% identical to any of SEQ ID NO. 58-SEQ ID NO. 121. In a particular embodiment, A is PilA of SEQ ID NO. 58.

In another embodiment, the fusion proteins of formula (I) are defined wherein A is an immunogenic fragment of PilA from *H. influenzae*. In another embodiment, A is an immunogenic fragment of PilA wherein PilA is approximately at least 75%, 80%, 85%, 90%, 92%, 95%, 98% or 99% identical to SEQ ID NO. 58. For example, A is an immunogenic fragment of PilA wherein PilA has an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset SEQ ID NO. 58 through SEQ ID NO. 121. In an additional embodiment, A is an immunogenic fragment of PilA wherein PilA is at least 95% identical to any of SEQ ID NO. 58-SEQ ID NO. 121. In a particular embodiment, A is an immunogenic fragment of PilA from *H. influenzae* strain 86-028NP wherein PilA is SEQ ID NO. 58.

```
PilA from H. influenzae strain 86-028NP - SEQ ID
NO. 58
MKLTTQQTLK KGFTLIELMI VIAIIAILAT IAIPSYQNYT

KKAAVSELLQ ASAPYKADVE LCVYSTNETT NCTGGKNGIA

ADITTAKGYV KSVTTSNGAI TVKGDGTLAN MEYILQATGN

AATGVTWTTT CKGTDASLFP ANFCGSVTQL
```

In another embodiment, A is an immunogenic fragment of PilA approximately at least 75%, 80%, 85%, 90%, 92%, 95%, 98% or 99% identical to SEQ ID NO. 127. More specifically, in one embodiment A is SEQ ID NO. 127, a fragment consisting of amino acids 40-149 of SEQ ID NO. 58.

```
Amino acids 40-149 of PilA from H. influenzae
strain 86-028NP - SEQ ID NO. 127.
T KKAAVSELLQ ASAPYKADVE LCVYSTNETT NCTGGKNGIA

ADITTAKGYV KSVTTSNGAI TVKGDGTLAN MEYILQATGN

AATGVTWTTT CKGTDASLFP ANFCGSVTQ
```

In another embodiment, A is an immunogenic fragment of PilA consisting of amino acids 40-149 from any of SEQ ID NO. 58-SEQ ID NO. 121. In an additional embodiment, A is an immunogenic fragment at least 95% identical to amino acids 40-149 from any of SEQ ID NO. 58-SEQ ID NO. 121.

In one embodiment, the fusion proteins of formula (I) are defined wherein Y is selected from the group consisting of GG, SG and SS. In another embodiment, the fusion proteins of formula (I) are defined wherein Y is GG or SG. In one particular embodiment, Y is GG.

In one embodiment, the fusion proteins of formula (I) are defined wherein o is 1. In another embodiment, o is 0.

In one embodiment, the fusion proteins of formula (I) are defined wherein B is PilA from *H. influenzae* or an immunogenic fragment of PilA from *H. influenzae* when A is Protein E from *H. influenzae* or an immunogenic fragment of Protein E from *H. influenzae*. For example, B is PilA from *H. influenzae* strain 86-028NP. In another embodiment, B is PilA from *H. influenzae* having an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, B is PilA wherein PilA is approximately at least 75%, 80%, 85%, 90%, 92%, 95%, 98% or 99% identical to SEQ ID NO. 58. In another embodiment, B is PilA wherein PilA is at least 95%, 98% or 99% identical to any of SEQ ID NO. 58-SEQ ID NO. 121. In a particular embodiment, B is PilA of SEQ ID NO. 58.

In another embodiment, B is PilA wherein PilA is at least 95%, 98% or 99% identical to any of SEQ ID NO. 58-SEQ ID NO. 121 and A is PE wherein PE is at least 95%, 98% or 99% identical to any of SEQ ID NO. 4-SEQ ID NO. 57.

In another embodiment, the fusion proteins of formula (I) are defined wherein B is an immunogenic fragment of PilA from *H. influenzae* when A is an immunogenic fragment of Protein E from *H. influenzae*. For example, B is an immunogenic fragment of the PilA from *H. influenzae* strain 86-028NP. In another embodiment, B is an immunogenic fragment of PilA wherein PilA is approximately at least 80%, 85%, 90%, 95%, 98% or 99% identical to SEQ ID NO: 58. In another embodiment, B is an immunogenic fragment of PilA wherein PilA has an amino acid selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, B is an immunogenic fragment of PilA wherein PilA is at least 95%, 98% or 99% identical to any of SEQ ID NO. 58-SEQ ID NO. 121. In a particular embodiment, B is an immunogenic fragment of PilA from *H. influenzae* wherein PilA has the amino acid sequence set forth in SEQ ID NO. 58. In another embodiment, B is an immunogenic fragment of PilA consisting of amino acids 40-149 from any of SEQ ID NO. 58-SEQ ID NO. 121. More specifically, in one embodiment B is the fragment of PilA as set forth in SEQ ID NO. 127. In an additional embodiment, B is an immunogenic fragment at least 95%, 98% or 99% identical to amino acids 40-149 of any of SEQ ID NO. 58-SEQ ID NO. 121.

In one particular embodiment, B is the fragment of PilA as set forth in SEQ ID NO. 127 and A is an immunogenic fragment of Protein E selected from the group consisting of SEQ ID NO. 122, SEQ ID NO. 124, SEQ ID NO. 125 and SEQ ID NO. 126. More particularly, B is the fragment of PilA as set forth in SEQ ID NO. 127 and A is the fragment of Protein E as set forth in SEQ ID NO. 124, amino acids 19-160 of Protein E from SEQ ID NO. 4. In another embodiment, B is the fragment of PilA as set forth in SEQ ID NO. 127 and A is the fragment of Protein E as set forth in SEQ ID NO. 125.

In another embodiment, B is an immunogenic fragment of PilA wherein PilA is at least 95% identical to any of SEQ ID NO. 58-SEQ ID NO. 121 and A is an immunogenic fragment of PE wherein PE is at least 95% identical to any of SEQ ID NO. 4-SEQ ID NO. 57.

In another embodiment, the fusion proteins of formula (I) are defined wherein B is Protein E from *H. influenzae* when A is PilA from *H. influenzae*. For example, B is Protein E having an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, the fusion proteins of formula (I) are defined wherein B is Protein E wherein Protein E is approximately at least 75%, 80%, 85%, 90%, 95%, 98% or 99% identical to the Protein E amino acid sequence set forth in SEQ ID NO: 4. In another embodiment, B is Protein E wherein Protein E is approximately 90%, 95%, 98%, or 99% identical to the Protein E amino acid sequence set forth in SEQ ID NO: 4. For example, B is Protein E wherein Protein E is at least 95% identical to Protein E as set forth in SEQ ID NO. 4. In another embodiment, B is Protein E wherein Protein E is at least 95% identical to any of SEQ ID NO. 4-SEQ ID NO. 57. In a particular embodiment, B is Protein E having the amino acid sequence set forth in SEQ ID NO. 4.

In another embodiment, the fusion proteins of formula (I) are defined wherein B is an immunogenic fragment of Protein E from *H. influenzae* when A is an immunogenic fragment of PilA from *H. influenzae*. For example, B is an immunogenic fragment of Protein E wherein Protein E has an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, the fusion proteins of formula (I) are defined wherein B is an immunogenic fragment of Protein E wherein Protein E is approximately at least 75%, 80%, 85%, 90%, 95%, 98% or 99% identical to the Protein E amino acid sequence set forth in SEQ ID NO. 4. In another embodiment, B is an immunogenic fragment of Protein E wherein Protein E is approximately 90% to 100% identical to the Protein E amino acid sequence set forth in SEQ ID NO: 4. In a particular embodiment, B is an immunogenic fragment of Protein E having the amino acid sequence set forth in SEQ ID NO. 4. In an additional embodiment, B is an immunogenic fragment of Protein E, wherein Protein E is at least 95% identical to any of SEQ ID NO. 4-SEQ ID NO. 57.

In another embodiment, B is a fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125) and amino acids 22-160 of SEQ ID NO. 4 (SEQ ID NO. 126). In another embodiment, B is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). More specifically, in one embodiment, B is the fragment of Protein E as set forth in SEQ ID NO. 123, amino acids 18-160 of SEQ ID NO. 4.

In one particular embodiment B is an immunogenic fragment of Protein E as set forth in SEQ ID NO. 123, amino acids 18-160 of SEQ ID NO. 4, when A is an immunogenic fragment of PilA as set forth in SEQ ID NO. 127.

In one embodiment, the fusion proteins of formula (I) are defined wherein p is 0. In another embodiment, the fusion proteins of formula (I) are defined wherein p is 1.

In one embodiment, the fusion protein of formula (I) is selected from the group consisting of SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202 and SEQ ID NO. 204; or any subset thereof. In another embodiment, the fusion protein of formula (I) is approximately 85%, 88%, 90%, 92%, 95% or 98% identical to any of SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202 or SEQ ID NO. 204.

In one embodiment the fusion protein formula (I) is the fusion protein of SEQ ID NO. 148 wherein the signal peptide has been removed SEQ ID NO. 177 (QIQKAEQN DVKLAPPTDV RSGYIRLVKN VNYYIDSESI WVDN-QEPQIV HFDAWNLDK GLYVYPEPKR YARSVRQYKI LNCANYHLTQ VRTDFYDEFW GQGLRAAPKK QKKHTLSLTP DTTLYNAAQI ICANYGEAFS VDKKG-GTKKA AVSELLQASA PYKADVELCV YSTNETTNCT GGKNGIAADI TTAKGYVKSV TTSNGAITVK GDGT-LANMEY ILQATGNAAT GVTWTTTCKG TDASLF-PANF CGSVTQ).

In one embodiment the fusion protein of formula (I) is the fusion protein of SEQ ID NO. 194 wherein the signal peptide has been removed SEQ ID NO. 219 (IQKAEQND VKLAPPTDVR SGYIRLVKNV NYYIDSESIW VDN-QEPQIVH FDAWNLDKG LYVYPEPKRY ARS-VRQYKIL NCANYHLTQV RTDFYDEFWG QGLRAAP-KKQ KKHTLSLTPD TTLYNAAQII CANYGEAFSV DKKGGTKKAA VSELLQASAP YKADVELCVY STNETTNCTG GKNGIAADIT TAKGYVKSVT TSN-GAITVKG DGTLANMEYI LQATGNAATG VTWTTTCKGT DASLFPANFC GSVTQ).

*Streptococcus pneumoniae* Capsular Saccharide Conjugates

The term capsular saccharide includes capsular polysaccharides and oligosaccharides derivable from the capsular polysaccharide. An oligosaccharide contains at least 4 sugar residues. The terms conjugate and conjugated relate to a capsular saccharide covalently bonded to a carrier protein.

In an immunogenic composition, the total number of saccharide serotypes is optionally less than or equal to 23. In one embodiment the immunogenic composition comprises less than 23, 22, 21, 20, 19, 18, 17, 16, 15, 14, or 13 *Streptococcus pneumoniae* saccharides, optionally the immunogenic composition comprising 10-23 serotypes, 10-16 serotypes, 10-15 serotypes, 10-14 serotypes, 10-13 serotypes or 10-12 serotypes.

In one embodiment the *Streptococcus pneumoniae* capsular saccharide conjugates will be derived from the following serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F, although it is appreciated that one or two other serotypes could be substituted depending on the age of the recipient receiving the vaccine and the geographical location where the immunogenic composition will be administered. For example, a 7 valent immunogenic composition may comprise saccharides from serotypes 4, 6B, 9V, 14, 18C, 19F and 23F. A 10 valent immunogenic composition may further comprise saccharides derived from serotypes 1, 5 and 7F. A 12 valent immunogenic composition may further comprise saccharides derived from serotypes 6A, 19A. A 15 valent immunogenic composition may further comprise saccharides derived from serotypes 22F and 33F.

Further saccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

The term "carrier protein" is intended to cover both small peptides and large polypeptides (>10 kDa). The carrier protein may be any peptide or protein. It may comprise one or more T-helper epitopes. The carrier protein may be tetanus toxoid (TT), tetanus toxoid fragment C, non-toxic mutants of tetanus toxin [note all such variants of TT are considered to be the same type of carrier protein for the purposes of this invention], polypeptides comprising tetanus toxin T-cell epitopes such as N19 (WO2006/067632), diphtheria toxoid (DT), CRM197 (cross reacting material 197), other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 (where CRM stands for cross reacting material) and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (outer membrane protein C from meningococcus usually extracted from *N. meningitidis* serogroup B-EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7), pneumococcal surface protein PspA (WO 02/091998), iron uptake proteins (WO 01/72337), toxin A or toxin B of *Clostridium difficile* (WO 00/61761), *H. influenzae* Protein D (EP594610 and WO 00/56360), pneumococcal PhtA (WO 98/18930, also referred to Sp36), pneumococcal PhtD (poly histidine triad D disclosed in WO 00/37105, and is also referred to Sp036D), pneumococcal PhtB (poly histidine triad B disclosed in WO 00/37105, and is also referred to Sp036B), or PhtE (poly histidine triad E disclosed in WO00/30299 and is referred to as BVH-3).

In one embodiment the *Streptococcus pneumoniae* capsular saccharide conjugates are conjugated to a carrier protein independently selected from the group consisting of tetanus toxoid (TT), fragment C of TT, diphtheria toxoid, CRM197 (cross reacting material 197), detoxified pneumolysin, protein D (from *H. influenzae*), PhtD, PhtDE (a protein containing poly histidine triad protein D and poly histidine triad protein E) and N19. In a further embodiment the *Streptococcus pneumoniae* capsular saccharide conjugates are all independently conjugated to CRM197.

The term 'conjugated to' in this context means that the protein is covalently bonded to a saccharide; in this situation the protein is acting as a carrier protein.

In one embodiment the immunogenic composition comprises at least one *Streptococcus pneumoniae* capsular saccharide conjugated to protein D. In one embodiment a minority of conjugated *Streptococcus pneumoniae* saccharides are conjugated to protein D wherein the term 'minority' refers to less than half of the total number of saccharides in the composition being conjugated to protein D. In a further embodiment the immunogenic composition comprises between 1-20, 1-18, 1-16, 1-14, 1-12, 1-10, 1-9, 1-8, 1-7, 1-6, 1-5, 1-4, 1-4 or 1-2 *Streptococcus pneumoniae* capsular saccharide conjugated to protein D. In one embodiment the immunogenic composition comprises at least one *Streptococcus pneumoniae* capsular saccharides conjugated to diphtheria toxoid. In a further embodiment the immunogenic composition comprises 19F is conjugated to diphtheria toxoid. In one embodiment the immunogenic composition comprises at least one *Streptococcus pneumoniae* capsular saccharides conjugated to tetanus toxoid. In a further embodiment the immunogenic composition comprises 18C is conjugated to tetanus toxoid.

In one embodiment the immunogenic composition comprises a conjugated serotype 1 saccharide conjugated to protein D or CRM197. In one embodiment the immunogenic composition comprises a conjugated serotype 4 saccharide conjugated to protein D or CRM197. In one embodiment the immunogenic composition comprises a conjugated serotype 5 saccharide wherein the serotype 5 saccharide is conjugated to protein D or CRM197. In one embodiment the immunogenic composition comprises a conjugated serotype 6B saccharide wherein the serotype 6B saccharide is conjugated to protein D or CRM197. In one embodiment the immunogenic composition comprises a conjugated serotype 7F saccharide is wherein the serotype 7F saccharide is conjugated to protein D or CRM197. In one embodiment the immunogenic composition comprises a conjugated serotype 9V saccharide wherein the 9V saccharide is conjugated to protein D or CRM197. In one embodiment the immunogenic composition comprises a conjugated serotype 14 saccharide wherein the serotype 14 saccharide is conjugated to protein D or CRM197. In one embodiment the immunogenic composition comprises a conjugated serotype 18C saccharide wherein the serotype 18C saccharide is conjugated to tetanus toxoid or CRM197. In one embodiment the immunogenic composition comprises a conjugated 19F saccharide wherein the serotype 19F saccharide is conjugated to diphtheria toxoid or CRM197. In one embodiment the immunogenic composition comprises a conjugated 23F saccharide wherein the serotype 23F saccharide is conjugated to protein D or CRM197. In one embodiment the immunogenic composition comprises a conjugated 6A saccharide conjugated to CRM197. In one embodiment the immunogenic composition comprises a conjugated 19A saccharide conjugated to CRM197.

In one embodiment the immunogenic composition comprises a *Streptococcus pneumoniae* serotype 1 saccharide conjugated to protein D, a *Streptococcus pneumoniae* serotype 4 saccharide conjugated to protein D, a *Streptococcus pneumoniae* serotype 5 saccharide conjugated to protein D, a *Streptococcus pneumoniae* serotype 6B saccharide conjugated to protein D, a *Streptococcus pneumoniae* serotype 7F saccharide conjugated to protein D, a *Streptococcus pneumoniae* serotype 9V saccharide conjugated to protein D, a *Streptococcus pneumoniae* serotype 14 saccharide conjugated to protein D, a *Streptococcus pneumoniae* serotype 23F saccharide conjugated to protein D, a *Streptococcus pneumoniae* serotype 18C saccharide conjugated to tetanus toxoid and a *Streptococcus pneumoniae* 19F saccharide conjugated to diphtheria toxoid. In one embodiment the immunogenic composition further comprises a *Streptococcus pneumoniae* serotype 6A conjugated to CRM197 and a *Streptococcus pneumoniae* serotype 19A conjugated to CRM197.

Optionally the ratio of carrier protein to *S. pneumoniae* saccharide is between 1:5 and 5:1; 1:2 and 2.5:1; 1:1 and 2:1 (w/w). In an embodiment, the majority of the conjugates, for example 6, 7, 8, 9 or more of the conjugates have a ratio of carrier protein to saccharide that is greater than 1:1, for example 1.1:1, 1.2:1, 1.3:1, 1.4:1, 1.5:1 or 1.6:1.

In general, the immunogenic composition of the invention may comprise a dose of each saccharide conjugate between 0.1 and 20 µg, 1 and 5 µg, 1 and 10 µg or 1 and 3 µg of saccharide.

In an embodiment, the immunogenic composition of the invention contains each *S. pneumoniae* capsular saccharide conjugate at a dose of between 0.1-20 µg; 0.5-10 µg; 0.5-5 µg or 1-3 µg of saccharide. In an embodiment, capsular saccharides may be present at different dosages, for example some capsular saccharides may be present at a dose of exactly 1 µg or some capsular saccharides may be present at a dose of exactly 3 µg. In an embodiment, saccharides from serotypes 3, 18C and 19F (or 4, 18C and 19F) are present at a higher dose than other saccharides. In one aspect of this embodiment, serotypes 3, 18C and 19F (or 4, 18C and 19F) are present at a dose of around or exactly 3 µg whilst other saccharides in the immunogenic composition are present at a dose of around or exactly 1 µg. In one embodiment serotypes 1, 5, 6B, 7F, 9V, 14 and 23F are present at a dose of around or exactly 1 µg.

The term "saccharide" throughout this specification may indicate polysaccharide or oligosaccharide and includes both. Polysaccharides are isolated from bacteria and may be sized to some degree by known methods (see for example EP497524 and EP497525) and optionally by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

Capsular polysaccharides of *Streptococcus pneumoniae* comprise repeating oligosaccharide units which may contain up to 8 sugar residues. For a review of the oligosaccharide units for the key *Streptococcus pneumoniae* serotypes see JONES, Christopher. Vaccines based on the cell surface carbohydrates of pathogenic bacteria. An. Acad. Bras. Ciênc., June 2005, vol. 77, no. 2, p. 293-324. ISSN 0001-3765. In one embodiment, a capsular saccharide antigen may be a full length polysaccharide, however in others it may be one oligosaccharide unit, or a shorter than native length saccharide chain of repeating oligosaccharide units. In one embodiment, all of the saccharides present in the vaccine are polysaccharides. Full length polysaccharides may be "sized" i.e. their size may be reduced by various methods such as acid hydrolysis treatment, hydrogen peroxide treatment, sizing by Emulsiflex® followed by a hydrogen peroxide treatment to generate oligosaccharide fragments or microfluidization.

In one embodiment the immunogenic composition further comprises unconjugated *S. penumoniae* saccharides of serotypes different from those conjugated, such that the number of conjugated and unconjugated saccharide serotypes is less than or equal to 23.

Conjugation

The saccharide conjugates present in the immunogenic compositions of the invention may be conjugated to a carrier protein using any conjugation technique.

In an embodiment, the *Streptococcus pneumoniae* saccharide is conjugated to the carrier protein via a linker, for instance a bifunctional linker. The linker is optionally heterobifunctional or homobifunctional, having for example a reactive amino group and a reactive carboxylic acid group, two reactive amino groups or two reactive carboxylic acid groups. The linker has for example between 4 and 20, 4 and 12, 5 and 10 carbon atoms. A possible linker is adipic acid dihydrazide (ADH). Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. No. 4,673,574, U.S. Pat. No. 4,808,700), hexane diamine and 6-aminocaproic acid (U.S. Pat. No. 4,459,286). In an embodiment, ADH is used as a linker for conjugating saccharide from serotype 18C.

The saccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or STAB, or SIA, or SBAP). Optionally, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbodiimides, carbiinides, hydrazides, active esters, norborane, p-nitrobenzoic acid, N-hydroxysuccinimide, S—NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid dihydrazide (ADH) to the protein carrier by Carbodiimide condensation (Chu C. et al Infect. Immunity, 1983 245 256), for example using EDAC (1-Ethyl-3-(3-dimethylaminopropyl)carbodiimide hydrochloride).

In an embodiment, a hydroxyl group (optionally an activated hydroxyl group for example a hydroxyl group activated to make a cyanate ester [e.g. using CDAP]) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH may be conjugated to a carboxylic acid group on a protein, for example by using carbodiimide chemistry, for example by using EDAC. In an embodiment, the pneumococcal capsular saccharide(s) is conjugated to the linker first before the linker is conjugated to the carrier protein. Alternatively the linker may be conjugated to the carrier before conjugation to the saccharide.

A combination of techniques may also be used, with some saccharide-protein conjugates being prepared by CDAP, and some by reductive amination.

In general the following types of chemical groups on a protein carrier can be used for coupling/conjugation:
A) Carboxyl (for instance via aspartic acid or glutamic acid). In one embodiment this group is linked to amino groups on saccharides directly or to an amino group on a linker with carbodiimide chemistry e.g. with EDAC.
B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.
C) Sulphydryl (for instance via cysteine). In one embodiment this group is linked to a bromo or chloro acetylated saccharide or linker with maleimide chemistry. In one embodiment this group is activated/modified with bis diazobenzidine.
D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:

Saccharide-OH+CNBr or CDAP→cyanate ester+NH2-Prot→conjugate

Saccharide-aldehyde+NH2-Prot→Schiff base+NaCNBH3→conjugate

Saccharide-COOH+NH2-Prot+EDAC→conjugate

Saccharide-NH2+COOH-Prot+EDAC→conjugate

Indirect Coupling Via Spacer (Linker) Approaches:

Saccharide-OH+CNBr or CDAP→cyanate ester+NH2—NH2→saccharide-NH2+COOH-Prot+EDAC→conjugate Saccharide-OH+CNBr or CDAP→cyanate ester+NH2—SH→saccharide-SH+SH-Prot (native Protein with an exposed cysteine or obtained after modification of amino groups of the protein by SPDP for instance)→saccharide-S—S-Prot Saccharide-OH+CNBr or CDAP→cyanate ester+NH2—SH→saccharide-SH+maleimide-Prot (modification of amino groups)→conjugate Saccharide-OH+CNBr or CDAP→cyanate ester+NH2—SH→Saccharide-SH+haloacetylated-Prot→Conjugate Saccharide-COOH+EDAC+NH2—NH2→saccharide-NH2+EDAC+COOH-Prot→conjugate Saccharide-COOH+EDAC+NH2—SH→saccharide-SH+SH-Prot (native Protein with an exposed cysteine or obtained after modification of amino groups of the protein by SPDP for instance)→saccharide-S—S-Prot Saccharide-COOH+EDAC+NH2—SH→saccharide-SH+maleimide-Prot (modification of amino groups)→conjugate Saccharide-COOH+EDAC+NH2—SH→Saccharide-SH+haloacetylated-Prot→Conjugate Saccharide-Aldehyde+NH2—NH2→saccharide-NH2+EDAC+COOH-Prot→conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues.

In one embodiment at least 1, 2, 3, 4, 5, 6, 7, 8, 9, 10, 11, 12, 13, 14, 15, 16, 17, 18, 19, 20, 21, 22, or 23 S. pneumoniae saccharides are conjugated to a carrier protein through reductive amination. In one embodiment less than 23, 22, 21, 20, 19, 18, 17, 16, 15, 14, 13, 12, 11, 10, 9, 8, 7, 6, 5, 4, 3, 2 or 1 S. pneumoniae saccharides are conjugated to a carrier protein through reductive amination. In one embodiment between 1 and 23, 2 and 22, 3 and 21, 4 and 20, 5 and 19, 6 and 18, 7 and 17, 8 and 16, 9 and 15, 10 and 14, 11 and 13, 1 and 23, and 22, 1 and 21, 1 and 20, 1 and 19, 1 and 18, 1 and 17, 1 and 16, 1 and 15, 1 and 14, 1 and 13, 1 and 12, 1 and 11, 1 and 10, 1 and 9, 1 and 8, 1 and 7, 1 and 6, 1 and 5, 1 and 4, 1 and 3, or 1 or 2 S. pneumoniae saccharides are conjugated to a carrier protein through reductive amination. In a further embodiment all of the S. pneumoniae capsular saccharides are conjugated to a carrier protein through reductive amination.

In one embodiment at least 1, 2, 3, 4, 5, 6, 7, 8, 9, 10, 11, 12, 13, 14, 15, 16, 17, 18, 19, 20, 21, 22, or 23 S. pneumoniae saccharides are conjugated to a carrier protein through CDAP chemistry. In one embodiment less than 23, 22, 21, 20, 19, 18, 17, 16, 15, 14, 13, 12, 11, 10, 9, 8, 7, 6, 5, 4, 3, 2 or 1 S. pneumoniae saccharides are conjugated to a carrier protein through CDAP chemistry. In one embodiment between 1 and 23, 2 and 22, 3 and 21, 4 and 20, 5 and 19, 6 and 18, 7 and 17, 8 and 16, 9 and 15, 10 and 14, 11 and 13, 1 and 23, and 22, 1 and 21, and 23, 10 and 22, 10 and 21, 10 and 20, 10 and 19, 10 and 18, 10 and 17, 10 and 16, 10 and 15, 10 and 14, 10 and 13, 10 and 12, 10 and 11, 1 and 20, 1 and 19, 1 and 18, 1 and 17, 1 and 16, 1 and 15, 1 and 14, 1 and 13, 1 and 12, 1 and 11, 1 and 10, 1 and 9, 1 and 8, 1 and 7, 1 and 6, 1 and 5, 1 and 4, 1 and 3, or 1 or 2 S. pneumoniae saccharides are conjugated to a carrier protein through CDAP chemistry. In a further embodiment all of the S. pneumoniae capsular saccharides are conjugated to a carrier protein through CDAP chemistry.

In one embodiment the immunogenic composition of the invention comprises at least 1, 2, 3, 4, 5, 6, 7, 8, 9, 10, 11, 12, 13, 14, 15, 16, 17, 18, 19, 20, 21 or 22 saccharides conjugated to a carrier protein through reductive amination and comprises at least 1, 2, 3, 4, 5, 6, 7, 8, 9, 10, 11, 12, 13, 14, 15, 16, 17, 18, 19, 20, 21, or 22 saccharides conjugated to a carrier protein through a chemistry other than reductive amination for example CDAP chemistry.

In an embodiment capsular saccharides from at least one of the serotypes selected from the group consisting of serotypes 1, 3, 19A and 19F are conjugated through a chemistry other than reductive amination and at least one of the serotypes selected from the group consisting of serotypes 4, 5, 6A, 6B, 6C, 7F, 9V, 14, 18C and 23F are conjugated through reductive amination. In an embodiment, the immunogenic composition of the invention comprises S. pneumoniae capsular saccharide(s) from serotype 1 or 3 or 19A or 19F; 1 and 3; 1 and 19A; 1 and 19F; 3 and 19A; 3 and 19F; 19A and 19F; 1, 3 and 19A; 1, 3 and 19F, 1, 19A and 19F; 3, 19A and 19F or 1, 3, 19A and 19F conjugated to a protein carrier through a chemistry other than reductive animation. In an embodiment, 19F is conjugated to a carrier protein through a chemistry other than reductive amination. In an embodiment, the immunogenic composition of the invention comprises S. pneumoniae capsular saccharide from serotype 1 or 3 or 19A or 19F; 1 and 3; 1 and 19A; 1 and 19F; 3 and 19A; 3 and 19F; 19A and 19F; 1, 3 and 19A; 1, 3 and 19F, 1, 19A and 19F; 3, 19A and 19F or 1, 3, 19A and 19F conjugated to a protein carrier through cyanylation chemistry such as CDAP chemistry. In an embodiment, 19F is conjugated to a carrier protein by CDAP chemistry. In an embodiment of the invention, the following S. pneumoniae capsular saccharide or saccharides is/are conjugated to a carrier protein by reductive amination; serotype 4, 5, 6A, 6B, 7F, 9V, 14, 18C or 23F, 4 and 5, 4 and 6A, 4 and 6B, 4 and 7F, 4 and 9V, 4 and 14, 4 and 18C, 4 and 23F, 5 and 6A, 5 and 6B, 5 and 7F, 5 and 9V, 5 and 14, 5 and 18C, 5 and 23F, 6A and 6B, 6A and 7F, 6A and 9V, 6A and 14, 6A and 18C, 6A and 23F, 6B and 7F, 6B and 9V, 6B and 14, 6B and 18C, 6B and 23F, 7F and 9V, 7F and 14, 7F and 18C, 7F and 23F, 9V and 14, 9V and 18C, 9V and 23F, 14 and 18C, 14 and 23F or 18C and 23F. In an embodiment, serotype 23F is conjugated to a carrier protein by reductive amination chemistry.

Unconjugated or Conjugated Streptococcus pneumoniae Protein

The immunogenic compositions of the invention may comprise at least one unconjugated or conjugated S. pneu-

*moniae* protein. In one embodiment the at least one unconjugated or conjugated *S. pneumoniae* protein is selected from the group consisting of Poly Histidine Triad family (PhtX), detoxified pneumolysin (dPly), Choline Binding Protein Family (CbpX), CbpX truncates, LytX (autolytic enzymes) family, LytX truncates, CbpX truncate-LytX truncate chimeric proteins, PcpA (Pneumococcal Choline Binding protein A), PspA (Pneumococcal Surface Protein A), PsaA (Pneumococcal Surface Adhesin Protein A), Sp128, Sp101 (*Streptococcus pneumoniae* 101), Sp130 (*Streptococcus pneumoniae* 130), SP125 (*Streptococcus pneumoniae* 125) and SP133 (*Streptococcus pneumoniae* 133).

The Pht (Poly Histidine Triad) family comprises proteins PhtA, PhtB, PhtD, and PhtE. Note that the Pht family can be referred to as either the Poly Histidine Triad family or the Pneumococcal Histidine Triad family, thus the terms 'Poly Histidine Triad' and 'Pneumococcal Histidine Triad' can be considered to be interchangeable. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and *Neisseria*. In one embodiment of the invention, the Pht protein of the invention is PhtD. It is understood, however, that the terms PhtA, PhtB, PhtD and PhtE refer to proteins having sequences disclosed in the citations below as well as naturally-occurring (and man-made) variants thereof that have a sequence homology that is at least 90% identical to the referenced proteins. Optionally it is at least 95% identical or at least 97% identical.

With regards to the PhtX proteins, PhtA is disclosed in WO 98/18930, and is also referred to Sp36. As noted above, it is a protein from the Pht family and has the type II signal motif of LXXC. PhtD is disclosed in WO 00/37105, and is also referred to Sp036D. As noted above, it also is a protein from the Pht family and has the type II LXXC signal motif. In one embodiment the term 'PhtD' refers to SEQ ID NO:220. PhtB is disclosed in WO 00/37105, and is also referred to Sp036B. Another member of the PhtB family is the C3-Degrading Polypeptide, as disclosed in WO 00/17370. This protein also is from the Pht family and has the type II LXXC signal motif. For example, an immunologically functional equivalent is the protein Sp42 disclosed in WO 98/18930. A PhtB truncate (approximately 79 kD) is disclosed in WO99/15675 which is also considered a member of the Pht family. PhtE is disclosed in WO00/39299 and is referred to as BVH-3. Where any Pht protein is referred to herein, it is meant that immunogenic fragments or fusions thereof of the Pht protein can be used. For example, a reference to PhtX includes immunogenic fragments or fusions thereof from any Pht protein. A reference to PhtD or PhtB does not exclude PhtDE (a fusion protein comprising PhtD and PhtE) or PhtBE (a fusion protein comprising PhtB and PhtE), respectively, as found, for example, in WO0198334.

In one embodiment the at least one unconjugated to conjugated *Streptococccus pneumoniae* protein comprises at least one protein from the Poly histidine Triad family (for example, the protein may be selected from the group consisting of PhtD, PhtBD and PhtDE fusion protein). In a further embodiment the at least one unconjugated or conjugated *Streptococcus pneumoniae* protein is a PhtD protein. In a further embodiment the PhtD protein comprises an amino acid sequence at least 85%, 90%, 95%, 98%, 99% or 100% identical to the sequence at amino acids 21-838 of Sequence ID No. 4 of WO00/37105.

In one embodiment the at least one unconjugated or conjugated *Streptococcus pneumoniae* protein is detoxified pneumolysin (dPly). In one embodiment the pneumolysin has been chemically detoxified. In a further embodiment the pneumolysin has been chemically detoxified. In a yet further embodiment the pneumolysin has been both chemically and genetically detoxified.

In a further embodiment the immunogenic composition of the invention comprises detoxified pneumolysin (dPly) and PhtD. In a further embodiment the immunogenic composition of the invention comprises unconjugated detoxified pneumolysin (dPly) and unconjugated PhtD.

Concerning the Choline Binding Protein family (CbpX), members of that family were originally identified as pneumococcal proteins that could be purified by choline-affinity chromatography. The choline binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions (R1 and/or R2), a proline rich region (P) and a conserved choline binding region (C), made up of multiple repeats, that comprises approximately one half of the protein. As used in this application, the term "Choline Binding Protein family (CbpX)" includes proteins from the group consisting of Choline Binding Proteins as identified in WO97/41151, PbcA, SpsA, PspC, CbpA, CbpD and CbpG. CbpA is disclosed in WO97/41151. CbpD and CbpG are disclosed in WO00/29434. PspC is disclosed in WO97/09994. PbcA is disclosed in WO98/21337.5 psA is a choline binding protein disclosed in WO 98/39450. Optionally the Choline Binding Proteins are selected from the group consisting of CbpA, PbcA, SpsA and PspC.

An embodiment of the invention comprises CbpX truncates wherein "CbpX" is defined above and "truncates" refers to CbpX proteins lacking 50% or more of the Choline binding region (C). Optionally such proteins lack the entire choline binding region. Optionally, the protein truncates lack (i) the choline binding region and (ii) a portion of the N-terminal half of the protein as well, yet retain at least one repeat region (R1 or R2). Optionally, the truncate retains 2 repeat regions (R1 and R2). Examples of such embodiments are NR1×R2 and R1×R2 as illustrated in WO99/51266 or WO99/51188, however, other choline binding proteins lacking a similar choline binding region are also contemplated within the scope of this invention.

The LytX family is membrane associated proteins associated with cell lysis. The N-terminal domain comprises choline binding domain(s). However the LytX family does not have all the features found in the CbpX family noted above. For the present invention, the LytX family is considered distinct from the CbpX family. In contrast with the CbpX family, the LytX family C-terminal domain contains the catalytic domain of the LytX protein. The family comprises LytA, LytB and LytC. With regards to the LytX family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. An embodiment of the invention comprises LytC.

Another embodiment comprises LytX truncates wherein "LytX" is defined above and "truncates" refers to LytX proteins lacking 50% or more of the Choline binding region.

Optionally such proteins lack the entire choline binding region. Yet another embodiment of this invention comprises CbpX truncate-LytX truncate chimeric proteins or fusion-proteins. Optionally the fusion protein comprises NR1×R2 (or R1×R2) of CbpX and the C-terminal portion (Cterm, i.e., the protein without the choline binding domains) of LytX (e.g., LytCCterm or Sp91Cterm). Optionally CbpX is selected from the group consisting of CbpA, PbcA, SpsA and PspC. Optionally, it is CbpA. Optionally, LytX is LytC (also referred to as Sp91). Another embodiment of the present invention is a PspA or PsaA truncate lacking the choline binding domain (C) and expressed as a fusion protein with LytX. Optionally, LytX is LytC.

With regards to PsaA and PspA, both are discussed in the art. For example, PsaA and transmembrane deletion variants thereof have been described by Berry & Paton, Infect Immun 1996 December; 64(12):5255-62. PspA and transmembrane deletion variants thereof have been described in, for example, U.S. Pat. No. 5,804,193, WO 92/14488, and WO 99/53940.

With regards to PcpA, this protein has been described in the art, for example PcpA has been described in WO2011/075823. The term 'PcpA' refers to a protein comprising at least 80%, 85%, 90%, 95%, 98%, 99% or 100% identical to SEQ ID NO:2 or 7 from WO2011/075823 or fragments of at least 100, 150, 200, 25 or more consecutive amino acids of SEQ ID NO:2 or 7 from WO2011/075823.

Sp128 and Sp130 are disclosed in WO00/76540. Sp125 is an example of a pneumococcal surface protein with the Cell Wall Anchored motif of LPXTG (where X is any amino acid). Proteins within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase. Sp101 is disclosed in WO 98/06734 (where it has the reference #y85993). It is characterized by a Type I signal sequence. Sp133 is disclosed in WO 98/06734 (where it has the reference #y85992). It is also characterized by a Type I signal sequence.

Any of these further *S. pneumoniae* proteins may be present is an unconjugated or conjugated form. One or more *S. pneumoniae* proteins is optionally conjugated to an *S. pneumoniae* saccharide (described in the section entitled *Streptococcus pneumoniae* capsular saccharide conjugates above). Optionally one or more *S. pneumoniae* proteins is conjugated to a saccharide from a different bacterium.

The term 'conjugated to' in this context means that the protein is covalently bonded to a saccharide, in this situation the protein is acting as a carrier protein.

In an embodiment the at least one further unconjugated or conjugated *S. pneumoniae* protein comprises a Poly Histidine family (PhtX) protein selected from the group consisting of PhtB, PhtE, PhtA, PhtBD and PhtDE.

Adjuvants

In one embodiment the immunogenic composition further comprises an adjuvant.

Suitable adjuvants include, but are not limited to, aluminium salts (for example, aluminium phosphate or aluminium hydroxide), monophosphoryl lipid A (for example 3D-MPL), saponins (for example QS21), oil in water emulsions, blebs or outer membrane vesicle preparations from Gram negative bacterial strains (such as those taught by WO02/09746), lipid A or derivatives thereof, alkyl glucosamide phosphates or combinations of two or more of these adjuvants. In one embodiment the adjuvant is aluminium phosphate. In a further embodiment the adjuvant comprises 100-750, 150-600, 200-500, 250-450, 300-400, or around 350 μg aluminium as aluminium phosphate per human dose.

Vaccines

The present invention provides a vaccine comprising the immunogenic compositions of the invention. Embodiments herein relating to "immunogenic compositions" of the invention are also applicable to embodiments relating to "vaccines" of the invention, and vice versa. In an embodiment, the vaccine comprises the immunogenic composition of the invention and a pharmaceutically acceptable excipient.

The vaccines of the invention may be administered by any suitable delivery route, such as intradermal, mucosal e.g. intranasal, oral, intramuscular or subcutaneous. Other delivery routes are well known in the art. Vaccine preparation is generally described in Vaccine Design ("The subunit and adjuvant approach" (eds Powell M. F. & Newman M. J.) (1995) Plenum Press New York).

In one aspect, the immunogenic composition of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

A further aspect of the invention is a method of making a vaccine of the invention comprising the steps of mixing the unconjugated *S. pneumoniae* protein with the adjuvant composition.

In one aspect of the invention there is provided a method of immunizing a subject against diseases caused by *Streptococcus pneumoniae* infection comprising administering to the subject a therapeutically effective dose of the immunogenic composition or vaccine of the invention. In a further aspect of the invention there is provided a method of immunizing a subject against diseases caused by *Haemophilus influenzae* infection comprising administering to the subject a therapeutically effective dose of the immunogenic composition or vaccine of the invention. In a further embodiment there is provided a method of immunizing a subject against diseases caused by *Streptococcus pneumoniae* and *Haemophilus influenzae* infection comprising administering to the subject a therapeutically effective dose of the immunogenic composition or vaccine of the invention. In one embodiment the diseases comprise at least one disease selected from the group consisting of pneumonia, invasive pneumococcal disease (IPD), exacerbations of chronic obstructive pulmonary disease (COPD), otitis media, meningitis, bacteraemia, and conjunctivitis. In one embodiment the subject is a mammalian subject. In a further embodiment the mammalian subject is selected from the group consisting of mouse, guinea pig and human. In one embodiment the subject is an adult human, optionally an elderly human. In a further embodiment the subject is an infant human.

In a further aspect of the invention is provided an immunogenic composition or vaccine of the invention for use in the treatment or prevention of disease caused by *Streptococcus pneumoniae* infection. In a further aspect of the invention there is provided an immunogenic composition or vaccine of the invention for use in the treatment or prevention of disease caused by *Haemophilus influenzae* infection. In a further embodiment there is provided an immunogenic composition or vaccine of the invention for use in the treatment or prevention of disease caused by *Streptococcus pneumoniae* and *Haemophilus influenzae* infection. In one embodiment the use comprises administration of the immunogenic composition to an adult human host, optionally an elderly human host. In a further embodiment the use comprises administration of the immunogenic composition to an infant host. In a further embodiment the diseases comprise at least one disease selected from the group consisting of pneumonia, invasive pneumococcal disease (IPD), exacerbations of chronic obstructive pulmonary disease (COPD), otitis media, meningitis, bacteraemia, and conjunctivitis.

In a further aspect of the invention there is provided a use of the immunogenic composition or vaccine of the invention in the manufacture of a medicament for the treatment or prevention of diseases caused by *Streptococcus pneumoniae* infection. In a further aspect of the invention there is provided of use of the immunogenic composition or vaccine of the invention in the manufacture of a medicament for the treatment or prevention of diseases caused by *Haemophilus influenzae* infection. In a further embodiment there is provided a use of the immunogenic composition or vaccine of the invention in the manufacture of a medicament for the treatment or prevention of diseases caused by *Haemophilus influenzae* and *Streptococcus pneumoniae* infection. In one embodiment the diseases comprise at least one disease selected from the group consisting of pneumonia, invasive pneumococcal disease (IPD), exacerbations of chronic obstructive pulmonary disease (COPD), otitis media, meningitis, bacteraemia, and conjunctivitis, In one embodiment the use comprises administration of the immunogenic composition or vaccine of the invention to a host selected from the group consisting of an adult human host, an elderly human host and an infant human host.

Fusion proteins of formula (I) and *Streptococcus pneumoniae* capsular saccharide conjugates are useful as immunogens in subjects such as mammals, particularly humans. In particular, the fusion proteins of formula (I) and *Streptococcus pneumoniae* capsular saccharide conjugates are useful in inducing an immune response against *H. influenzae* in subjects, particularly humans. Additionally, the fusion proteins of formula (I) and *Streptococcus pneumoniae* capsular saccharide conjugates are useful in inducing an immune response against *Streptococcus pneumoniae* in subjects, particularly humans. More specifically, the fusion proteins of formula (I) are useful in the treatment or prevention of otitis media and/or AECOPD and/or pneumonia.

In one embodiment, the invention further provides a method for the treatment or prevention of otitis media in a subject in need thereof comprising administering to said subject a therapeutically effective amount of an immunogenic composition comprising the fusion proteins of formula (I) and *Streptococcus pneumoniae* capsular saccharide conjugates as described herein. In another embodiment, the invention provides a method for the treatment or prevention of acute exacerbations of chronic obstructive pulmonary disease (AECOPD) in a subject in need thereof comprising administering to said subject a therapeutically effective amount of an immunogenic composition comprising the fusion proteins of formula (I) and *Streptococcus pneumoniae* capsular saccharide conjugates as described herein.

In another embodiment, the invention provides a method for the treatment or prevention of pneumonia in a subject in need thereof comprising administering to said subject a therapeutically effective amount of an immunogenic composition comprising the fusion proteins of formula (I) and *Streptococcus pneumoniae* capsular saccharide conjugates as described herein.

In another embodiment, the invention provides a method for the treatment or prevention of a *H. influenzae* infection or disease in a subject in need thereof, said method comprising administering to said subject a therapeutically effective amount of an immunogenic composition comprising the fusion proteins of formula (I) and *Streptococcus pneumoniae* capsular saccharide conjugates as described herein.

In another embodiment, the invention provides a method for the treatment or prevention of a *S. pneumoniae* infection or disease in a subject in need thereof, said method comprising administering to said subject a therapeutically effective amount of an immunogenic composition comprising the fusion proteins of formula (I) and *Streptococcus pneumoniae* capsular saccharide conjugates as described herein.

Further Definitions

Unless otherwise explained or defined herein, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen may be approximate. Thus, where a concentration is indicated to be (for example) approximately 200 pg, it is intended that the concentration includes values slightly more or slightly less than ("about" or "~") 200 pg Although methods and materials similar or equivalent to those described herein can be used in the practice or testing of this disclosure, suitable methods and materials are described below The term "comprises" means "includes". Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

A "subject" as used herein is a mammal, including humans, non-human primates, and non-primate mammals such as members of the rodent genus (including but not limited to mice and rats) and members of the order Lagomorpha (including but not limited to rabbits).

As used herein, "adjuvant" means a compound or substance that, when administered to a subject in conjunction with a vaccine, immunotherapeutic, or other antigen- or immunogen-containing composition, increases or enhances the subject's immune response to the administered antigen or immunogen (as compared to the immune response that would be obtained in the absence of adjuvant). This is to be distinguished from "adjuvant therapy", defined by the National Cancer Institute of the United States Institutes of Health in the context of cancer treatment as additional treatment given after the primary treatment, to lower the risk that the cancer will recur.

Conservative substitutions are well known and are generally set up as the default scoring matrices in sequence alignment computer programs. These programs include PAM250 (Dayhoft M. O. et al., (1978), "A model of evolutionary changes in proteins", In "Atlas of Protein sequence and structure" 5(3) M. O. Dayhoft (ed.), 345-352), National Biomedical Research Foundation, Washington, and Blosum 62 (Steven Henikoft and Jorja G. Henikoft (1992), "Amino acid substitution matrices from protein blocks"), *Proc. Natl. Acad. Sci. USA* 89 (Biochemistry): 10915-10919. The invention further provides fusion proteins of formula (I) containing conservative amino acid substitutions. For example, the fusion proteins of formula (I) may contain a conservative substitution of any amino acid from PE or PilA of *H. influenzae* as described in any of the sequences set forth herein (for example, any PE sequence set forth in SEQ ID NO. 4-SEQ ID NO. 57 and/or any PilA sequence set forth in SEQ ID NO. 58-SEQ ID NO. 121)

As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide.

A heterologous signal peptide may be cleaved from a fusion protein construct by signal peptide peptidases during or after protein transportation or secretion. For example, the signal peptide peptidase is signal peptide peptidase I. A "heterologous" signal peptide is one which is not associated with the protein as it exists in nature.

As used herein "treatment" means the prevention of occurrence of symptoms of the condition or disease in a subject, the prevention of recurrence of symptoms of the condition or disease in a subject, the delay of recurrence of symptoms of the condition or disease in a subject, the decrease in severity or frequency of symptoms of the condition or disease in a subject, slowing or eliminating the progression of the condition and the partial or total elimination of symptoms of the disease or condition in a subject.

As used herein, "optionally" means that the subsequently described event(s) may or may not occur, and includes both event(s) that occur and events that do not occur.

All references or patent applications cited within this patent specification are incorporated by reference herein.

As used herein 'infant' refers to a human 0-2 years old.

As used herein 'adult' refers to a human more than 18 years old.

As used herein 'elderly adult' refers to a human more than 60 years old, optionally more than 65 years old.

EXAMPLES

In the examples, the following terms have the designated meaning:

6×his=six histidines;
xg=centrifugal force (number gravities)
ATP=adenosine triphosphate;
BCA=bicinchoninic acid;
BSA=bovine serum albumin;
° C.=degrees Celsius;
$CaCl_2$=calcium chloride;
CV=column volume;
DNA=deoxyribonucleic acid;
DSC=differential scanning calorimetry;
DTT=dithiothreitol;
dNTP=deoxynucleoside triphosphate;
EDTA=ethylenediaminetetraacetic acid;
FT=flow through;
HCl=hydrogen chloride;
His=his=histidine;
HEPES=4-(2-hydroxyethyl)-1-piperazineethanesulfonic acid;
IMAC=immobilized metal affinity chromatography;
IPTG=isopropyl β-D-1-thiogalactopyranoside;
KCl=potassium chloride;
$K_2HPO_4$=dibasic potassium phosphate;
$KH_2PO_4$=monobasic potassium phosphate;
LDS=lithium dodecyl sulfate;
L=liter;
MES=2-(N-morpholino)ethanesulfonic acid;
$MgCl_2$=magnesium chloride;
ml=milliliter;
RPM=revolutions per minute;
min=minute;
mM=millimolar;
μL=microliter;
NaCl=sodium chloride;
$Na_2HPO_4$=dibasic sodium phosphate;
$NaH_2PO_4$=monobasic sodium phosphate;
ng=nanogram;
nm=nanometer;
O/N=overnight;
PBS=phosphate buffered saline;
PCR=polymerase chain reaction;
SB=sample buffer;
sec=second;
w/v=weight/volume
PS=polysaccharide and may be used interchangeably with the term 'saccharide'.

1. EXAMPLES

Example 1

Fusion Proteins

Fusion proteins were produced with different signal peptides and amino acid linker sequences. These fusion proteins allowed for secretion of both Protein E and PilA (or fragments thereof) without being restricted to a single bacterial strain. The fusion protein is released into the periplasm after removal of the heterologous signal peptide by a signal peptide peptidase. Fusion protein purified from the bacteria does not contain the heterologous signal peptide. "Purified" proteins are removed from the bacteria and lack the signal peptide.

The following table describes fusion protein constructs made.

TABLE 3

Fusion Protein Constructs containing PilA and Protein E.

| ConstructID | N-terminal | | | | | | | C-Terminal |
|---|---|---|---|---|---|---|---|---|
| LVL312 | flgI sp | | E | ProtE fragment (A.A.: 40-149 of SEQ ID NO. 58, SEQ ID NO. 127) | G G | PilA fragment (A.A.: 18 to 160 of SEQ ID NO. 4, SEQ ID NO. 2) | | GGHHHH HH |
| A.A. | 1 | | 19 | 21                              130 | 133 | 275 | | 276     283 |
| LVL291 | peIB sp | | | ProtE fragment (A.A.: 19 to 160 of SEQ ID NO. 4, SEQ ID NO. 124) | G G | PilA fragment (A.A.: 40.149 of SEQ ID NO. 58, SEQ ID NO. 127) | | GGHHHH HH |
| A.A. | 1 | | 22 | 23                              164 | 167 | 276 | | 277     284 |
| LVL268 | peIB sp | | D | ProtE fragment (A.A.: 20 to 160 of SEQ ID NO. 4, SEQ ID NO. 125) | G G | PilA fragment (A.A.: 40-149 of SEQ ID NO. 58, SEQ ID NO. 127) | | GGHHHH HH |
| A.A. | 1 | | 22 | 24                              164 | 167 | 276 | | 277     284 |
| LVL269 | nadA sp | | AT ND DD | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) | | GGHHH HHH |
| A.A. | 1 | | 23  24-29 | 30                              168 | 171 | 280 | | 281     288 |
| LVL270 | M HH HH HH | | | ProtE fragment (A.A.: 17 to 160 of SEQ ID NO. 4, SEQ ID NO. 122) | G G | PilA fragment (A.A.: 40-149 of SEQ ID NO. 58, SEQ ID NO. 127) | | |
| A.A. | 1 | | | 7  8                            151 | 154 | | | 263 |
| LVL315 | peIB sp | | M D | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) | | GGHHHHHH |
| | 1 | | 22 | 25                              163 | 166 | 275 | | 276     283 |
| LVL317 | peIB sp | | | ProtE fragment (A.A.: 19 to 160 of SEQ ID NO. 4, SEQ ID NO. 124) | G G | PilA fragment (A.A.: 40-149 of SEQ ID NO. 58, SEQ ID NO. 127) | | |
| A.A. | 1 | | | 22  23                          164 | 167 | | | 276 |
| LVL318 | peIB sp | | M D | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) | | |
| A.A. | 1 | | 22 | 25                              163 | 166 | | | 275 |
| LVL702 | peIB sp | | | ProtE fragment (A.A.: 20 to 160 of SEQ ID NO. 4, SEQ ID NO. 125) | G G | PilA fragment (A.A.: 40-149 of SEQ ID NO. 58, SEQ ID NO 127) | | GGHHHHH H |
| A.A. | 1 | | | 22  23                          163 | 166 | 275 | | 283 |
| LVL736 | peIB sp | | | ProtE fragment (A.A.: 17 to 160 of SEQ ID NO. 4, SEQ ID NO. 122) | G G | PilA fragment (A.A.: 40-149 of SEQ ID NO. 58, SEQ ID NO 127) | | GG HH HH HH |
| A.A. | 1 | | | 22  23                          166 | 169 | 278 | | 286 |
| LVL737 | peIB sp | | | ProtE fragment (AA.: 18 to 160 of SEQ ID NO. 4, SEQ ID NO. 123) | G G | PilA fragment (A.A.: 40-149 of SEQ ID NO. 58, SEQ ID NO. 127) | | GGH HHH HH |
| A.A. | 1 | | | 22  23                          165 | 168 | 277 | | 285 |
| LVL738 | peIB sp | | | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) | | GGHHHHHH |
| A.A. | 1 | | | 22  23                          161 | 164 | 273 | | 281 |

TABLE 3-continued

Fusion Protein Constructs containing PiIA and Protein E.

| ConstructID | N-terminal | | | | | C-Terminal |
|---|---|---|---|---|---|---|
| LVL739 | peIB sp | ProtE fragment (A.A.: 23 to 160 of SEQ ID NO. 4, SEQ ID NO. 179) | G G | PiIA fragment (A.A.: 40-149 of SEQ ID NO. 58, SEQ ID NO. 127) | | GG HHRH HH |
| A.A. | 1 | 22 23 | 160 | 163 | | 272 280 |
| LVL740 | peIB sp | ProtE fragment (A.A.: 24 to 160 of SEQ ID NO. 4, SEQ ID NO. 180) | G G | PiIA fragment (A.A.: 40-149 of SEQ ID NO. 58, SEQ ID NO. 127) | | GGHHHHH H |
| A.A. | | 22 23 | 159 | 162 | | 271 279 |
| LVL735 | peIB sp | ProtE fragment (A.A.: 20 to 160 of SEQ ID NO. 4, SEQ ID NO. 125) | | G G | PiIA fragment (A.A.: 40-149 of SEQ ID NO. 58, SEQ ID NO. 127) | |
| A.A. | 1 | 22 23 | | 163 | 166 | 275 |
| LVL778 | peIB sp | ProtE fragment (A.A.: 17 to 160 of SEQ ID NO. 4, SEQ ID NO. 122) | | G G | PiIA fragment (A.A.: 40-149 of SEQ ID NO. 58, SEQ ID NO. 127) | |
| A.A. | 1 | 22 23 | | 166 | 169 | 278 |
| LVL779 | peIB sp | ProtE fragment (A.A.: 18 to 160 of SEQ ID NO. 4, SEQ ID NO. 123) | | G G | PiIA fragment (A.A.: 40-149 of SEQ ID NO. 58, SEQ ID NO. 127) | |
| A.A. | 1 | 22 23 | | 165 | 168 | 277 |
| LVL780 | peIB sp | ProtE fragment (A.A.: 22 to 160 of SEQ ID NO. 4, SEQ ID NO. 126) | | G G | PiIA fragment (A.A.: 40-149 of SEQ ID NO. 58, SEQ ID NO. 127) | |
| A.A. | 1 | 22 23 | | 161 | 164 | 273 |
| LVL781 | peIB sp | ProtE fragment (A.A.: 23 to 160 of SEQ ID NO. 4, SEQ ID NO. 179) | | G G | PiIA fragment (A.A.: 40-149 of SEQ ID NO. 58, SEQ ID NO. 127) | |
| A.A. | 1 | 22 23 | | 160 | 163 | 272 |
| LVL782 | peIB sp | ProtE fragment (A.A.: 24 to 160 of SEQ ID NO. 4, SEQ ID NO. 180) | | G G | PiIA fragment (A.A.: 40-149 of SEQ ID NO. 58, SEQ ID NO. 127) | |
| A.A. | 1 | 22 23 | | 159 | 162 | 271 | sp = signal peptide;
A.A. = amino acid
The DNA and amino acid sequences for each of the signal peptides and plasmids listed in Table 3 are set forth below.

Signal Sequences:

```
pelB signal peptide (DNA) - SEQ ID NO. 129:
atgaaatacctgctgccgaccgctgctgctggtctgctgctcctcgctgc ccagccggcgatggcc pelB signal peptide (Amino Acid) - SEQ ID NO. 130:
MKYLLPTAAA GLLLLAAQPA MA FlgI signal peptide (DNA) - SEQ ID NO. 131:
atgattaaatttctctctgcattaattcttctactggtcacgacggcggc tcaggct FlgI signal peptide (Amino Acid) - SEQ ID NO. 132:
MIKFLSALIL LLVTTAAQA
```

```
NadA signal peptide (DNA) - SEQ ID NO. 133:
atgaaacactttccatccaaagtactgaccacagccatccttgccactttt ctgtagcggcgcactggca NadA signal peptide (Amino Acid) - SEQ ID NO. 134:
MKHFPSKVLT TAILATFCSG ALA
```

Fusion Protein Construct Sequences:

The single underlined portion of the amino acid sequences is from PilA from *Haemophilus influenzae* strain 86-028NP. The embolded underlined portion of the amino acid sequences was derived from Protein E from *Haemophilus influenza* strain 772.

LVL312 (DNA) - SEQ ID NO. 135:
atgattaaatttctctctgcattaattcttctactggtcacgacggcggctcaggctgagactaaaaaagcagcggtatctgaattactg caagcgtcagcgccttataaggctgatgtggaattatgtgtatatagcacaaatgaaacaacaaactgtacgggtggaaaaaatg gtattgcagcagatataaccacagcaaaaggctatgtaaaatcagtgacaacaagcaacggtgcaataacagtaaaagggggat ggcacattggcaaatatggaatatattttgcaagctacaggtaatgctgcaacaggtgtaacttggacaacaacttgcaaaggaac ggatgcctcttatttccagcaaattttttgcggaagtgtcacacaaggcggcgcgcagattcagaaggctgaacaaaatgatgtgaa gctggcaccgccgactgatgtacgaagcggatatatacgtttggtaaagaatgtgaattattacatcgatagtgaatcgatctgggtg gataaccaagagccacaaattgtacattttgatgcagtggtgaatttagataagggattgtatgthatcctgagcctaaacgttatgca cgttctgttcgtcagtataagatcttgaattgtgcaaattatcatttaactcaagtacgaactgatttctatgatgaattttggggacagggt ttgcgggcagcacctaaaaagcaaaagaaacatacgttaagtttaacacctgatacaacgctttataatgctgctcagattatttgtg cgaactatggtgaagcattttcagttgataaaaaaggcggccaccaccaccaccaccactaa LVL312 (protein): (flgI sp)(E)(PilA aa 40-149)(GG)(ProtE aa 18-160)(GGHHHHHH) - SEQ ID NO. 136
MIKFLSALIL LLVTTAAQAE <u>TKKAAVSELL QASAPYKADV ELCVYSTNET TNCTGGKNGI</u>

<u>AADITTAKGY VKSVTTSNGA ITVKGDGTLA NMEYILQATG NAATGVTWTT TCKGTDASLF</u>

<u>PANFCGSVTQ GGAQIQKAEQ NDVKLAPPTD VRSGYIRLVK NVNYYIDSES IWVDNQEPQI</u>

<u>VHFDAVVNLD KGLYVYPEPK RYARSVRQYK ILNCANYHLT QVRTDFYDEF</u>

<u>WGQGLRAAPK KQKKHTLSLT PDTTLYNAAQ IICANYGEAF SVDKKGGHHH HHH</u>

LVL291 (DNA) - SEQ ID NO. 137:
atgaaatacctgctgccgaccgctgctgctggtctgctgctcctcgctgcccagccggcgatggcccagattcagaaggctgaaca aaatgatgtgaagctggcaccgccgactgatgtacgaagcggatatatacgtttggtaaagaatgtgaattattacatcgatagtga atcgatctgggtggataaccaagagccacaaattgtacattttgatgcagtggtgaatttagataagggattgtatgtttatcctgagcc taaacgttatgcacgttctgttcgtcagtataagatcttgaattgtgcaaattatcatttaactcaagtacgaactgatttctatgatgaattt tggggacagggtttgcgggcagcacctaaaaagcaaaagaaacatacgttaagtttaacacctgatacaacgctttataatgctgc tcagattatttgtgcgaactatggtgaagcattttcagttgataaaaaaggcggcactaaaaaagcagcggtatctgaattactgcaa gcgtcagcgccttataaggctgatgtggaattatgtgtatatagcacaaatgaaacaacaaactgtacgggtggaaaaaatggtatt gcagcagatataaccacagcaaaaggctatgtaaaatcagtgacaacaagcaacggtgcaataacagtaaaagggggatggc acattggcaaatatggaatatattttgcaagctacaggtaatgctgcaacaggtgtaacttggacaacaacttgcaaaggaacgga tgcctcttatttccagcaaattttttgcggaagtgtcacacaaggcggccaccaccaccaccaccactaa LVL291 (Protein)(pelB sp)(ProtE aa 19-160)(GG)(PilA aa40-149)(GGHHHHHH) - SEQ ID NO. 138
MKYLLPTAAA GLLLLAAQPA MA<u>QIQKAEQN DVKLAPPTDV RSGYIRLVKN VNYYIDSESI</u>

<u>WVDNQEPQIV HFDAVVNLDK GLYVYPEPKR YARSVRQYKI LNCANYHLTQ</u>

<u>VRTDFYDEFW GQGLRAAPKK QKKHTLSLTP DTTLYNAAQI ICANYGEAFS VDKKGGTKKA</u>

<u>AVSELLQASA PYKADVELCV YSTNETTNCT GGKNGIAADI TTAKGYVKSV TTSNGAITVK</u>

<u>GDGTLANMEY ILQATGNAAT GVTWTTTCKG TDASLFPANF CGSVTQGGHH HHH</u>

LVL268 (DNA) - SEQ ID NO. 139:
atgaaatacctgctgccgaccgctgctgctggtctgctgctcctcgctgcccagccggcgatggccgatattcagaaggctgaaca aaatgatgtgaagctggcaccgccgactgatgtacgaagcggatatatacgtttggtaaagaatgtgaattattacatcgatagtga atcgatctgggtggataaccaagagccacaaattgtacattttgatgcagtggtgaatttagataagggattgtatgtttatcctgagcc taaacgttatgcacgttctgttcgtcagtataagatcttgaattgtgcaaattatcatttaactcaagtacgaactgatttctatgatgaattt tggggacagggtttgcgggcagcacctaaaaagcaaaagaaacatacgttaagtttaacacctgatacaacgctttataatgctgc tcagattatttgtgcgaactatggtgaagcattttcagttgataaaaaaggcggcactaaaaaagcagcggtatctgaattactgcaa gcgtcagcgccttataaggctgatgtggaattatgtgtatatagcacaaatgaaacaacaaactgtacgggtggaaaaaatggtatt gcagcagatataaccacagcaaaaggctatgtaaaatcagtgacaacaagcaacggtgcaataacagtaaaagggggatggc -continued acattggcaaatatggaatatattttgcaagctacaggtaatgctgcaacaggtgtaacttggacaacaacttgcaaaggaacgga tgcctctttatttccagcaaatttttgcggaagtgtcacacaaggcggccaccaccaccaccac LVL268 (protein): (pelB sp)(D)(ProtE aa 20-160)(GG)(PilA aa40-149)(GGHHHHHH) - SEQ ID NO. 140:
MKYLLPTAAA GLLLLAAQPA MAD<u>IQKAEQN DVKLAPPTDV RSGYIRLVKN VNYYIDSESI</u>

<u>WVDNQEPQIV HFDAVVNLDK GLYVYPEPKR YARSVRQYKL LNCANYHLTQ</u>

<u>VRTDFYDEFW GQGLRAAPKK QKKHTLSLTP DTTLYNAAQI ICANYGEAFS VDKKGGTKKA</u>

<u>AVSELLQASA PYKADVELCV YSTNETTNCT GGKNGIAADI TTAKGYVKSV TTSNGAITVK</u>

<u>GDGTLANMEY ILQATGNAAT GVTWTTTCKG TDASLFPANF CGSVTQ</u>GGHH HHHH

LVL269 (DNA) - SEQ ID NO. 141:
atgaaacactttccatccaaagtactgaccacagccatccttgccactttctgtagcggcgcactggcagccacaaacgacgacg ataaggctgaacaaaatgatgtgaagctggcaccgccgactgatgtacgaagcggatatatacgtttggtaaagaatgtgaattat tcatcgatagtgaatcgatctgggtggataaccaagagccacaaattgtacattttgatgcagtggtgaatttagataagggattgtat gtttatcctgagcctaaacgttatgcacgttctgttcgtcagtataagatcttgaattgtgcaaattatcatttaactcaagtacgaactgat ttctatgatgaattttggggacaggtttgcgggcagcacctaaaaagcaaaagaaacatacgttaagtttaacacctgatacaac gctttataatgctgctcagattatttgtgcgaactatggtgaagcattttcagttgataaaaaaggcggcactaaaaaagcagcggtat ctgaattactgcaagcgtcagcgccttataaggctgatgtggaattatgtgtatatagcacaaatgaaacaacaaactgtacgggtg gaaaaaatggtattgcagcagatataaccacagcaaaaggctatgtaaaatcagtgacaacaagcaacggtgcaataacagta aaaggggatggcacattggcaaatatggaatatattttgcaagctacaggtaatgctgcaacaggtgtaacttggacaacaacttg caaaggaacggatgcctctttatttccagcaaatttttgcggaagtgtcacacaaggcggccaccaccaccaccactaa LVL269 (protein): (nadA sp)(ATNDDD)(ProtE aa 22-160)(GG)(PilA aa 40-149)(GGHHHHHH) - SEQ ID NO. 142
MKHFPSKVLT TAILATFCSG ALAATNDDD<u>K AEQNDVKLAP PTDVRSGYIR LVKNVNYYID</u>

<u>SESIWVDNQE PQIVHFDAVV NLDKGLYVYP EPKRYARSVR QYKILNCANY HLTQVRTDFY</u>

<u>DEFWGQGLRA APKKQKKHTL SLTPDTTLYN AAQIICANYG EAFSVDKKGG TKKAAVSELL</u>

<u>QASAPYKADV ELCVYSTNET TNCTGGKNGI AADITTAKGY VKSVTTSNGA ITVKGDGTLA</u>

<u>NMEYILQATG NAATGVTWTT TCKGTDASLF PANFCGSVTQ</u> GGHHHHHH

LVL270 (DNA) - SEQ ID NO. 143:
atgcaccaccaccaccaccacagcgcgcagattcagaaggctgaacaaaatgatgtgaagctggcaccgccgactgatgtacg aagcggatatatacgtttggtaaagaatgtgaattattacatcgatagtgaatcgatctgggtggataaccaagagccacaaattgta cattttgatgcagtggtgaatttagataagggattgtatgtttatcctgagcctaaacgttatgcacgttctgttcgtcagtataagatcttg aattgtgcaaattatcatttaactcaagtacgaactgatttctatgatgaattttggggacaggtttgcggcagcacctaaaaagca aaagaaacatacgttaagtttaacacctgatacaacgctttataatgctgctcagattatttgtgcgaactatggtgaagcattttcagtt gataaaaaaggcggcactaaaaaagcagcggtatctgaattactgcaagcgtcagcgccttataaggctgatgtggaattatgtgt atatagcacaaatgaaacaacaaactgtacgggtggaaaaaatggtattgcagcagatataaccacagcaaaaggctatgtaa aatcagtgacaacaagcaacggtgcaataacagtaaaaggggatggcacattggcaaatatggaatatattttgcaagctacag gtaatgctgcaacaggtgtaacttggacaacaacttgcaaaggaacggatgcctctttatttccagcaaatttttgcggaagtgtcac acaataa LVL270 (protein): (MHHHHHH)(ProtE aa 17-160)(GG)(PilA aa40-149) - SEQ ID NO. 144:
MHHHHHH<u>SAQ IQKAEQNDVK LAPPTDVRSG YIRLVKNVNY YIDSESIWVD NQEPQINHFD</u>

<u>AVVNLDKGLY VYPEPKRYAR SVRQYKILNC ANYHLTQVRT DFYDEFWGQG</u>

<u>LRAAPKKQKK HTLSLTPDTT LYNAAQIICA NYGEAFSVDK KGGTKKAAVS ELLQASAPYK</u>

<u>ADVELCVYST NETTNCTGGK NGIAADITTA KGYVKSVTTS NGAITVKGDG TLANMEYILQ</u>

<u>ATGNAATGVT WTTTCKGTDA SLFPANFCGS VTQ</u>

LVL315 (DNA) - SEQ ID NO. 145:
atgaaatacctgctgccgaccgctgctgctggtctgctgctcctcgctgcccagccggcgatggccatggataaggctgaacaaaa
tgatgtgaagctggcaccgccgactgatgtacgaagcggatatatacgtttggtaaagaatgtgaattattacatcgatagtgaatcg
atctgggtggataaccaagagccacaaattgtacattttgatgcagtggtgaatttagataagggattgtatgtttatcctgagcctaaa
cgttatgcacgttctgttcgtcagtataagatcttgaattgtgcaaattatcatttaactcaagtacgaactgatttctatgatgaattttggg
gacagggtttgcgggcagcacctaaaaagcaaaagaaacatacgttaagtttaacacctgatacaacgctttataatgctgctcag
attatttgtgcgaactatggtgaacattttcagttgataaaaaaggcggcactaaaaaagcagcggtatctgaattactgcaagcgt
cagcgccttataaggctgatgtggaattatgtgtatatagcacaaatgaaacaacaaactgtacgggtgaaaaaatggtattgca
gcagatataaccacagcaaaaggctatgtaaaatcagtgacaacaagcaacggtgcaataacagtaaaaggggatggcacat
tggcaaatatggaatatattttgcaagctacaggtaatgctgcaacaggtgtaacttggacaacaacttgcaaaggaacggatgcc
tctttatttccagcaaattttttgcggaagtgtcacacaaggcggccaccaccaccaccaccactaa LVL315 (protein): (pelB sp)(MD)(ProtE aa 22-160)(GG)(PilA aa40-149)(GGHHHHHH) - SEQ
ID NO. 146:
MKYLLPTAAA GLLLLAAQPA MAMDKAEQND VKLAPPTDVR SGYIRLVKNV NYYIDSESIW

VDNQEPQIVH FDAVVNLDKG LYVYPEPKRY ARSVRQYKIL NCANYHLTQV

RTDFYDEFWG QGLRAAPKKQ KKHTLSLTPD TTLYNAAQII CANYGEAFSV DKKGGTKKAA

VSELLQASAP YKADVELCVY STNETTNCTG GKNGIAADIT TAKGYVKSVT TSNGAITVKG

DGTLANMEYI LQATGNAATG VTWTTTCKGT DASLFPANCF GSVTQGGHHH HHH

LVL317 (DNA) - SEQ ID NO. 147:
atgaaatacctgctgccgaccgctgctgctggtctgctgctcctcgctgcccagccggcgatggcccatgattcagaaggctgaaca
aaatgatgtgaagctggcaccgccgactgatgtacgaagcggatatatacgtttggtaaagaatgtgaattattacatcgatagtga
atcgatctgggtggataaccaagagccacaaattgtacattttgatgcagtggtgaatttagataagggattgtatgtttatcctgagcc
taaacgttatgcacgttctgttcgtcagtataagatcttgaattgtgcaaattatcatttaactcaagtacgaactgatttctatgatgaattt
tggggacagggtttgcgggcagcacctaaaaagcaaaagaaacatacgttaagtttaacacctgatacaacgctttataatgctgc
tcagattatttgtgcgaatatggtgaagcattttcagttgataaaaaaggcggcactaaaaaagcagcggtatctgaatactgcaa
gcgtcagcgccttataaggctgatgtggaattatgtgtatatagcacaaatgaaacaacaaactgtacgggtggaaaaaatggtatt
gcagcagatataaccacagcaaaaggctatgtaaaatcagtgacaacaagcaacggtgcaataacagtaaaaggggatggc
acattggcaaatatggaatatattttgcaagctacaggtaatgctgcaacaggtgtaacttggacaacaacttgcaaaggaacgga
tgcctctttatttccagcaaattttttgcggaagtgtcacacaataa LVL317 (protein): (pelB sp)(ProtE aa 19-160)(GG)(PilA aa40-149) - SEQ ID NO. 148:
MKYLLPTAAA GLLLLAAQPA MAQIQKAEQN DVKLAPPTDV RSGYIRLVKN VNYYIDSESI

WVDNQEPQIV HFDAVVNLDK GLYVYPEPKR YARSVRQYKI LNCANYHLTQ

VRTDFYDEFW GQGLRAAPKK QKKHTLSLTP DTTLYNAAQI ICANYGEAFS VDKKGGTKKA

AVSELLQASA PYKADVELCV YSTNETTNCT GGKNGIAADI TTAKGYVKSV TTSNGAITVK

GDGTLANMEY ILQATGNAAT GVTWTTTCKG TDASLFPANF CGSVTQ

LVL318 (DNA) - SEQ ID NO. 149:
atgaaatacctgctgccgaccgctgctgctggtctgctgctcctcgctgcccagccggcgatggccatggataaggctgaacaaaa
tgatgtgaagctggcaccgccgactgatgtacgaagcggatatatacgtttggtaaagaatgtgaattattacatcgatagtgaatcg
atctgggtggataaccaagagccacaaattgtacattttgatgcagtggtgaatttagataagggattgtatgtttatcctgagcctaaa
cgttatgcacgttctgttcgtcagtataagatcttgaattgtgcaaattatcatttaactcaagtacgaactgatttctatgatgaattttggg
gacagggtttgcgggcagcacctaaaaagcaaaagaaacatacgttaagtttaacacctgatacaacgctttataatgctgctcag
attatttgtgcgaactatggtgaagcattttcagttgataaaaaaggcggcactaaaaaagcagcggtatctgaattactgcaagcgt
cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacat tggcaaatatggaatatattttgcaagctacaggtaatgctgcaacaggtgtaacttggacaacaacttgcaaaggaacggatgcc tctttatttccagcaaattttgcggaagtgtcacacaataa LVL318 (protein): (pelB sp)(MD)(ProtE aa 22-160)(GG)(PilA aa40-149) - SEQ ID NO. 150:
MKYLLPTAAA GLLLLAAQPA MAMDKAEQND VKLAPPTDVR SGYIRLVKNV NYYIDSESIW

VDNQEPQIVH FDAVVNLDKG LYVYPEPKRY ARSVRQYKIL NCANYHLTQV

RTDFYDEFWG QGLRAAPKKQ KKHTLSLTPD TTLYNAAQII CANYGEAFSV DKKGGTKKAA

VSELLQASAP YKADVELCVY STNETTNCTG GKNGIAADIT TAKGYVKSVT TSNGAITVKG

DGTLANMEYI LQATGNAATG VTWTTTCKGT DASLFPANFC GSVTQ

LVL702 (DNA) - SEQ ID NO. 181:
atgaaatacctgctgccgaccgctgctgctggtctgctgctcctcgctgcccagccggcgatggccattcagaaggctgaacaaaa tgatgtgaagctggcaccgccgactgatgtacgaagcggatatatacgtttggtaaagaatgtgaattattacatcgatagtgaatcg atctgggtggataaccaagagccacaaattgtacattttgatgcagtggtgaatttagataagggattgtatgtttatcctgagcctaaa cgttatgcacgttctgttcgtcagtataagatcttgaattgtgcaaattatcatttaactcaagtacgaactgatttctatgatgaattttggg gacagggtttgcgggcagcacctaaaaagcaaagaaacatacgttaagtttaacacctgatacaacgctttataatgctgctcag attatttgtgcgaactatggtgaagcattttcagttgataaaaaaggcggcactaaaaaagcagcggtatctgaattactgcaagcgt cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacat tggcaaatatggaatatattttgcaagctacaggtaatgctgcaacaggtgtaacttggacaacaacttgcaaaggaacggatgcc tctttatttccagcaaattttgcggaagtgtcacacaaggcggccaccaccaccaccaccac LVL702 (protein): (pelB sp)(ProtE aa 20-160)(GG)(PilA aa40-149)(GGHHHHHH) - SEQ ID
NO. 182:
MKYLLPTAAA GLLLLAAQPA MAIQKAEQND VKLAPPTDVR SGYIRLVKNV NYYIDSESIW

VDNQEPQIVH FDAVVNLDKG LYVYPEPKRY ARSVRQYKIL NCANYHLTQV

RTDFYDEFWG QGLRAAPKKQ KKHTLSLTPD TTLYNAAQII CANYGEAFSV DKKGGTKKAA

VSELLQASAP YKADVELCVY STNETTNCTG GKNGIAADIT TAKGYVKSVT TSNGAITVKG

DGTLANMEYI LQATGNAATG VTWTTTCKGT DASLFPANFC GSVTQGGHHH HHH

LVL736 (DNA) - SEQ ID NO. 183:
atgaaatacctgctgccgaccgctgctgctggtctgctgctcctcgctgcccagccggcgatggccagcgcccagattcagaaggc tgaacaaaatgatgtgaagctggcaccgccgactgatgtacgaagcggatatatacgtttggtaaagaatgtgaattattacatcga tagtgaatcgatctgggtggataaccaagagccacaaattgtacattttgatgcagtggtgaatttagataagggattgtatgtttatcct gagcctaaacgttatgcacgttctgttcgtcagtataagatcttgaattgtgcaaattatcatttaactcaagtacgaactgatttctatgat gaattttggggacagggtttgcgggcagcacctaaaaagcaaagaaacatacgttaagtttaacacctgatacaacgctttataa tgctgctcagattatttgtgcgaactatggtgaagcattttcagttgataaaaaaggcggcactaaaaaagcagcggtatctgaatta ctgcaagcgtcagcgccttataaggctgatgtggaattatgtgtatatagcacaaatgaaacaacaaactgtacgggtggaaaaa atggtattgcagcagatataaccacagcaaaaggctatgtaaaatcagtgacaacaagcaacggtgcaataacagtaaaaggg gatggcacattggcaaatatggaatatattttgcaagctacaggtaatgctgcaacaggtgtaacttggacaacaacttgcaaagg aacggatgcctctttatttccagcaaattttgcggaagtgtcacacaaggcggccaccaccaccaccaccac LVL736 (protein): (pelB sp)(ProtE aa 17-160)(GG)(PilA aa40-149)(GGHHHHHH) - SEQ ID
NO. 184:
MKYLLPTAAA GLLLLAAQPA MASAQIQKAE QNDVKLAPPT DVRSGYIRLV KNVNYYIDSE

SIWVDNQEPQ IVHFDAVVNL DKGLYVYPEP KRYARSVRQY KILNCANYHL TQVRTDFYDE

FWGQGLRAAP KKQKKHTLSL TPDTTLYNAA QIICANYGEA FSVDKKGGTK KAAVSELLQA

SAPYKADVEL CVYSTNETTN CTGGKNGIAA DITTAKGYVK SVTTSNGAIT VKGDGTLANM

EYILQATGNA ATGVTWTTTC KGTDASLFPA NFCGSVTQGG HHHHHH

LVL737 (DNA) - SEQ ID NO. 185:
atgaaatacctgctgccgaccgctgctgctggtctgctgctcctcgctgcccagccggcgatggccgcccagattcagaaggctga acaaaatgatgtgaagctggcaccgccgactgatgtacgaagcggatatatacgtttggtaaagaatgtgaattattacatcgatag tgaatcgatctgggtggataaccaagagccacaaattgtacattttgatgcagtggtgaatttagataagggattgtatgtttatcctga gcctaaacgttatgcacgttctgttcgtcagtataagatcttgaattgtgcaaattatcatttaactcaagtacgaactgatttctatgatga attttggggacaggggtttgcgggcagcacctaaaaagcaaaagaaacatacgttaagttaacacctgatacaacgctttataatgc tgctcagattatttgtgcgaactatggtgaagcattttcagttgataaaaaaggcggcactaaaaaagcagcggtatctgaattactg caagcgtcagcgccttataaggctgatgtggaattatgtgtatatagcacaaatgaaacaacaaactgtacgggtggaaaaaatg gtattgcagcagatataaccacagcaaaaggctatgtaaaatcagtgacaacaagcaacggtgcaataacagtaaaaggggat ggcacattggcaaatatggaatatattttgcaagctacaggtaatgctgcaacaggtgtaacttggacaacaacttgcaaaggaac ggatgcctcttatttccagcaaatttttgcggaagtgtcacacaaggcggccaccaccaccaccaccac LVL737 (protein): (pelB sp)(ProtE aa 18-160)(GG)(PilA aa40-149)(GGHHHHHH) - SEQ ID
NO. 186:
MKYLLPTAAA GLLLLAAQPA MAAQIQKAEQ NDVKLAPPTD VRSGYIRLVK NVNYYIDSES

IWVDNQEPQI VHFDAVVNLD KGLYVYPEPK RYARSVRQYK ILNCANYHLT QVRTDFYDEF

WGQGLRAAPK KQKKHTLSLT PDTTLYNAAQ IICANYGEAF SVDKKGGTKK AAVSELLQAS

APYKADVELC VYSTNETTNC TGGKNGIAAD ITTAKGYVKS VTTSNGAITV KGDGTLANME

YILQATGNAA TGVTWTTTCK GTDASLFPAN FCGSVTQGGH HHHH

LVL738 (DNA) - SEQ ID NO. 187:
atgaaatacctgctgccgaccgctgctgctggtctgctgctcctcgctgcccagccggcgatggccaaggctgaacaaaatgatgt gaagctggcaccgccgactgatgtacgaagcggatatatacgtttggtaaagaatgtgaattattacatcgatagtgaatcgatctg ggtggataaccaagagccacaaattgtacattttgatgcagtggtgaatttagataagggattgtatgtttatcctgagcctaaacgtta tgcacgttctgttcgtcagtataagatcttgaattgtgcaaattatcatttaactcaagtacgaactgatttctatgatgaattttggggaca gggtttgcgggcagcacctaaaaagcaaaagaaacatacgttaagtttaacacctgatacaacgctttataatgctgctcagattatt tgtgcgaactatggtgaagcattttcagttgataaaaaaggcggcactaaaaaagcagcggtatctgaatactgcaagcgtcagc gccttataaggctgatgtggaattatgtgtatatagcacaaatgaaacaacaaactgtacgggtggaaaaaatggtattgcagcag atataaccacagcaaaaggctatgtaaaatcagtgacaacaagcaacggtgcaataacagtaaaagggggatggcacattggc aaatatggaatatattttgcaagctacaggtaatgctgcaacaggtgtaacttggacaacaacttgcaaaggaacggatgcctcttt atttccagcaaatttttgcggaagtgtcacacaaggcggccaccaccaccaccaccac LVL738 (protein): (pelB sp)(ProtE aa 22-160)(GG)(PilA aa40-149)(GGHHHHHH) - SEQ ID
NO. 188:
MKYLLPTAAA GLLLLAAQPA MAKAEQNDVK LAPPTDVRSG YIRLVKNVNY YIDSESIWVD

NQEPQIVHFD AVVNLDKGLY VYPEPKRYAR SVRQYKILNC ANYHLTQVRT

DFYDEFWGQG LRAAPKKQKK HTLSLTPDTT LYNAAQIICA NYGEAFSVDK KGGTKKAAVS

ELLQASAPYK ADVELCVYST NETTNCTGGK NGIAADITTA KGYVKSVTTS NGAITVKGDG

TLANMEYILQ ATGNAATGVT WTTTCKGTDA SLFPANFCGS VTQGGHHHHH H

LVL739 (DNA) - SEQ ID NO. 189:
ATGAAATACCTGCTGCCGACCGCTGCTGCTGGTCTGCTGCTCCTCGCTGCCCAGCCGGC

GATGGCCGCTGAACAAAATGATGTGAAGCTGGCACCGCCGACTGATGTACGAAGCGGAT

ATATACGTTTGGTAAAGAATGTGAATTATTACATCGATAGTGAATCGATCTGGGTGGATAA

CCAAGAGCCACAAATTGTACATTTTGATGCAGTGGTGAATTTAGATAAGGGATTGTATGTT

TATCCTGAGCCTAAACGTTATGCACGTTCTGTTCGTCAGTATAAGATCTTGAATTGTGCAA

ATTATCATTTAACTCAAGTACGAACTGATTTCTATGATGAATTTTGGGGACAGGGTTTGCG

GGCAGCACCTAAAAAGCAAAAGAAACATACGTTAAGTTTAACACCTGATACAACGCTTTAT

AATGCTGCTCAGATTATTTGTGCGAACTATGGTGAAGCATTTTCAGTTGATAAAAAAGGC

GGCACTAAAAAAGCAGCGGTATCTGAATTACTGCAAGCGTCAGCGCCTTATAAGGCTGAT

GTGGAATTATGTGTATATAGCACAAATGAAACAACAAACTGTACGGGTGGAAAAAATGGT

ATTGCAGCAGATATAACCACAGCAAAAGGCTATGTAAAATCAGTGACAACAAGCAACGGT

GCAATAACAGTAAAAGGGGATGGCACATTGGCAAATATGGAATATATTTTGCAAGCTACA

GGTAATGCTGCAACAGGTGTAACTTGGACAACAACTTGCAAAGGAACGGATGCCTCTTTA

TTTCCAGCAAATTTTTGCGGAAGTGTCACACAAGGCGGCCACCACCACCACCACCAC

LVL739 (protein): (pelB sp)(ProtE aa 23-160)(GG)(PilA aa40-149)(GGHHHHHH) - SEQ ID
NO. 190:
MKYLLPTAAA GLLLLAAQPA M<u>AEQNDVKL APPTDVRSGY IRLVKNVNYY IDSESIWVDN</u>

<u>QEPQIVHFDA VVNLDKGLYV YPEPKRYARS VRQYKILNCA NYHLTQVRTD</u>

<u>FYDEFWGQGL RAAPKKQKKH TLSLTPDTTL YNAAQIICAN YGEAFSVDKK</u> GG<u>TKKAAVSE</u>

<u>LLQASAPYKA DVELCVYSTN ETTNCTGGKN GIAADITTAK GYVKSVTTSN GAITVKGDGT</u>

<u>LANMEYILQA TGNAATGVTW TTTCKGTDAS LFPANFCGSV TQ</u>GGHHHHHH

LVL740 (DNA) - SEQ ID NO. 191:
atgaaatacctgctgccgaccgctgctgctggtctgctgctcctcgctgcccagccggcgatggccgaacaaaatgatgtgaagct ggcaccgccgactgatgtacgaagcggatatatacgtttggtaaagaatgtgaattattacatcgatagtgaatcgatctgggtggat aaccaagagccacaaattgtacattttgatgcagtggtgaatttagataagggattgtatgtttatcctgagcctaaacgttatgcacgt tctgttcgtcagtataagatcttgaattgtgcaaattatcatttaactcaagtacgaactgatttctatgatgaattttggggacagggtttg cgggcagcacctaaaaagcaaaagaaacatacgttaagtttaacacctgatacaacgctttataatgctgctcagattatttgtgcg aactatggtgaagcattttcagttgataaaaaaggcggcactaaaaaagcagcggtatctgaattactgcaagcgtcagcgccttat aaggctgatgtggaattatgtgtatatagcacaaatgaaacaacaaactgtacgggtggaaaaaatggtattgcagcagatataa ccacagcaaaaggctatgtaaaatcagtgacaacaagcaacggtgcaataacagtaaaaggggatggcacattggcaaatat ggaatatattttgcaagctacaggtaatgctgcaacaggtgtaacttggacaacaacttgcaaaggaacggatgcctcttatttcca gcaaattttgcggaagtgtcacacaaggcggccaccaccaccaccac LVL740 (protein): (pelB sp)(ProtE aa 24-160)(GG)(PilA aa40-149)(GGHHHHHH) - SEQ ID
NO. 192:
MKYLLPTAAA GLLLLAAQPA M<u>AEQNDVKLA PPTDVRSGYI RLVKNVNYYI DSESIWVDNQ</u>

<u>EPQIVHFDAV VNLDKGLYVY PEPKRYARSV RQYKILNCAN YHLTQVRTDF YDEFWGQGLR</u>

<u>AAPKKQKKHT LSLTPDTTLY NAAQIICANY GEAFSVDKKG</u> G<u>TKKAAVSEL LQASAPYKAD</u>

<u>VELCVYSTNE TTNCTGGKNG IAADITTAKG YVKSVTTSNG AITVKGDGTL ANMEYILQAT</u>

<u>GNAATGVTWT TTCKGTDASL FPANFCGSVT Q</u>GGHHHHHH

LVL735 (DNA) - SEQ ID NO. 193:
ATGAAATACCTGCTGCCGACCGCTGCTGCTGGTCTGCTGCTCCTCGCTGCCCAGCCGGC

GATGGCCATTCAGAAGGCTGAACAAAATGATGTGAAGCTGGCACCGCCGACTGATGTAC

GAAGCGGATATATACGTTTGGTAAAGAATGTGAATTATTACATCGATAGTGAATCGATCTG

```
GGTGGATAACCAAGAGCCACAAATTGTACATTTTGATGCAGTGGTGAATTTAGATAAGGG

ATTGTATGTTTATCCTGAGCCTAAACGTTATGCACGTTCTGTTCGTCAGTATAAGATCTTG

AATTGTGCAAATTATCATTTAACTCAAGTACGAACTGATTTCTATGATGAATTTTGGGGAC

AGGGTTTGCGGGCAGCACCTAAAAAGCAAAAGAAACATACGTTAAGTTTAACACCTGATA

CAACGCTTTATAATGCTGCTCAGATTATTTGTGCGAACTATGGTGAAGCATTTTCAGTTGA

TAAAAAAGGCGGCACTAAAAAAGCAGCGGTATCTGAATTACTGCAAGCGTCAGCGCCTTA

TAAGGCTGATGTGGAATTATGTGTATATAGCACAAATGAAACAACAAACTGTACGGGTGG

AAAAAATGGTATTGCAGCAGATATAACCACAGCAAAAGGCTATGTAAAATCAGTGACAAC

AAGCAACGGTGCAATAACAGTAAAAGGGGATGGCACATTGGCAAATATGGAATATATTTT

GCAAGCTACAGGTAATGCTGCAACAGGTGTAACTTGGACAACAACTTGCAAAGGAACGG

ATGCCTCTTTATTTCCAGCAAATTTTTGCGGAAGTGTCACACAA
```

LVL735 (protein): (pelB sp)(ProtE aa 20-160)(GG)(PilA aa40-149) - SEQ ID NO. 194:
MKYLLPTAAA GLLLLAAQPA MA<u>IQKAEQND VKLAPPTDVR SGYIRLVKNV NYYIDSESIW</u>

<u>VDNQEPQIVH FDAVVNLDKG LYVYPEPKRY ARSVRQYKIL NCANYHLTQV</u>

<u>RTDFYDEFWG QGLRAAPKKQ KKHTLSLTPD TTLYNAAQII CANYGEAFSV DKKGGTKKAA</u>

<u>VSELLQASAP YKADVELCVY STNETTNCTG GKNGIAADIT TAKGYVKSVT TSNGAITVKG</u>

<u>DGTLANMEYI LQATGNAATG VTWTTTCKGT DASLFPANFC GSVTQ</u>

LVL778 (DNA) - SEQ ID NO. 195:
```
atgaaatacctgctgccgaccgctgctgctggtctgctgctcctcgctgcccagccggcgatggccagcgcccagattcagaaggc tgaacaaaatgatgtgaagctggcaccgccgactgatgtacgaagcggatatatacgtttggtaaagaatgtgaattattacatcga tagtgaatcgatctgggtggataaccaagagccacaaattgtacattttgatgcagtggtgaatttagataagggattgtatgtttatcct gagcctaaacgttatgcacgttctgttcgtcagtataagatcttgaattgtgcaaattatcatttaactcaagtacgaactgatttctatgat gaattttggggacagggtttgcgggcagcacctaaaaagcaaaagaaacatacgttaagtttaacacctgatacaacgctttataa tgctgctcagattatttgtgcgaactatggtgaagcattttcagttgataaaaaaggcggcactaaaaaagcagcggtatctgaatta ctgcaagctcagcgccttataaggctgatgtggaattatgtgtatatagcacaaatgaaacaacaaactgtacgggtggaaaaa atggtattgcagcagatataaccacagcaaaaggctatgtaaaatcagtgacaacaagcaacggtgcaataacagtaaaaggg gatggcacattggcaaatatggaatatattttgcaagctacaggtaatgctgcaacaggtgtaacttggacaacaacttgcaaagg aacggatgcctctttatttccagcaaattttgcggaagtgtcacacaa
```

LVL778 (protein): (pelB sp)(ProtE aa 17-160)(GG)(PilA aa40-149) - SEQ ID NO. 196:
MKYLLPTAAA GLLLLAAQPA MA<u>SAQIQKAE QNDVKLAPPT DVRSGYIRLV KNVNYYIDSE</u>

<u>SIWVDNQEPQ IVHFDAVVNL DKGLYVYPEP KRYARSVRQY KILNCANYHL TQVRTDFYDE</u>

<u>FWGQGLRAAP KKQKKHTLSL TPDTTLYNAA QIICANYGEA FSVDKKGGTK KAAVSELLQA</u>

<u>SAPYKADVEL CVYSTNETTN CTGGKNGIAA DITTAKGYVK SVTTSNGAIT VKGDGTLANM</u>

<u>EYILQATGNA ATGVTWTTTC KGTDASLFPA NFCGSVTQ</u>

LVL779 (DNA) - SEQ ID NO. 197:
```
atgaaatacctgctgccgaccgctgctgctggtctgctgctcctcgctgcccagccggcgatggccgcccagattcagaaggctga acaaaatgatgtgaagctggcaccgccgactgatgtacgaagcggatatatacgtttggtaaagaatgtgaattattacatcgatag tgaatcgatctgggtggataaccaagagccacaaattgtacattttgatgcagtggtgaatttagataagggattgtatgtttatcctga gcctaaacgttatgcacgttctgttcgtcagtataagatcttgaattgtgcaaattatcatttaactcaagtacgaactgatttctatgatga attttggggacagggtttgcgggcagcacctaaaaagcaaaagaaacatacgttaagtttaacacctgatacaacgctttataatgc tgctcagattatttgtgcgaactatggtgaagcattttcagttgataaaaaaggcggcactaaaaaagcagcggtatctgaataactg caagcgtcagcgccttataaggctgatgtggaattatgtgtatatagcacaaatgaaacaacaaactgtacgggtggaaaaaatg
``` gtattgcagcagatataaccacagcaaaaggctatgtaaaatcagtgacaacaagcaacggtgcaataacagtaaaagggat ggcacattggcaaatatggaatatattttgcaagctacaggtaatgctgcaacaggtgtaacttggacaacaacttgcaaaggaac ggatgcctcttttatttccagcaaattttttgcggaagtgtcacacaa LVL779 (protein): (pelB sp)(ProtE aa 18-160)(GG)(PilA aa40-149) - SEQ ID NO. 198:
MKYLLPTAAA GLLLLAAQPA M<u>AAQIQKAEQ NDVKLAPPTD VRSGYIRLVK NVNYYIDSES</u>

<u>IWVDNQEPQI VHFDAVVNLD KGLYVYPEPK RYARSVRQYK ILNCANYHLT QVRTDFYDEF</u>

<u>WGQGLRAAPK KQKKHTLSLT PDTTLYNAAQ IICANYGEAF SVDKKGGTKK AAVSELLQAS</u>

<u>APYKADVELC VYSTNETTNC TGGKNGIAAD ITTAKGYVKS VTTSNGAITV KGDGTLANME</u>

<u>YILQATGNAA TGVTWTTTCK GTDASLFPAN FCGSVTQ</u>

LVL780 (DNA) - SEQ ID NO. 199:
atgaaatacctgctgccgaccgctgctgctggtctgctgctcctcgctgcccagccggcgatggccaaggctgaacaaaatgatgt gaagctggcaccgccgactgatgtacgaagcggatatatacgtttggtaaagaatgtgaattattacatcgatagtgaatcgatctg ggtggataaccaagagccacaaattgtacattttgatgcagtggtgaatttagataagggattgtatgtttatcctgagcctaaacgtta tgcacgttctgttcgtcagtataagatcttgaattgtgcaaattatcatttaactcaagtacgaactgatttctatgatgaattttggggaca gggtttgcgggcagcacctaaaaagcaaaagaaacatacgttaagtttaacacctgatacaacgctttataatgctgctcagattatt tgtgcgaactatggtgaagcattttcagttgataaaaaaggcggcactaaaaaagcagcggtatctgaattactgcaagcgtcagc gccttataaggctgatgtggaattatgtgtatatagcacaaatgaaacaacaaactgtacgggtggaaaaaatggtattgcagcag atataaccacagcaaaaggctatgtaaaatcagtgacaacaagcaacggtgcaataacagtaaaagggggatggcacattggc aaatatggaatatattttgcaagctacaggtaatgctgcaacaggtgtaacttggacaacaacttgcaaaggaacggatgcctcttt atttccagcaaattttttgcggaagtgtcacacaa LVL780 (protein): (pelB sp)(ProtE aa 22-160)(GG)(PilA aa40-149) - SEQ ID NO. 200:
MKYLLPTAAA GLLLLAAQPA M<u>AKAEQNDVK LAPPTDVRSG YIRLVKNVNY YIDSESIWVD</u>

<u>NQEPQIVHFD AVVNLDKGLY VYPEPKRYAR SVRQYKILNC ANYHLTQVRT</u>

<u>DFYDEFWGQG LRAAPKKQKK HTLSLTPDTT LYNAAQIICA NYGEAFSVDK KGGTKKAAVS</u>

<u>ELLQASAPYK ADVELCVYST NETTNCTGGK NGIAADITTA KGYVKSVTTS NGAITVKGDG</u>

<u>TLANMEYILQ ATGNAATGVT WTTTCKGTDA SLFPANFCGS VTQ</u>

LVL781 (DNA) - SEQ ID NO. 201:
Atgaaatacctgctgccgaccgctgctgctggtctgctgctcctcgctgcccagccggcgatggccgctgaacaaaatgatgtgaa gctggcaccgccgactgatgtacgaagcggatatatacgtttggtaaagaatgtgaattattacatcgatagtgaatcgatctgggtg gataaccaagagccacaaattgtacattttgatgcagtggtgaatttagataagggattgtatgthatcctgagcctaaacgttatgca cgttctgttcgtcagtataagatcttgaattgtgcaaattatcatttaactcaagtacgaactgatttctatgatgaattttggggacagggt ttgcgggcagcacctaaaaagcaaaagaaacatacgttaagtttaacacctgatacaacgctttataatgctgctcagattatttgtg cgaactatggtgaagcattttcagttgataaaaaaggcggcactaaaaaagcagcggtatctgaattactgcaagcgtcagcgcct tataaggctgatgtggaattatgtgtatatagcacaaatgaaacaacaaactgtacgggtggaaaaaatggtattgcagcagatat aaccacagcaaaaggctatgtaaaatcagtgacaacaagcaacggtgcaataacagtaaaagggggatggcacattggcaaat atggaatatattttgcaagctacaggtaatgctgcaacaggtgtaacttggacaacaacttgcaaaggaacggatgcctcttttatttcc agcaaattttttgcggaagtgtcacacaa LVL781 (protein): (pelB sp)(ProtE aa 23-160)(GG)(PilA aa40-149) - SEQ ID NO. 202:
MKYLLPTAAA GLLLLAAQPA M<u>AAEQNDVKL APPTDVRSGY IRLVKNVNYY IDSESIWVDN</u>

<u>QEPQIVHFDA VVNLDKGLYV YPEPKRYARS VRQYKILNCA NYHLTQVRTD</u>

<u>FYDEFWGQGL RAAPKKQKKH TLSLTPDTTL YNAAQIICAN YGEAFSVDKK GGTKKAAVSE</u>

<u>LLQASAPYKA DVELCVYSTN ETTNCTGGKN GIAADITTAK GYVKSVTTSN GAITVKGDGT</u>

<u>LANMEYILQA TGNAATGVTW TTTCKGTDAS LFPANFCGSV TQ</u>

```
LVL782 (DNA) - SEQ ID NO. 203:
atgaaatacctgctgccgaccgctgctgctggtctgctgctcctcgctgcccagccggcgatggccgaacaaaatgatgtgaagct ggcaccgccgactgatgtacgaagcggatatatacgtttggtaaagaatgtgaattattacatcgatagtgaatcgatctgggtggat aaccaagagccacaaattgtacattttgatgcagtggtgaatttagataagggattgtatgtttatcctgagcctaaacgttatgcacgt tctgttcgtcagtataagatcttgaattgtgcaaattatcatttaactcaagtacgaactgatttctatgatgaattttggggacagggtttg cgggcagcacctaaaaagcaaagaaacatacgttaagtttaacacctgatacaacgctttataatgctgctcagattatttgtgcg aactatggtgaagcattttcagttgataaaaaaggcggcactaaaaaagcagcggtatctgaattactgcaagcgtcagcgcc ttat aaggctgatgtggaattatgtgtatatagcacaaatgaaacaacaaactgtacgggtggaaaaaatggtattgcagcagatataa ccacagcaaaaggctatgtaaaatcagtgacaacaagcaacggtgcaataacagtaaaagggatggcacattggcaaatat ggaatatattttgcaagctacaggtaatgctgcaacaggtgtaacttggacaacaacttgcaaaggaacggatgcctctttatttcca gcaaattttttgcggaagtgtcacacaa LVL782 (protein): (pelB sp)(ProtE aa 24-160)(GG)(PilA aa40-149) - SEQ ID NO. 204:
MKYLLPTAAA GLLLLAAQPA MAEQNDVKLA PPTDVRSGYI RLVKNVNYYI DSESIWVDNQ

EPQIVHFDAV VNLDKGLYVV PEPKRYARSV RQYKILNCAN YHLTQVRTDF YDEFWGQGLR

AAPKKQKKHT LSLTPDTTLY NAAQIICANY GEAFSVDKKG GTKKAAVSEL LQASAPYKAD

VELCVYSTNE TTNCTGGKNG IAADITTAKG YVKSVTTSNG AITVKGDGTL ANMEYILQAT

GNAATGVTWT TTCKGTDASL FPANFCGSVT Q
```

The full length sequence for PE and PilA from which the above sequences were obtained are set forth in SEQ ID NO. 4 (PE) and SEQ ID NO. 58 (PilA), respectively.

Example 2

Vector Construction and Transformation

Primers for amplifying PE from *H. influenzae* strain 772 were designed based on the sequence of *H. influenzae* strain Hi Rd. The 5' primer sequence contains one nucleotide difference compared to the NTHi 772 sequence, introducing an amino acid difference at position 24 when compared with the currently reported NTHi 772 genome sequence. Amino acid #24 in the fusion protein constructs is E (glutamic acid) instead of K (lysine) as found in NTHi 772.

```
DNA Sequence for PE from H. influenzae strain Rd. - SEQ ID NO. 151
atgaaaaaaattattttaacattatcacttgggttacttaccgcttgttctgctcaaatccaaaaggctgaacaaaatgatgtgaagctggc accgccgactgatgtacgaagcggatatatacgtttggtaaagaatgtgaattattacatcgatagtgaatcgatctgggtggataacc aagagccacaaattgtacattttgatgctgtggtgaatttagataggggattgtatgtttatcctgagcctaaacgttatgcacgttctgttcg tcagtataagattttgaattgtgcaaattatcatttaactcaaatacgaactgatttctatgatgaattttggggacagggtttgcgggcagc acctaaaaagcaaagaaacatacgttaagtttaacacctgatacaacgctttataatgctgctcagattatttgtgcaaattatggtaaa gcattttcagttgataaaaaataa Protein Sequence for PE from H. influenzae strain Rd. - SEQ ID NO. 152
MKKIILTLSL GLLTACSAQI QKAEQNDVKL APPTDVRSGY IRLVKNVNYY IDSESIWVDN

QEPQIVHFDA VVNLDRGLYV YPEPKRYARS VRQYKILNCA NYHLTQIRTD FYDEFWGQGL

RAAPKKQKKH TLSLTPDTTL YNAAQIICAN YGKAFSVDKK

DNA Sequence for PE from H. influenzae strain 772 (as set forth in: Microbes & Infection,
Corrigendum to "Identification of a novel Haemophilus influenzae protein important for adhesion
to epithelia cells" [Microbes Infect. 10 (2008) 87-97], available online Jul. 6, 2010, "Article in
Press")) - SEQ ID NO. 153
atgaaaaaaattattttaacattatcacttgggttacttactgcctgttctgctcaaatccaaaaggctaaacaaaatgatgtgaagctggc accgccgactgatgtacgaagcggatatatacgtttggtaaagaatgtgaattattacatcgatagtgaatcgatctgggtggataacc
```

-continued

```
aagagccacaaattgtacattttgatgcagtggtgaatttagataagggattgtatgtttatcctgagcctaaacgttatgcacgttctgttc gtcagtataagatcttgaattgtgcaaattatcatttaactcaagtacgaactgatttctatgatgaattttggggacagggtttgcgggcag cacctaaaaagcaaaagaaacatacgttaagtttaacacctgatacaacgctttataatgctgctcagattatttgtgcgaactatggtg aagcattttcagttgataaaaaa
```

Protein Sequence for PE from *H. influenzae* strain 772 (as set forth in: Microbes & Infection, Corrigendum to "Identification of a novel *Haemophilus influenzae* protein important for adhesion to epithelia cells" [Microbes Infect. 10 (2008) 87-97], available online Jul. 6, 2010, "Article in Press")) - SEQ ID NO. 154

MKKIILTLSL GLLTACSAQI QKAKQNDVKL APPTDVRSGY IRLVKNVNYY IDSESIWVDN

QEPQIVHFDA VVNLDKGLYV YPEPKRYARS VRQYKILNCA NYHLTQVRTD FYDEFWGQGL

RAAPKKQKKH TLSLTPDTTL YNAAQIICAN YGEAFSVDKK

Vector Construction:

To generate LVL312, LVL291, LVL268, LVL269, LVL270, LVL702, LVL735, LVL778, LVL779, LVL780, LVL781 and LVL782, a polymerase chain reaction (PCR) preparation of the following components was prepared (specific components are subsequently exemplified): 36.6 µl of deionized water, 5 µl of buffer #1 10×, 5 µl of dNTPs 2 mM, 2 µl MgCl$_2$ 25 mM, 0.4 µl of primer #1 (50 µM), 0.4 µl of primer #2 (50 µM), 0.5 µl of template (100 ng/µl) and 0.4 µl of KOD HiFi DNA polymerase 2.5 units/µl (NOVAGEN®) was formulated. Polymerase chain reaction involved 25 cycles of 15 seconds of denaturation at 98° C., 2 seconds for annealing at 55° C. and 20 seconds of primer extension at 72° C. The PCR products were purified using QIAQUICK® PCR purification kit (QIAGEN®). This product was used under conditions recommended by the supplier which were: the addition of 5 volumes Buffer PB, provided in the QIAQUICK® PCR purification kit, to 1 volume of the PCR preparation. The PCR preparation with Buffer PB was subsequently mixed by vortex. A QIAQUICK® column was placed into a 2 ml collection tube. To bind DNA in the PCR preparation to the column, the mixed sample was applied to the QIAQUICK® column and centrifuged for 30-60 seconds at 14 000 RPM. The flow-through was discarded and the QIAQUICK® column was placed back in the same tube. To wash the bound DNA 0.75 ml Buffer PE, provided in the QIAQUICK® PCR purification kit, was added to the QIA-QUICK® column, and the column was centrifuged for 30-60 seconds at 14 000 RPM. The flow-through was discarded and the QIAQUICK® column was placed back in the same tube. The QIAQUICK® column was centrifuged once more in the 2 ml collection tube for 1 minute to remove residual wash buffer. Each QIAQUICK® column was placed in a clean 1.5 ml microcentrifuge tube. To elute the DNA, 33 µl water was added to the center of the QIA-QUICK® membrane and the column was centrifuged for 1 minute at 14 000 RPM. Restriction enzymes and buffer related were obtained from New England BioLabs. For example, approximately 5 µl of pET26b vector (100 ng/µl), 2 µl of NEBuffer 2 (New England Biolabs, 1×NEBuffer 2: 50 mM NaCl, 10 mM Tris-HCl, 10 mM MgCl$_2$, 1 mM dithiothreitol, pH 7.9 at 25° C.), 1 µl of NdeI (20 000 units/ml), 1 µl of HindIII (20 000 units/ml) and 11 µl of deionized water were mixed and incubated for two hours at 37° C. for DNA digestion. Thereafter, a second step of purification was performed using the QIAQUICK® PCR purification kit (QIAGEN®) with the procedure described above.

Ligation was performed using Quick T4 DNA ligase and Quick Ligation Reaction Buffer from New England Bio-Labs. For example, around 10 ng of vector and 30 ng of insert in 10 µl of deionized water were mixed with 10 µl of 2× Quick Ligation Reaction Buffer (New England Biolabs, 132 mM Tris-HCl, 20 mM MgCl$_2$, 2 mM dithiothreitol, 2 mM ATP, 15% polyethylene glycol, pH 7.6 at 25° C.) and 1 µl of Quick T4 DNA ligase (New England Biolabs). The enzymatic reaction was incubated for 5 minutes at room temperature before transformation.

To generate LVL315, LVL317, LVL318, LVL736, LVL737, LVL738, LVL739 and LVL740, a PCR preparation of the following components was prepared: 40 µl of deionized water, 5 µl of reaction buffer 10×, 1 µl of dNTPs mix, 1 µl of primer #1 (10 µM), 1 µl of primer #2 (10 µM), 1 µl of template (25 ng/µl) and 1 µl of PfuUltra High-Fidelity DNA polymerase 2.5 units/µl (QuikChange II Site-Directed Mutagenesis Kit, Agilent Technologies, Stratagene Division) was formulated. Polymerase chain reaction involved one cycle of denaturation at 95° C. for 30 sec, 18 cycles of 30 sec of denaturation at 95° C., 1 min for annealing at 55° C. and 5 min 30 sec of primer extension at 68° C. The PCR products were digested using 1 µl of DpnI restriction enzyme at 37° C. for one hour before transformation.

A detailed list of PCR primer sequences used for amplifications is illustrated in Table 4.

To generate pRIT16711, the PE gene fragment coding for amino acids 22 to 160 of SEQ ID NO. 4, which excludes the sequence coding for its corresponding secretion signal, was amplified by PCR from genomic DNA of NTHi strain 772. The amplification primers were designed based on the available strain Hi Rd sequence (at that time, the 772 sequence was not known). The 5' primer sequence contains one mutation compared to the NTHi 772 sequence (sequence as now available), introducing one amino acid difference in PE coding sequence at position 24, glutamic acid (E) instead of lysine (K). After PCR amplification, the insert was cloned in the pET-26(+) expression vector (NOVAGEN®) using BamHI and XhoI restriction sites.

To generate pRIT16671, a DNA fragment coding for a PilA gene fragment (amino acids 40 to 149 of SEQ ID NO. 58, SEQ ID NO. 127), which excludes its leader peptide as well as a portion of the predicted hydrophobic alpha helix, was amplified from genomic DNA of NTHi strain 86-028NP and cloned into the pET15 expression vector. The vector pRIT16790 (containing amino acids 40 to 149 from NTHi strain 86-028NP) was used as a template to generate the vector pRIT16671. The PilA gene fragment was amplified by PCR using the vector pRIT16790 and primers MDES PILA-3 and MDES PILA-4. The PilA fragment was cloned into the pET-26 expression vector using NdeI/XhoI restriction sites. The DNA sequence encoding six histidine (his)

amino acids was incorporated into the 5' primer to add six histidines (6×his) at the N-terminal end of the PilA sequence (MDES PILA-3).

To generate LVL312 (FlgI signal peptide-E-PilA fragment-GG-PE fragment-GGHHHHHH), a polymerase chain reaction was performed to amplify the PilA gene (amino acids 40-149/strain 86-028NP) using the pRIT16671 vector as a template and primers CAN534 and CAN537. DNA sequence corresponding to FlgI signal peptide (sp) and glutamic acid (E) amino acid was incorporated into the 5' primer (CAN534). To link the PilA sequence to PE sequence, DNA sequence corresponding to the two glycine (GG) amino acids linker and the N-terminal PE amino acids were incorporated into the 3' primer (CAN537). Another polymerase chain reaction was performed to amplify the PE gene (amino acids 18-160) using pRIT16711 vector as a template and primers CAN536 and CAN538. DNA sequence corresponding to the C-terminal PilA amino acids and GG amino acids were incorporated into the 5' primer to link pilA to PE sequence (CAN536). DNA sequence corresponding to the GG amino acids linker and 6×his amino acids were incorporated into the 3' primer (CAN538). Finally, to generate LVL312, a third polymerase chain reaction was performed to amplify the PilA and PE genes in fusion with the FlgI signal peptide at the N-terminus, a glutamic acid (E) amino acid between FlgI and pilA, a GG linker between PilA and PE sequences and a GG linker between PE and the 6×his amino acids at the C-terminus. To achieve this amplification, the products of the two polymerase chain reactions described above were used as a template with primers CAN534 and CAN538. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL291 (pelB signal peptide-PE fragment-GG-PilA fragment-GG-6×his), a polymerase chain reaction was performed to amplify the PE gene (amino acids 19-160) using the pRIT16711 vector as a template and primers CAN544 and CAN546. DNA sequence corresponding to pelB signal peptide (sp) amino acids was incorporated into the 5' primer (CAN544). To link the PilA sequence to the PE sequence, DNA sequence corresponding to GG amino acids linker and the N-terminal PilA amino acids were incorporated into the 3' primer (CAN546). Another polymerase chain reaction was performed to amplify the PilA gene (amino acids 40-149 of SEQ ID NO. 58, SEQ ID NO. 127) using the pRIT16671 vector as a template with primers CAN545 and CAN535. DNA sequence corresponding to the C-terminal PE amino acids and GG amino acids were incorporated into the 5' primer (CAN545) to link the PilA sequence to the PE sequence. DNA sequence corresponding to linker GG amino acids and 6×his amino acids were incorporated into the 3' primer (CAN535). Finally, to generate LVL291, a third polymerase chain reaction was performed to amplify the PE and PilA genes in fusion with the pelB signal peptide at the N-terminus, a GG linker between the PE and PilA sequences and a GG linker between PilA and 6×his amino acids at the C-terminus. To achieve this amplification, the products of two polymerase chain reactions described above were used as a template with primers CAN544 and CAN535. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL268 (pelB signal peptide-D-PE fragment-GG-PilA fragment-GG-6×his), a polymerase chain reaction was performed to amplify the PE gene (amino acids 20-160) using the pRIT16711 vector as a template with primers CAN547 and CAN546. DNA sequence corresponding to the pelB signal peptide (sp) amino acids and aspartic acid (D) amino acid were incorporated into the 5' primer (CAN547). To link the PilA sequence to the PE sequence, DNA sequence corresponding to GG amino acids linker and the N-terminal PilA amino acids were incorporated into the 3' primer (CAN546). Another polymerase chain reaction was performed to amplify the PilA gene (amino acids 40-149/NTHi strain 86-028NP) using the pRIT16671 vector as a template with CAN545 and CAN535. DNA sequence corresponding to the C-terminal PE amino acids and GG amino acids were incorporated into the 5' primer (CAN545) to link the PilA sequence to the PE sequence. DNA sequence corresponding to linker GG amino acids and 6×his amino acids were incorporated into the 3' primer (CAN535). Finally, to generate LVL268, a third polymerase chain reaction was performed to amplify the PE and PilA genes in fusion with the pelB signal peptide at the N-terminus, a D amino acid between pelB signal peptide and PE, a GG linker between PE and pilA sequences and a GG linker between PilA and 6×his amino acids in C-term. To achieve this amplification, the products of the two polymerase chain reactions described above were used as a template with primers CAN547 and CAN535. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL269 (NadA signal peptide-ATNDDD-PE fragment-GG-PilA fragment-GG-6×his), a polymerase chain reaction was performed to amplify the PE gene (amino acids 22-160 of SEQ ID NO. 4) using the pRIT16711 vector as a template with primers CAN548 and CAN546. DNA sequence corresponding to pelB signal peptide (sp) amino acids and ATNDDD amino acids were incorporated into the 5' primer (CAN548). To link the PilA sequence to the PE sequence, DNA sequence corresponding to the GG amino acids linker and the N-terminal PilA amino acids were incorporated into the 3' primer (CAN546). Another polymerase chain reaction was performed to amplify the PilA gene (amino acids 40-149 of SEQ ID NO. 58, SEQ ID NO. 127) using the pRIT16671 vector as a template with primers CAN545 and CAN535. DNA sequence corresponding to the C-terminal PE amino acids and GG amino acids were incorporated into the 5' primer to link the PilA sequence to the PE sequence (CAN545). DNA sequence corresponding to linker GG amino acids and 6×his amino acids were incorporated into the 3' primer (CAN535). Finally, to generate LVL269, a third polymerase chain reaction was performed to amplify the PE and PilA gene in fusion with the NadA signal peptide at the N-terminus, ATNDDD amino acids between the pelB signal peptide and PE, a GG linker between the PE and pilA sequences and a GG linker between PilA and 6×his amino acids at the C-terminus. To achieve this amplification, the products of the two polymerase chain reactions describe above were used as a template with primers CAN548 and CAN535. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL270 (M-6×His-PE fragment-GG-PilA fragment), a polymerase chain reaction was performed to amplify the PE gene (amino acids 17-160) using the pRIT16711 vector as a template with primers CAN540 and CAN542. DNA sequence corresponding to 6×his amino acids were incorporated into the 5' primer (CAN540). To link the PilA sequence to the PE sequence, DNA sequence corresponding to the GG amino acids linker and the N-terminal PilA amino acids were incorporated into the 3' primer (CAN542). Another polymerase chain reaction was performed to amplify the PilA gene (amino acids 40-149/NTHi strain 86-028NP) using pRIT16671 vector as a template with primers CAN541 and CAN543. DNA sequence corresponding to the C-terminal PE amino acids and GG amino acids were incorporated into the 5' primer (CAN541) to link the PilA to the PE sequence. Finally, to generate LVL270, a third polymerase chain reaction was performed to amplify the 6-his-PE-GG-PilA gene in fusion. To achieve this amplification, the products of the two polymerase chain reactions describe above were used as a template with primers CAN540 and CAN543. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL315 (pelB signal peptide-MD-PE fragment-GG-PilA fragment-GG-6×his), a site-directed mutagenesis was performed to change the N-terminal PE amino acid sequence from QIQ to MD using LVL291 as a template with primers CAN670 and CAN671 and the QuikChange II Site-Directed Mutagenesis Kit (Agilent Technologies, Stratagene Division).

To generate LVL317 (pelB signal peptide-PE fragment-GG-pilA fragment), a site-directed mutagenesis was performed to incorporate a stop codon between the PilA gene and the DNA sequence corresponding to GGHHHHHH amino acid residues (SEQ ID NO: 3) using LVL291 as a template with primers CAN678 and CAN679 and the QuikChange II Site-Directed Mutagenesis Kit (Agilent Technologies, Stratagene Division).

To generate LVL318 (pelB signal peptide-MD-PE-GG-PilA), a site-directed mutagenesis was performed to incorporate a stop codon between the PilA gene and the DNA sequence corresponding to GGHHHHHH amino acid residues (SEQ ID NO: 3) using LVL315 as a template with primers CAN678 and CAN679 and the QuikChange II Site-Directed Mutagenesis Kit (Agilent Technologies, Stratagene Division).

To generate LVL702 (LVL291 ΔQ), a polymerase chain reaction was performed using the LVL291 vector as template and primers CAN1517 and CAN1518. Deletion of three nucleotides corresponding to the amino acid Q at the position 23 on LVL291 sequence was incorporated to the 5' primer. The only difference between LVL702 and LVL291 is the deletion of amino acid Q at the position 23 on LVL291 sequence. NdeI and HindIII restriction sites were incorporated into the 5' and 3' primers respectively. The generated PCR product was then inserted into the pET-26b(+) cloning vector (NOVAGEN®).

To generate LVL735 (LVL317 ΔQ), a polymerase chain reaction was performed using the LVL317 vector as template and primers CAN1517 and CAN1519. Deletion of three nucleotides corresponding to the amino acid Q at the position 23 on LVL317 sequence was incorporated to the 5' primer. The only difference between LVL735 and LVL317 is the deletion of amino acid Q at the position 23 on LVL317 sequence. NdeI and HindIII restriction sites were incorporated into the 5' and 3' primers respectively. The generated PCR product was then inserted into the pET-26b(+) cloning vector (NOVAGEN®).

To generate LVL736 (LVL291+SA), a site-directed mutagenesis was performed to add amino acids S and A between amino acid 22 and 23 on LVL291 sequence. LVL291 was used as template with primers CAN1531 and CAN1532 and the QuikChange II Site-Directed Mutagenesis Kit (Agilent Technologies, Stratagene Division).

To generate LVL737 (LVL291+A), a site-directed mutagenesis was performed to add amino acid A between amino acid 22 and 23 on LVL291 sequence. LVL291 was used as template with primers CAN1529 and CAN1530 and the QuikChange II Site-Directed Mutagenesis Kit (Agilent Technologies, Stratagene Division).

To generate LVL738 (LVL291 ΔQIQ), a site-directed mutagenesis was performed to delete amino acids Q, I and Q at positions 23 to 25 on LVL291 sequence. LVL291 was used as template with primers CAN1523 and CAN1524 and the QuikChange II Site-Directed Mutagenesis Kit (Agilent Technologies, Stratagene Division).

To generate LVL739 (LVL291 ΔQIQK), a site-directed mutagenesis was performed to delete amino acids Q, I, Q and K at positions 23 to 26 on LVL291 sequence. LVL291 was used as template with primers CAN1525 and CAN1526 and the QuikChange II Site-Directed Mutagenesis Kit (Agilent Technologies, Stratagene Division).

To generate LVL740 (LVL291 ΔQIQKA), a site-directed mutagenesis was performed to delete amino acids Q, I, Q, K and A at positions 23 to 27 on LVL291 sequence. LVL291 was used as template with primers CAN1527 and CAN1528 and the QuikChange II Site-Directed Mutagenesis Kit (Agilent Technologies, Stratagene Division).

To generate LVL778 (LVL736 Δ6×His tag), LVL779 (LVL737 Δ6×His tag), LVL780 (LVL738 Δ6×His tag), LVL781 (LVL739 Δ6×His tag) and LVL782 (LVL740 Δ6×His tag) a polymerase chain reaction was performed using the LVL736, LVL737, LVL738, LVL739 and LVL740 vectors as template, respectively, with primers CAN1669 and CAN543. Deletion of 6×His tag corresponds to the amino acid sequence GGHHHHHH (SEQ ID NO: 3) at the C-terminal sequences. This deletion was incorporated to the 3' primer. NdeI and HindIII restriction sites were incorporated into the 5' and 3' primers respectively. The generated PCR product was then inserted into the pET-26b(+) cloning vector (NOVAGEN®).

TABLE 4

PCR primer sequences used for PE, PilA and PE-PilA amplifications

| Primer ID | DNA Sequence 5'-3' |
|---|---|
| CAN534 | CACACACATATGATTAAATTTCTCTCTGCATTAATTCTTCTACTGGTCACGACG GCGGCTCAGGCTGAGACTAAAAAAGCAGCGGTATCTG (SEQ ID NO. 155) |
| CAN535 | TGTGTGAAGCTTTTAGTGGTGGTGGTGGTGGCCGCCTTGTGTGACACTT CCGCAAAAATTTGC (SEQ ID NO. 156) |

TABLE 4-continued

PCR primer sequences used for PE, PilA and PE-PilA amplifications

| Primer ID | DNA Sequence 5'-3' |
|---|---|
| CAN536 | TTTGCGGAAGTGTCACACAAGGCGGCGCGCAGATTCAGAAGGCTGAACAAA ATGATGT (SEQ ID NO. 157) |
| CAN537 | ACATCATTTTGTTCAGCCTTCTGAATCTGCGCGCCGCCTTGTGTGACACTTCC GCAAA (SEQ ID NO. 158) |
| CAN538 | TGTGTGAAGCTTTTAGTGGTGGTGGTGGTGGCCGCCTTTTTTATCAACT GAAAATG (SEQ ID NO. 159) |
| CAN540 | CACACACATATGCACCACCACCACCACCACAGCGCGCAGATTCAGAAGGCT GAACAAAATGATGT (SEQ ID NO. 160) |
| CAN541 | CATTTTCAGTTGATAAAAAAGGCGGCACTAAAAAAGCAGCGGTATC (SEQ ID NO. 161) |
| CAN542 | GATACCGCTGCTTTTTTAGTGCCGCCTTTTTTATCAACTGAAAATG (SEQ ID NO. 162) |
| CAN543 | TGTGTGAAGCTTTTATTGTGTGACACTTCCGCAAA (SEQ ID NO. 163) |
| CAN544 | CACACACATATGAAATACCTGCTGCCGACCGCTGCTGCTGGTCTGCTGCTCC TCGCTGCCCAGCCGGCGATGGCCCAGATTCAGAAGGCTGAACAAAATGATG T (SEQ ID NO. 164) |
| CAN545 | GCATTTTCAGTTGATAAAAAAGGCGGCACTAAAAAAGCAGCGGTATCTG (SEQ ID NO. 165) |
| CAN546 | CAGATACCGCTGCTTTTTTAGTGCCGCCTTTTTTATCAACTGAAAATGC (SEQ ID NO. 166) |
| CAN547 | CACACACATATGAAATACCTGCTGCCGACCGCTGCTGCTGGTCTGCTGCTCC TCGCTGCCCAGCCGGCGATGGCCGATATTCAGAAGGCTGAACAAAATGATG T (SEQ ID NO. 167) |
| CAN548 | CACACACATATGAAACTTTCCATCCAAAGTACTGACCACAGCCATCCTTGC CACTTTCTGTAGCGGCGCACTGGCAGCCACAAACGACGACGATAAGGCTGA ACAAAATGATG (SEQ ID NO. 168) |
| CAN670 | GCCGGCGATGGCCATGGATAAGGCTGAACAAAATG (SEQ ID NO. 169) |
| CAN671 | CATTTTGTTCAGCCTTATCCATGGCCATCGCCGGC (SEQ ID NO. 170) |
| CAN678 | GGAAGTGTCACACAATAAGGCGGCCACCACCACC (SEQ ID NO. 171) |
| CAN679 | GGTGGTGGTGGCCGCCTTATTGTGTGACACTTCC (SEQ ID NO. 172) |
| CAN1517 | GATATACATATGAAATACCTGCTGCCGACCGCTGCTGCTGGTCTGCTGCTCC TCGCTGCCCAGCCGGCGATGGCCATTCAGAAGGCTGAACAAAA (SEQ ID NO. 205) |
| CAN1518 | GGCCGCAAGCTTTTAGTGGTGGTGGTGGTGGCCGCC (SEQ ID NO. 206) |
| CAN1519 | GGCCGCAAGCTTTTATTGTGTGACACTTCC (SEQ ID NO. 207) |
| CAN1523 | GCTGCCCAGCCGGCGATGGCCAAGGCTGAACAAAATGATGTG (SEQ ID NO. 208) |
| CAN1524 | CACATCATTTTGTTCAGCCTTGGCCATCGCCGGCTGGGCAGC (SEQ ID NO. 209) |
| CAN1525 | GCTGCCCAGCCGGCGATGGCCGCTGAACAAAATGATGTGAAGC (SEQ ID NO. 210) |
| CAN1526 | GCTTCACATCATTTTGTTCAGCGGCCATCGCCGGCTGGGCAGC (SEQ ID NO. 211) |
| CAN1527 | GCTGCCCAGCCGGCGATGGCCGAACAAAATGATGTGAAGCTGG (SEQ ID NO. 212) |

TABLE 4-continued

PCR primer sequences used for PE, PilA and PE-PilA amplifications

| Primer ID | DNA Sequence 5'-3' |
|---|---|
| CAN1528 | CCAGCTTCACATCATTTTGTTCGGCCATCGCCGGCTGGGCAGC (SEQ ID NO. 213) |
| CAN1529 | GCTGCCCAGCCGGCGATGGCCGCCCAGATTCAGAAGGCTGAAC (SEQ ID NO. 214) |
| CAN1530 | GTTCAGCCTTCTGAATCTGGGCGGCCATCGCCGGCTGGGCAGC (SEQ ID NO. 215) |
| CAN1531 | GCTGCCCAGCCGGCGATGGCCAGCGCCCAGATTCAGAAGGCTGAAC (SEQ ID NO. 216) |
| CAN1532 | GTTCAGCCTTCTGAATCTGGGCGCTGGCCATCGCCGGCTGGGCAGC (SEQ ID NO. 217) |
| CAN1669 | CACACACATATGAAATACCTGCTGCCGACC (SEQ ID NO. 218) |
| MDesPILA-3 | GAATTCCATATGCACCATCACCATCACCATACTAAAAAAGCAGCGGTATCTGAA (SEQ ID NO. 173) |
| MDesPILA-4 | GCGCCGCTCGAGTCATTGTGTGACACTTCCGC (SEQ ID NO. 174) |
| MnoNTHi-44 | GCCCAGCCGGCGATGGCCCAGATCCAGAAGGCTGAACAAAATG (SEQ ID NO. 175) |
| MnoNTHi-45 | CATTTTGTTCAGCCTTCTGGATCTGGGCCATCGCCGGCTGGGC (SEQ ID NO. 176) |

Transformation

Escherichia coli BLR (DE3) or E. coli HMS (DE3) cells were transformed with plasmid DNA according to standard methods with $CaCl_2$-treated cells. (Hanahan D. <<Plasmid transformation by Simanis.>> In Glover, D. M. (Ed), DNA cloning. IRL Press London. (1985): p. 109-135.). Briefly, BLR (DE3) or HMS174(DE3) competent cells were gently thawed on ice. Approximately 4 µl of plasmid (10-100 ng) were mixed using 50-100 µl competent cells. Thereafter, this formulation was incubated on ice for 30 min. To perform the transformation reaction, the formulation was heat pulsed at 42° C. for 45 seconds then incubated on ice for 2 minutes. Approximately 0.5 ml of SOC medium (Super Optimal broth with Catabolite repression) was added to the transformed cells and the cell culture was incubated at 37° C. for one hour before plating on Luria-Bertani (LB) agar with 50 ug/ml kanamycin. Around 100 µl of transformed cell culture was plated and incubated overnight at 37° C.

BLR (DE3): BLR is a recA⁻ derivative of BL21 (F-ompT hsdSB(rB-mB-) gal dcm (DE3). This E. coli strain used for expression of recombinant proteins improves plasmid monomer yields and may help stabilize target plasmids containing repetitive sequences or whose products may cause the loss of the DE3 prophage. (Studier, F. W. (1991) J. Mol. Biol. 219: 37-44). The detailed genotype of E. coli BLR (DE3) has been published by NOVAGEN®. (F-ompT hsdSB (rB-mB-) gal dcm Δ(srl-recA)306::Tn10 (TetR) (DE3).

HMS174 (DE3): HMS174 strains provide the recA mutation in a K-12 background. Like BLR, these strains may stabilize certain target genes whose products may cause the loss of the DE3 prophage. The detailed genotype of E. coli HMS174 (DE3) has been published by NOVAGEN®. (F-recA1 hsdR(rK12-mK12+) (DE3) (Rif R).

Production Using BLR (DE3) and Characterization of His Tagged Constructs are Described in Example 3 Through Example 6

Example 3

Protein Expression Using Shake Flask

Generally, one confluent agar plate inoculated with Escherichia coli BLR (DE3) transformed with recombinant plasmid was stripped, resuspended in culture media and used to inoculate 800 ml of LB broth (Becton, Dickinson and Company)±1% (weight/volume, w/v) glucose (Laboratoire MAT, catalogue number: GR-0101) and 50 µg/ml kanamycin (Sigma) to obtain $O.D._{600\ nm}$ between 0.1 and 0.2. Cultures were incubated at 37° C. with agitation of 250 RPM to reach an $O.D._{600\ nm}$ of ~0.8.

One ml of each culture was then collected, centrifuged at 14 000 RPM for 5 minutes and supernatants and pellets were frozen at −20° C. separately.

At an $O.D._{600\ nm}$~0.8, the BLR (DE3) cultures were cooled down (−20° C., 20 minutes or 4° C., 1 hour, preferably at 4° C. for 1 hour) before inducing the expression of the recombinant protein by addition of 1 mM isopropyl β-D-1-thiogalactopyranoside (IPTG; EMD Chemicals Inc., catalogue number: 5815) and incubation overnight at 16, 22 and 30° C., or 3 hours at 37° C. with agitation of 250 RPM, preferably overnight at 22° C. After the induction period the cultures were centrifuged at 14 000 RPM for 5 minutes or 6 000 RPM for 15 minutes and supernatant (media fraction sample) and pellets (containing soluble and insoluble fractions) were frozen at −20° C. separately.

These conditions are used for periplasmic protein expression.

Example 4

Protein Purification Using Shake Flask, Cell Pastes, His Tagged Constructs

Each bacterial pellet obtained after induction was resuspended in 20 mM 4-(2-hydroxyethyl)-1-piperazineethanesulfonic acid (HEPES) buffer (pH 8.0) containing 500 mM NaCl, 10 mM imidazole and Roche COMPLETE® Protease Inhibitor Cocktail (1 tablet/50 ml of HEPES buffer containing 500 mM NaCl, Roche COMPLETE® ULTRA tablets, Roche Diagnostics Corporation).

Alternatively, 20 to 50 mM bicine buffer may be used instead of HEPES buffer containing NaCl. For example, 20 mM bicine buffer may be used. Bacteria were lysed using a Constant System 1.1 KW 2×30 000 PSI (pounds per square inch). Soluble (supernatant) and insoluble (pellet) components were separated by centrifugation at 20 000 g for 20 min at 4° C.

6-His tagged-proteins were purified under native conditions on immobilized metal affinity chromatography (IMAC) using PROFINIA™ protein purification protocol (Bio-Rad Laboratories, Inc.). The soluble components were loaded on a 5 ml His Trap column (Bio-Rad Laboratories, Inc.) preequilibrated with the same buffer used for bacterial resuspension; the soluble components were added at up to 5 ml/min (producing a "flow through fraction") After loading on the column, the column was washed with 10 column volumes of the same buffer at a rate of 10 ml/min (producing a "wash fraction #1). A second wash using 20 mM bicine buffer or 20 mM HEPES buffer (pH 8.0) containing 500 mM NaCl and 20 mM imidazole was performed, producing a "wash fraction #2). Elution was performed using 2 column volumes of 20 mM HEPES buffer or 50 mM bicine buffer (pH 8.0) containing 500 mM NaCl and 250 mM imidazole at a rate of 10 ml/min, producing an "elution fraction".

To improve the purity of the protein, positive elution fractions from IMAC were pooled and loaded on a size exclusion chromatography (SEC) column (HILOAD™ SUPERDEX™ 200 26/60 from GE Healthcare) preequilibrated in phosphate buffered saline without calcium or magnesium (NaCl 137 mM, KCl 2.7 mM, $Na_2HPO_4$ 8.1 mM, $KH_2PO_4$ 1.47 mM, pH 7.4). Samples from elution fractions were analyzed by sodium dodecyl sulfate polyacrylamide gel electrophoresis (SDS-PAGE). Samples were concentrated using Centricon 10 000 MW (Millipore).

Protein concentration was determined using spectrometer.

Example 5

SDS-PAGE and Western Blot Analysis of His Tapped Constructs & SDS-PAGE Analysis of Non-His Tapped LVL317 & LVL318 Constructs Soluble and Insoluble Fraction Preparation For example, 1 ml of culture after induction (see, for example, Example 3 above) was centrifuged at 14 000 RPM for 2 min. The pellet was resolubilized using 40 µl of BUGBUSTER® Protein Extraction Reagent (NOVAGEN®, EMD4 Biosciences, Merck), creating a cell suspension. The cell suspension was incubated on a rotating platform for 10 min at room temperature. The cell suspension was then centrifuged at 14 000 RPM for 2 min to separate the soluble fraction. The resulting pellet (insoluble fraction) was resolubilized using 70 µl of deionized water, 5 µl of dithiothreitol (DTT) 1M and 25 µl of NUPAGE® LDS (Lithium Dodecyl Sulphate) Sample Buffer 4× (INVITROGEN™). The soluble fraction (supernatant from the cell suspension of the resolubilized pellet) was added to 30 µl of deionized water, 5 µl of DTT 1M and 25 µl of LDS Sample Buffer 4×.

Media Fraction Preparation

For example, to prepare the media fraction, 100 µl of the supernatant from the induced whole cell culture following centrifugation (see, for example, Example 3 above) was concentrated by adding 500 µl of RC reagent I (Bio-Rad Laboratories, Inc.); the sample was mixed and incubated for 1 min at room temperature. Then, 500 µl of Reagent II (Bio-Rad Laboratories, Inc.) was added to the sample and mixed. This formulation was centrifuged at 14 000 RPM for 10 min. The pellet was resolubilized using 28 µl of deionized water, 2 µl of DTT 1M and 10 µl of LDS SB 4×.

Purification Fraction Preparation

For example, purified proteins (for example, obtained as described in Example 4) were prepared for SDS-PAGE analysis by adding 70 l of sample, 5 l of DTT 1M and 25 l of LDS Sample Buffer 4×.

SDS-PAGE Analysis and Transfer to Nitrocellulose Membrane

SDS-PAGE analysis and transfer to nitrocellulose membrane were performed according to manufacturer's recommendations (Invitrogen) using NUPAGE® Bis-Tris 4-12% gels. Preparations of samples, buffers and migration conditions were done under conditions recommended by the suppliers.

In one example, the gel was loaded with a 20 ul sample from a master mix comprising 70 µl of a purified protein fraction, 5 µl of DTT 1M and 25 µl of LDS SB 4×.

After samples were run on NUPAGE® Bis-Tris 4-12% gels, the proteins were transferred to nitrocellulose membranes.

Nitrocellulose membranes were blocked for 30 minutes at 37° C., 60 RPM using 3% milk/PBS 1× fresh solution. After the blocking incubation, Primary Antibodies were added (6×His Tag® antibody, Abcam PLC, catalogue number: ab9108) at a dilution of: 1:1000 in 3% milk/PBS 1× fresh solution for 1 hour at 37° C., 60 RPM. After that, membranes were washed three times, for 5 minutes each, at room temperature using 0.02% polsorbate 20 (for example, TWEEN™ 20)/PBS 1×. Secondary Antibodies (alkaline phosphatase (AP) Rabbit anti-IgG (H+L) rabbit, Jackson ImmunoResearch Laboratories, Inc.) were added at dilution 1:14 000 using 3% milk/PBS 1× fresh solution. Membranes were incubated for 1 hour at 37° C., 60 RPM. After that, membranes were washed three times for 5 minutes at room temperature using 0.02% polysorbate 20 (for example, TWEEN™ 20)/PBS 1× before the membrane expositions to 5-bromo-4-chloro-3-indolyl phosphate/nitro blue tetrazolium (for example, BCIP®/NBT from Sigma-Aldrich®, 1 tablet/10 ml water).

See FIG. 1 for SDS-PAGE of induced bacterial extracts for fusion protein constructs LVL291, LVL268 and LVL269. Insoluble fraction (I), Soluble fraction (S) and Culture Media fraction (M) were loaded for LVL291, LVL268 and LVL269 before and after induction (ind).

Figure 2:
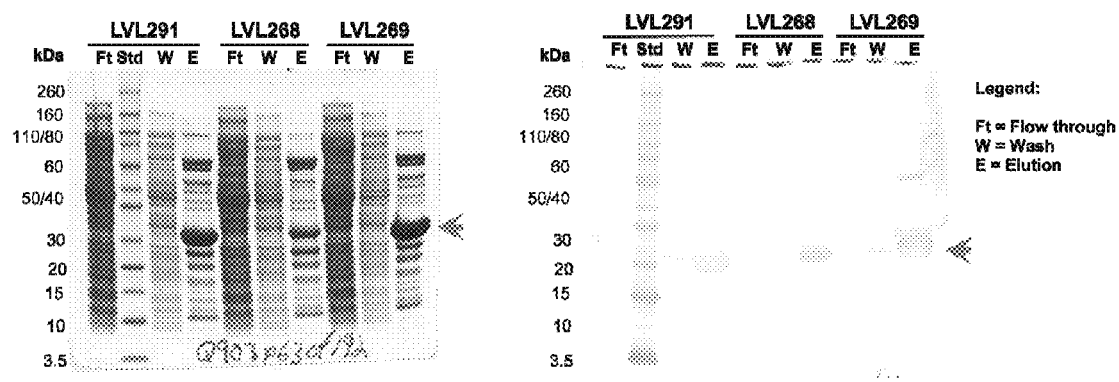
FIG. 2. SDS-PAGE and Western blot related to purification extracts for fusion protein constructs LVL291, LVL268 and LVL269. Flow through fraction (Ft), Wash fraction (W) and Elution fraction (E) were loaded for purification of LVL291, LVL268 and LVL269. Anti-his tag was used to probe extracts.

See FIG. 2 for SDS-PAGE and Western blot related to purification extracts for fusion protein constructs LVL291, LVL268 and LVL269. Flow through fraction (Ft), Wash fraction (W) and Elution fraction (E) were loaded for purification of LVL291, LVL268 and LVL269. Anti-his tag was used to probe extracts.

Figure 3:
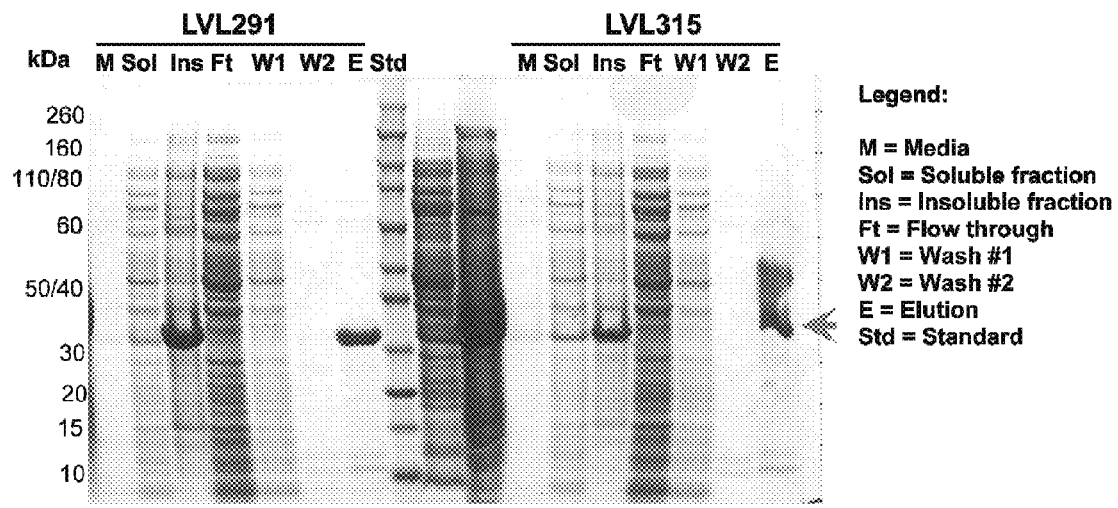
FIG. 3. SDS-PAGE of induced bacterial and purification extracts for fusion protein constructs LVL291 and LVL315. Culture Media fraction (M), Soluble fraction (Sol), Insoluble fraction (Ins), Flow through fraction (Ft), Wash fraction #1 (W1), Wash fraction #2 (W2) and Elution fraction (E) were loaded for LVL291 and LVL315.

See FIG. 3 for SDS-PAGE of induced bacterial and purification extracts for fusion protein constructs LVL291 and LVL315. Culture Media fraction (M), Soluble fraction (Sol), Insoluble fraction (Ins), Flow through fraction (Ft), Wash fraction #1 (W1), Wash fraction #2 (W2) and Elution fraction (E) were loaded for LVL291 and LVL315.

Figure 4:
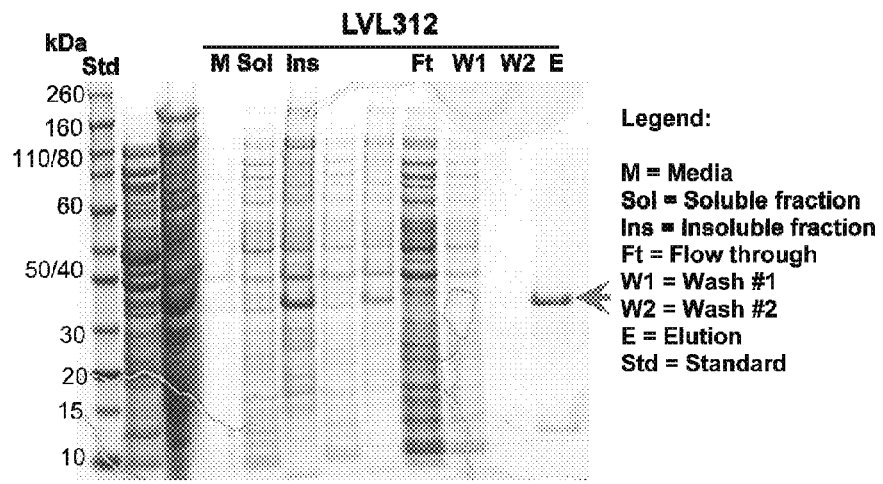
FIG. 4. SDS-PAGE of induced bacterial and purification extracts for fusion protein construct LVL312. Culture Media fraction (M), Soluble fraction (Sol), Insoluble fraction (Ins), Flow Through fraction (Ft), Wash fraction #1 (W1), Wash fraction #2 (W2) and Elution fraction (E) were loaded for LVL312.

See FIG. 4 for SDS-PAGE of induced bacterial and purification extracts for fusion protein construct LVL312.

Culture Media fraction (M), Soluble fraction (Sol), Insoluble fraction (Ins), Flow Through fraction (Ft), Wash fraction #1 (W1), Wash fraction #2 (W2) and Elution fraction (E) were loaded for LVL312.

Figure 25:
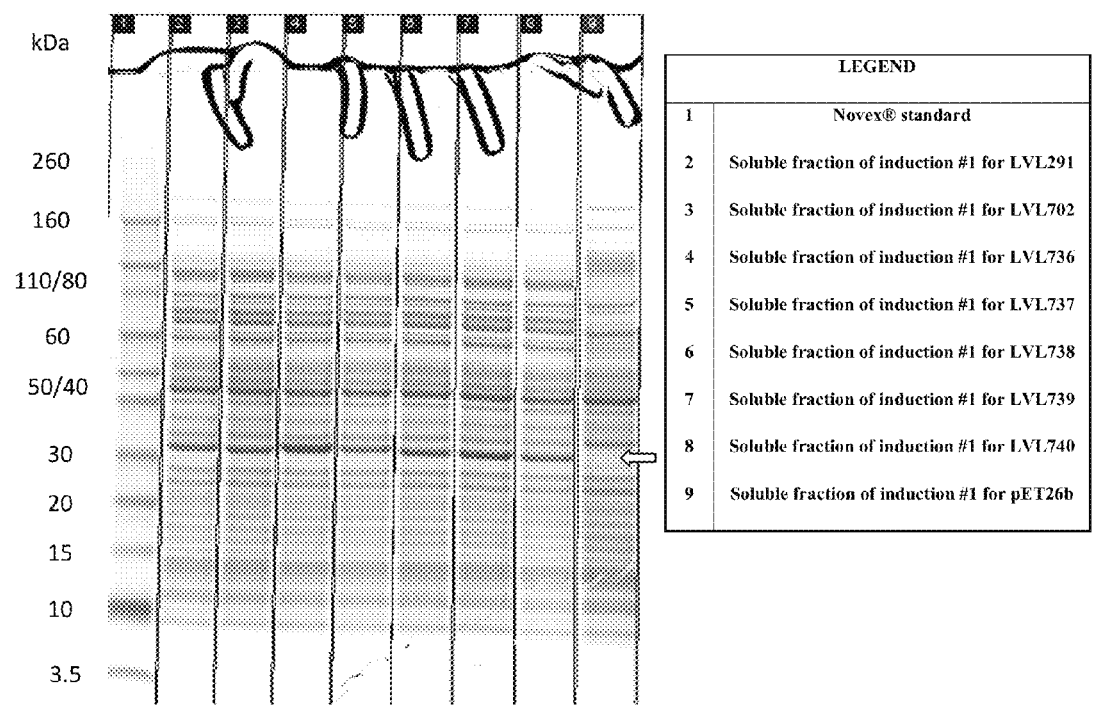
FIG. 25. SDS-PAGE of soluble fractions of induced bacterial extracts for fusion protein constructs LVL291, LVL702, LVL736, LVL737, LVL738, LVL739, LVL740 and pET26b vector (negative control). (a) Experiment 1 (b) Experiment 2 (c) Experiment 3. PE-PilA fusion protein indicated by arrow.
Figure 25:
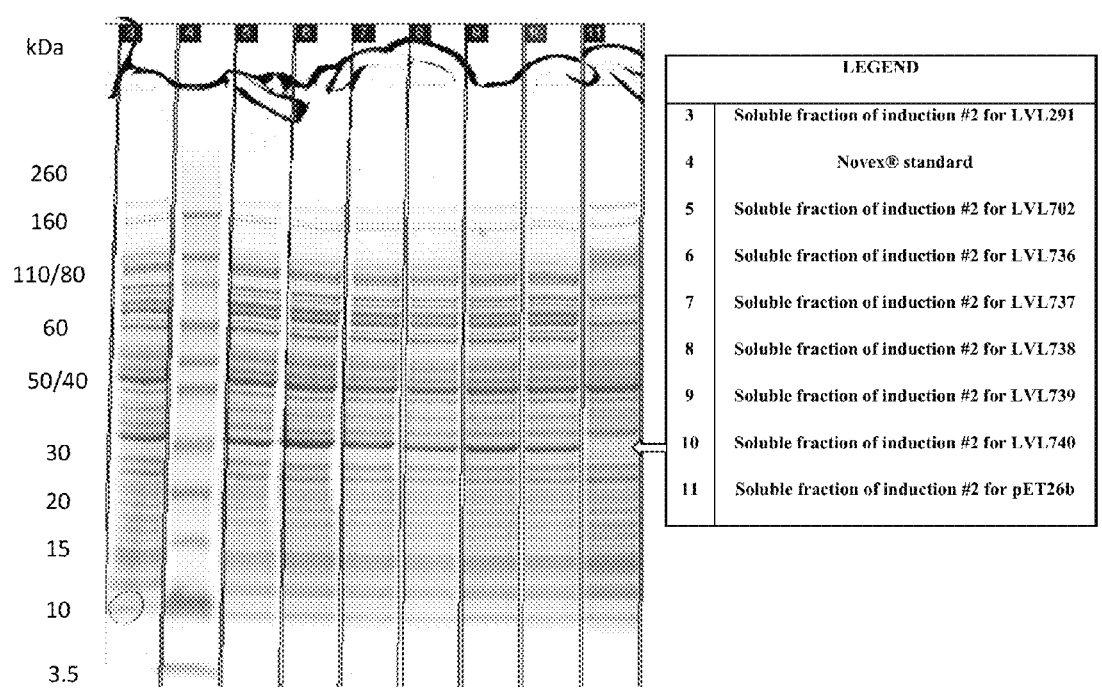
Figure 25:
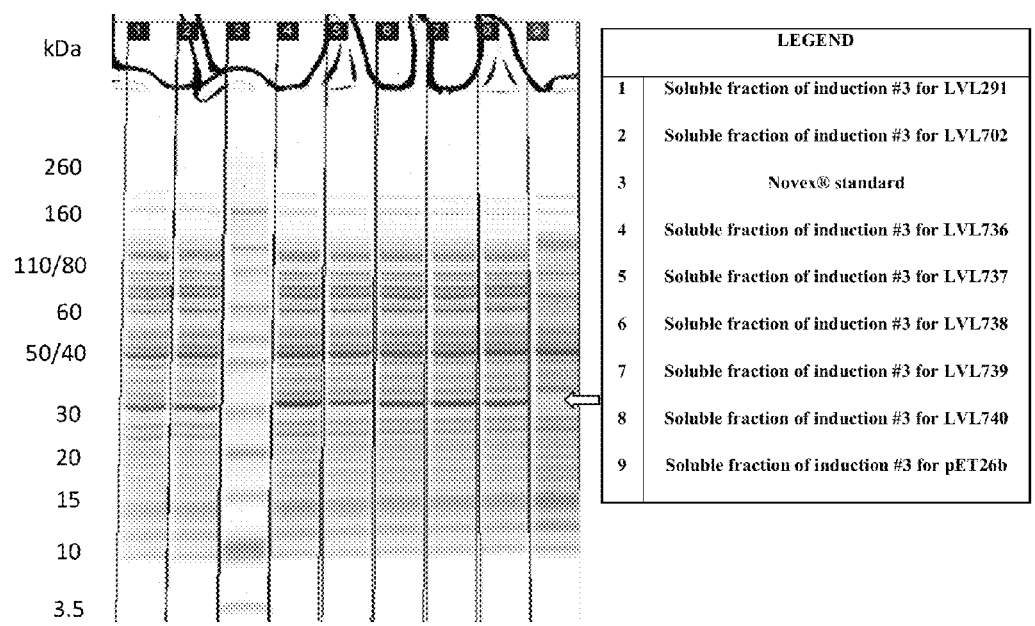

See FIG. 25 for SDS-PAGE of soluble fractions from induced bacterial extracts for fusion protein constructs LVL291, LVL702, LVL736, LVL737, LVL738, LVL739, LVL740 and pET26b vector (negative control). (a) Experiment 1 (b) Experiment 2 (c) Experiment 3. PE-PilA fusion protein indicated by arrow.

Figure 26:
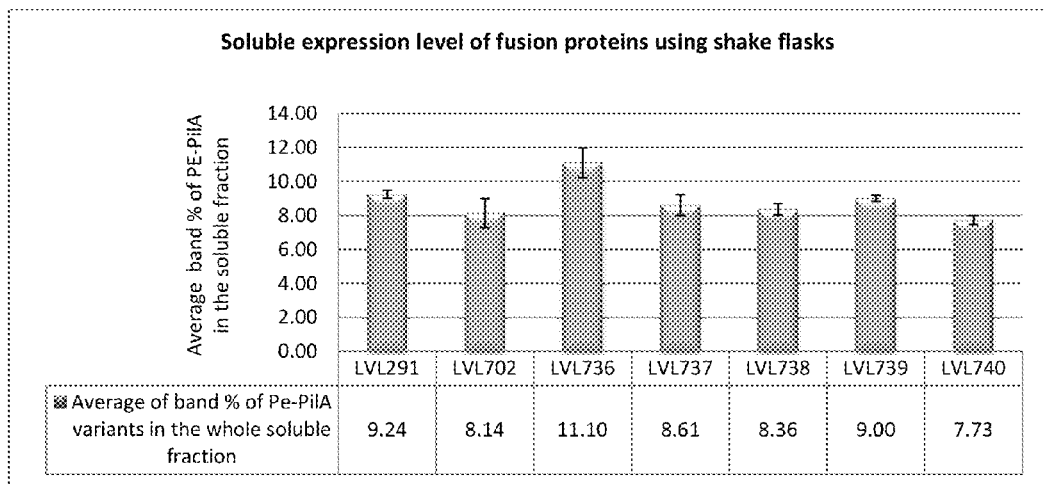
FIG. 26. The average band percentage of fusion protein in the soluble fraction from Experiments 1, 2 and 3.

See FIG. 26 for the average band percentage of fusion protein in the soluble fraction from Experiments 1, 2 and 3.

Figure 5:
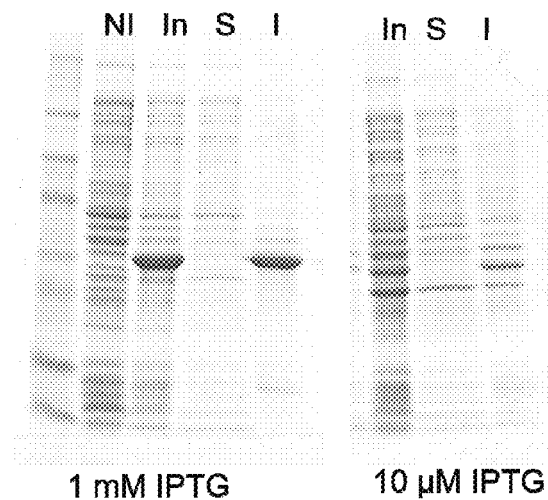
FIG. 5. SDS-PAGE of induced (1 mM and 10 µM IPTG) bacterial extracts for fusion protein construct LVL317. Extracts from before (NI) and after induction (In), Soluble fraction (S), Insoluble fraction (I).
Figure 6:
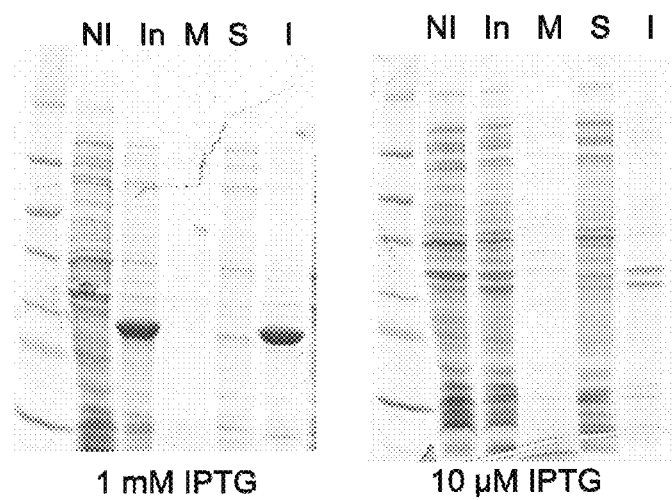
FIG. 6. SDS-PAGE of induced (1 mM and 10 µM IPTG) bacterial extracts for fusion protein construct LVL318. Extracts from before (NI) and after induction (In), Culture Media fraction (M), Soluble fraction (S), Insoluble fraction (I).

LVL317 and LVL318 bacterial extracts used in the SDS-PAGE analysis in FIG. 5 and FIG. 6, respectively, were prepared generally as described above.

FIG. 5. SDS-PAGE of induced (1 mM and 10 μM IPTG) bacterial extracts for fusion protein construct LVL317. Extracts from before (NI) and after induction (In), Soluble fraction (S), Insoluble fraction (I).

FIG. 6. SDS-PAGE of induced (1 mM and 10 μM IPTG) bacterial extracts for fusion protein construct LVL318. Extracts from before (NI) and after induction (In), Culture Media fraction (M), Soluble fraction (S), Insoluble fraction (I).

Proteins separate by SDS-PAGE were transferred to an Immobilon-P membrane. The Coomassie Blue stained protein bands were cut and placed in a sequenator reactor. Sequencing was carried out according to manufacturer's protocol using an Applied Biosystems PROCISE® Protein Sequencer, model 494-cLC.

TABLE 5

Shake flask protein expression profiles and signal peptide cleavage for fusion protein constructs.

| Fusion Protein Construct ID | Description N-term → C-term | Protein Expression profile | Signal peptide cleavage |
|---|---|---|---|
| LVL312 | FlgI sp - E - PilA fragment - GG - PE fragment - GGHHHHHH | In: +++<br>So: +<br>Se: + | Confirmed |
| LVL291 | PelB sp - PE fragment - GG - PilA fragment - GGHHHHHH | In: +++<br>So: ++<br>Se: + | Confirmed |
| LVL268 | PelB sp - D - PE fragment - GG - PilA fragment - GGHHHHHH | In: +++<br>So: ++<br>Se: + | Confirmed |
| LVL269 | NadA sp - ATNDDD - PE fragment - GG - PilA fragment - GGHHHHHH | In: +++<br>So: ++<br>Se: + | Confirmed |
| LVL270 | MHHHHHH - PE fragment - GG - PilA fragment | In: +<br>So: −<br>Se: − | Not tested |
| LVL315 | PelB sp - MD - PE fragment - GG - PilA fragment - GGHHHHHH | In: +++<br>So: ++<br>Se: + | Confirmed |
| LVL317 | PelB - PE fragment - GG - PilA fragment | In: +++<br>So: +<br>Se: Nt | Confirmed |
| LVL318 | PelB sp - MD - PE fragment - GG - PilA fragment | In: +++<br>So: +<br>Se: − | |
| LVL702 | PelB sp - PE fragment - GG - PilA fragment - GGHHHHHH | In: +++<br>So: ++<br>Se: Nt | Confirmed |
| LVL736 | PelB sp - PE fragment - GG - PilA fragment - GGHHHHHH | In: +++<br>So: ++<br>Se: Nt | Confirmed |
| LVL737 | PelB sp - PE fragment - GG - PilA fragment - GGHHHHHH | In: +++<br>So: ++<br>Se: Nt | Confirmed |
| LVL738 | PelB sp - PE fragment - GG - PilA fragment - GGHHHHHH | In: +++<br>So: ++<br>Se: Nt | Confirmed |
| LVL739 | PelB sp - PE fragment - GG - PilA fragment - GGHHHHHH | In: +++<br>So: ++<br>Se: Nt | Confirmed |
| LVL740 | PelB sp - PE fragment - GG - PilA fragment - GGHHHHHH | In: +++<br>So: ++<br>Se: Nt | Confirmed |

So = Soluble fraction.
In = Insoluble fraction.
Se = Protein Secreted in the media fraction.
Nt = Not tested.
The following rating were based on a visual inspection (coomassie)
+: low expression;
++: medium expression;
+++: high expression;
−: no expression

Example 6

LVL291 Fusion Protein Characterization

Physical Properties of LVL291: Folding of PE and PilA in LVL291 & Melting Point

Circular Dichroism:

Analysis of Secondary Structure

Circular dichroism (CD) is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative abundance of each secondary structure type in a given protein sample can be calculated by comparison to reference spectra.

Far UV spectra are measured using an optical path of 0.01 cm from 178 to 250 nm, with a 1 nm resolution and bandwidth on a Jasco J-720 spectropolarimeter. Temperature of the cell is maintained at 23° C. by a Peltier thermostated RTE-111 cell block. A nitrogen flow of 10 L/min is maintained during the measurements.

Figure 7:
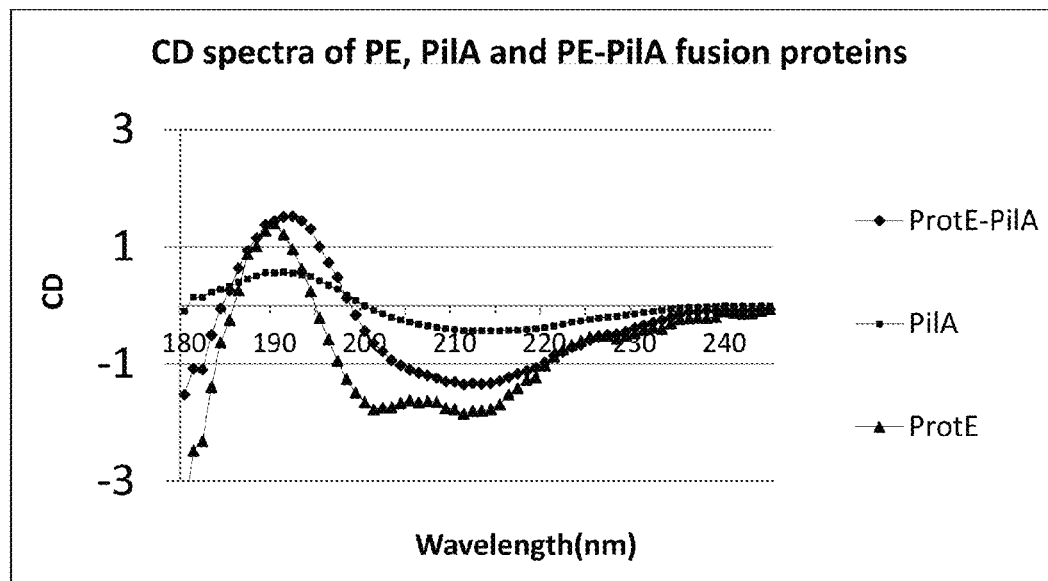
FIG. 7. CD spectra of PE, PilA and PE-PilA fusion proteins.

Results:

The far-UV CD spectra obtained for PE (from construct pRIT16762), PilA (from construct pRIT 16790) and PE-PilA proteins are characteristic of folded proteins containing a mix of alpha and beta structures, but PE is significantly richer in alpha helix than PilA and PE-PilA (FIG. 7, CD spectra of PE, PilA and PE-PilA fusion proteins).

In order to evaluate the integrity of the folding of PE and PilA individual proteins once bound together in a chimeric protein and then verify a possible interaction between both, difference spectra were calculated.

Figure 8:
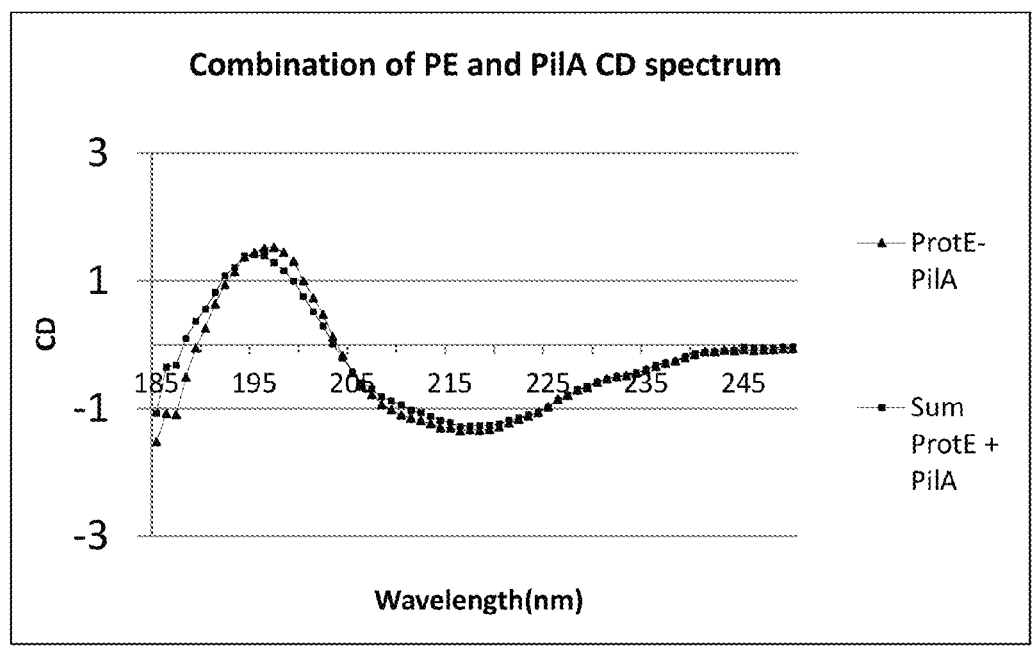
FIG. 8. Combination of PE and PilA CD spectrum.

When the PE and PilA far-UV spectra are combined, the resulting spectrum superposes to the spectrum of PE-PilA chimer (FIG. 8, Combination of PE and PilA CD spectrum). This result suggests that the PE-PilA chimer contains all the secondary structures that are detected in the individual components. It also suggests that the fusion of the proteins has no major impact on the secondary structures of the individual components and consequently that the folding of PE and PilA is not significantly different whether the proteins are separate or in fusion.

Melting Point Evaluation:

In order to evaluate if the expression in fusion has an impact on the thermodynamic properties of the individual proteins, the melting points of PE, PilA and PE-PilA have been evaluated by monitoring the defolding of the alpha helix with temperature by circular dichroism.

The presence of alpha helix is characterized by a minimum in the Circular dichroism signal at 222 nm, so a significant increase in CD signal at 222 nm during temperature increase is an indication of protein denaturation. The determination of the temperature at which the protein undergoes loss in secondary structure allows the determination of the melting point (Tm), which corresponds to the temperature at which half of the proteins have lost their structure.

Melting point can be determined by identification of the inflexion point on the thermal denaturation curve obtained from a temperature versus CD 222 nm plot.

Figure 9:
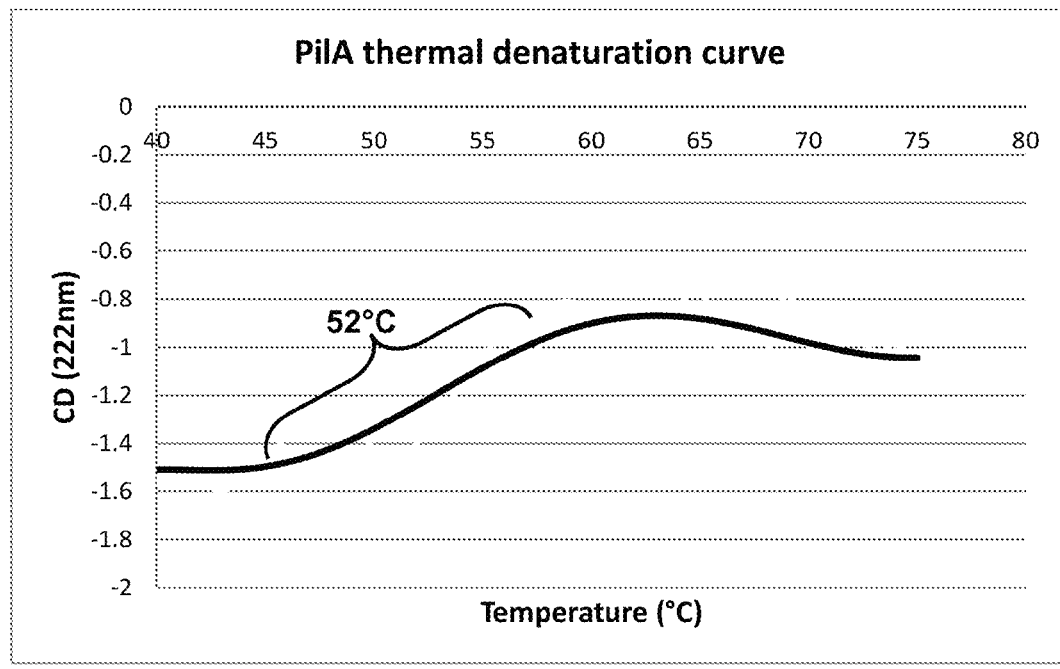
FIG. 9. PilA thermal denaturation curve.
Figure 10:
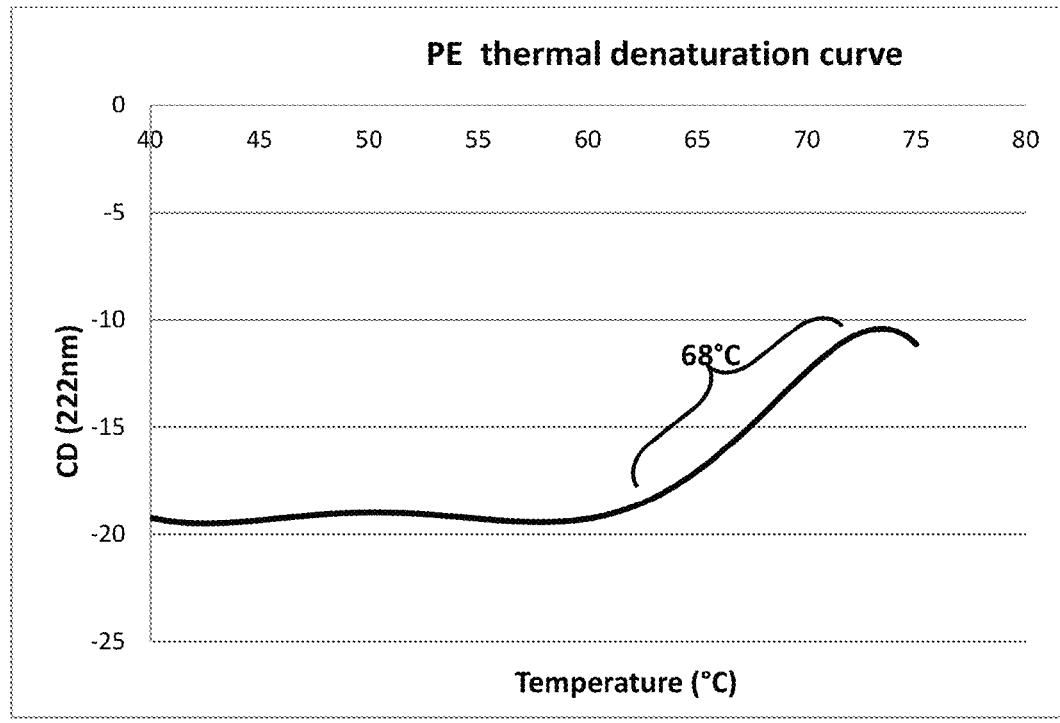
FIG. 10. PE denaturation curve.

Melting point of PilA and PE as determined by far-UV CD are respectively of 52° C. and 68° C. (FIG. 9, PilA thermal denaturation curve; FIG. 10, PE thermal denaturation curve).

Figure 11:
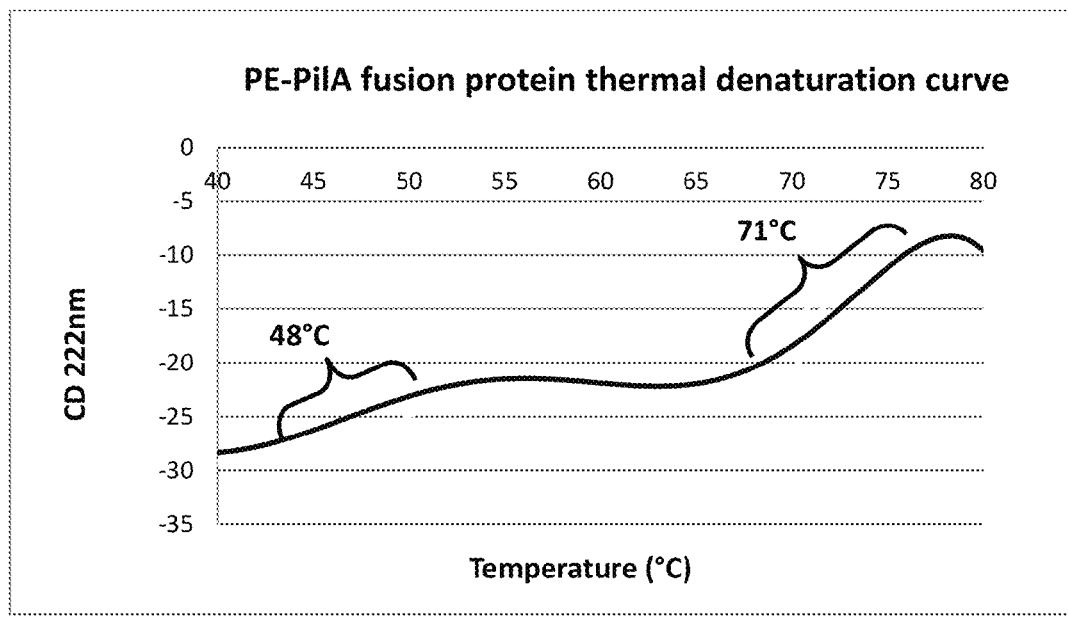
FIG. 11. PE-PilA fusion protein thermal denaturation curve.

The PE-PilA fusion protein exhibits two distinct Tm's at 48° C. and 71° C. (FIG. 11, PE-PilA fusion protein thermal denaturation curve). Those values indicate that the PE and PilA proteins are still independently folded when bound into a chimer and that they defold at a similar temperature whether they are separate or in fusion. The observation that the defolding of the PilA portion at 48° C. doesn't cause precipitation or impact the Tm of the PE portion at 71° C. is a strong indication that the interaction between PE and PilA within the fusion is minimal and that they don't have a major observable impact on each other. The melting points of proteins are sensitive to various external conditions, including buffer composition or presence of interacting molecules; that no major variation is observed upon fusion of PE and PilA is a strong indication of the preservation of most of the structure and of the properties of both PE and PilA when they are bound together.

Example 7

Fermentation Process

Fusion proteins of the invention may be prepared by methods known by those skilled in the art.

Example 8

Protein Purification of PE, PilA, and LVL317

PE Protein Purification from pRIT16762:

To generate the pRIT16762 expression vector, the pRIT16711 vector was digested using BamHI and NcoI restriction enzymes in order to delete 6 amino acid residues between the signal sequence (pelB) and PE. The vector obtained was named pRIT16712. In this vector, there are 3 amino acids between the signal sequence pelB and PE: MDP. In a second step, a site directed mutagenesis was performed to change amino acid sequence from MDP to QIQ using pRIT16712 as template with primers MnoNTHi-44 and MnoNTHi-45 (described in Table 4) and the QuikChange II Site-Directed Mutagenesis Kit (Agilent Technologies, Stratagene Division).

Working seed of E. coli BLR(DE3) containing PE QIQ (from the pRIT16762 construct) was thawed from −80° C. and used to prepare 100 ml of pre-culture in LB broth by overnight incubation at 37° C. under agitation at 215 RPM. After overnight incubation, eight flasks containing 800 ml of LB APS were inoculated with 12.5 ml of pre-culture and $OD_{600}$ measured at around 0.06. The cultures were incubated 3 h at 37° C. with shaking. At a $OD_{600}$ of around 0.9, 1 mM IPTG was added to start the induction. During the induction, the cultures were incubated 19 h at 22° C. with shaking. After induction, $OD_{600}$ was at around 2.2. The cell cultures were transferred into 1 L centrifuge bags placed inside 1 L bottles and centrifuged at 4° C. for 30 minutes at 6,000×g and supernatant discarded. 1 ml aliquots of culture pre- and post-induction and supernatant were kept for future analysis.

Lysis of the BLR(DE3) Induced with PE QIQ

The centrifuge bags were removed from the centrifugation bottles, opened and the pellet was expulsed from the bag into a beaker. The eight pellets were pulled together and resuspended in 100 ml of binding buffer (20 mM Hepes, 10 mM imidazole, 500 mM NaCl, pH 8.01). The E. coli BLR (DE3) containing the PE QIQ construct were disrupted with the TS Series Bench Top cell disrupter from Constant Systems Ltd. (1×30 kPsi; 1×15 kPsi). The lysate was centrifuged 30 minutes, 6000 RPM, 4° C. The supernatant was kept and loaded on an IMAC column.

IMAC Purification of PE QIQ

IMAC column (BioRad, Bio-Scale Mini Profinity IMAC cartridge 5 ml) was equilibrated with 5CV of Binding buffer (20 mM HEPES, 10 mM imidazole, 500 mM NaCl, pH 8.01) at 5 ml/min. 100 ml of lysate supernatant was loaded on the IMAC at 2.5 mL/min. Flow-through was collected in 50 ml fractions for future analysis. The column was washed with 3CV of Binding buffer to remove unbound protein. Sample containing unbound proteins was collected in one aliquot of 15 ml in a 50 ml tube. The column was washed with 2CV of Wash buffer (20 mM HEPES, 20 mM imidazole, 500 mM NaCl, pH 8.01) collected in 2 ml fractions in a 96 well plate. The bound protein was then eluted with 6CV of 100% Elution buffer (20 mM HEPES, 250 mM imidazole, 500 mM NaCl, pH 8.01). The eluted protein was collected in 2 ml fractions in 96-well plates. Wash and elution were performed at 5 ml/min.

Size Exclusion Chromatography (SEC) on the IMAC Pool of PE QIQ

SEC column (GE healthcare, HILOAD™ 26/60 SUPERDEX™ 75 prep grade, 60 cm height approx 319 ml volume) was equilibrated with 3CV of SEC buffer (20 mM HEPES, 150 mM NaCl, pH8.49). 11 ml of IMAC eluate was loaded onto the column at a flow rate of 2.5 ml/min. 2 ml fractions were collected from 0.3CV to 0.9CV. Two runs were performed then fractions were analyzed by SDS-PAGE. Fractions from the two runs containing Prot E protein were pooled together ("SEC pool", 48 ml approx total volume). 500 mM of Arginine was added to the SEC pool.

Dosage of the PE QIQ Pooled Samples Generated in the Above SEC Protocol

The SEC pool was dosed with the RCDC (Reducing Agent and Detergent Compatible) method from the Bio-Rad RC DC™ kit following manufacturer's protocol:

For each tested sample and standard, 25 µL was distributed in microfuge tubes in duplicate. 125 µL of Bio-Rad RC Reagent I was added into each tube; each tube was vortexed and incubate for 1 minute at room temperature. 125 µL of Bio-Rad RC Reagent II is added into each tube; each tube is vortexed and then centrifuged at 14,000×g for 5 minutes. Supernatants are discarded by inverting the tubes on clean, adsorbent tissue paper allowing the liquid to drain completely from the tubes. 25.4 µL of Reagent A (already prepared by mixing 20 µL of Reagent S per 1 ml of Reagent A) is added to each tube; each tube is vortexed and incubated at room temperature for 5 minutes, or until precipitate is completely dissolved. Vortex before proceeding to next step. Add 200 µL of DC reagent B to each tube and vortex immediately. Incubate at room temperature for 15 minutes. Transfer all samples to a 96-well plate and read the absorbance at 750 nm to determine the protein concentration for each unknown protein sample.

The ProtE concentration was 1.069 mg/ml

PilA His-Tagged Protein Purification:

PilA was purified following the general procedure below:
 E. coli cells containing a construct encoding PilA or a fragment thereof are suspended in BUGBUSTER® and BENZONASE® nuclease (NOVAGEN®), for example 10 ml BUGBUSTER® and 10 ul BENZONASE® nuclease. The cell lysate is mixed at room temperature on a rotating platform, for example, for 15 minutes. The cell lysate is centrifuged at 4° C., for example at 16,000 g for 20 minutes. The supernatant containing the protein is added to a Ni NTA column containing Ni NTA HIS.BIND® resin and mixed at 4° C., for example for 1 hour. The column may consist of 2 ml of Ni NTA HIS.BIND® resin (NOVAGEN®) and 10 ml 1× Binding Buffer (from NOVAGEN®'s Ni-NTA Buffer Kit). The column flow through is then collected. The resin is washed two times with 1× wash buffer, for example, containing 300 mM NaCl, 50 mM NaH$_2$PO$_4$, 25 mM imidazone, pH 8.0). The wash is collected by gravity flow. The protein is eluted from the column with 1× elution buffer, for example, 300 mM NaCl, 50 mM NaH$_2$PO$_4$, 250 mM imidazone, pH 8.0. The protein may be further purified by dialysis with the Binding Buffer and rerun over a Ni NTA column as described above.

Thrombin Cleavage of PilA.

PilA is then incubated with thrombin (diluted 1/50) at room temperature for 16 h, to remove the histidine tag.

Size Exclusion Chromatography (SEC) on PilA Cleaved with Thrombin.

SEC column (GE healthcare, HILOAD™ 26/60 SUPERDEX™ 75 prep grade, 60 cm height approx 319 ml volume) was equilibrated with 5CV of SEC buffer (20 mM HEPES, 150 mM NaCl, pH8.52). Approximately 10 ml of cleaved PilA was loaded onto the column at a flow rate of 2.5 ml/min. 2 ml fractions collected from 0.3CV to 0.9CV. Two runs were performed then fractions were analyzed by SDS-PAGE. Fractions from the two runs containing cleaved PilA protein were pooled together ("SEC pool", 52 ml approx total volume).

Dosage of PilA, SEC Pool.

The SEC pool was dosed with the RCDC method as described above. The cleaved PilA concentration was at 5.37 mg/ml.

Dialysis of the PilA SEC Pool with PBS 1× pH 7.4 (Dialysis Factor=1600) and Dosage by RCDC The concentration post-dialysis determined by RCDC was at 3.0 mg/ml.

Purification of LVL317

Osmotic Shock

Since LVL317 fusion protein is expressed and processed in bacterial periplasm, the protein was extracted by osmotic shock.

Frozen (−20° C.) harvested E. coli B2448 cell paste containing LVL317 from 4 L of fermentor culture were pooled and resuspended in a hypertonic buffer consisting of 24 mM Tris-HCl, 16% (w/v) sucrose, 9.9% (w/v) glucose, 10 mM EDTA, pH 8.0 up to a final volume of 4 L. The suspension was mixed gently for 30 min at room temperature using a 3-blade propeller installed on RW 16 basic stirrer, at medium speed. The suspension was centrifuged at 15,900×g for 30 minutes at room temperature. Supernatant (SN1) was kept for gel analysis.

The resulting pellet was resuspended in a hypotonic solution; 38 mM MgCl$_2$, and mixed for 30 min at room temperature. The mixture was centrifuged at 15,900×g for 30 minutes at room temperature and the antigen recovered in the supernatant (SN2).

A clarification of the SN2 was performed by filtration through a 0.45/0.2 µm polyethersulfone Sartorius Sartopore 2 MidiCap filter, at 600 ml/min of flow rate.

The SN2 was diluted 1:3 with 20 mM NaH$_2$PO$_4$—Na$_2$HPO$_4$, pH 7.0, the pH adjusted to 7.0 if necessary and another clarification by filtration through a 0.45/0.2 µm polyethersulfone Sartorius Sartopore 2 MidiCap filter, at 600 ml/min was performed.

SP SEPHAROSE™ Fast Flow (SP FF) Chromatography

The diluted/filtered SN2 was loaded and captured on a strong cationic exchanger resin (SP SEPHAROSE™ FF-GE Healthcare) in a 14 cm ID (internal diameter)×20 cm length column (column volume 3100 ml) equilibrated with 2CV of 20 mM $NaH_2PO_4/Na_2HPO_4$ buffer pH 7.0. After washing the column with 5CV of 20 mM $NaH_2PO_4/Na_2HPO_4$ buffer pH 7.0, the antigen (contained within LVL317) was eluted by increasing the concentration of NaCl up to 100 mM in the same washing buffer.

Figure 12:
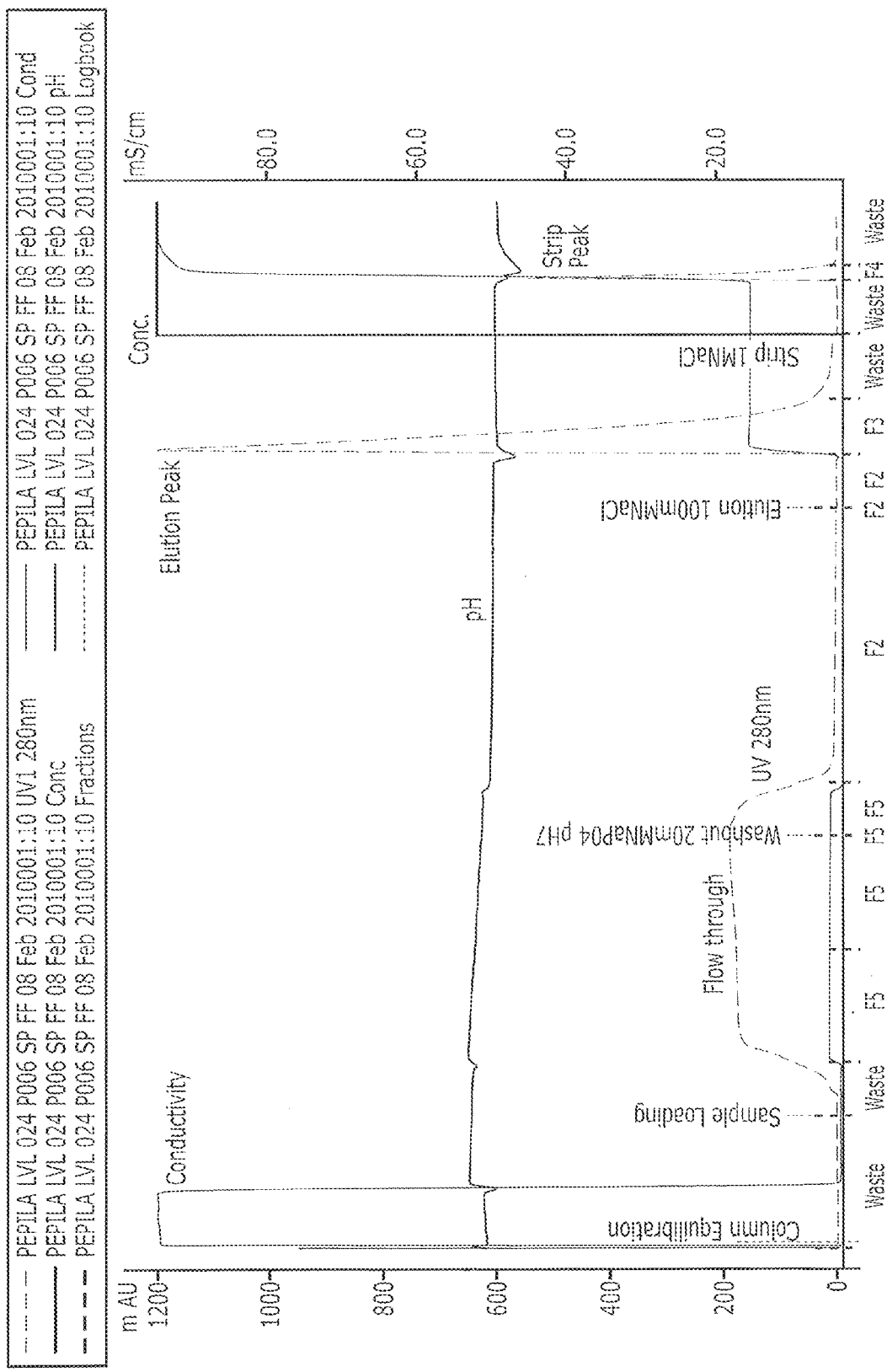
FIG. 12. Typical SP Sepharose™ Fast Flow chromatogram.

See FIG. 12 for a typical SP SEPHAROSE™ Fast Flow chromatogram.

Q SEPHAROSE™ Fast Flow (Q FF) Chromatography

The antigen present in the SP FF Eluate was diluted 1:4 with a 20 mM Tris pH 8.5, pH adjusted to 8.5 if necessary and passed through a strong anionic exchanger resin (Q SEPHAROSE™ FF-GE Healthcare) in a 14 cm ID×11.8 cm length column (column volume 1800 ml) equilibrated with 2CV of 20 mM Tris buffer pH 8.5. The antigen was recovered in the flow-through fraction.

Figure 13:
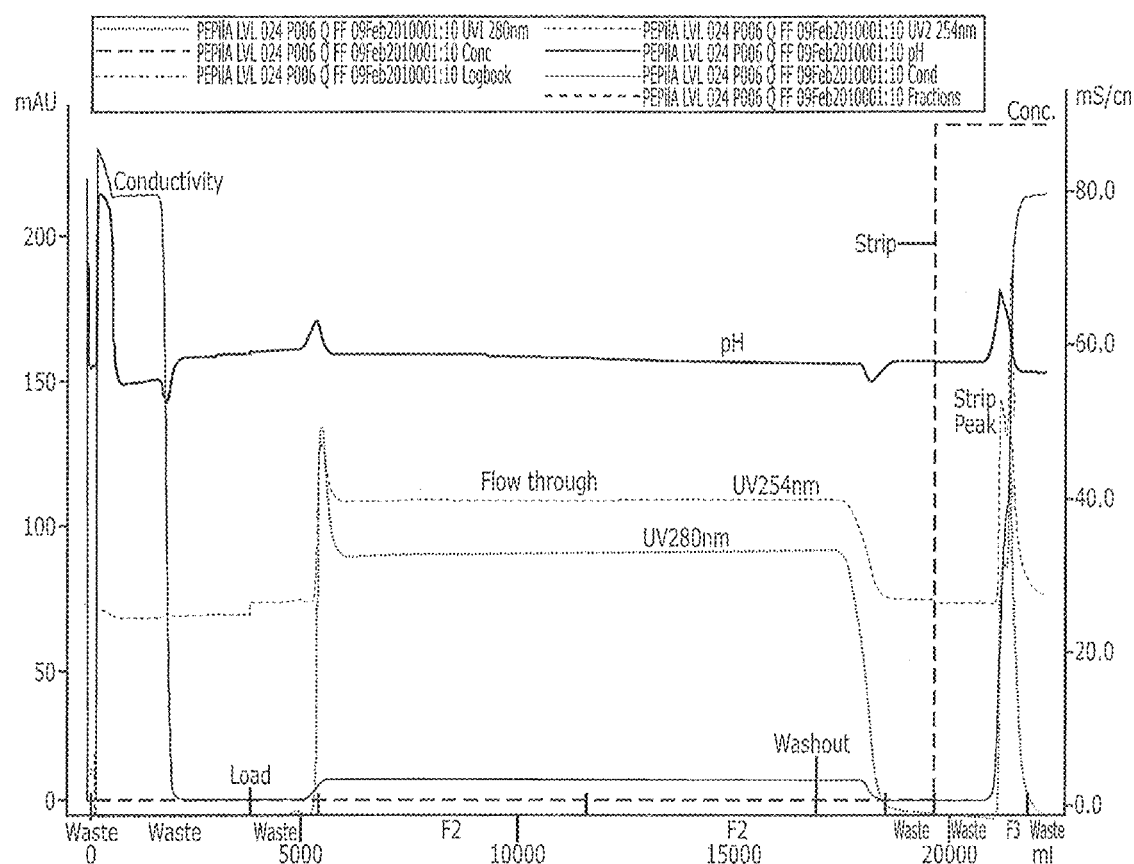
FIG. 13. Typical Q Sepharose™ Fast Flow chromatogram.

See FIG. 13 for a typical Q SEPHAROSE™ Fast Flow chromatogram.

Concentration, Diaflitration, Polysorbate 80 Addition and Sterile Filtration

The Q FF flow-through containing the antigen was concentrated up to 0.7-0.8 mg/ml based on chromatogram UV and diafiltered with 5DV of 10 mM $KH_2PO_4/K_2HPO_4$ buffer pH 6.5 using a Pellicon-2™ 10 kDa cutoff membrane (Millipore).

Using a 5% stock solution, polysorbate 80 (for example, TWEEN™ 80) was added to the ultrafiltration retentate and agitated for 30 minutes with magnetic stirrer at 130 rpm at 4° C. The final concentration of polysorbate 80 was 0.04%. Ultrafiltration retentate was sterilized by filtration through a 0.45/0.2 μm Cellulose Acetate membrane (Sartobran 300, Sartorius). The purified bulk was stored at −20° C. or −80° C. Absolute protein concentration was measured by AAA (Amino Acid Analysis) at 0.737 mg/ml.

Example 9

Use of Polysorbate 80

A titration experiment indicated that the addition of polysorbate 80, specifically, TWEEN™ 80 to a final concentration of 0.04% (w/v) to the purified bulk prior to sterile filtration reduced filamentous particle formation and aggregation.

According to DSC analysis, TWEEN™ 80 reduced the degree of structural change (30-45° C.) seen after freeze/thaw cycles after storage at −20° C. and after storage 4 days at 4° C., −20° C. and −80° C. and 37° C.

Example 10

SDS-PAGE and Western Blot Analysis of LVL317

SDS-PAGE and Western Blot Analysis:

NUPAGE®, Bis-Tris 4-12% gel was loaded as described below with 10 μg of sample in NUPAGE® LDS sample buffer containing 50 mM DTT heated 5 min at 95° C. (20 μL of sample was loaded for samples having low concentration). Migration: 35 minutes at 200 Volts at room temperature (RT) in NUPAGE® MES Running Buffer. Gel Stained 2 hours in Instant blue (Novexin cat.: ISB01L) and destained overnight in water.

Lane Contents:

1: MW standard (10 μL)  2: Start (total fraction) (10 μg)  3: SN1 non filtered (10 μg)
4: SN2 not filtered (10 μg)  5: Not extracted (10 μg)  6: Load SP FF (10 μg)
7: Flow through SP FF (6.9 μg)  8: Wash SP FF (20 μL)  9: Elution SP FF (10 μg)
10: Strip SP FF (10 μg)  11: Load Q FF (8.9 μg)  12: Elution Q FF (9.8 μg)
13: Strip Q FF (4.8 μg)  14: TFF retentate before0.04% TWEEN™ 80 spiked (10 μg)
15: Purified bulk Not filtered 0.04% TWEEN™ 80 spiked (10 μg)
16: Purified bulk Sterile Filtered 0.04% TWEEN™ 80 spiked (10 μg)
17: Purified bulk Sterile Filtered 0.04% TWEEN™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

Figure 14:
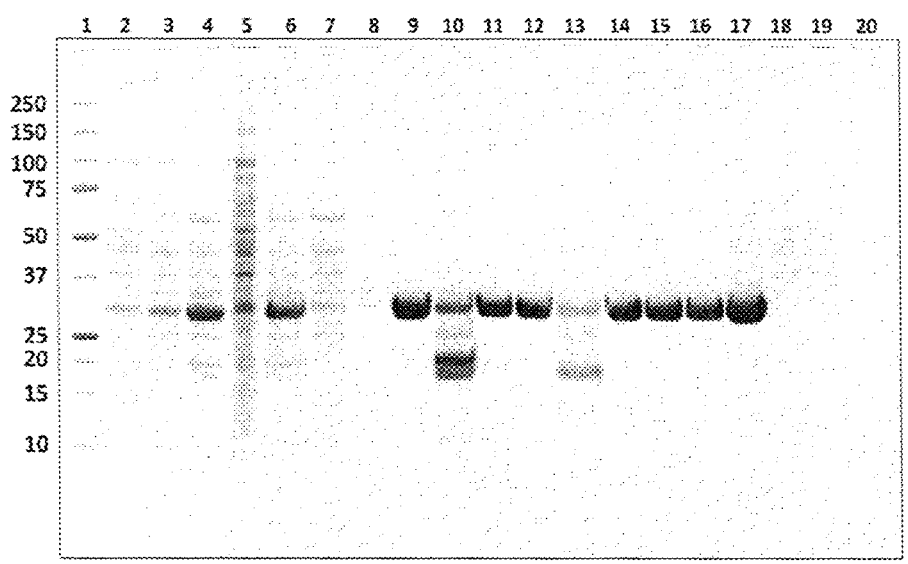
FIG. 14. SDS-PAGE of In-process samples from purification process of PE-PilA fusion protein.

See FIG. 14 for a SDS-PAGE of In-process samples from purification process of PE-PilA fusion protein.

For Western Blot, proteins were transferred at 4° C. overnight at 30 Volts in NUPAGE® transfer buffer+20% Methanol, 0.1% SDS on nitrocellulose membrane. Membranes were blocked 1 hour with 50 mM Tris, 150 mM NaCl pH 7.4+5% non-fat dry milk, incubated 2 hours in rabbit polyclonal primary antibody diluted in blocking buffer (anti-Prot-E 1/50 000 and anti-*E coli* (BLR) 1/1 000), washed 3×5 minutes in 50 mM Tris pH 7.4+0.05% Tween 20, incubated 1 hour in secondary antibody (goat anti-rabbit conjugated to alkaline phosphatase diluted 1/5000 in blocking buffer), washed 3×5 minutes in wash buffer and developed in BCIP/NBT substrate (1 tablet per 10 ml). All incubations performed in 25 ml per membrane.

Figure 15:
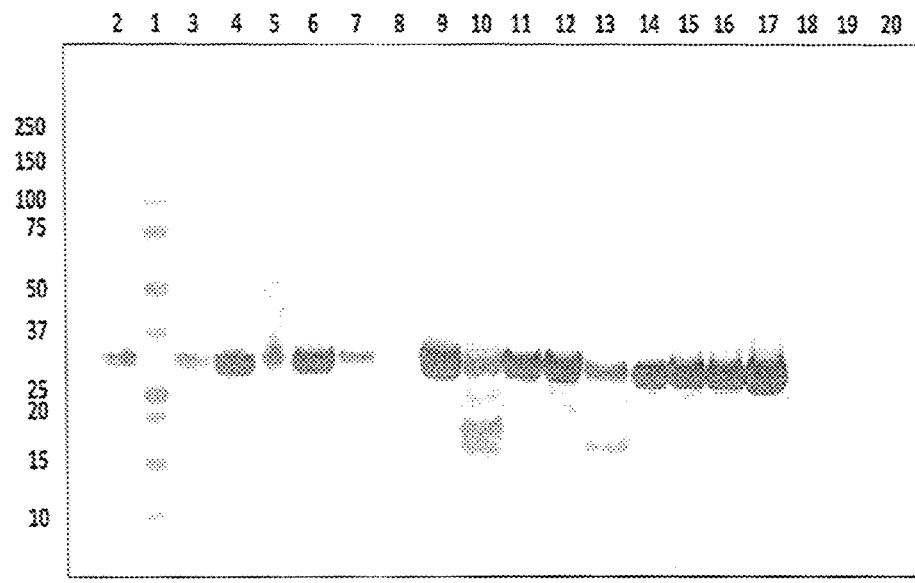
FIG. 15. Western Blot of In-process samples of purification process from PE-PilA fusion protein. Blot using rabbit polyclonal anti-PE.

See FIG. 15 for a Western Blot of In-process samples of purification process from PE-PilA fusion protein. Blot using rabbit polyclonal anti-PE.

Lane Contents:

1: MW standard (10 μL)  2: Start (total fraction) (10 μg)  3: SN1 non filtered (10 μg)
4: SN2 not filtered (10 μg)  5: Not extracted (10 μg)  6: Load SP FF (10 μg)
7: Flow through SP FF (6.9 μg)  8: Wash SP FF (20 μL)  9: Elution SP FF (10 μg)
10: Strip SP FF (10 μg)  11: Load Q FF (8.9 μg)  12: Elution Q FF (9.8 μg)
13: Strip Q FF (4.8 μg)  14: TFF retentate before0.04% TWEEN™ 80 spiked (10 μg)
15: Purified bulk Not filtered 0.04% TWEEN™ 80 spiked (10 μg)
16: Purified bulk Sterile Filtered 0.04% TWEEN™ 80 spiked (10 μg)

17: Purified bulk Sterile Filtered 0.04% TWEEN ™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

Figure 16:
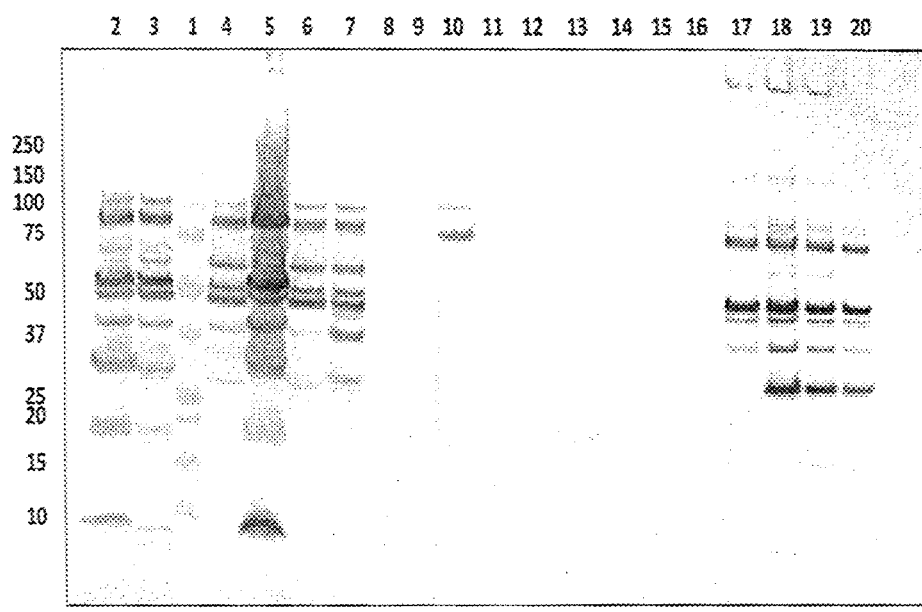
FIG. 16. Western Blot of In-process samples of purification process from PE-PilA fusion protein. Blot using rabbit polyclonal anti-*E. coli* (BLR).
Figure 17:
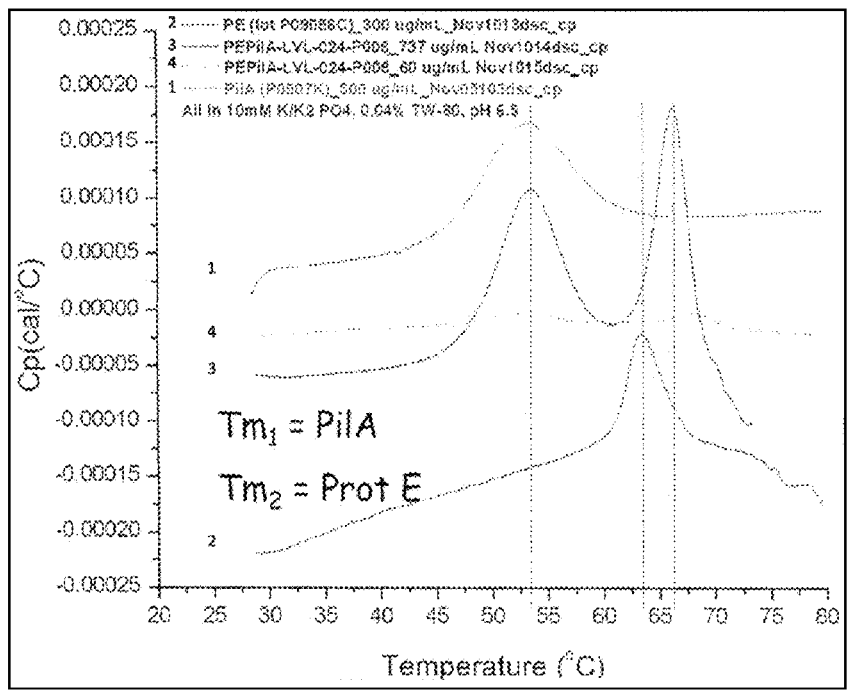
FIG. 17. Thermal transition of PE-PilA fusion protein and PE and PilA proteins. Curves: PilA (1), Protein E (Prot E, PE) (2), PE-PilA Purified Bulk not diluted, 737 µg/ml (3), and PE-PilA Purified Bulk diluted at Final Container concentration 60 µg/ml (4).

See FIG. 16 for a Western Blot of In-process samples of purification process from PE-PilA fusion protein. Blot using rabbit polyclonal anti-*E. coli* (BLR).
Lane Contents:

1: MW standard (10 μL)
2: Start (total fraction) (10 μg)
3: SN1 non filtered (10 μg)
4: SN2 not filtered (10 μg)
5: Not extracted (10 μg)
6: Load SP FF (10 μg)
7: Flow through SP FF (6.9 μg)
8: Wash SP FF (20 μL)
9: Elution SP FF (10 μg)
10: Strip SP FF (10 μg)
11: Load Q FF (8.9 μg)
12: Elution Q FF (9.8 μg)
13: Strip Q FF (4.8 μg)
14: TFF retentate before0.04% TWEEN™ 80 spiked (10 μg)
15: Purified bulk Not filtered 0.04% TWEEN ™ 80 spiked (10 μg)
16: Purified bulk Sterile Filtered 0.04% TWEEN ™ 80 spiked (10 μg)
17: Purified bulk Sterile Filtered 0.04% TWEEN ™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

SDS-PAGE and Western Blot Figures Comments:

The PE-PilA fusion protein migrates at 30 kDa. The extraction by osmotic shock extracts the fusion protein expressed and processed in bacteria periplasm and reduced contamination from bacteria. Small loss of fusion protein during hypertonic treatment (lane 3). A small proportion is not extracted by hypotonic treatment and remains associated with cells (lane 5). Small loss in SP FF Flow through (lane 7) and in strip fraction of both columns (lanes 10 and 13). Since the total volume of strip fraction is low the loss of fusion protein is not significant. Degraded bands are visible in strip fractions but not in final product. No significant contamination from *E. coli* host cell proteins in purified bulk (lane 16).

Analysis of LVL735 and LVL778 yielded similar profiles as LVL317.

Example 11

Melting Point Data for PE, PilA and LVL317

Thermal transition of PE-PilA fusion non His-tagged protein (LVL317) was compared with the thermal transition of both PE his-tagged (as described in Example 8) and cleaved PilA (as described in Example 8) proteins, purified as described above.

Before DSC, PE and PilA were dialyzed overnight in 10 mM $K_2HPO_4/KH_2PO_4$ pH 6.5+0.04% Tween 80 (1:250 sample:buffer volume ratio) to have them in the same buffer as the fusion protein. After dialysis, proteins concentration was measured by BCA and adjusted to 300 μg/ml (PE) and 500 μg/ml (PilA).

Analysis done on VP™-DSC from MicroCal, LLC (part of GE Healthcare). The final dialysis buffer was used as reference and subtracted from the scans. DSC scan rate 90° C./hr. In order to evaluate the capacity to measure the thermal transition in the Final Container (FC) after formulation, the fusion protein was diluted to the FC concentration (60 μg/ml). Final container data not shown.
Results:

| | |
|---|---|
| 1—PilA | Tm: 53° C. |
| 2—Protein E | Tm: 63 |
| 3—PE-PilA PB (Purified Bulk) not diluted 737 μg/ml | $Tm_1$: 53.7° C. and $Tm_2$: 66.1° C. |
| 4—PE-PilA PB diluted at FC concentration 60 μg/ml | Tm1: 53.2° C. and Tm2: 67.6° C. |

Two transitions were detected in the purified fusion protein (LVL317) (curves 3 and 4).

The $Tm_1$ (53.7° C.) of the PE-PilA fusion protein is similar to PilA transition (53° C.).

Significant shift of $Tm_2$ in PE-PilA (66.1° C.) as compared to PE transition (63° C.). The fusion of both domains seems to stabilize the PE fragment.

The shift of $Tm_2$ in the diluted fusion protein as compared to undiluted is a concentration artifact arising from the steep decreasing slope typical of aggregation which is concentration dependant.

Antigen folding analysis of LVL735 and LVL778 were similar to that of LVL317.

Example 12

Figure 18:
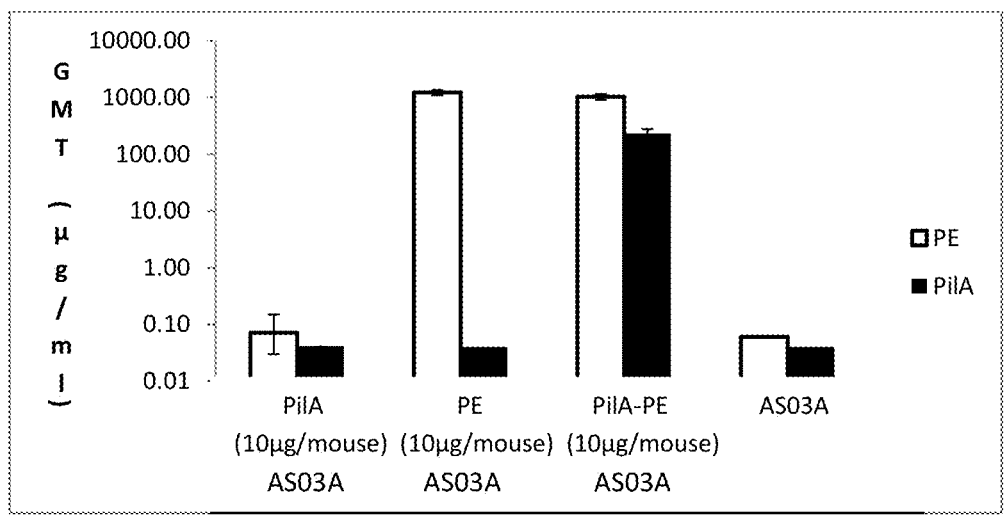
FIG. 18. Antibody responses against LVL291 PE-PilA fusion protein and against monovalent PE and PilA in the Balb/c mouse model.

PE-PilA Fusion Protein Construct LVL291
Anti-PilA Immunogenicity Response in Balb/c Mice The immune response directed against purified LVL291 PE-PilA fusion protein (the LVL291 fusion protein without the heterologous signal peptide) formulated in $AS03_A$ was evaluated in Balb/c mice. Animals (20 mice/group) were immunized by the intramuscular route at days 0, 14 and 28 with 10 μg of PE (from vector pRIT16762), PilA (from vector pRIT16790) or PE-PilA, each formulated in $AS03_A$. The control group was vaccinated with $AS03_A$ alone. Antibody response directed against each antigen was determined in individual sera collected at day 42. No antibody response was obtained with the negative control. As shown in FIG. 18, the antibody response directed against PilA was higher in mice immunized with the PE-PilA fusion compared to antibody response in mice immunized with monovalent PilA. The antibody responses directed against PE were similar in mice immunized with the fusion protein and mice immunized with monovalent PE. GMT=geometric means titer. Data were captured and analyzed with the SOFT-MAX® Pro Software (Molecular Devices) running under WINDOWS®(Microsoft); the four parameters logistic log function was used to calculate the standard curve. The four-parameter logistic-log function describes, with a high degree of accuracy, the curve of the reference serum displaying a pronounced sigmoïdal shape when plotted on an optical density-versus-concentration (log) scale. Antibody concentrations were calculated at each dilution of mice serum samples by interpolation of the standard curve. The antibody in quality control sera and in unknown serum samples is obtained by averaging the values from all dilutions that fall within the working range (10-80%) of the dilution curve of the reference. Results are shown in FIG. 18, which graphs the antibody responses against LVL291 PE-PilA fusion protein and against monovalent PE and PilA in the Balb/c mouse model.

Example 13

Murine Nasopharyngeal Colonization Model. Immunization with PE-PilA. Challenge with NTHi Strain 86-028NP and NTHi Strain 3224A Balb/c female mice (20/group) were immunized intranasally at days 0 and 14 with 6 µg of a purified PE-PilA fusion protein (LVL291 for challenge with 86-028NP; LVL317 for challenge with strain 3224A) formulated with LT (heat labile toxin of *Escheria coli*) and on day 28 with 6 µg of a purified PE-PilA fusion protein in phosphate buffered saline (PBS). Control mice (20/group) were vaccinated with LT alone. Mice were subsequently challenged intranasally with $5 \times 10^6$ CFU (colony forming units) of homologous NTHi strain 86-028NP and heterologous NTHi strain 3224A. Homology and heterology are determined by reference to the NTHi strain with which the mice were immunized. Bacterial colonies were counted in nasal cavities removed 1 and 2 days after the challenge. D1=day 1. D2=day 2. PE-PilA vaccination increased the clearance of NTHi strain 86-028NP and strain 3224A in the nasopharynx at day 1 and day 2 post challenge.

For the experiment performed with NTHi strain 86-028NP: A 2-way fixed ANOVA was performed using the log 10 values of the counts as response, the fixed factors being the group (4 levels) and the day (2 levels). The assumption of variance heterogeneity was rejected and a model with heterogeneous variances was fitted to the data. No significant interaction was detected between the 2 factors. The group fusion PE-PilA (6 µg per mouse) significantly reduced CFU compared with the control group (LT); the geometric mean ratio being equal to 0.06 with a 95% confidence interval of 0.01, 0.25.

For the experiment conducted with NTHi strain 3224A: A 3-way fixed ANOVA was performed using the log 10 values as response, the fixed factors being the group, the day, and the experiment. The Shapiro-Wilk and Levene's test did not reject the assumptions of normality and of homogeneity of variances. No significant interaction between any of the 2 factors or between the 3 factors was detected and only main factors were kept in the analysis. PE-PilA/LT significantly reduced CFU compared with the control group; the geometric mean ratio being equal to 0.11 with a 95% confidence interval of 0.02, 0.61.

Figure 19:
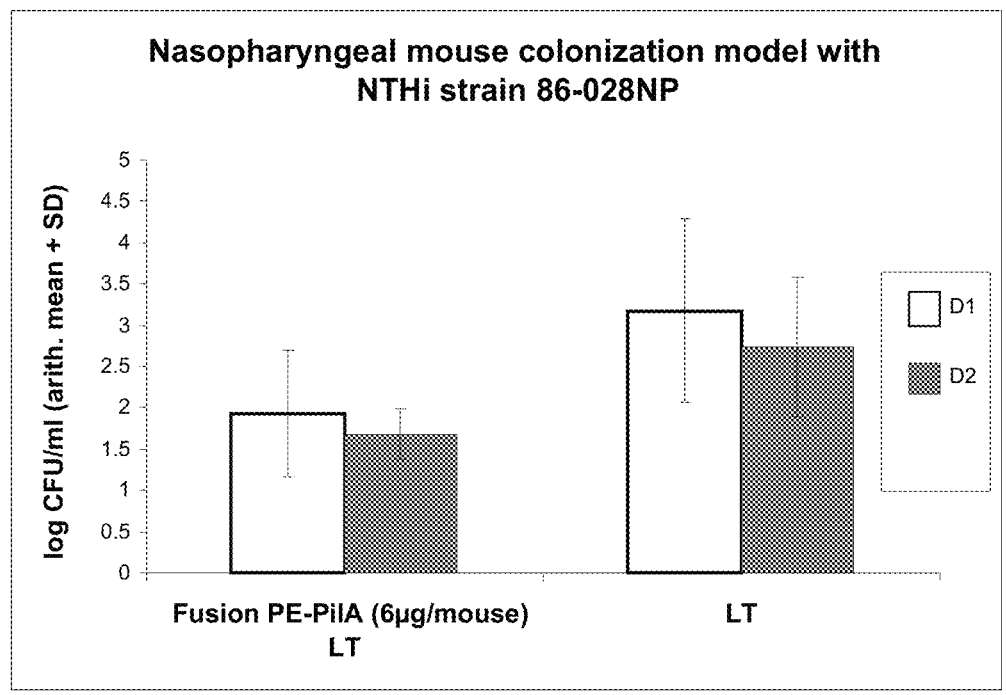
FIG. 19. Effect of PE-PilA fusion protein vaccination on NTHi strain 86-028NP bacterial clearance in mouse nasopharynx.

See FIG. 19 for effect of PE-PilA fusion protein vaccination on NTHi strain 86-028NP bacterial clearance in mouse nasopharynx.

Figure 20:
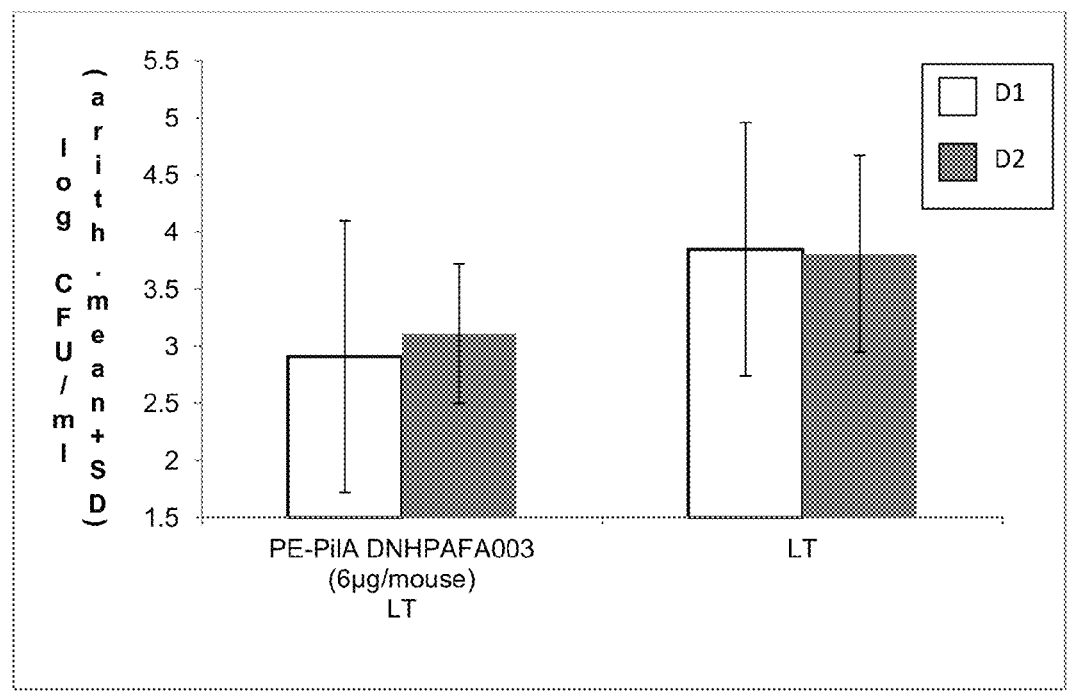
FIG. 20. Effect of PE-PilA fusion protein vaccination on NTHi strain 3224A bacterial clearance in mouse nasopharynx.

See FIG. 20 for effect of PE-PilA fusion protein vaccination on NTHi strain 3224A bacterial clearance in mouse nasopharynx.

Example 14

Murine Nasopharyngeal Colonization Model. Immunization with PilA. Challenge with NTHi Strain 3219C Female OF1 mice (20 mice/group) were immunized intranasally at days 0 and 14 with 3 µg PilA (from vector 16790) formulated with LT and at day 28 with 3 µg PilA in PBS. Control mice were vaccinated with LT alone. Mice were subsequently challenged intranasally with $5 \times 10^6$ CFU of NTHi strain 3219C. Bacterial colonies were counted in nasal cavities removed 3 and 4 days after the challenge. D3=day 3. D4=day 4.

Figure 21:
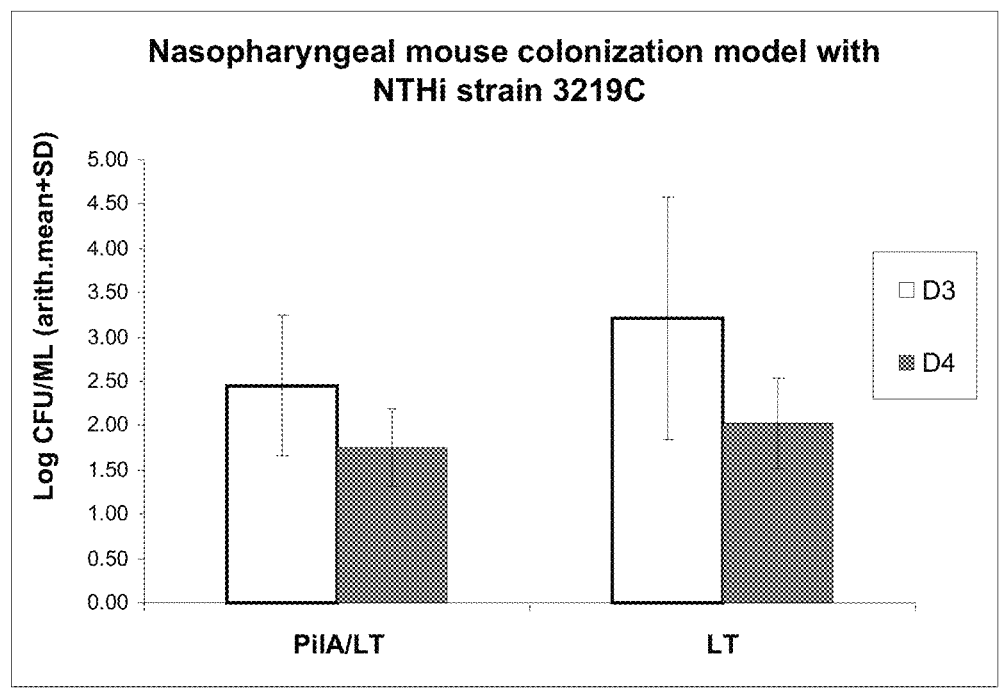
FIG. 21. Effect of PilA vaccination on bacterial clearance in mouse nasopharynx.

See FIG. 21 for effect of PilA vaccination on bacterial clearance in mouse nasopharynx.

Example 15

Murine Nasopharyngeal Colonization Model. Immunization with PE. Challenge with NTHi Strain 3224A Balb/c female mice (20 mice/group) were immunized intranasally at days 0 and 14 with 3 µg PE (from vector pRIT16762) formulated with LT and at day 28 with 3 µg PE in PBS. Control mice were vaccinated with LT alone. Mice were subsequently challenged intranasally with $5 \times 10^6$ CFU of NTHi strain 3224A. Bacterial colonies were counted in nasal cavities removed 3 and 4 days after the challenge. 10 mice were examined on day 3 (D3). 10 mice were examined on day 4 (D4). PE vaccination increased significantly the clearance of NTHi in the naso-pharynx at day 4 post challenge (FIG. 22), using on the Dunn test for statistical analysis.

Figure 22:
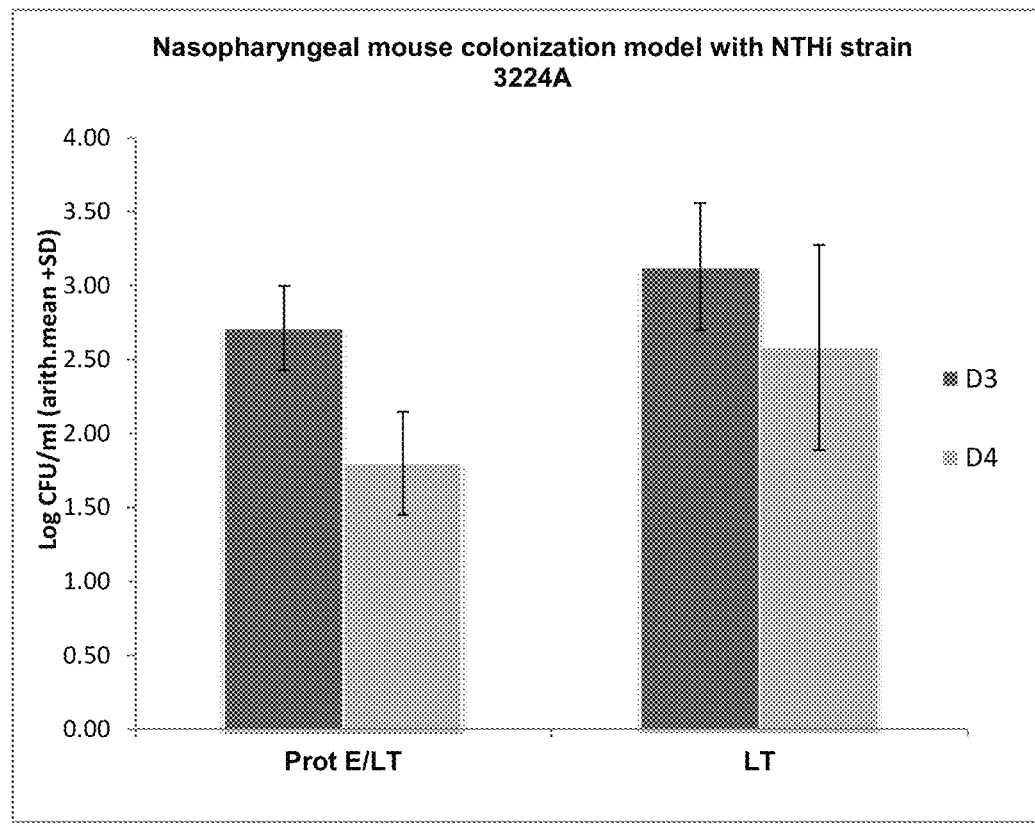
FIG. 22. Effect of PE vaccination on bacterial clearance in mouse nasopharynx.

See FIG. 22 for effect of PE vaccination on bacterial clearance in the nasopharynx of mice.

Example 16

Vibronectin Binding. Inhibition of Vibronectin Binding by LVL317 & LVL735 PE-PilA Fusion Protein The ability of PE in the purified LVL317 PE-PilA fusion protein construct to bind to vitronectin was evaluated. Microtiter plates (POLYSORP™, Nunc, Thermo Fisher Scientific) were coated with PE (from vector pRIT16762) or with purified LVL317 PE-PilA fusion protein (10 µg/ml). Plates were washed four times with NaCl 150 mM-polysorbate 20, 0.05% (for example, TWEEN™ 20) and blocked for one to two hours with PBS-BSA 1%. After four washings, vitronectin (Vitronectin from human plasma, SIGMA-ALDRICH®) was added (10 µg/ml), two fold diluted (12 dilutions), and the plates were incubated for 1 h at room temperature. The plates were then washed 4 times with NaCl 150 mM-polysorbate 20, 0.05% (for example TWEEN™ 20) After washings, the bound vitronectin was detected using peroxydase sheep anti-human vitronectin (US Biological) followed by the addition of ortho-phenylene diamine/$H_2O_2$ substrate. The color developed is directly proportional to the amount of antibody fixed to the vitronectin.

Figure 23:
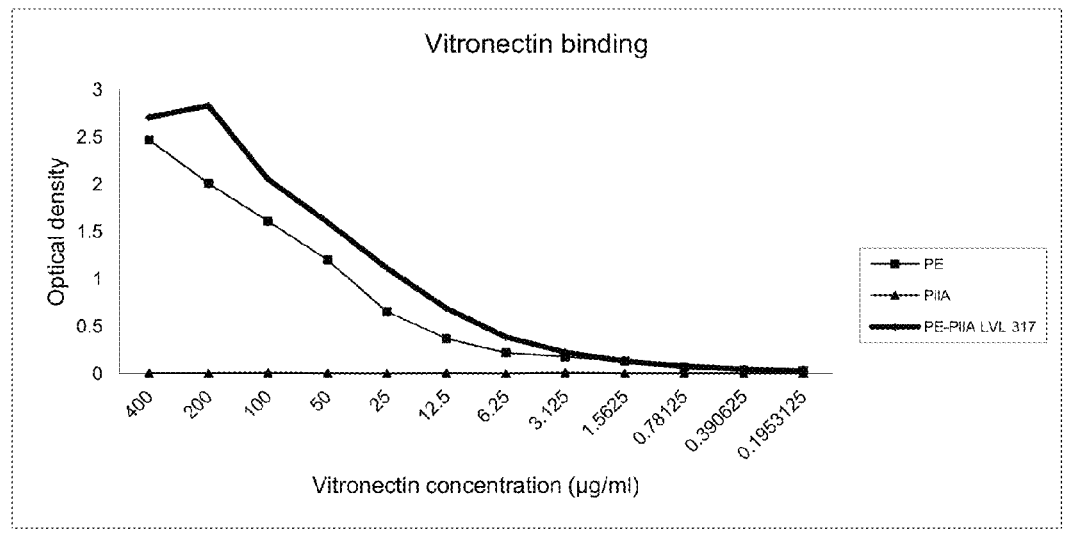
FIG. 23. (a) LVL317 PE-PilA fusion protein binding to vitronectin and (b) LVL317 and LVL735 PE-PilA fusion protein bound to vitronectin.
Figure 23:
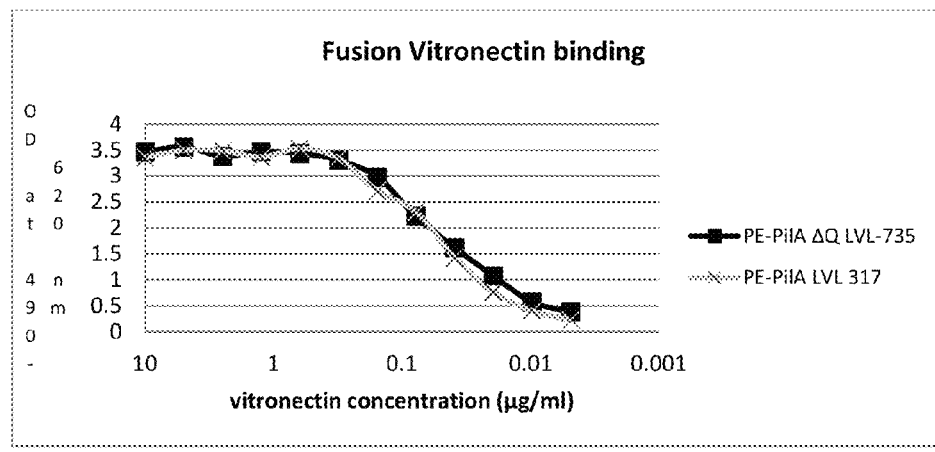

See FIG. 23 for (a) LVL317 PE-PilA fusion protein bound to vitronectin. PilA=PilA from NTHi strain 86-028NP (as described for pRIT16790); PE=Protein E (as described for pRIT16762) and (b) LVL317 and LVL735 PE-PilA fusion protein bound to vitronectin.

Example 17

Vibronectin Binding. Inhibition of Vibronectin Binding by Antibodies Directed Against the LVL291 PE-PilA Fusion Protein Microtiter plates (POLYSORP™, Nunc, Thermo Fisher Scientific) were coated with PE (from vector pRIT16762) or with purified PE-PilA fusion protein (10 µg/ml). Plates were washed four times with NaCl 150 mM-polysorbate 20, 0.05% (for example, TWEEN™ 20) and blocked for two hours with PBS-BSA 1%. After washings, vitronectin (Vitronectin from human plasma, SIGMA-ALDRICH®) was added at 50 µg/ml and purified antibodies anti-PE-PilA (produced and purified in house) were two-fold serially diluted and incubated for 1 h at room temperature. The plates were then washed 4 times with NaCl 150 mM-polysorbate 20, 0.05% (for example, TWEEN™ 20). After four washings, the bound vitronectin was detected using peroxydase sheep anti-Vitronectin (US Biological) followed by the addition of ortho-phenylene diamine/$H_2O_2$ substrate. The color developed is directly proportional to the amount of antibody fixed to the vitronectin.

Inhibition of vitronectin binding to PE by polyclonal antibodies directed against PE-PilA was observed.

Figure 24:
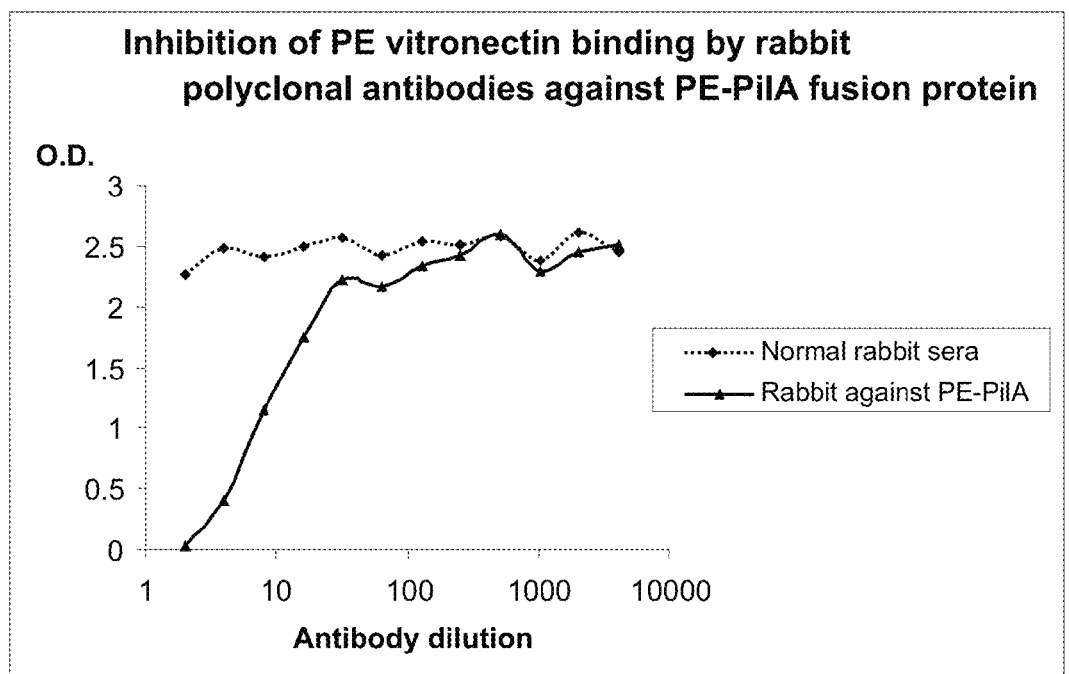
FIG. 24. Inhibition of vitronectin binding by polyclonal antibodies against PE-PilA fusion protein.

See FIG. 24 for inhibition of vitronectin binding by polyclonal antibodies against PE-PilA fusion protein.

Example 18

Antigenicity of LVL291 PE-PilA Fusion Protein. ELISA

Purified LVL291 PE-PilA fusion protein was validated in an antigenicity test with monovalent proteins as control. The fusion protein was tested in a sandwich ELISA developed with polyclonal antibodies (rabbit and guinea pig) generated against the PE gene fragment coding for amino acids 22 to 160 of SEQ ID NO: 4 (as described for pRIT16711) or against PilA from NTHi strain 86-028NP (from vector pRIT16790).

PilA or PE was added at 100 ng/ml and serially two fold diluted. After 30 minutes incubation and after washing, the bound antigen was detected by a rabbit polyclonal serum obtained after immunisation with PE or PilA. The bound antibodies were detected using a peroxydase anti-rabbit Ig (Jackson ImmunoResearch Laboratories, Inc.) followed by the addition of ortho-phenylene-diamine/$H_2O_2$ substrate. The color developed is directly proportional to the amount of antigen present. Absorbance readings were measured using a spectrophotometer for microtiter plates. The antigenicity of the samples was determined by comparison to the curve of the full length PE or full length PilA reference antigen and is expressed in ug/ml. The reference represented 100% of antigenicity.

As observed in the Table 6: Antigenicity was observed with the purified LVL291 PE-PilA fusion protein compared to the monovalent PE and PilA antigens.

TABLE 6

Relative antigenicity obtained with purified LVL291 PE-PilA fusion protein in the antigenicity test.

|  | PE relative antigenicity (%) |
| --- | --- |
| Protein E as Reference | 100 |
| PE-PilA | 130-148 |
| PilA as Reference | 100 |
| PE-PilA | 120-152 |

Example 19

Immunogenicity of LVL735 PE-PilA Fusion Protein

Female Balb/c mice (n=34) were immunized by the intramuscular route at days 0, 14 and 28 with 50 µl of vaccine formulation containing 1, 0.2 or 0.04 µg of PE-PilA fusion protein LVL317 or LVL735 formulated within $AS01_E$ or $AIPO_4$ (aluminium phosphate). The antibody responses to PE and PilA were determined in individual sera collected at day 42 and the IgG level against PE and PilA was measured and expressed in µg/ml.

Figure 27:
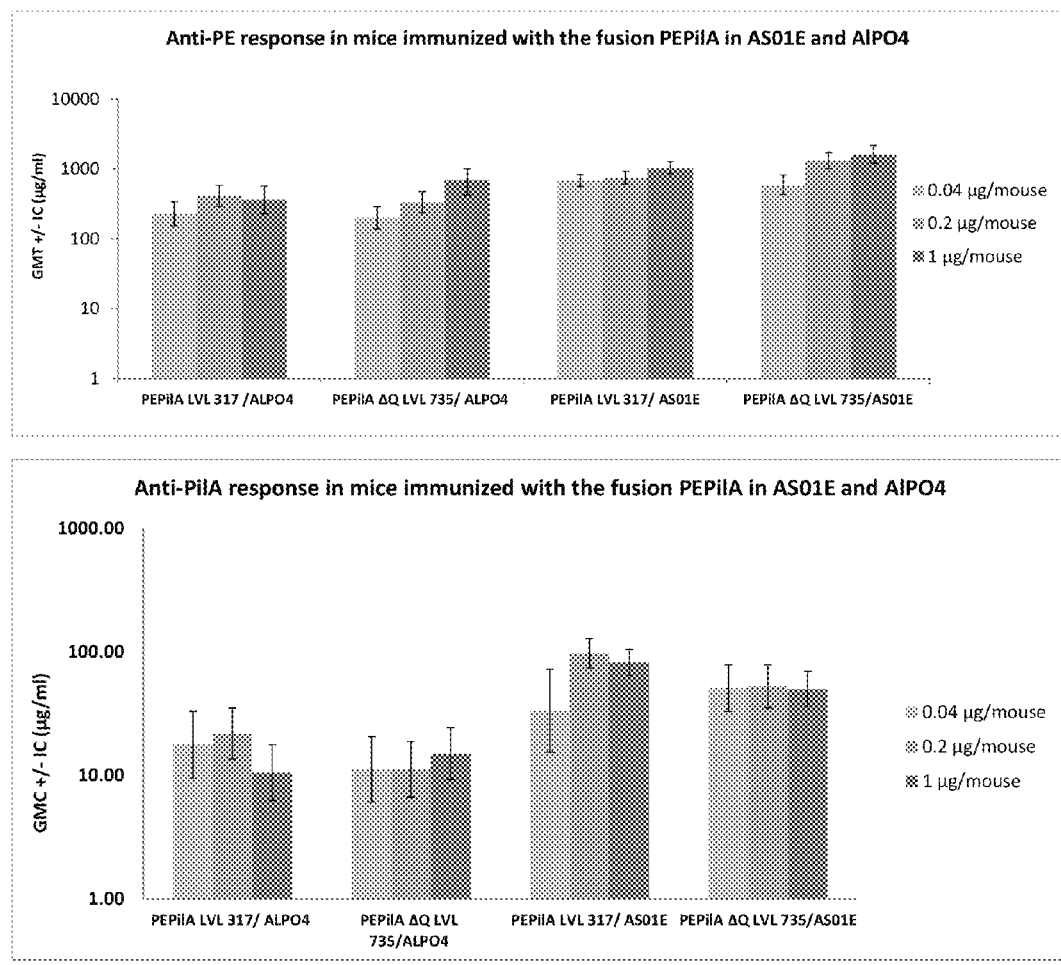
FIG. 27. PE and PilA antibody response to LVL317 and LVL735.

See FIG. 27 for PE and PilA antibody response to LVL317 and LVL735. GMC=geometric mean concentration. GMT=geometric means titer. IC=confidence intervals.

Example 20

Protective Efficacy of the LVL735 and LVL317 Fusion Proteins in a Mouse Model of Non-Typeable *Haemophilus influenzae* Nasopharyngeal Colonization Female Balb/c mice were intranasally immunized at days 0 and 14 with 10 µl of vaccine formulation containing 5.8 µg of LVL735 or LVL317 admixed with 0.5 µg of *E. coli* labile toxin (LT). A booster dose of 5.8 µg of non-adjuvanted LVL735 or LVL317 was administered at day 28. Control mice were vaccinated with LT alone at days 0 and 14, and PBS at day 28. Animals were intranasally challenged with $5 \times 10^6$ cfu of NTHi 3224A strain at day 42. Bacterial colonies were counted in nasal cavities removed 1 and 2 days after the challenge (n=10/time-point).

Nasal cavities are homogenized in medium and a bacterial quantification is performed. Results are well expressed in CFU/ml.

Figure 28:
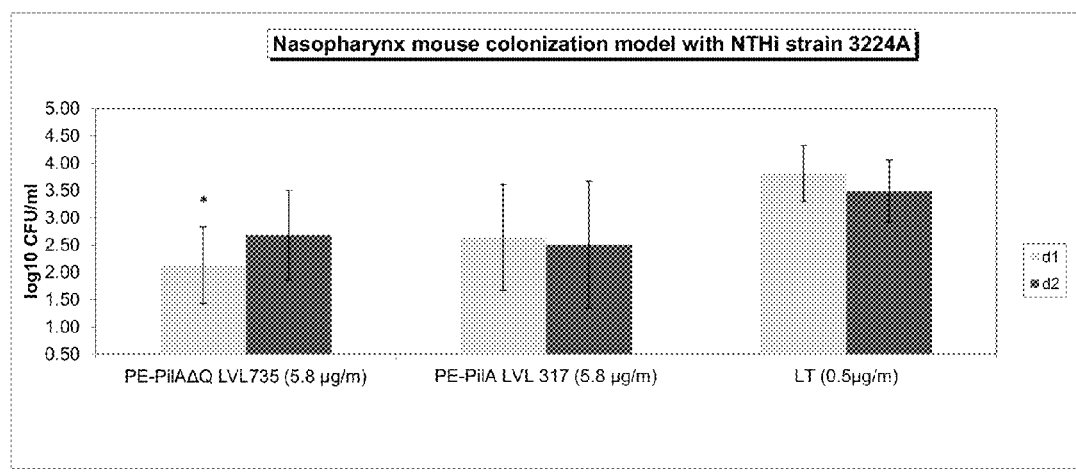
FIG. 28. Effect of LVL735 and LVL317 vaccination on bacterial clearance in a mouse model of non-typeable *Haemophilus influenzae* nasopharyngeal colonization.
Figure 29:
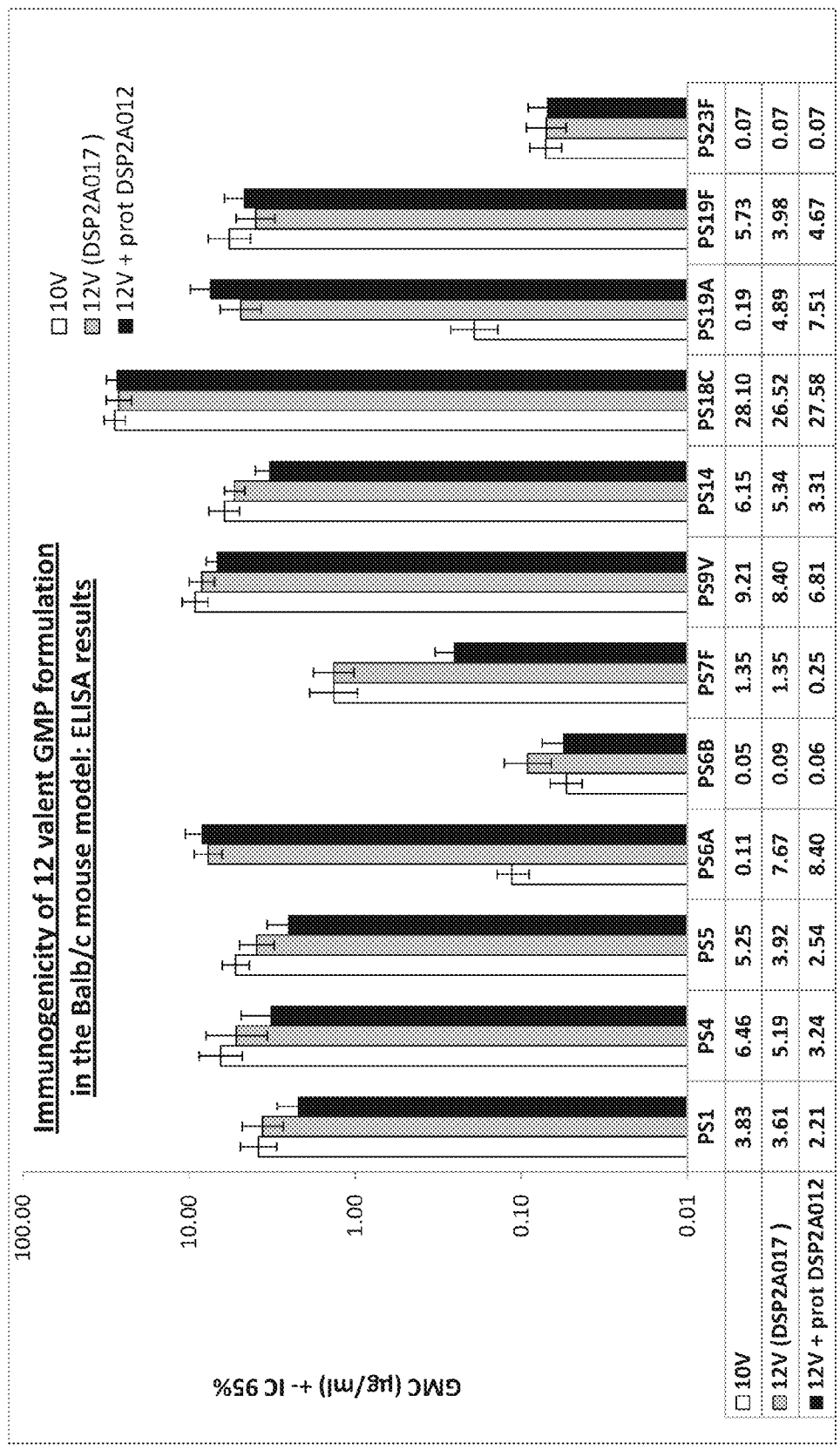
FIG. 29. Graph comparing the immunogenicity of a composition comprising 12 saccharide conjugates, PhtD, dPly and PE-PilA (12V+prot) with a composition comprising 12 saccharide conjugates (12V) and a composition comprising 10 saccharide conjugates (10V) as measured after injection of mice using an anti-saccharide ELISA assay. GMC=geometric mean concentration. IC=confidence intervals.
Figure 30:
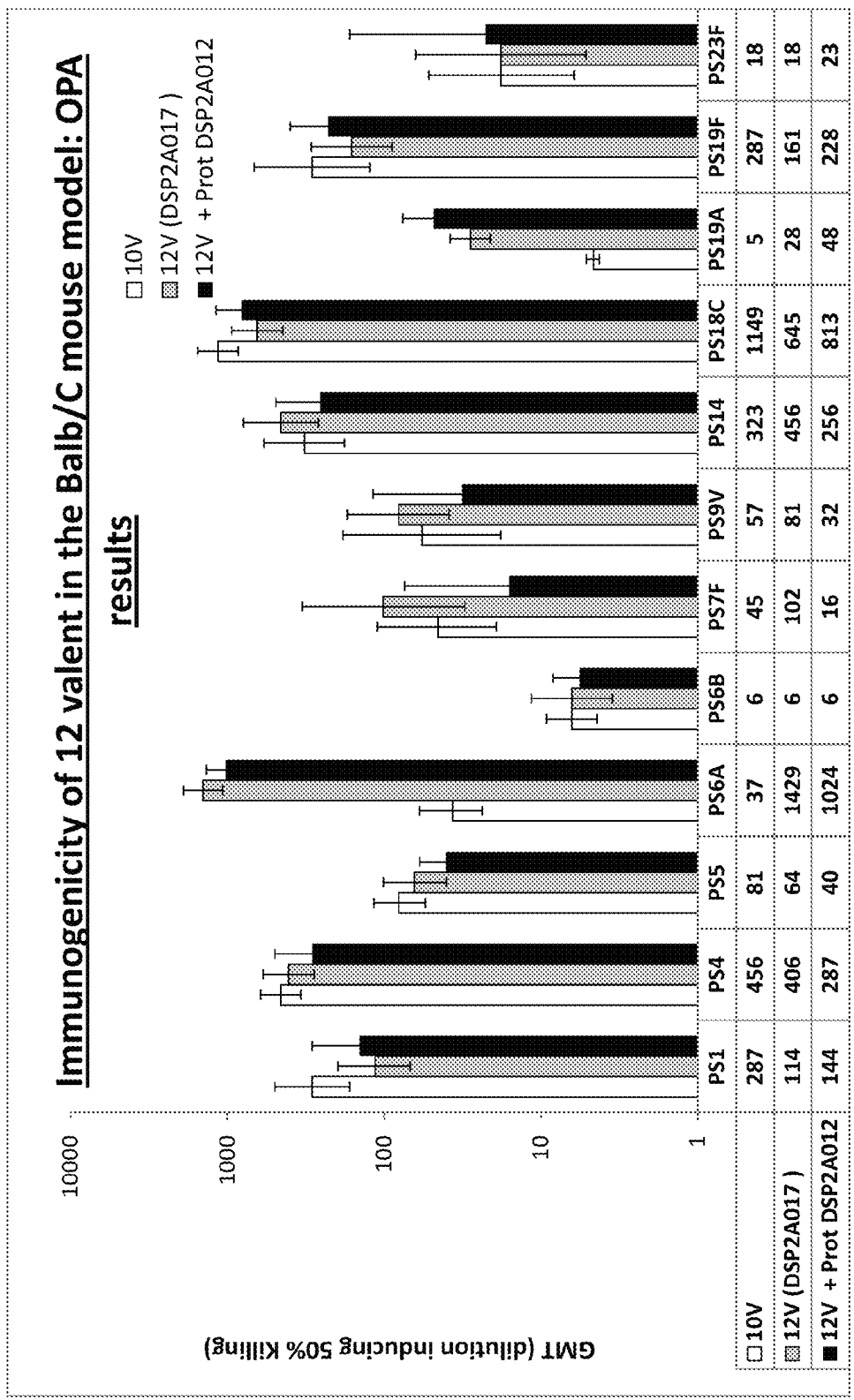
FIG. 30. Graph comparing the immunogenicity of a composition comprising 12 saccharide conjugates, PhtD, dPly and PE-PilA (12V+prot) with a composition comprising 12 saccharide conjugates (12V) and a composition comprising 10 saccharide conjugates (10V) as measured after injection of mice using an opsonophagocytosis assay. GMT=geometric means titer.

See FIG. 28 for the effect of LVL735 and LVL317 vaccination on bacterial clearance in a mouse model of non-typeable *Haemophilus influenzae* nasopharyngeal colonization.

Example 21

Formulation of Multivalent Vaccines Comprising a PE-PilA Fusion Protein 3 vaccines were designed:

10V:

A ten valent (10V) vaccine containing the following ten *S. pneumoniae* capsular saccharide conjugates: capsular saccharide from serotype 1 conjugated to protein D (1-PD), capsular saccharide from serotype 4 conjugated to protein D (4-PD), capsular saccharide from serotype 5 conjugated to protein D (5-PD), capsular saccharide from serotype 6B conjugated to protein D (6B-PD), capsular saccharide from serotype 7F conjugated to protein D (7F-PD), capsular saccharide from serotype 9V conjugated to protein D (9V-PD), capsular saccharide from serotype 14 conjugated to protein D (14-PD), capsular saccharide from serotype 23F conjugated to protein D (23F-PD), capsular saccharide from serotype 18C conjugated to tetanus toxoid (18C-TT) and capsular saccharide from serotype 19F conjugated to Diphtheria Toxin (19F-DT).

12V:

A twelve valent (12V) vaccine containing the same ten *S. pneumoniae* capsular saccharide conjugates as 10V with an additional two *S. pneumoniae* saccharide conjugates, 19A conjugated to CRM197 (19ACRM) and 6A conjugated to CRM197 (6ACRM).

12V+ Proteins (12V+prot):

A vaccine containing the same twelve *S. pneumoniae* capsular saccharide conjugates as 12V with the addition of PhtD, dPly and PE-PilA fusion protein.

Preparation of dPly:

Pneumococcal pneumolysin was prepared and detoxified as described in WO2004/081515 and WO2006/32499 using formaldehyde detoxification.

Expression and Purification of PhtD:

Expression of PhtD:

The PhtD protein is a member of the pneumococcal histidine-triad (Pht) protein family characterized by the presence of histidine-triads. PhtD is a 838 aa-molecule and carries 5 histidine triads (see MedImmune WO00/37105 SEQ ID NO: 4 for amino acid sequence and SEQ ID NO: 5 for DNA sequence). PhtD also contains a proline-rich region in the middle (amino acid position 348-380). PhtD has a 20 aa-N-terminal signal sequence. Preparation and purification of PhtD is described in WO2007/071710 (see, for example, Example 1b). The sequence of amino acids 21-838 of SEQ ID NO:4 from WO00/37105 corresponds to SEQ ID NO:220.

SEQ ID NO: 220

```
Ser Tyr Glu Leu Gly Arg His Gln Ala Gly Gln Val Lys Lys Glu Ser Asn Arg Val Ser Tyr Ile

Asp Gly Asp Gln Ala Gly Gln Lys Ala Glu Asn Leu Thr Pro Asp Glu Val Ser Lys Arg Glu Gly

Ile Asn Ala Glu Gln Ile Val Ile Lys Ile Thr Asp Gln Gly Tyr Val Thr Ser His Gly Asp His Tyr

His Tyr Tyr Asn Gly Lys Val Pro Tyr Asp Ala Ile Ile Ser Glu Glu Leu Leu Met Lys Asp Pro Asn

Tyr Gln Leu Lys Asp Ser Asp Ile Val Asn Glu Ile Lys Gly Gly Tyr Val Ile Lys Val Asp Gly Lys

Tyr Tyr Val Tyr Leu Lys Asp Ala Ala His Ala Asp Asn Ile Arg Thr Lys Glu Glu Ile Lys Arg

Gln Lys Gln Glu His Ser His Asn His Gly Gly Gly Ser Asn Asp Gln Ala Val Val Ala Ala Arg

Ala Gln Gly Arg Tyr Thr Thr Asp Asp Gly Tyr Ile Phe Asn Ala Ser Asp Ile Ile Glu Asp Thr Gly

Asp Ala Tyr Ile Val Pro His Gly Asp His Tyr His Tyr Ile Pro Lys Asn Glu Leu Ser Ala Ser Glu

Leu Ala Ala Ala Glu Ala Tyr Trp Asn Gly Lys Gln Gly Ser Arg Pro Ser Ser Ser Ser Ser Tyr Asn

Ala Asn Pro Ala Gln Pro Arg Leu Ser Glu Asn His Asn Leu Thr Val Thr Pro Thr Tyr His Gln

Asn Gln Gly Glu Asn Ile Ser Ser Leu Leu Arg Glu Leu Tyr Ala Lys Pro Leu Ser Glu Arg His

Val Glu Ser Asp Gly Leu Ile Phe Asp Pro Ala Gln Ile Thr Ser Arg Thr Ala Arg Gly Val Ala Val

Pro His Gly Asn His Tyr His Phe Ile Pro Tyr Glu Gln Met Ser Glu Leu Glu Lys Arg Ile Ala Arg

Ile Ile Pro Leu Arg Tyr Arg Ser Asn His Trp Val Pro Asp Ser Arg Pro Glu Gln Pro Ser Pro Gln

Ser Thr Pro Glu Pro Ser Pro Ser Pro Gln Pro Ala Pro Asn Pro Gln Pro Ala Pro Ser Asn Pro Ile

Asp Glu Lys Leu Val Lys Glu Ala Val Arg Lys Val Gly Asp Gly Tyr Val Phe Glu Glu Asn Gly

Val Ser Arg Tyr Ile Pro Ala Lys Asp Leu Ser Ala Glu Thr Ala Ala Gly Ile Asp Ser Lys Leu Ala

Lys Gln Glu Ser Leu Ser His Lys Leu Gly Ala Lys Lys Thr Asp Leu Pro Ser Ser Asp Arg Glu

Phe Tyr Asn Lys Ala Tyr Asp Leu Leu Ala Arg Ile His Gln Asp Leu Leu Asp Asn Lys Gly Arg

Gln Val Asp Phe Glu Ala Leu Asp Asn Leu Leu Glu Arg Leu Lys Asp Val Pro Ser Asp Lys Val

Lys Leu Val Asp Asp Ile Leu Ala Phe Leu Ala Pro Ile Arg His Pro Glu Arg Leu Gly Lys Pro

Asn Ala Gln Ile Thr Tyr Thr Asp Asp Glu Ile Gln Val Ala Lys Leu Ala Gly Lys Tyr Thr Thr Glu

Asp Gly Tyr Ile Phe Asp Pro Arg Asp Ile Thr Ser Asp Glu Gly Asp Ala Tyr Val Thr Pro His Met
```

-continued

Thr His Ser His Trp Ile Lys Lys Asp Ser Leu Ser Glu Ala Glu Arg Ala Ala Ala Gln Ala Tyr Ala

Lys Glu Lys Gly Leu Thr Pro Pro Ser Thr Asp His Gln Asp Ser Gly Asn Thr Glu Ala Lys Gly

Ala Glu Ala Ile Tyr Asn Arg Val Lys Ala Ala Lys Lys Val Pro Leu Asp Arg Met Pro Tyr Asn

Leu Gln Tyr Thr Val Glu Val Lys Asn Gly Ser Leu Ile Ile Pro His Tyr Asp His Tyr His Asn Ile

Lys Phe Glu Trp Phe Asp Glu Gly Leu Tyr Glu Ala Pro Lys Gly Tyr Thr Leu Glu Asp Leu Leu

Ala Thr Val Lys Tyr Tyr Val Glu His Pro Asn Glu Arg Pro His Ser Asp Asn Gly Phe Gly Asn

Ala Ser Asp His Val Arg Lys Asn Lys Val Asp Gln Asp Ser Lys Pro Asp Glu Asp Lys Glu His

Asp Glu Val Ser Glu Pro Thr His Pro Glu Ser Asp Glu Lys Glu Asn His Ala Gly Leu Asn Pro

Ser Ala Asp Asn Leu Tyr Lys Pro Ser Thr Asp Thr Glu Glu Thr Glu Glu Glu Ala Glu Asp Thr

Thr Asp Glu Ala Glu Ile Pro Gln Val Glu Asn Ser Val Ile Asn Ala Lys Ile Ala Asp Ala Glu Ala

Leu Leu Glu Lys Val Thr Asp Pro Ser Ile Arg Gln Asn Ala Met Glu Thr Leu Thr Gly Leu Lys

Ser Ser Leu Leu Leu Gly Thr Lys Asp Asn Asn Thr Ile Ser Ala Glu Val Asp Ser Leu Leu Ala

Leu Leu Lys Glu Ser Gln Pro Ala Pro Ile

Expression of Protein D

Protein D was expressed as described in WO2007/071710

Expression and Purification of CRM197 E. coli:

In order to improve the yield of process for the production of CRM197, alternative expression modes were evaluated with a target of a 10-fold increase of process yield. The selected construction was expressed in *Escherichia coli* strain (B834 (DE3)) as a fusion between FlgI signal sequence from *E. coli* (19aa) and CRM197 (537aa). The signal sequence is cleaved upon transport to the periplasm. The CRM197 is extracted by osmotic shock before being purified. The purification process is similar to the one disclosed in WO2006/100108 except that an additional chromatographic step (Phenyl Sepharose) was added between the Q-Sepharose-XL and hydroxyapatite steps and the last chromatographic step on the octyl-Sepharose 4FF was removed.

Preparation of Conjugates

It is well known in the art how to make purified pneumococcal polysaccharides. For the purposes of these examples the polysaccharides were made essentially as described in EP072513 or by closely-related methods. Before conjugation the polysaccharides may be sized by microfluidisation as described below.

The activation and coupling conditions are specific for each polysaccharide. These are given in Table 1. Sized polysaccharide (except for 6B and 23F) was dissolved in NaCl 2M, NaCl 0.2M or in water for injection (WFI). The optimal polysaccharide concentration was evaluated for all the serotypes. All serotypes except serotype 18C were conjugated directly to the carrier protein as detailed below.

From a 100 mg/ml stock solution in acetonitrile or acetonitrile/water (50%/50%) solution, CDAP (1-cyano-4-dimethylaminopyridinium tetrafluoroborate) (CDAP/PS ratio 0.5-1.5 mg/mg PS) was added to the polysaccharide solution. 1.5 minute later, 0.2M-0.3M NaOH was added to obtain the specific activation pH. The activation of the polysaccharide was performed at this pH for 3 minutes at 25° C. Purified protein (protein D, CRM197 or DT) (the quantity depends on the initial PS/carrier protein ratio) was added to the activated polysaccharide and the coupling reaction was performed at the specific pH for up to 2 hour (depending upon serotype) under pH regulation. In order to quench un-reacted cyanate ester groups, a 2M glycine solution was then added to the mixture. The pH was adjusted to the quenching pH (pH 9.0). The solution was stirred for 30 minutes at 25° C. and then incubatedovernight at 2-8° C. with continuous slow stirring.

Preparation of 18C:

18C was linked to the carrier protein via a linker—Adipic acid dihydrazide (ADH) Polysaccharide serotype 18C was microfluidized before conjugation.

Derivatization of tetanus toxoid with EDAC (2-Ethyl-3-(3-dimethylaminopropyl) carbodiimide hydrochloride)

For derivatization of the tetanus toxoid, purified TT was diluted at 25 mg/ml in 0.2M NaCl and the ADH spacer was added in order to reach a final concentration of 0.2M. When the dissolution of the spacer was complete, the pH was adjusted to 6.2. EDAC (1-ethyl-3-(3-dimethylaminopropyl) carbodiimide) was then added to reach a final concentration of 0.02M and the mixture was stirred for 1 hour under pH regulation. The reaction of condensation was stopped by increasing pH up to 9.0 for at least 30 minutes at 25° C.

Derivatized TT was then diafiltrated (10 kDa CO membrane) in order to remove residual ADH and EDAC reagent.

$TT_{AH}$ (Tetanus toxoid conjugated to an ADH linker) bulk was finally sterile filtered until coupling step and stored at −70° C.

Chemical Coupling of $TT_{AH}$ to PS 18C

Details of the conjugation parameters can be found in Table 1.

2 grams of microfluidized PS were diluted at the defined concentration in water and adjusted to 2M NaCl by NaCl powder addition.

CDAP solution (100 mg/ml freshly prepared in 50/50 v/v acetonitrile/WFI) was added to reach the appropriate CDAP/PS ratio.

The pH was raised up to the activation pH 9.0 by the addition of 0.3M NaOH and was stabilised at this pH until addition of $TT_{AH}$.

After 3 minutes, derivatized $TT_{AH}$ (20 mg/ml in 0.2 M NaCl) was added to reach a ratio $TT_{AH}$/PS of 2; the pH was regulated to the coupling pH 9.0. The solution was left one hour under pH regulation.

For quenching, a 2M glycine solution, was added to the mixture PS/TT$_{AH}$/CDAP.

The pH was adjusted to the quenching pH (pH 9.0).

The solution was stirred for 30 min at 25° C., and then overnight at 2-8° C. with continuous slow stirring.

Specific Activation/Coupling/Quenching Conditions
of *S. Pneumoniae* Capsular Saccharide-Protein
D/TT/DT/PhtD/Ply Conjugates Where "µfluid" appears in a row header, it indicates that the saccharide was sized by microfluidisation before conjugation. Sizes of saccharides following microfluidisation are given in table 2.

TABLE 1

Specific activation/coupling/quenching conditions of *S. pneumoniae* capsular saccharide-Protein D/TT/DT/CRM197 conjugates

| Serotype | 1 µfluid | 4 µfluid | 5 mfluid | 6A mfluid | 6B | 7F µfluid |
|---|---|---|---|---|---|---|
| PS conc. (mg/ml) | 2.27 | 2.37 | 7.1 | 10 | 5.0 | 5.0 |
| PS dissolution | WFI | WFI | WFI | NaCl 2M | NaCl 2M | NaCl 2M |
| Carrier conc. (mg/ml) | 10.0 PD | 10.0 PD | 5.0 PD | 10 CRM197 | 5.0 PD | 10.0 PD |
| Initial PROT/PS Ratio (w/w) | 1.65/1 | 1.60/1 | 1/1 | 1/1 | 1.1/1 | 1.2/1 |
| CDAP conc. (mg/mg PS) | 0.55 | 0.55 | 0.79 | 1.0 | 0.83 | 0.75 |
| pH$_a$ = pH$_c$ = pH$_q$ | 9.0/9.0/9.0 | 9.5/9.5/9.0 | 9.0/9.0/9.0 | 9.5/9.5/9.0 | 9.5/9.5/9.0 | 9.5/9.5/9.0 |

| Serotype | 9V µfluid | 14 µfluid | 18C µfluid | 19A µfluid | 19F µfluid | 23F |
|---|---|---|---|---|---|---|
| PS conc. (mg/ml) | 5.0 | 5.0 | 4.5 | 15.0 | 9.0 | 2.38 |
| PS dissolution | NaCl 2M | NaCl 2M | NaCl 2M | NaCl 2M | NaCl 2M | NaCl 2M |
| Carrier protein conc. (mg/ml) | 10.0 | 10.0 | 20.0 (TT) | 15.0 (CRM197) | 20.0 (DT) | 5.0 |
| Initial carrier protein/PS Ratio (w/w) | 1.2/1 | 1.2/1 | 2/1 | 1.5/1 | 1.5/1 | 1/1 |
| CDAP conc. (mg/mg PS) | 0.50 | 0.75 | 0.75 | 1.5 | 1.5 | 0.79 |
| pH$_a$ = pH$_c$ = pH$_q$ | 9.5/9.5/9.0 | 9.5/9.5/9.0 | 9.0/9.0/9.0 | 9.0/9.0/9.0 | 9.0/9.0/9.0 | 9.5/9.5/9.0 |

Note:
pH$_{a,c,q}$ corresponds to the pH for activation, coupling and quenching, respectively Purification of the Conjugates:

The conjugates were purified by gel filtration using a Sephacryl S400HR gel filtration column equilibrated with 0.15M NaCl (except S500HR was used as buffer for 18C and 20 mM acetate containing 1.15MNaCl pH6.2 was used for 19A) to remove small molecules (including DMAP) and unconjugated saccharide and protein. Based on the different molecular sizes of the reaction components, PS-PD, PS-TT, PS-CRM197 or PS-DT conjugates are eluted first, followed by free PS, then by free protein carrier and finally DMAP and other salts (NaCl, glycine). Fractions containing conjugates are detected by UV$_{280\ nm}$. Fractions are pooled according to their Kd, sterile filtered (0.22 µm) and stored at +2-8° C. The PS/Protein ratios in the conjugate preparations were determined.

Formulation of the Vaccines

The 10V vaccine contains *S. pneumoniae* capsular saccharide serotype 1, 4, 5, 6B, 7F, 9V, 14, 18C, 19F and 23F conjugates adsorbed onto aluminium phosphate together at a human dose of 1, 3, 1, 1, 1, 1, 1, 3, 3, 1 µg (the saccharides were individually adsorbed to aluminium phosphate, they were then mixed together and the level of aluminium phosphate adjusted to 500 µg).

The 12V vaccine was made in the same way as the 10V vaccine with additional serotypes 19A and 6A conjugates at doses of 2 µg adsorbed onto aluminium phosphate added.

The 12V+ proteins vaccine was made in the same way as the 12V vaccine except proteins PhtD, dPly and PE-PilA were added. The PE-PilA was produced as described herein. The 12 conjugates and the proteins were mixed together using the dosages described for 12V above and the proteins at dosages of 30 µg each (note that this refers to 30 µg of PE-PilA, not 30 µg of PE and 30 µg of PilA).

Example 22

Comparison of the Immunogenicity of 10V, 12V and 12V+ Proteins Vaccines in Mice

Description of the Anti-Pneumococcal Polysaccharide PS (Polysaccharide) ELISA

Microplates were coated for 2 hours at 37° C. with capsular polysaccharide (CPS) (100 µl per well of 2.5 µg/ml of PS1 and PS3, 5 µg/ml of PS4, 5, 6A, 6B, 7F, 9V or 14; 10 µg/ml of PS19A and 23F or 40 µg/ml of PS18C and PS19F in PBS). The plates were washed three times with NaCl 150 mM (0.9%)-Polysorbate 20 0.05%. Sera was diluted (1/2 for 6A and 6B and 1/10 for the other serotypes) in PBS-Polysorbate20 0.05% containing CPS (1 mg CPS/ml of non diluted serum except or 6A and 6B which was at 2.5 mg/ml) V/V and incubated for 1 hour at 37° C. in order to neutralize antibodies directed to the CPS. The sera from mice immunised as described in the section entitled 'immunogenicity of three vaccine formulations in mice' or a reference (an internal reference calibrated with Chrompure mouse IgG) was added to the microwells and serially diluted 100 µl (two-fold dilution step) in PBS-Polysorbate20 0.05%. The plates were incubated under agitation for 30 minutes at room temperature. The plates were washed as above and anti-mouse IgG antibodies conjugated to peroxidase (100 µl per well) was added, the plates were incubated for 30 minutes at room temperature with shaking. After washing, the substrate (4 mg of OPDA (ortho phenylen-diamine) in 10 ml of citrate 0.1M pH 4.5-4.6 and 5 µl of $H_2O_2$) was added to each well (100 µl) and the plates incubated for 15 minutes in the dark. The reaction was stopped by addition of HCl 1N (50 µl). The absorbance was read at 490 nm or 620 nm for the reference using a spectrophotometer. The color developed is directly proportional to the amount of antibody present in the serum.

Description of the ELISA to Measure PD, PE and PilA Antibodies

Plates were coated overnight at 4° C. with 100 µl per well of 2 µg/ml of PD (1 mg/ml), 2 µg/ml of PE (1500 µg/ml), 2 µg/ml of PilA (3660 µg/ml) in carbonate buffer pH 9.6. The plates were washed four times with NaCl 0.9% Polysorbate 20 0.05%. For PE and PilA ELISA, the plates were saturated for 30 min at room temperature (with shaking) with PBS-BSA1%. After washing, sera from mice immunised as described in the section entitled 'immunogenicity of three vaccine formulations in mice' or a reference (an internal reference calibrated with Chrompure mouse IgG) was added to microwells and serially diluted 100 µl (two-fold dilution step) in PBS Polysorbate 20 0.05% (for the PD assay) and PBS Polysorbate 20 0.05% BSA 0.1% (for the PE and PilA assay). The plates were then incubated for 30 min at room temperature with agitation. After washing, the plates were incubated with an anti-mouse IgG antibody conjugated to peroxidaseperoxidase (100 µl per well) at room temperature for 30 minutes with shaking. The plates were then washed as above and the substrate conjugate (4 mg of OPDA (ortho phenylen-diamine) in 10 ml of citrate 0.1M pH 4.5-4.6 and 5 µl of $H_2O_2$) as added to each well (100 µl) for 15 min in darkness. The reaction was stopped by addition of HCl 1N 50 µl and the absorbance was read at 490 nm (620 nm for the reference).

Description of the ELISA to Measure PhtD and dPly Antibodies

Plates were coated for 2 hours at 37° C. with 100 µl per well of 1 µg/ml of PhtD (1021 µg/ml) or 4 µg/ml of Ply (367 µg/ml). The plates were then washed three times with NaCl 0.09% Polysorbate 0.05%. After washing, sera from mice immunised as described in the section entitled 'immunogenicity of three vaccine formulations in mice' or a reference (an internal reference calibrated with Chrompure mouse IgG) (was added to microwells and serially diluted 100 µl (two-fold dilution step) in PBS Polysorbate 20 0.05%. The plates were incubated for 30 min at room temperature with agitation. After washing, the plates were incubated with an anti-mouse IgG antibody conjugated to peroxidase (100 µl per well) at room temperature for 30 minutes with shaking. The plates were washed as above and the substrate conjugate (4 mg of OPDA in 10 ml of citrate 0.1M ph 4.5 and 5 µl of $H_2O_2$) was added to each well (100 µl) for 15 min in darkness. The reaction was stopped by addition of HCl 1N 50 µl and the absorbance was read at 490 nm (620 nm for the reference filter).

Description of Opsonophagocytosis Assay (OPA)

Serum samples were heated for 45 min at 56° C. to inactivate any remaining endogenous complement. Twenty-five microliters aliquots of each 1:2 diluted serum sample were two-fold serially diluted in 25 µl OPA buffer (HBSS (Hank's Balanced Salt Solution)—14.4% inactivated FCS (Foetal Calf Serum)) per well of a 96-well round bottom microtitre plate. Subsequently, 25 µl of a mixture of activated HL-60 cells (1×107 cells/ml), freshly thawed pneumococcal working seed and freshly thawed baby rabbit complement in an e.g. 4/2/1 ratio (v/v/v) (except for serotypes 1, 6B and 6A for which the ratio was 4/2/2) were added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min, the plate is kept on ice until use. A 20 µl aliquot of each well of the plate was then transferred into the corresponding well of a 96-well flat bottom microplate and 50 µl of Todd-Hewitt Broth-0.9% agar was added to each well. After overnight incubation at 37° C. and 5% $CO_2$, pneumococcal colonies which appeared in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Immunogenicity of Three Vaccine Formulations in Mice.

2 groups of 27 female Balb/c mice distributed in 2 experiments were immunized by intramuscular (IM) injections on days 0, 14 and 28 with 1/10 human dose of different formulation including Proteins alone (PhtD, dPly and PEPilA), Prevnar 13™ (a commercially available Streptococcal vaccine—results not presented) 10V, 12V (DSP2A017) and 12V+ proteins (DSP2A012) GMP lots. Mice received in a different leg (mimicking co-administration at different sites in infants in clinical trials) $\frac{1}{10}^{th}$ human dose of Infanrix Hexa™ (a vaccine comprising diphtheria toxoid, tetanus toxoid, pertussis toxoid, filamentous haemmagglutinin, pertactin, hepatitis B surface antigen, inactivated polio virus types 1, 2 and 3 and *Haemophilus influenzae* b saccharide (PRP)).

Anti-IgG levels and opsonophagocytosis titers were determined respectively in individual and pooled sera collected at day 42.

The potential of the 12V+ proteins vaccine to induce IgG antibody titers and opsonic activity was evaluated and compared to that of the 12V and 10V vaccines.

Sera from mice injected with the different formulations were tested in ELISA (as described above) against the polysaccharide serotypes and proteins and in OPA against the 12 polysaccharide serotypes.

The 12V+ proteins vaccine induced similar response to the 12V for most serotypes.

Figure 31:
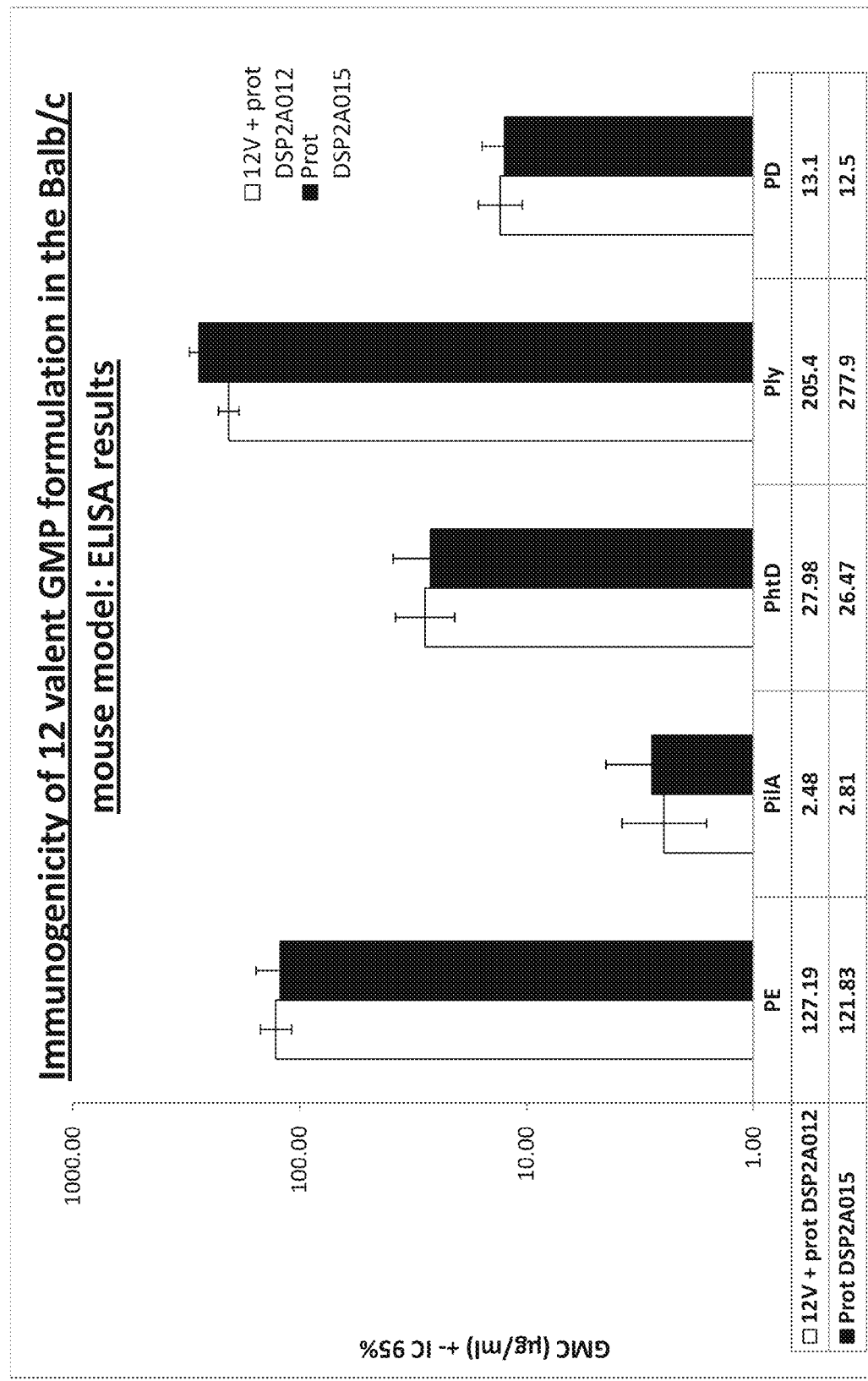
FIG. 31. Graph comparing the immunogenicity of a composition comprising 12 saccharide conjugates, PhtD, dPly and PE-PilA (12V+prot) with a composition comprising PhtD, dPly and PE-PilA alone (prot) as measured after injection of mice using an anti-protein ELISA assay. GMC=geometric mean concentration. IC=confidence intervals.
Figure 32:
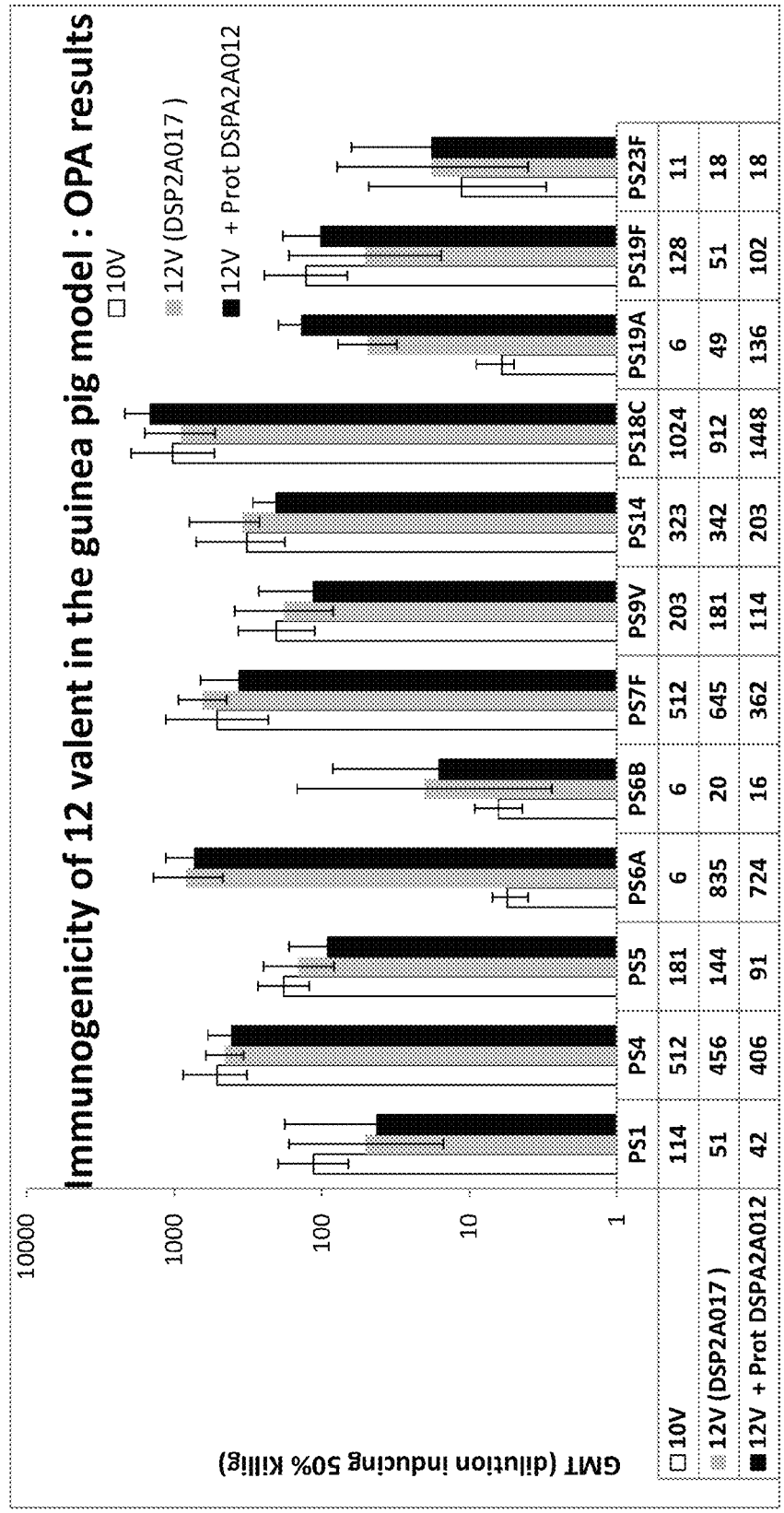
FIG. 32. Graph comparing the immunogenicity of a composition comprising 12 saccharide conjugates, PhtD, dPly and PE-PilA (12V+prot) with a composition comprising 12 saccharide conjugates (12V) and a composition comprising 10 saccharide conjugates (10V) as measured after injection of guinea pigs using an opsonophagocytosis assay. GMT=geometric means titer.
Figure 33:
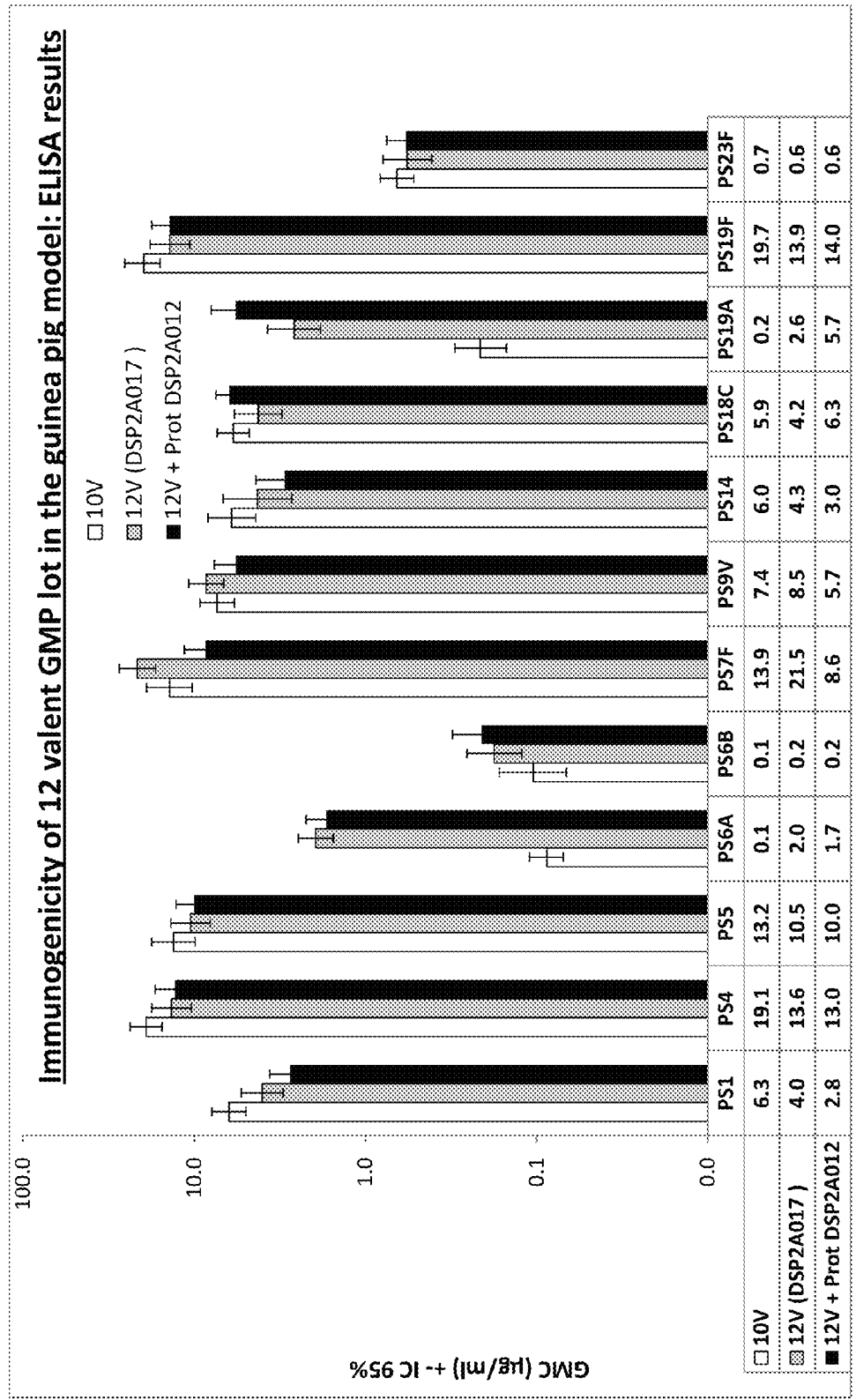
FIG. 33. Graph comparing the immunogenic of a composition comprising 12 saccharide conjugates, PhtD, dPly and PE-PilA (12V+prot) with a composition comprising 12 saccharide conjugates (12V) and a composition comprising 10 saccharide conjugates (10V) as measured after injection of guinea pigs using an anti-saccharide ELISA. GMC=geometric mean concentration. IC=confidence intervals.

The results in FIG. 31 demonstrated that there was no stastical difference between the PE, PilA, PhtD, Ply and PD antibody responses measured for the 12V+ formulation and a formulation that did not comprises the *S. pneumoniae* saccharide conjugates.

Example 23

Comparison of the Immunogenicity of 10V, 12V and 12V+ Protein Vaccines in Guinea Pigs Description of ELISA Anti-Pneumococcal Polyssacharide PS Microplates were coated for 2 hours at 37° C. with 100 µl per well of 2.5 µg/ml of PS1, 5 µg/ml of PS4, 5, 6A, 6B, 7F, 9V or 14; 10 µg/ml of PS19A and 23F, 40 µg/ml of PS18C and PS19F or Affinipure Goat anti-guinea pig IgG (2.4 mg/ml) diluted to 2 µg/ml for the reference wells in PBS. The plates were washed three times with NaCl 150 mM (0.9%)-Polysorbate20 0.05%. Pooled serum from each group was diluted (½ for P δ 6A and 6B and ¹⁄₁₀ for all the other serotypes) in PBS-Polysorbate20 0.05% containing CPS (1 mg CPS/ml of non diluted serum except for 6A and 6B at 2.5 mg/ml) V/V and incubated for 1 hour at 37° C. in order to neutralize antibodies directed to CPS. The serum from guinea pigs immunised as described in the section entitled 'immunogenicity of three vaccine formulations in guinea pigs' was added to the microwells and serially diluted 100 µl (two-fold dilution step) in PBS-Polysorbate20 0.05% or a reference (Chrompure guinea pig IgG (11 mg/ml) diluted to 0.25 µg/ml in PBS-polysorbate20 0.05%) was added. The plates were incubated under agitation for 30 minutes at room temperature. The plates were washed as above and anti-guinea pig IgG antibodies conjugated to peroxidase (100 µl per well) were added and the plates incubated for 30 minutes at room temperature with shaking. After washing, the substrate (4 mg of OPDA in 10 ml of citrate 0.1M pH 4.5-4.6 and 5 µl of $H_2O_2$) was added to each well (100 µl) and incubated for 15 minutes in the dark. The reaction was stopped by addition of HCl 1N. Absorbance was read at 490 nm (620 nm for the reference) using a spectrophotometer. The color developed is directly proportional to the amount of antibody present in the serum.

Description of the ELISA to Measure Anti PD, PE, and PilA Antibodies

Plates were coated for 2 hours at 37° C. with 100 µl per well of 2 µg/ml of PD (1 mg/ml), 2 µg/ml of PE (1500 µg/ml), or 2 µg/ml of PilA (3660 µg/ml) in carbonate buffer pH 9.6 in PBS or Affinipure Goat anti-guinea pig IgG (2.4 mg/ml) diluted to 2 µg/m for the reference wells in PBS. The plates were washed 4 times with NaCl 0.9% Polysorbate 20 0.05%. For PE and PilA ELISAs (this step was not carried out for the PD and Ply ELISAs), the plates were saturated 30 min at room temperature with PBS-BSA1%. After washing, sera from guinea pigs immunised as described in the section entitled 'immunogenicity of three formulations in guinea pigs' or a reference serum sample (an internal reference calibrated with Chrompure guinea pig IgG) was added to microwells and serially diluted 100 µl (two-fold dilution step) in PBS Polysorbate 20 0.05% (for the PD ELISA) and PBS Polysorbate 20 0.05% BSA 0.1% for the PE and PilA ELISAs. The plates were incubated for 30 min at room temperature. After washing, the plates were incubated with an anti-guinea pig IgG antibody conjugated to peroxydase (100 µl per well) at room temperature for 30 minutes with shaking. Plates were washed as above and the substrate conjugate (4 mg of OPDA in 10 ml of citrate 0.1M pH 4.5-4.6 and 5 µl of $H_2O_2$) was added to each well (100 µl) for 15 min in darkness. The reaction was stopped by addition of HCl 1N 50 µl and the absorbance is read at 490 nm (620 nm for the reference filter).

Description of the ELISA to Measure PhtD and dPly Antibodies

Plates were coated for 2 hours at 37° C. with 100 µl per well of 1 µg/ml of PhtD (1021 µg/ml) or 2 µg/ml Ply (376 µg/ml) in PBS. The plates were then washed 4 times with NaCl 0.9% Polysorbate 20 0.05%. After washing, sera from guinea pigs immunised as described in the section entitled 'immunogenicity of three vaccine formulations in guinea pigs' or a reference (an internal reference calibrated with Chrompure guinea pig IgG) was added to microwells and serially diluted 100 µl (two-fold dilution step) in PBS Polysorbate 20 0.05%. The plates were incubated for 30 min at room temperature with agitation. After washing, the plates were incubated with an anti-guinea pig IgG antibody conjugated to peroxydase (100 µl per well) at room temperature for 30 minutes with shaking. Plates were washed as above and the substrate conjugate (4 mg of OPDA in 10 ml of citrate 0.1M pH 4.5-4.6 and 5 µl of $H_2O_2$) was added to each well (100 µl) for 15 min in darkness. The reaction was stopped by addition of HCl 1N 50 µl and the absorbance was read at 490 nm (620 nm for the reference filter).

Opsonophagocytosis Assay

Serum samples were heated for 45 min at 56° C. to inactivate any remaining endogenous complement. Twenty-five microliters aliquots of each 1:2 diluted serum sample was two-fold serially diluted in 25 µl OPA buffer (HBSS (Hank's Balanced Salt Solution)—14.4% inactivated FCS (foetal calf serum)) per well of a 96-well round bottom microtitre plate. Subsequently, 25 µl of a mixture of activated HL-60 cells (1×107 cells/ml), freshly thawed pneumococcal working seed and freshly thawed baby rabbit complement in an e.g. 4/2/1 ratio (v/v/v) (except for serotypes 1,6B and 6A for which the ratio was 4/2/2) was added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min (the plate should be kept on ice until further use. A 20 µl aliquot of each well of the plate was then transferred into the corresponding well of a 96-well flat bottom microplate and 50 µl of Todd-Hewitt Broth-0.9% agar was added to each well. After overnight incubation at 37° C. and 5% CO2, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Immunogenicity of Three Formulations in Guinea Pigs 2 groups of 17 guinea pigs distributed in 2 experiments were immunized by intramuscular (IM) injections on days 0, 14 and 28 with ¼ human dose of different formulation including Proteins alone (PhtD, dPly and PEPilA), Prevnar 13(™ a commercially available Streptococcal vaccine—results not presented) 10V, 12V (DSP2A017) and 12V+ proteins (DSP2A012) GMP lots. Guinea pigs received in a different leg (mimicking co-administration at different sites in infants in clinical trials) ¼ of human dose of Infanrix Hexa((™ a vaccine comprising diphtheria toxoid, tetanus toxoid, pertussis toxoid, filamentous haemmagglutinin, pertactin, hepatitis B surface antigen, inactivated polio virus types 1, 2 and 3 and *Haemophilus influenzae* b saccharide (PRP). Anti-IgG levels and opsonophagocytosis titers were determined respectively in individual and pooled sera collected at days 42.

The IgG antibody titers and opsonic activity was evaluated and compared between the 12V+ proteins, 12V and 10V vaccines.

Sera from guinea pigs injected with the different formulations were tested in ELISA against the polysaccharide serotypes and proteins and in OPA against the 12 serotypes in the formulation. The 12V+ proteins induced similar responses to the 12V formulation.

Figure 34:
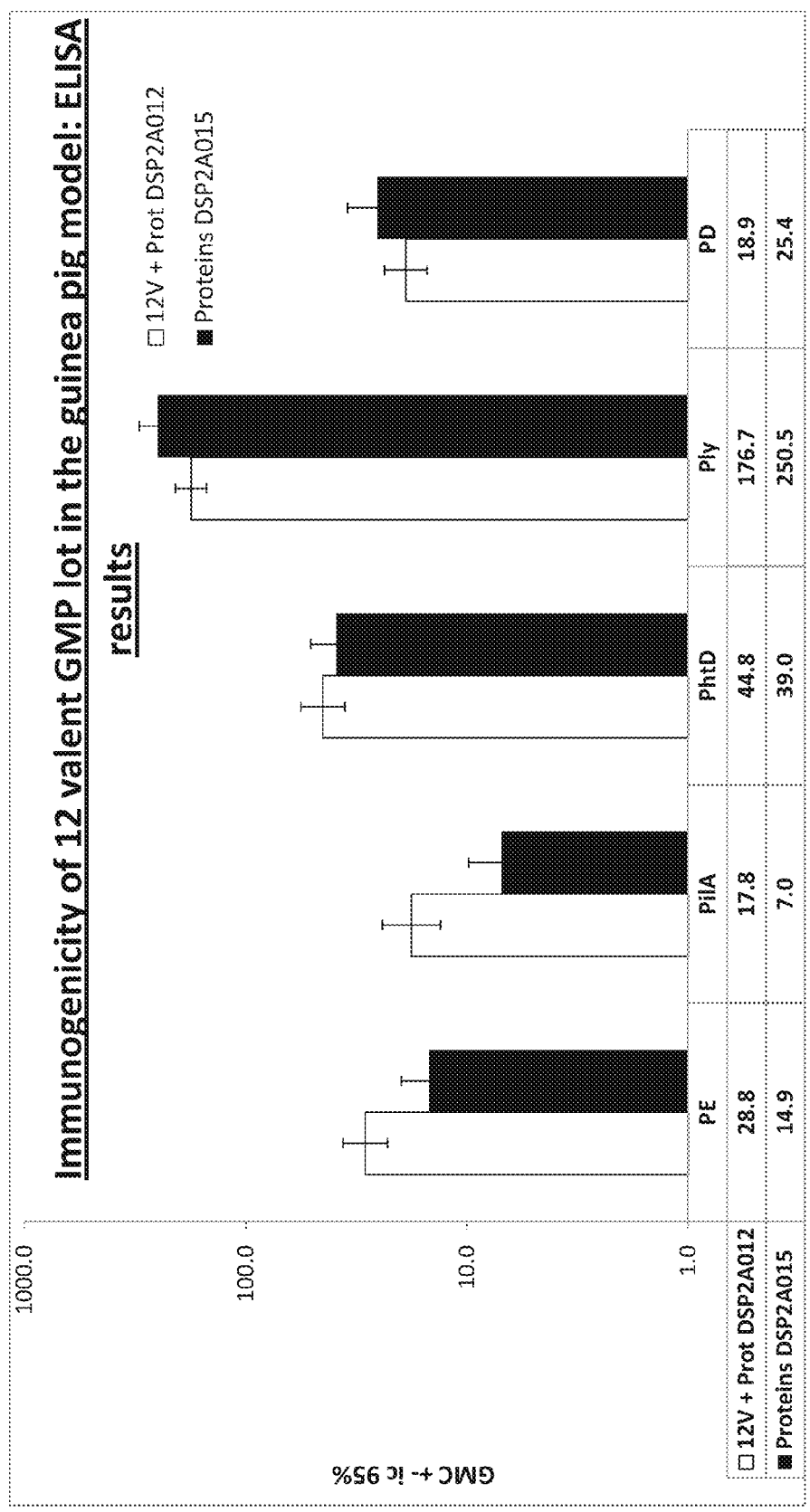
FIG. 34. Graph comparing the immunogenic of a composition comprising 12 saccharide conjugates, PhtD, dPly and PE-PilA (12V+prot) with a composition comprising PhtD, dPly and PE-PilA alone (prot) as measured after injection of guinea pigs using an anti-protein ELISA. GMC=geometric mean concentration. ic=confidence intervals.

The results in FIG. 34 demonstrated that there is no negative impact on the immunogenicity of the 12 valent conjugates when they are combined with PEPilA.

The results obtained with the 12V+ proteins GMP formulation demonstrated immunogenicity of the 10V polysaccharides as well as the proteins and support the clinical evaluation of this formulation.

We claim:

1. An immunogenic composition comprising: (i) 1 or more *Streptococcus pneumoniae* capsular saccharide conjugates; and (ii) a fusion protein component comprising (a) an immunogenic fragment of Protein E wherein the amino acid sequence of the immunogenic fragment of Protein E has a sequence that is SEQ ID NO. 124 or SEQ ID NO. 125, and (b) an immunogenic fragment of PilA from *Haemophilus influenzae*, wherein the amino acid sequence of the immunogenic fragment of PilA has at least 95%, identity, over the entire length, to SEQ ID NO. 127, wherein the immunogenic fragment of protein E is covalently linked to immunogenic fragment of PilA to form the fusion protein.

2. The immunogenic composition of claim 1 wherein the immunogenic fragment of Protein E is a polypeptide having an amino acid sequence of SEQ ID NO. 124.

3. The immunogenic composition of claim 1 wherein the immunogenic fragment of Protein E is a polypeptide having the amino acid sequence of SEQ ID NO. 125.

4. The immunogenic composition of claim 1 wherein the immunogenic fragment of PilA is a polypeptide comprising a sequence having at least 98% identity, over the entire length, to SEQ ID NO. 127.

5. The immunogenic composition of claim 1 wherein the immunogenic fragment of PilA is a polypeptide having an amino acid sequence that is SEQ ID NO. 127.

6. The immunogenic composition of claim 1 wherein the fusion protein is at least 95%, identical to SEQ ID NO. 194.

7. The immunogenic composition of claim 1 wherein the 1 or more *Streptococcus pneumoniae* capsular saccharide conjugates comprises a conjugated saccharide selected from the group consisting of a *Streptococcus pneumoniae* serotype 1, serotype 4, serotype 5, serotype 6B, serotype 9V, a serotype 14, a serotype 18C, a serotype 19F and a serotype 23F capsular saccharide conjugate.

8. The immunogenic composition of claim 1 or claim 7 wherein the 1 or more *Streptococcus pneumoniae* capsular saccharide conjugates comprises a conjugated saccharide selected from the group consisting of a conjugated serotype 1 saccharide, a conjugated serotype 5 saccharide and a conjugated serotype 7F saccharide.

9. The immunogenic composition of claim 1 or claim 7 wherein the 1 or more *Streptococcus pneumoniae* capsular saccharide conjugates are conjugated to a carrier protein independently selected from the group consisting of tetanus toxoid (TT), fragment C of TT, diphtheria toxoid, CRM197 (cross reacting material 197), Pneumolysin, protein D (from *H. influenzae*), PhtD (Poly Histidine Triad D), PhtDE (a fusion between Pneumococal Histidine Triad D and E) and N19.

10. The immunogenic composition of claim 1 or claim 7 wherein the *Streptococcus pneumoniae* capsular saccharide conjugates are all independently conjugated to CRM197.

11. The immunogenic composition of claim 1 or claim 7 wherein the 1 or more *Streptococcus pneumoniae* capsular saccharide conjugates comprises a serotype 1 saccharide conjugated to protein D, a serotype 4 saccharide conjugated to protein D, a serotype 5 saccharide conjugated to protein D, a serotype 6B saccharide conjugated to protein D, a serotype 7F saccharide conjugated to protein D, a serotype 9V saccharide conjugated to protein D, a serotype 14 saccharide conjugated to protein D, a serotype 23F saccharide conjugated to protein D, a serotype 18C saccharide conjugated to tetanus toxoid and a serotype 19F saccharide conjugated to diphtheria toxoid.

12. The immunogenic composition of claim 1 wherein the immunogenic composition further comprises at least one unconjugated or conjugated *Streptococcus pneumoniae* protein.

13. The immunogenic composition of claim 12 wherein the at least one unconjugated or conjugated *Streptococcus pneumoniae* protein is a PhtD protein.

14. The immunogenic composition of claim 12 wherein the at least one unconjugated or conjugated *Streptococcus pneumoniae* protein is detoxified pneumolysin (dPly).

15. A vaccine comprising the immunogenic composition of claim 1 or claim 7 and a pharmaceutically acceptable excipient.

16. A method of immunizing a subject against diseases caused by *Streptococcus pneumoniae* infection comprising administering to the subject a therapeutically effective dose of the immunogenic composition of claim 1 or claim 7 or the vaccine of claim 15.

17. A method of immunizing a subject against diseases caused by *Haemophilus influenzae* infection comprising administering to the subject a therapeutically effective dose of the immunogenic composition of claim 1 or claim 7 or the vaccine of claim 15.

18. An immunogenic composition comprising a fusion protein wherein the amino acid sequence of the fusion protein is SEQ ID NO. 219.

19. An immunogenic composition comprising a fusion protein wherein the amino acid sequence of the fusion protein is SEQ ID NO. 177.

* * * * *